United States Patent
Arami et al.

(10) Patent No.: US 9,913,970 B2
(45) Date of Patent: Mar. 13, 2018

(54) APPLICATOR

(71) Applicant: HISAMITSU PHARMACEUTICAL CO., INC., Tosu-shi, Saga (JP)

(72) Inventors: Shunsuke Arami, Tsukuba (JP); Makoto Ogura, Tsukuba (JP); Seiji Tokumoto, Tsukuba (JP)

(73) Assignee: HISAMITSU PHARMACEUTICAL CO., LTD., Tosu-Shi, Saga (JP)

( * ) Notice: Subject to any disclaimer, the term of this patent is extended or adjusted under 35 U.S.C. 154(b) by 319 days.

(21) Appl. No.: 14/654,029

(22) PCT Filed: Nov. 27, 2013

(86) PCT No.: PCT/JP2013/081944
§ 371 (c)(1),
(2) Date: Jun. 19, 2015

(87) PCT Pub. No.: WO2014/097837
PCT Pub. Date: Jun. 26, 2014

(65) Prior Publication Data
US 2015/0314117 A1 Nov. 5, 2015

(30) Foreign Application Priority Data
Dec. 21, 2012 (JP) ................... P2012-280198

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61M 5/1454* (2013.01);
(Continued)

(58) Field of Classification Search
CPC ...... A61M 37/0015; A61M 2037/0023; A61M 2037/003; A61M 2037/0038;
(Continued)

(56) References Cited

U.S. PATENT DOCUMENTS 6,334,856 B1 * 1/2002 Allen ................. A61B 5/14514
128/898
2002/0091357 A1 7/2002 Trautman et al.
(Continued)

FOREIGN PATENT DOCUMENTS

AU 2012201016 A1 3/2012
CA 2425312 A1 4/2002
(Continued)

OTHER PUBLICATIONS

European Search Report dated Nov. 21, 2016 corresponding to application No. 13864780.5-1501.
(Continued)

*Primary Examiner* — Bradley Osinski
*Assistant Examiner* — James D Ponton
(74) *Attorney, Agent, or Firm* — Nath, Goldberg & Meyer; Joshua B. Goldberg; Tanya E. Harkins

(57) ABSTRACT

An applicator includes a piston plate, a non-linear coil spring, a casing, a lock means and a release means. The casing includes a tubular main body part that houses therein the piston plate and the non-linear coil spring, and a cover part that is arranged on one end side of the main body part. The cover part and the piston plate sandwich the non-linear coil spring there between. The lock means locks the piston plate with the casing such that the piston plate is held at a retraction position thereof on the cover part side in a state where the cover part and the piston plate compress the non-linear coil spring. The release means releases a locked state where the piston plate is locked with the casing by the lock means and where the cover part and the piston plate compress the non-linear coil spring.

19 Claims, 99 Drawing Sheets

(51) Int. Cl.
    *A61M 5/145* (2006.01)
    *A61M 5/158* (2006.01)

(52) U.S. Cl.
    CPC ............ *A61M 2005/14506* (2013.01); *A61M 2005/1585* (2013.01); *A61M 2037/0023* (2013.01); *A61M 2037/0046* (2013.01)

(58) Field of Classification Search
    CPC .. A61M 2037/0046; A61M 2037/0053; A61M 2037/0061; A61M 5/14244; A61M 5/14248; A61M 2005/1585; A61K 9/0021; A61B 5/6849; A61B 5/6847; A61B 5/685
    See application file for complete search history.

(56) References Cited

U.S. PATENT DOCUMENTS

| | | | |
|---|---|---|---|
| 2002/0123675 A1* | 9/2002 | Trautman | A61B 17/205 600/309 |
| 2006/0074376 A1 | 4/2006 | Kwon | |
| 2008/0039805 A1 | 2/2008 | Frederickson et al. | |
| 2008/0156594 A1 | 7/2008 | Kobayashi | |
| 2009/0198189 A1 | 8/2009 | Simons et al. | |
| 2010/0222743 A1* | 9/2010 | Frederickson | A61B 17/205 604/136 |
| 2011/0275994 A1 | 11/2011 | Iwase et al. | |
| 2011/0276027 A1 | 11/2011 | Trautman et al. | |
| 2012/0010529 A1* | 1/2012 | Chickering, III | A61B 5/1411 600/576 |
| 2012/0130207 A1 | 5/2012 | O'dea et al. | |
| 2014/0039458 A1* | 2/2014 | Constantineau | A61M 5/158 604/508 |

FOREIGN PATENT DOCUMENTS

| | | |
|---|---|---|
| CA | 2490137 A1 | 12/2003 |
| CN | 1479589 A | 3/2004 |
| CN | 101513550 A | 8/2009 |
| CN | 102753234 A | 10/2012 |
| EP | 2399643 A1 | 12/2011 |
| JP | 2004510534 A | 4/2004 |
| JP | 2006500973 A | 1/2006 |
| JP | 2006-276200 A | 10/2006 |
| JP | 2007516781 A | 6/2007 |
| JP | 2008535587 A | 9/2008 |
| JP | 2010-211890 A | 9/2010 |
| JP | 4659332 B2 | 3/2011 |
| JP | 2012-100783 A | 5/2012 |
| JP | 2014-509208 A | 4/2014 |
| KR | 101111144 B1 | 2/2012 |
| TW | 201231109 A1 | 8/2012 |
| WO | 00/09184 A1 | 2/2000 |
| WO | 02/30300 A2 | 4/2002 |
| WO | 2005/123173 A1 | 12/2005 |
| WO | 2006/103727 A1 | 10/2006 |
| WO | 2007/124411 A1 | 11/2007 |
| WO | 2011075105 A1 | 6/2011 |
| WO | 2012046816 A1 | 4/2012 |
| WO | 2013/015136 A1 | 2/2015 |
| WO | 2013/051568 A1 | 3/2015 |

OTHER PUBLICATIONS

International Patent Application No. PCT/JP2013/081944, International Search Report dated Mar. 4, 2014, two (2) pages.
International Patent Application No. PCT/JP2013/081944, International Preliminary Report on Patentability dated Jul. 2, 2015, Seven (7) pages.
European Search Report dated Sep. 27, 2017 in corresponding with not Counterpart European Patent Application No. 14859702.4.
Office action received Nov. 17, 2017, in U.S. Appl. No. 15/032,709.

* cited by examiner

Fig.14
(a)
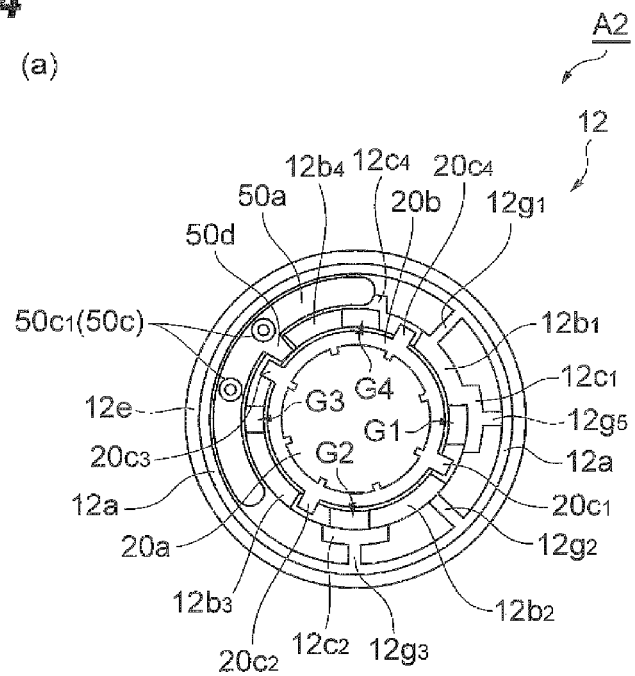
(b)
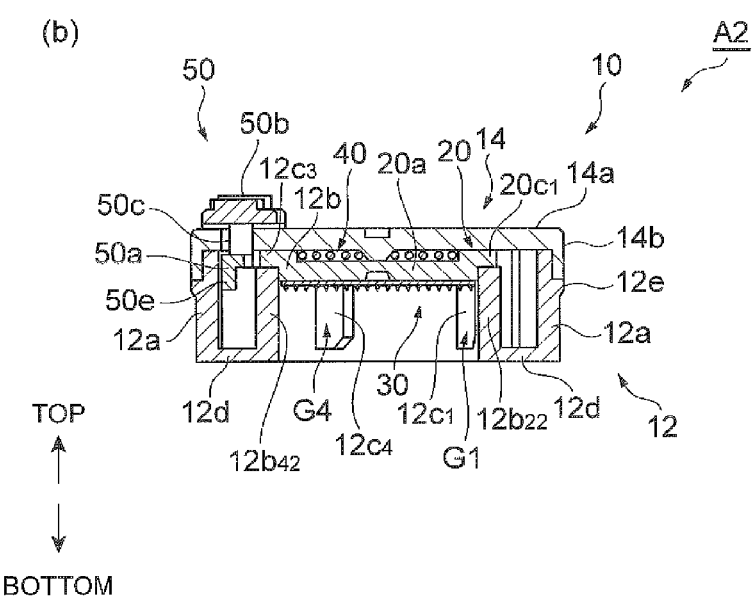
TOP
↑
↓
BOTTOM

Fig.15
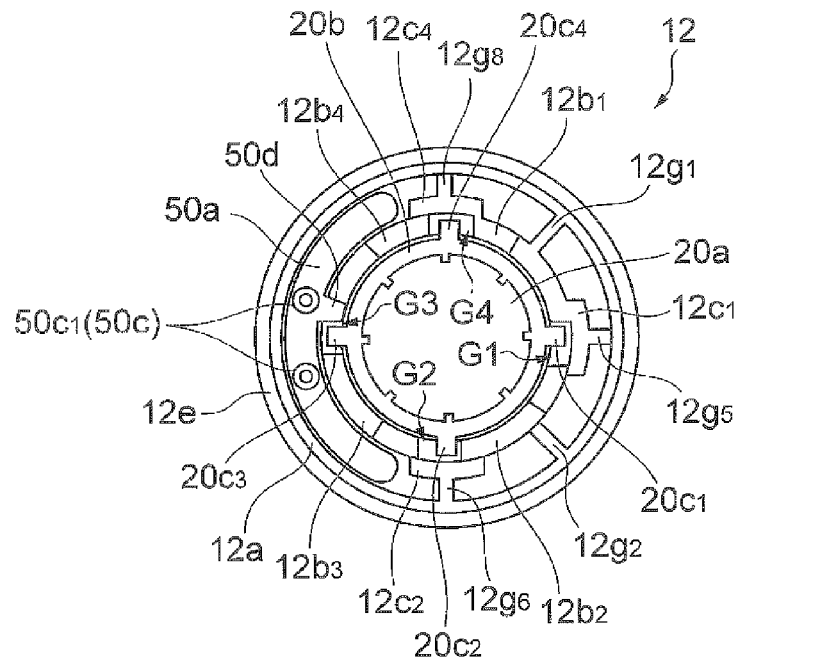
(a)
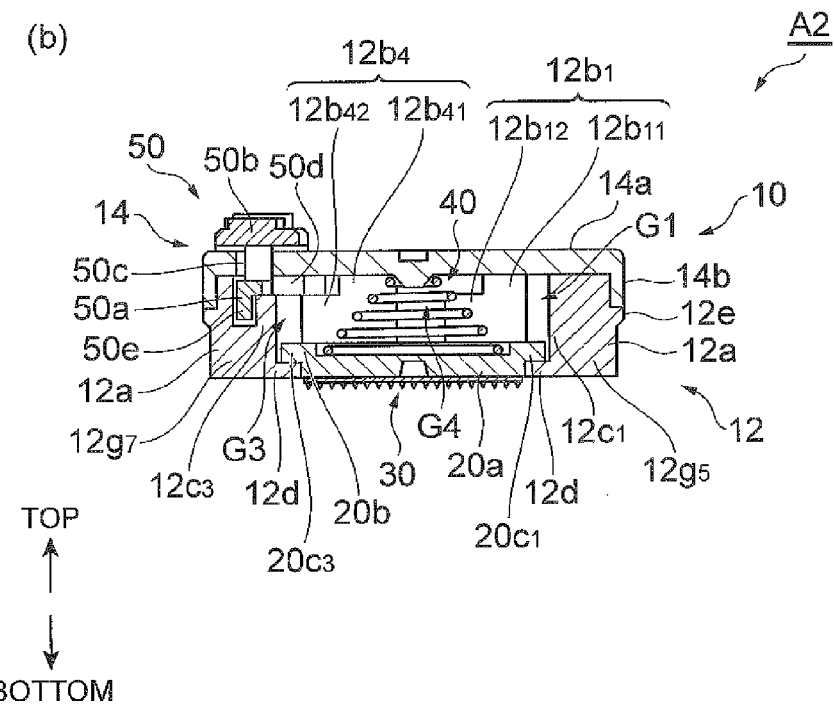
(b)

Fig.19
(a)
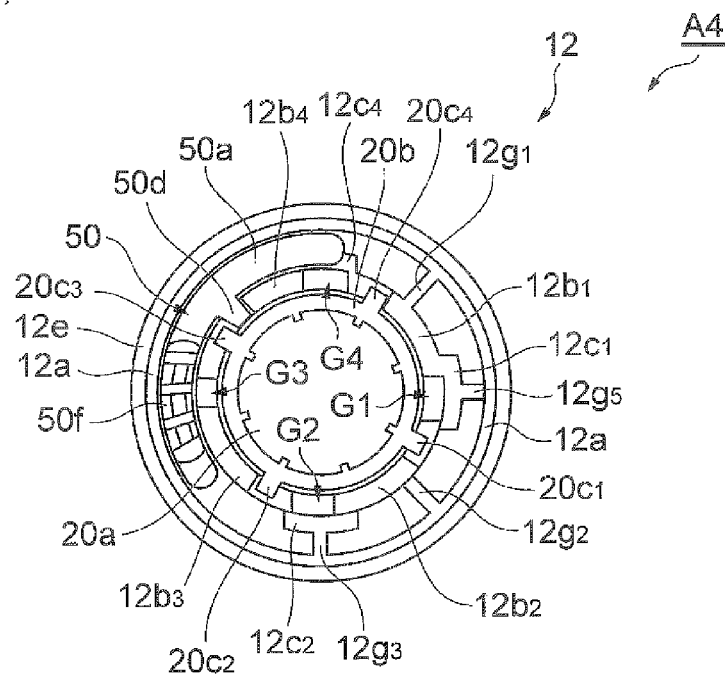
(b)
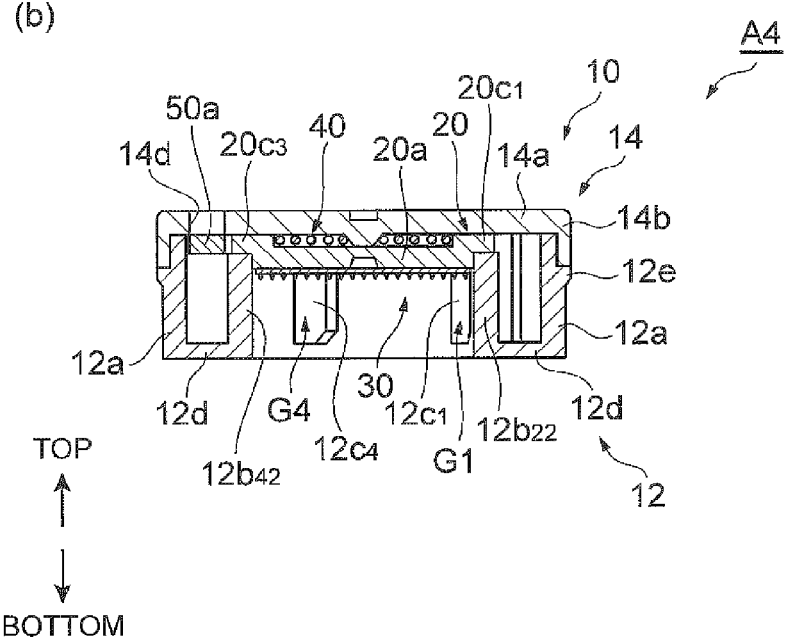

*Fig.20*
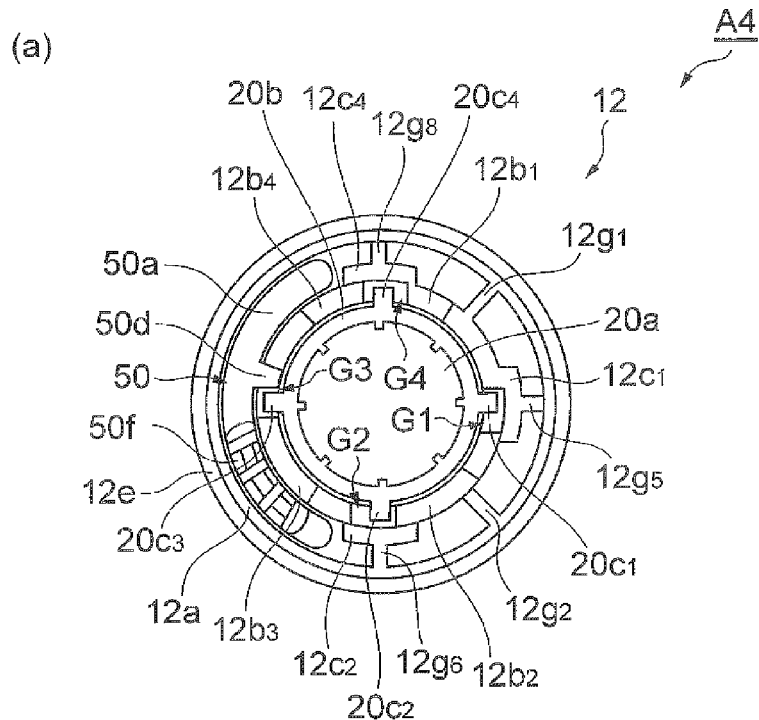
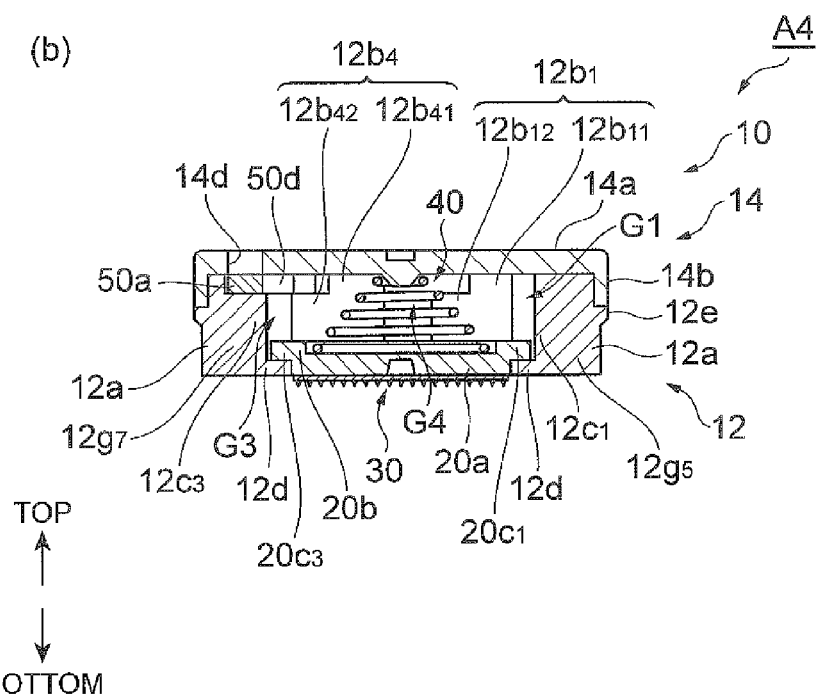

Fig.53
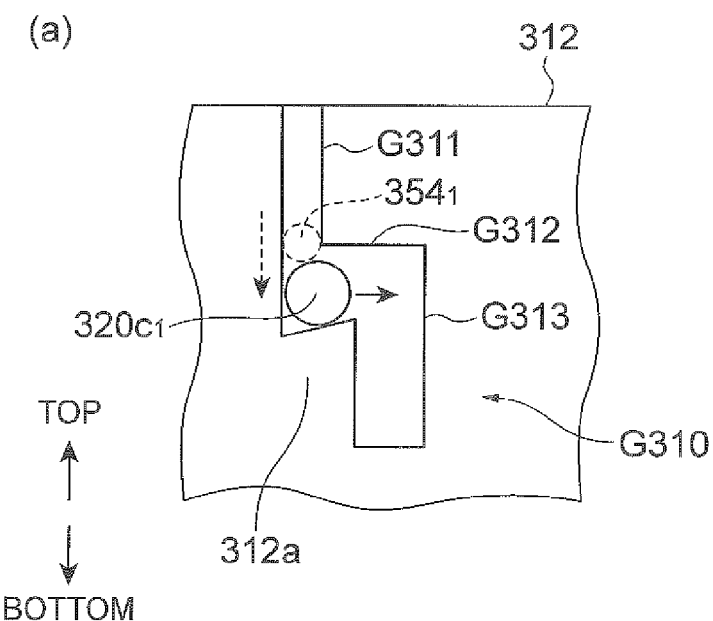
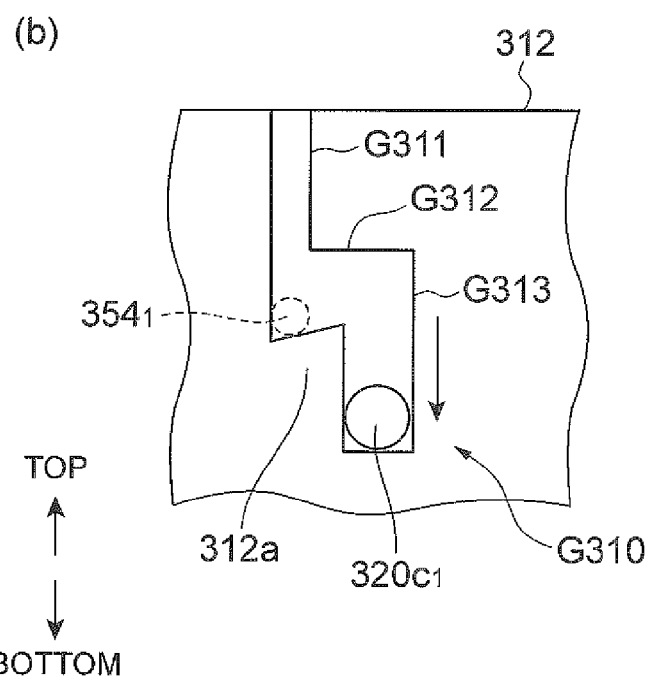

Fig.95 (a)
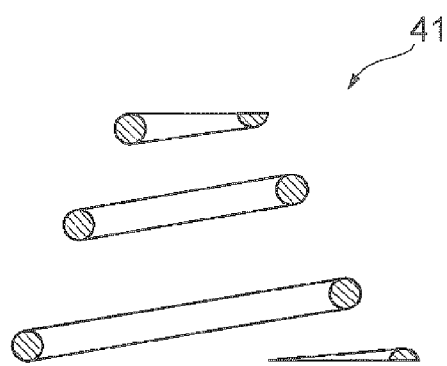
41
(b)
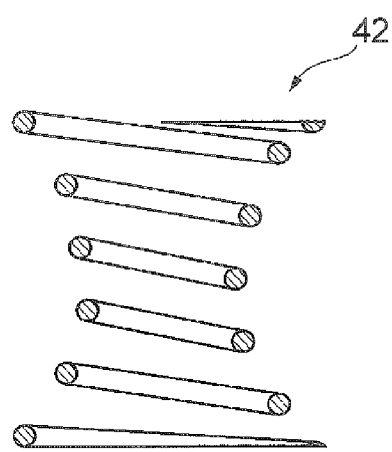
42
(c)
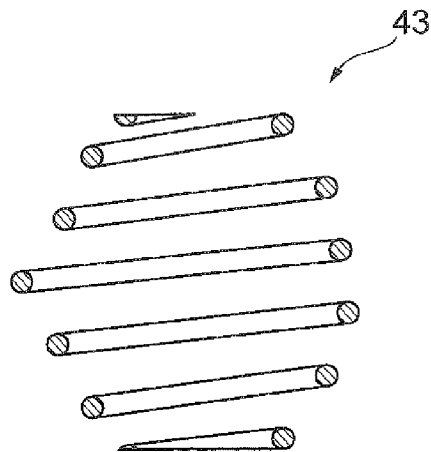
43

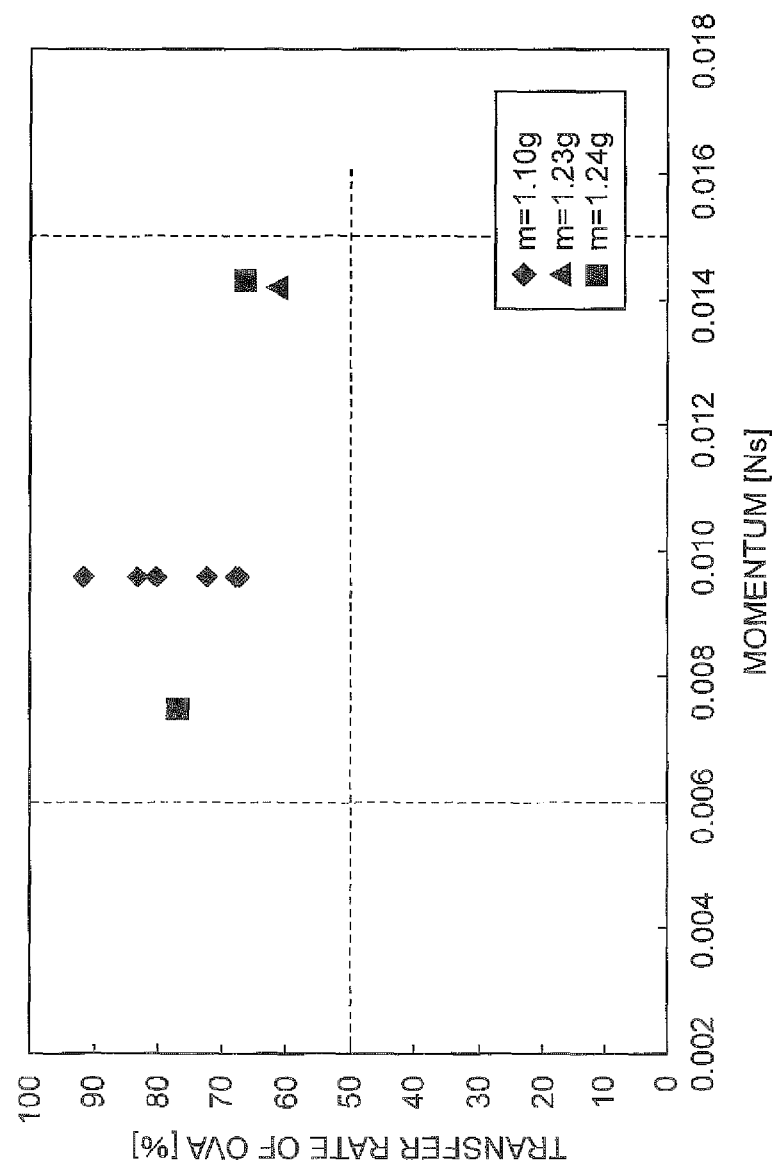

APPLICATOR

This is a National Phase Application filed under 35 U.S.C. 371 as a national stage of PCT/JP2013/081944, filed Nov. 27, 2013, an application claiming the benefit of Japanese Application No. P2012-280198, filed Dec. 21, 2012, the content of each of which is hereby incorporated by reference in its entirety.

TECHNICAL FIELD

The present invention relates to an applicator for transferring active ingredients into a body through a skin by a puncture in the skin.

BACKGROUND ART

Up to now, an applicator that holds a microneedle array by means of a latch mechanism or the like has been known, the microneedle array including a large number of microneedles each having a leading end to which a medical agent or the like is applied (see Patent Literatures 1 to 5). If the microneedle array held by the applicator is caused to collide against a skin by disengaging the latch mechanism, the microneedles are stuck into the skin, and active ingredients contained in the medical agent or the like are transferred into the body of an animal (for example, a human) through the skin.

CITATION LIST

Patent Literature

[Patent Literature 1] Japanese Patent No. 4659332
[Patent Literature 2] Japanese translation of PCT International Application No. 2007-516781
[Patent Literature 3] International Publication No. WO 2009/107806
[Patent Literature 4] International Publication No. WO 00/009184
[Patent Literature 5] U.S. Patent Application Publication No. 2011/276027

SUMMARY OF INVENTION

Technical Problem

Unfortunately, conventional applicators have a large size. For some medical agents and the like, a user may need to continue to wear an applicator for several tens of minutes after a puncture in the skin with microneedles, in order to sufficiently transfer active ingredients thereof into the user's body. Thus, a further reduction in size and weight of the applicators has been desired in order to further improve convenience in wearing and carrying.

In view of the above, one aspect of the present invention has an object to provide an applicator that can achieve a further reduction in size and weight.

Solution to Problem

An applicator according to one aspect of the present invention is an applicator for transferring an active ingredient into a body through a skin by a puncture in the skin with microneedles, the applicator comprising: a piston plate wherein the microneedles are arranged on one main surface side of the piston plate; a non-linear coil spring that is arranged on another main surface side of the piston plate and exerts an elastic force on the piston plate; a casing including: a tubular main body part that houses therein the piston plate and the non-linear coil spring; and a cover part that is arranged on one end side of the main body part, the cover part and the piston plate sandwiching the non-linear coil spring therebetween; and release means for releasing a locked state where the piston plate is locked with the casing by lock means such that the piston plate is held at a retraction position thereof on the cover part side in a state where the cover part and the piston plate compress the non-linear coil spring and where the cover part and the piston plate compress the non-linear coil spring. If the locked state is released by the release means, the piston plate is moved, by the biasing force of the non-linear coil spring, inside of the main body part to reach a position for action on the skin.

In the applicator according to one aspect of the present invention, the locked state where the piston plate is locked with the casing by the lock means is released by the release means. Consequently, the piston plate is moved, by the biasing force of the non-linear coil spring, inside of the main body part to reach the position for action on the skin. Thus, a member such as a shaft that extends in the axial direction of the main body part (the height direction of the applicator) does not need to be attached to the piston plate. Further, in the applicator according to one aspect of the present invention, the non-linear coil spring is used to exert a biasing force on the piston plate. When being compressed, the height of the non-linear coil spring becomes extremely smaller compared with general cylindrical coil springs. In this way, the height of the applicator itself can be made smaller, thus achieving a reduction in weight of the applicator.

Depending on the type of a medical agent or the like, the applicator needs to be held on the skin for a long time after a collision of the microneedles against the skin. Even in such a case, with the use of the applicator according to one aspect of the present invention that can achieve a reduction in size and weight, a user can put on clothing and move without any restriction with the applicator being attached to the skin. Moreover, because the applicator according to one aspect of the present invention is small, even in the case where the user freely moves in such a manner, the applicator is extremely unlikely to collide against another object (obstacle) to thereby cause the microneedles to come off the skin or to break and stay in the skin.

In the case of using a conventional large-size applicator, the user may have trouble in handling, and the large exterior appearance thereof may bring about a feeling of fear. In contrast, the applicator according to one aspect of the present invention that can achieve a reduction in size and weight can be easily handled, and a feeling of fear that the user may develop can be significantly reduced.

A needle density of the microneedles may be equal to or more than 500 needles/cm$^2$, a total weight of an actuation part including the piston plate, the non-linear coil spring, and the microneedles may be equal to or less than 1.5 g, and a momentum of the actuation part actuated by the biasing force of the non-linear coil spring may be 0.006 Ns to 0.015 Ns.

An applicator according to another aspect of the present invention is an applicator for transferring an active ingredient into a body through a skin by a puncture in the skin with microneedles, the applicator comprising: a piston plate that transmits an impact force to a microneedle array provided with the microneedles when one main surface of the piston plate collides against the microneedle array; a non-linear coil spring that is arranged on another main surface side of the piston plate and exerts an elastic force on the piston plate; a casing including: a tubular main body part that houses therein the piston plate and the non-linear coil spring; and a cover part that is arranged on one end side of the main body part, the cover part and the piston plate sandwiching the non-linear coil spring therebetween; lock means for locking the piston plate with the casing such that the piston plate is held at a retraction position thereof on the cover part side in a state where the cover part and the piston plate compress the non-linear coil spring; and release means for releasing a locked state where the piston plate is locked with the casing by the lock means and where the cover part and the piston plate compress the non-linear coil spring. If the locked state is released by the release means, the piston plate is moved, by the biasing force of the non-linear coil spring, inside of the main body part to reach a position for action on the skin.

In the applicator according to another aspect of the present invention, the locked state where the piston plate is locked with the casing by the lock means is released by the release means. Consequently, the piston plate is moved, by the biasing force of the non-linear coil spring, inside of the main body part to reach the position for action on the skin. Thus, a member such as a shaft that extends in the axial direction of the main body part (the height direction of the applicator) does not need to be attached to the piston plate. Further, in the applicator according to another aspect of the present invention, the non-linear coil spring is used to exert a biasing force on the piston plate. When being compressed, the height of the non-linear coil spring becomes extremely smaller compared with general cylindrical coil springs. In this way, the height of the applicator itself can be made smaller, thus achieving a reduction in weight of the applicator.

Depending on the type of a medical agent or the like, the applicator needs to be held on the skin for a long time after a collision of the microneedles against the skin. Even in such a case, with the use of the applicator according to another aspect of the present invention that can achieve a reduction in size and weight, a user can put on clothing and move without any restriction with the applicator being attached to the skin. Moreover, because the applicator according to another aspect of the present invention is small, even in the case where the user freely moves in such a manner, the applicator is extremely unlikely to collide against another object (obstacle) to thereby cause the microneedles to come off the skin or to break and stay in the skin.

In the case of using a conventional large-size applicator, the user may have trouble in handling, and the large exterior appearance thereof may bring about a feeling of fear. In contrast, the applicator according to another aspect of the present invention that can achieve a reduction in size and weight can be easily handled, and a feeling of fear that the user may develop can be significantly reduced.

The piston plate may be provided with a plurality of projections that protrude outward in a direction that intersects with a thickness direction of the piston plate. Guide means may be a plurality of opening parts that are formed on an inner circumferential surface of the main body part so as to extend along the axial direction of the main body part. The projections of the piston plate may be respectively movable inside of the opening parts in a state where the projections are respectively located inside of the opening parts. The lock means may be arranged at a position adjacent to each of the opening parts, and may be lockable with each of the projections of the piston plate. In this case, even if a member such as a shaft that extends in the axial direction of the main body part (the height direction of the applicator) is not attached to the piston plate, the locking of the piston plate with the lock means can be achieved by the plurality of projections and the lock means. Thus, the height of the applicator itself can be made further smaller.

The plurality of projections may be provided in a periphery of the piston plate. In this case, the plurality of projections laterally extend from the periphery of the piston plate, and hence the thickness of the piston plate including the plurality of projections is reduced. Thus, the height of the applicator itself can be made further smaller.

The lock means may be inclined so as to approach the cover part toward each of the opening parts. In this case, when the projections locked with the lock means respectively move toward the opening parts, the projections need to climb the slopes of the lock means. Thus, even if an impact or the like is applied from the outside to the applicator, the projections can be prevented from unintentionally moving into the opening parts.

Surfaces facing the other end side of the main body part, of the plurality of projections may be oblique surfaces that are inclined to the axial direction of the main body part so as to approach one end side of the main body part toward an outer side, and a bottom wall of the main body part that locks the plurality of projections that have reached the position for action on the skin may have oblique surfaces respectively corresponding to the oblique surfaces of the plurality of projections. In this case, when the piston plate reaches the position for action on the skin and the projections of the piston plate and the bottom wall of the main body part collide against each other, the impact force generated between the projections of the piston plate and the bottom wall of the main body part is distributed to the axial direction of the main body part and a direction orthogonal to the axial direction thereof. Accordingly, the mechanical strength of the applicator can be improved, and a collision sound generated when the projections of the piston plate and the bottom wall of the main body part collide against each other can be reduced. Moreover, because the impact force generated when the projections of the piston plate and the bottom wall of the main body part collide against each other is distributed, the reaction force that acts on the piston plate in the axial direction of the main body part becomes smaller. Accordingly, after the collision between the projections of the piston plate and the bottom wall of the main body part, the piston plate bounces less easily toward the cover part. As a result, the certainty of the puncture in the skin with the microneedles can be enhanced.

The guide means may be a plurality of opening parts that are formed on the inner circumferential surface of the main body part so as to extend obliquely to the axial direction when viewed from the direction orthogonal to the axial direction. In this case, the piston plate moves while rotating inside of the main body part, and reaches the position for action on the skin. Thus, even in the case where an impact force is generated in the piston plate when the piston plate reaches the position for action on the skin and where a reaction force acts on the piston plate, because the guide means extends obliquely to the axial direction, it is difficult for the piston plate to move back along the guide means. Accordingly, after the piston plate reaches the position for action on the skin, the piston plate bounces less easily toward the cover part. As a result, the certainty of the puncture in the skin with the microneedles can be enhanced.

The release means may exert a turning force on the piston plate to thereby release the locked state.

A through-hole that extends along a circumferential direction of the main body part may be formed in a side wall of the main body part. The release means may include: a first portion that is located inside of the casing and is locked with the piston plate; and a second portion that is connected to the first portion and passes through the through-hole to be located on an outer circumferential surface of the main body part. If the second portion is operated to be moved from one end side to the other end side of the through-hole, the first portion may exert a turning force on the piston plate, the projections may respectively reach the opening parts from the lock means, and the locked state may be released. In this case, the release means is located lateral to the casing, and hence the release means is suppressed from extending in the axial direction of the main body part (the height direction of the applicator). Thus, the height of the applicator itself can be made further smaller.

A through-hole may be formed in the cover part. The release means may include: a first portion that is located inside of the casing and is locked with the piston plate; and a second portion that is connected to the first portion and passes through the through-hole to be located on an outer surface of the cover part. If the second portion is operated to be moved from one end side to the other end side of the through-hole, the first portion may exert a turning force on the piston plate, the projections may respectively reach the opening parts from the lock means, and the locked state may be released.

A through-hole may be formed in the cover part. The release means may include: a base part that is arranged on an outer surface of the cover part and is turnable about the axis of the main body part; a knob part that is attached to the base part so as to be pivotable about a direction that intersects with the axial direction of the main body part; and a transmission part that extends from the base part to the inside of the casing through the through-hole and transmits a turning force of the base part to the piston plate. If the transmission part is moved from one end side to the other end side of the through-hole by operating the knob part, the transmission part may exert the turning force on the piston plate, the projections may respectively reach the opening parts from the lock means, and the locked state may be released. In this case, when the puncture in the skin is to be made using the applicator, it is sufficient to pivot the knob part and cause the knob part to stand up with respect to the base part (stand-up state). On the other hand, when the applicator is held on the skin, it is sufficient to lay down the knob part on the base part (lay-down state). Thus, the locked state can be easily released by the release member by means of the knob part. Further, in the case where the applicator is held on the skin, the height of the applicator can be made smaller by bringing the knob part into the lay-down state.

The release means may include an engagement part that engages the cover part with the piston plate. The cover part and the main body part may be configured as separate members. In the locked state, in a case where the cover part is biased by the non-linear coil spring so as to move away from the piston plate and where the cover part is at a separate position away from the piston plate, the engagement part of the release means may not engage the cover part with the piston plate. On the other hand, in the locked state, in a case where a pressing force against the biasing force of the non-linear coil spring is exerted on the cover part and where the cover part is at a close position adjacent to the piston plate, the engagement part of the release means may engage the cover part with the piston plate. If the cover part is turned in a state where the engagement part engages the cover part with the piston plate, the engagement part may exert a turning force on the piston plate, the projections may respectively reach the opening parts from the lock means, and the locked state may be released. In this case, the piston plate is not turned by the engagement part unless the cover part is turned while the pressing force against the biasing force of the non-linear coil spring is exerted on the cover part. Thus, the applicator can be prevented from malfunctioning.

The release means may be located so as to face an outer circumferential surface of the main body part. A through-hole may be formed at a position on a side wall of the main body part, the position being on a straight line connecting between the release means and the lock means. If the release means is pushed against the projections in the locked state while passing through the through-hole, a turning force for turning the piston plate may act on the piston plate by means of the release means, the projections may respectively reach the opening parts from the lock means, and the locked state may be released.

The release means may be a plate-like body having a triangular shape. An oblique side of the plate-like body may be opposed to the through-hole. If the release means is pushed against the projections in the locked state while passing through the through-hole and the projections thus slide on the oblique side, a turning force for turning the piston plate may act on the piston plate, the projections may respectively reach the opening parts from the lock means, and the locked state may be released.

The applicator may further comprise a stopper that restricts drive of the release means, to thereby prevent the release means from passing through the through-hole and coming into contact with the projections in the locked state. In this case, the applicator can be prevented from malfunctioning.

The release means may be attached to an outside of the main body part so as to be movable in the axial direction. When a pressing force is exerted on the release means and the release means moves from one end side to the other end side of the main body part, the release means may exert a turning force on the piston plate to thereby release the locked state. In this case, when the release means is pressed in the axial direction of the main body part and moves from one end side to the other end side of the main body part, the locked state of the piston plate is released, and the piston plate reaches a position for action on the skin. Thus, in the state where the applicator is pushed against the skin by means of the release member, the puncture in the skin with the microneedles is made. Accordingly, when the applicator is pushed against the skin, the skin is stretched by the applicator. As a result, at the time of the puncture, a tensile force can be applied to the surface of the skin, and hence the microneedles can be more easily stuck into the skin.

The release means may include: a first release member that is attached to an outside of the main body part so as to be movable in the axial direction; and a second release member that is arranged between the main body part and the first release member so as to be turnable in a circumferential direction of the main body part. The second release member may be provided with: first engagement projections that protrude toward the main body part and are respectively engageable with the projections of the piston plate; and second engagement projections that protrude toward the first release member. The first release member may be provided with housing opening parts that respectively house the second engagement projections therein. The housing opening parts may each have a side that extends obliquely to the axial direction when viewed from the direction orthogonal to the axial direction. When a pressing force is exerted on the first release member and the first release member moves from one end side to the other end side of the main body part, the second engagement projections may respectively slide on the sides of the housing opening parts while abutting against the sides thereof, and the first release member thus may turn the second release member. Along with the turn of the second release member, the first engagement projections may exert a turning force on the piston plate while being respectively engaged with the projections of the piston plate, the projections may respectively reach the opening parts from the lock means, and the locked state may be released. The release means may be attached to an outside of the main body part so as to be movable in the axial direction. The release means may be provided with engagement projections that are respectively located above the projections of the piston plate and respectively protrude toward the projections of the piston plate. The engagement projections may each have a side that extends obliquely to the axial direction when viewed from the direction orthogonal to the axial direction and is opposed to each of the projections of the piston plate. When a pressing force is exerted on the release means and the release means moves from one end side to the other end side of the main body part, the sides of the engagement projections may exert a turning force on the piston plate while being respectively engaged with the projections of the piston plate, the projections may respectively reach the opening parts from the lock means, and the locked state may be released.

A plurality of cutout groove parts that extend in a thickness direction of the piston plate may be formed in a peripheral part of the piston plate. The guide means may be a plurality of elongated protrusions that are formed on an inner circumferential surface of the main body part so as to extend along the axial direction of the main body part. The piston plate may be movable along the elongated protrusions inside of the main body part in a state where the cutout groove parts of the piston plate are respectively engaged with the corresponding elongated protrusions. The lock means may be configured by an end part on the cover part side of each of the elongated protrusions. The lock means may be lockable with the piston plate in a state where the cutout groove parts do not overlap with the elongated protrusions when viewed from the axial direction of the main body part. In this case, even if a member such as a shaft that extends in the axial direction of the main body part (the height direction of the applicator) is not attached to the piston plate, the locking of the piston plate with the lock means can be achieved by the plurality of cutout groove parts and the plurality of elongated protrusions. Thus, the height of the applicator itself can be made further smaller.

The guide means may be a plurality of elongated protrusions that are formed on the inner circumferential surface of the main body part so as to extend obliquely to the axial direction when viewed from the direction orthogonal to the axial direction. In this case, the piston plate moves while rotating inside of the main body part, and reaches the position for action on the skin. Thus, even in the case where an impact force is generated in the piston plate when the piston plate reaches the position for action on the skin and where a reaction force acts on the piston plate, because the guide means extends obliquely to the axial direction, it is difficult for the piston plate to move back along the guide means. Accordingly, after the piston plate reaches the position for action on the skin, the piston plate bounces less easily toward the cover part. As a result, the certainty of the puncture in the skin with the microneedles can be enhanced.

The release means may exert a turning force on the piston plate to thereby release the locked state.

A through-hole that extends along a circumferential direction of the main body part may be formed in a side wall of the main body part. The release means may include: a first portion that is located inside of the casing and is locked with the piston plate; and a second portion that is connected to the first portion and passes through the through-hole to be located on an outer circumferential surface of the main body part. If the second portion is operated to be moved from one end side to the other end side of the through-hole, the first portion may exert a turning force on the piston plate, the cutout grooves may respectively reach the elongated protrusions from the state where the cutout grooves do not overlap with the elongated protrusions, and the locked state may be released. In this case, the release means is located lateral to the casing, and hence the release means is suppressed from extending in the axial direction of the main body part (the height direction of the applicator). Thus, the height of the applicator itself can be made further smaller.

A through-hole may be formed in the cover part. The release means may include: a first portion that is located inside of the casing and is locked with the piston plate; and a second portion that is connected to the first portion and passes through the through-hole to be located on an outer surface of the cover part. If the second portion is operated to be moved from one end side to the other end side of the through-hole, the first portion may exert a turning force on the piston plate, the cutout grooves may respectively reach the elongated protrusions from the state where the cutout grooves do not overlap with the elongated protrusions, and the locked state may be released.

A through-hole may be formed in the cover part. The release means may include: a base part that is arranged on an outer surface of the cover part and is turnable about the axis of the main body part; a knob part that is attached to the base part so as to be pivotable about a direction that intersects with the axial direction of the main body part; and a transmission part that extends from the base part to the inside of the casing through the through-hole and transmits a turning force of the base part to the piston plate. If the transmission part is moved from one end side to the other end side of the through-hole by operating the knob part, the transmission part may exert the turning force on the piston plate, the cutout grooves may respectively reach the elongated protrusions from the state where the cutout grooves do not overlap with the elongated protrusions, and the locked state may be released. In this case, when the puncture in the skin is to be made using the applicator, it is sufficient to pivot the knob part and cause the knob part to stand up with respect to the base part (stand-up state). On the other hand, when the applicator is held on the skin, it is sufficient to lay down the knob part on the base part (lay-down state). Thus, the locked state can be easily released by the release member by means of the knob part. Further, in the case where the applicator is held on the skin, the height of the applicator can be made smaller by bringing the knob part into the lay-down state.

The release means may include an engagement part that engages the cover part with the piston plate. The cover part and the main body part may be configured as separate members. In the locked state, in a case where the cover part is biased by the non-linear coil spring so as to move away from the piston plate and where the cover part is at a separate position away from the piston plate, the engagement part of the release means may not engage the cover part with the piston plate. On the other hand, in the locked state, in a case where a pressing force against the biasing force of the non-linear coil spring is exerted on the cover part and where the cover part is at a close position adjacent to the piston plate, the engagement part of the release means may engage the cover part with the piston plate. If the cover part is turned in a state where the engagement part engages the cover part with the piston plate, the engagement part may exert a turning force on the piston plate, the cutout grooves may respectively reach the elongated protrusions from the state where the cutout grooves do not overlap with the elongated protrusions, and the locked state may be released. In this case, the piston plate is not turned by the engagement part unless the cover part is turned while the pressing force against the biasing force of the non-linear coil spring is exerted on the cover part. Thus, the applicator can be prevented from malfunctioning.

A concave part concaved toward a central part of the piston plate may be provided in the periphery of the piston plate. The release means may be located so as to face an outer circumferential surface of the main body part. A through-hole may be formed at a position on a side wall of the main body part, the position being on a straight line connecting between the release means and the lock means. If the release means is pushed against the concave part of the piston plate in the locked state while passing through the through-hole, a turning force for turning the piston plate may act on the piston plate by means of the release means, the cutout grooves may respectively reach the elongated protrusions from the state where the cutout grooves do not overlap with the elongated protrusions, and the locked state may be released.

The lock means may be an arm member provided to the piston plate. A through-hole through which the arm member is inserted may be formed in the cover part. The piston plate may be movable between a first position at which the arm member is locked with the cover part and is not passable through the through-hole and a second position at which the arm member is not locked with the cover part and is passable through the through-hole. When the piston plate is at the first position, the piston plate may be held at the retraction position thereof on the cover part side in the state where the cover part and the piston plate compress the non-linear coil spring. When the locked state is released by the release means and the piston plate moves to the second position, the piston plate may be moved by the biasing force of the non-linear coil spring inside of the main body part to reach the position for action on the skin. In this case, the size of the applicator is substantially determined in accordance with the total height of the arm member and the piston plate. Hence, if the height of the arm member is made smaller, the height of the applicator itself can be made further smaller.

The release means may exert a turning force on the piston plate with the intermediation of the arm member, and may move the piston plate from the first position to the second position, to thereby release the locked state.

The applicator may further comprise an engagement piece that is engaged with the piston plate that has reached the position for action on the skin. In this case, after the piston plate reaches the position for action on the skin, movement of the piston plate is restricted by the engagement piece. Thus, a bounce of the piston plate toward the cover part is suppressed by the engagement piece. As a result, the certainty of the puncture in the skin with the microneedles can be enhanced.

The non-linear coil spring may be a conical coil spring. In this case, the height thereof in a compressed state can be smaller, thus achieving a further reduction in size and weight of the applicator.

A metal wire that forms the conical coil spring may not overlap when viewed from an extending direction of a central line of the conical coil spring. In this case, if a load is applied to the conical coil spring along the extending direction of the central line, the height of the compressed conical coil spring becomes substantially coincident with the wire diameter. Thus, a further reduction in size and weight of the applicator can be achieved.

Advantageous Effects of Invention

According to the present invention, it is possible to provide an applicator that can achieve a further reduction in size and weight.

BRIEF DESCRIPTION OF DRAWINGS

FIG. 14 The (a) of FIG. 14 is a top view illustrating a state before an operation of the applicator according to the second embodiment, from which a cover part is detached, and (b) of FIG. 14 is a cross sectional view illustrating the state before the operation of the applicator according to the second embodiment.

FIG. 15 The (a) of FIG. 15 is a top view illustrating a state after the operation of the applicator according to the second embodiment, from which the cover part is detached, and (b) of FIG. 15 is a cross sectional view illustrating the state after the operation of the applicator according to the second embodiment.

FIG. 19 The (a) of FIG. 19 is a top view illustrating a state before an operation of the applicator according to the fourth embodiment, from which a cover part is detached, and (b) of FIG. 19 is a cross sectional view illustrating the state before the operation of the applicator according to the fourth embodiment.

FIG. 20 The (a) of FIG. 20 is a top view illustrating a state after the operation of the applicator according to the fourth embodiment, from which the cover part is detached, and (b) of FIG. 20 is a cross sectional view illustrating the state after the operation of the applicator according to the fourth embodiment.

FIG. 53 are enlarged side views each illustrating part of the applicator according to the tenth embodiment, for describing moving states of projections.

FIG. 95 The (a) of FIG. 95 is a cross sectional view illustrating another example of the conical coil spring, (b) of FIG. 95 is a cross sectional view illustrating an example of a non-linear coil spring, and (c) of FIG. 95 is a cross sectional view illustrating another example of the non-linear coil spring.

FIG. 99 is a graph illustrating a relation between momentum and the transfer rate of OVA according to an example.

DESCRIPTION OF EMBODIMENTS

Figure 1:
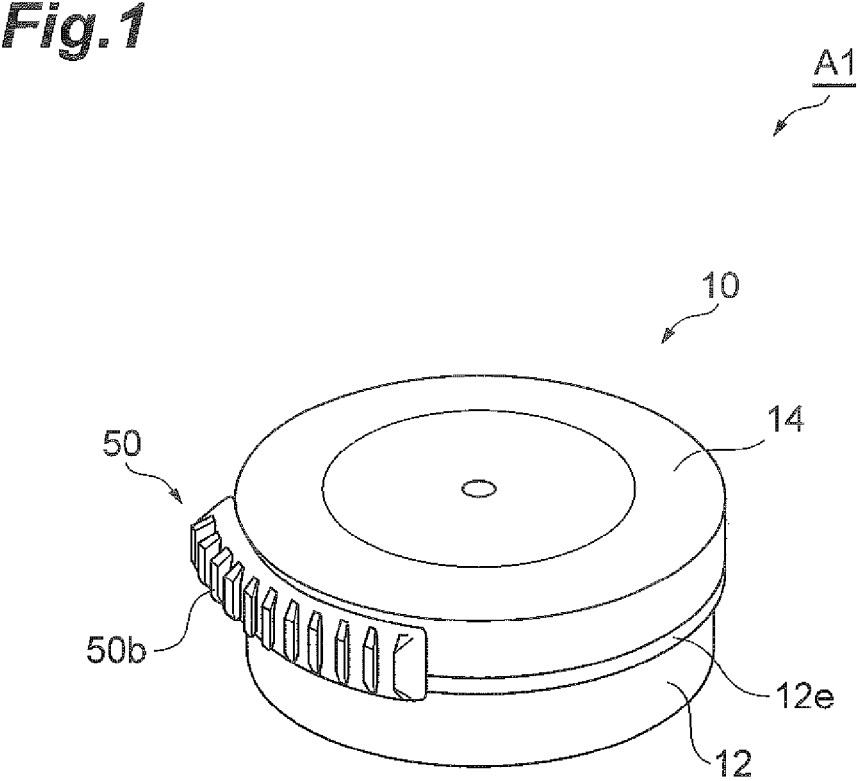
FIG. 1 is a perspective view of an applicator according to a first embodiment.

Embodiments of the present invention are described with reference to the drawings. The following present exemplary embodiments are given as examples for describing the present invention, and the present invention is not limited to the following contents. In the following description, the same elements or elements having the same functions are denoted by the same reference signs, and redundant description is omitted.

[1] First Embodiment

[1.1] Configuration of Applicator

A configuration of an applicator A1 according to a first embodiment is described with reference to FIG. 1 to FIG. 9. In the following description, the term "top" corresponds to the top direction of FIG. 1 to FIG. 3, and the term "bottom" corresponds to the bottom direction of FIG. 1 to FIG. 3. That is, the top-bottom direction corresponds to the height direction of the applicator A1.

The applicator A1 is a device for transferring active ingredients of a medical agent or the like into the body of an animal such as a human through a skin of the animal by a puncture in the skin with microneedles 32 (to be described later in detail). The applicator A1 includes a casing 10, a piston plate 20, a microneedle array 30, a conical coil spring 40, and a release member 50.

Figure 2:
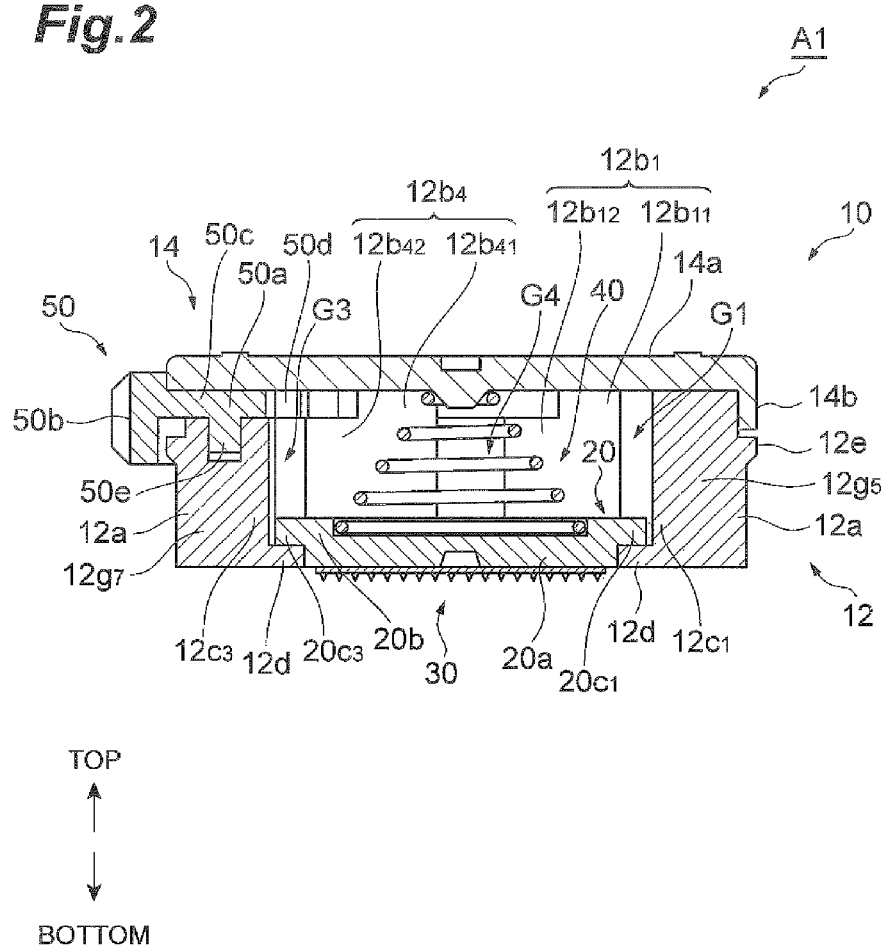
FIG. 2 is a cross sectional view illustrating a state after an operation of the applicator according to the first embodiment.
Figure 3:
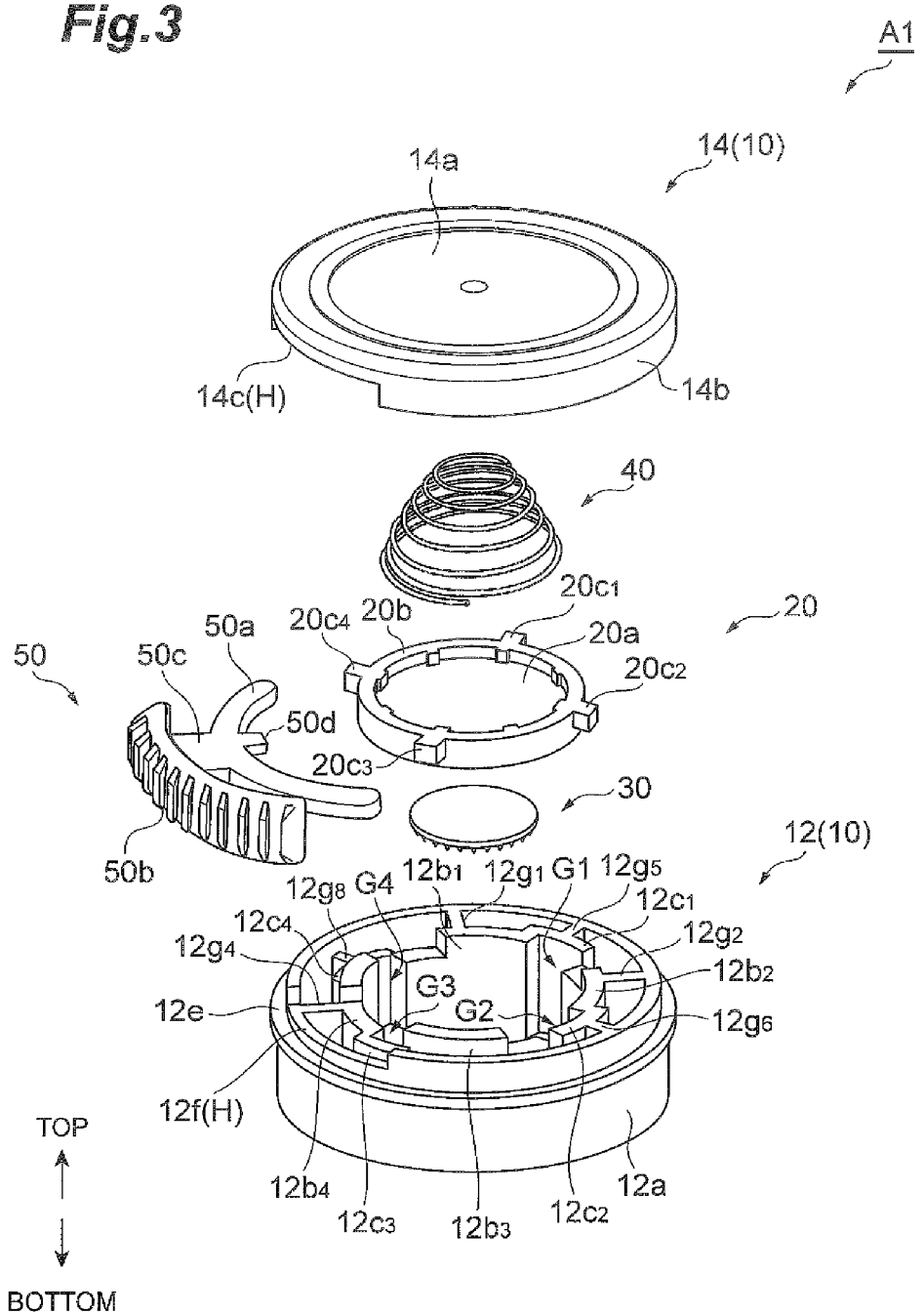
FIG. 3 is an exploded perspective view of the applicator according to the first embodiment.

As illustrated in FIG. 1 to FIG. 3, the casing 10 includes: a main body part 12 having the central axis that extends along the top-bottom direction and having a cylindrical shape; and a cover part 14 arranged on the upper end side of the main body part 12. The casing 10 has strength high enough to maintain the biasing force of the conical coil spring 40 (to be described later in detail). Examples of the material of the casing 10 include polycarbonate resin, ABS resin, and synthetic or natural resin materials such as polystyrene, polypropylene, and polyacetal (POM), and can also include silicon, silicon dioxide, ceramics, and metal (such as stainless steel, titanium, nickel, molybdenum, chromium, and cobalt). Glass fiber may be added to the above-mentioned resin materials for the purpose of increasing the strength and the like.

It is desirable that the applicator A1 have a shape that enables easy hold and enables easy application (easy puncture) of the microneedles 32 (to be described later) to the skin of the animal (including a human). Thus, the outer shape of the main body part 12 may be other than the cylindrical shape, and may be, for example, multangular or rounded. A recess or a step may be provided on the surface of the main body part 12. A fine groove may be formed on the surface of the main body part 12, or a non-slippery coating layer may be provided thereon, whereby the surface of the main body part 12 may be roughened. A through-hole may be formed in the main body part 12 for the purpose of reducing the air resistance and the weight.

As illustrated in FIG. 2 to FIG. 5, the main body part 12 includes: an outer wall 12a having a cylindrical shape; interior inner walls $12b_1$, $12b_2$, $12b_3$ and $12b_4$ each having a circular arc-like shape; exterior inner walls $12b_1$, $12b_2$, $12b_3$ and $12b_4$ each having a circular arc-like shape; and a bottom wall 12d having a circular ring-like shape. A flange member 12e having a circular ring-like shape is provided at a position closer to the upper end (closer to the cover part 14) on the outer circumferential surface of the outer wall 12a. The flange member 12e protrudes outward from the outer circumferential surface of the outer wall 12a. A cutout part 12f that extends in the circumferential direction is provided between the upper end of the outer wall 12a and the flange member 12e.

The interior inner walls $12b_1$, $12b_2$, $12b_3$ and $12b_4$ are located on the inner side of the outer wall 12a and on a circumference having the same radius. The interior inner walls $12b_1$, $12b_2$, $12b_3$ and $12b_4$ are arranged in the stated order in the clockwise direction when viewed from the upper end side (the cover part 14 side) of the main body part 12, with given intervals in the circumferential direction. That is, the interior inner wall $12b_1$ and the interior inner wall $12b_2$ are spaced apart from each other with a predetermined interval in the circumferential direction, the interior inner wall $12b_2$ and the interior inner wall $12b_3$ are spaced apart from each other with a predetermined interval in the circumferential direction, the interior inner wall $12b_3$ and the interior inner wall $12b_4$ are spaced apart from each other with a predetermined interval in the circumferential direction, and the interior inner wall $12b_4$ and the interior inner wall $12b_1$ are spaced apart from each other with a predetermined interval in the circumferential direction.

The circle formed by the interior inner walls $12b_1$, $12b_2$, $12b_3$ and $12b_4$ can be set to be equivalent to or slightly larger than the outer diameter of a main body 20a (to be described later) of the piston plate 20. The interval between the interior inner walls (of the interior inner walls $12b_1$, $12b_2$, $12b_3$ and $12b_4$) that are adjacent to each other in the circumferential direction can be set to be equivalent to or slightly larger than the widths of projections $20c_1$, $20c_2$, $20c_3$ and $20c_4$ (to be described later) of the piston plate 20. In the present exemplary embodiment, the central axis of the interior inner walls $12b_1$, $12b_2$, $12b_3$ and $12b_4$ is substantially coincident with the central axis of the outer wall 12a (main body part 12), but does not need to be coincident therewith.

A portion of the upper end of the interior inner wall $12b_1$ is cut out, the portion being closer to the interior inner wall $12b_4$. More specifically, the interior inner wall $12b_1$ includes: a first portion $12b_{11}$ having the upper end whose position is equivalent to the position of the upper end of the outer wall 12a; and a second portion $12b_{12}$ having the upper end whose position is closer to the bottom wall 12d than the first portion $12b_{11}$, in the top-bottom direction (the central axis direction of the main body part 12). That is, the first portion $12b_{11}$ and the second portion $12b_{12}$ form a step in the circumferential direction. The interior inner wall $12b_1$ and the outer wall 12a are coupled to each other by a coupling wall $12g_1$, whereby the rigidities of the two walls are enhanced. The position of the upper end of the coupling wall $12g_1$ is equivalent to the position of the upper end of the first portion $12b_{11}$. The interior inner wall $12b_1$, the outer wall 12a, and the coupling wall $12g_1$ can be integrally shaped.

A portion of the upper end of the interior inner wall $12b_2$ is cut out, the portion being closer to the interior inner wall $12b_1$. More specifically, the interior inner wall $12b_2$ includes: a first portion $12b_{21}$ having the upper end whose position is equivalent to the position of the upper end of the outer wall 12a; and a second portion $12b_{22}$ having the upper end whose position is closer to the bottom wall 12d than the first portion $12b_{21}$, in the top-bottom direction. That is, the first portion $12b_{21}$ and the second portion $12b_{22}$ form a step in the circumferential direction. The interior inner wall $12b_2$ and the outer wall 12a are coupled to each other by a coupling wall $12g_2$, whereby the rigidities of the two walls are enhanced. The position of the upper end of the coupling wall $12g_2$ is equivalent to the position of the upper end of the first portion $12b_{21}$. The interior inner wall $12b_2$, the outer wall 12a, and the coupling wall $12g_2$ can be integrally shaped.

A portion of the upper end of the interior inner wall $12b_3$ is cut out, the portion being closer to the interior inner wall $12b_2$. More specifically, the interior inner wall $12b_3$ includes: a first portion $12b_{31}$ having the upper end whose position is equivalent to the position of the upper end of the outer wall 12a; and a second portion $12b_{32}$ having the upper end whose position is closer to the bottom wall 12d than the first portion $12b_{31}$, in the top-bottom direction. That is, the first portion $12b_{31}$ and the second portion $12b_{32}$ form a step in the circumferential direction. The interior inner wall $12b_3$ and the outer wall 12a are coupled to each other by a coupling wall $12g_3$, whereby the rigidities of the two walls are enhanced. The position of the upper end of the coupling wall $12g_3$ is equivalent to the position of the upper end of the second portion $12b_{32}$. The interior inner wall $12b_3$, the outer wall 12a, and the coupling wall $12g_3$ can be integrally shaped.

A portion of the upper end of the interior inner wall $12b_4$ is cut out, the portion being closer to the interior inner wall $12b_3$. More specifically, the interior inner wall $12b_4$ includes: a first portion $12b_{41}$ having the upper end whose position is equivalent to the position of the upper end of the outer wall 12a; and a second portion $12b_{42}$ having the upper end whose position is closer to the bottom wall 12d than the first portion $12b_{41}$, in the top-bottom direction. That is, the first portion $12b_{41}$ and the second portion $12b_{42}$ form a step in the circumferential direction. The interior inner wall $12b_4$ and the outer wall 12a are coupled to each other by a coupling wall $12g_4$, whereby the rigidities of the two walls are enhanced. The position of the upper end of the coupling wall $12g_4$ is equivalent to the position of the upper end of the second portion $12b_{42}$. The interior inner wall $12b_4$, the outer wall 12a, and the coupling wall $12g_4$ can be integrally shaped.

The exterior inner walls $12c_1$, $12c_2$, $12c_3$ and $12c_4$ are located between the outer wall 12a and the interior inner walls $12b_1$, $12b_2$, $12b_3$ and $12b_4$ and on a circumference having the same radius. The difference between the radius of the circle formed by the exterior inner walls $12c_1$, $12c_2$, $12c_3$ and $12c_4$ and the radius of the circle formed by the interior inner walls $12b_1$, $12b_2$, $12b_3$ and $12b_4$, that is, the depths of groove parts G1, G2, G3 and G4 (to be described later) can be set to be equivalent to or slightly larger than the protruding lengths of the projections $20c_1$, $20c_2$, $20c_3$, and $20c_4$ (to be described later) of the piston plate 20. The exterior inner walls $12c_1$, $12c_2$, $12c_3$ and $12c_4$ are arranged in the stated order in the clockwise direction when viewed from the upper end side (the cover part 14 side) thereof, with given intervals in the circumferential direction. That is, the exterior inner wall $12c_1$ and the exterior inner wall $12c_2$ are spaced apart from each other with a predetermined interval in the circumferential direction, the exterior inner wall $12c_2$ and the exterior inner wall $12c_3$ are spaced apart from each other with a predetermined interval in the circumferential direction, the exterior inner wall $12c_3$ and the exterior inner wall $12c_4$ are spaced apart from each other with a predetermined interval in the circumferential direction, and the exterior inner wall $12c_4$ and the exterior inner wall $12c_1$ are spaced apart from each other with a predetermined interval in the circumferential direction.

A lateral part of the exterior inner wall $12c_1$ is connected to lateral parts of the interior inner walls $12b_1$ and $12b_2$. The exterior inner wall $12c_1$ and the interior inner walls $12b_1$ and $12b_2$ can be integrally shaped. Thus, the exterior inner wall $12c_1$ and the interior inner walls $12b_1$ and $12b_2$ form the groove part G1 that extends in the top-bottom direction, on the inner circumferential surface of the main body part 12. That is, the groove part G1 is adjacent to the second portion $12b_{22}$ of the interior inner wall $12b_2$. The position of the upper end of the exterior inner wall $12c_1$ is equivalent to the position of the upper end of the outer wall 12a, in the top-bottom direction. The exterior inner wall $12c_1$ and the outer wall 12a are coupled to each other by a coupling wall $12g_5$, whereby the rigidities of the two walls are enhanced. The position of the upper end of the coupling wall $12g_5$ is equivalent to the position of the upper end of the exterior inner wall $12c_1$. The exterior inner wall $12c_1$, the outer wall 12a, and the coupling wall $12g_5$ can be integrally shaped.

A lateral part of the exterior inner wall $12c_2$ is connected to lateral parts of the interior inner walls $12b_2$ and $12b_3$. The exterior inner wall $12c_2$ and the interior inner walls $12b_2$ and $12b_3$ can be integrally shaped. Thus, the exterior inner wall $12c_2$ and the interior inner walls $12b_2$ and $12b_3$ form the groove part G2 that extends in the top-bottom direction, on the inner circumferential surface of the main body part 12. That is, the groove part G2 is adjacent to the second portion $12b_{32}$ of the interior inner wall $12b_3$. The position of the upper end of the exterior inner wall $12c_2$ is equivalent to the position of the upper end of the outer wall 12a, in the top-bottom direction. The exterior inner wall $12c_2$ and the outer wall 12a are coupled to each other by a coupling wall $12g_6$, whereby the rigidities of the two walls are enhanced. The position of the upper end of the coupling wall $12g_6$ is equivalent to the position of the upper end of the exterior inner wall $12c_2$. The exterior inner wall $12c_2$, the outer wall 12a, and the coupling wall $12g_6$ can be integrally shaped.

A lateral part of the exterior inner wall $12c_3$ is connected to lateral parts of the interior inner walls $12b_3$ and $12b_4$. The exterior inner wall $12c_3$ and the interior inner walls $12b_3$ and $12b_4$ can be integrally shaped. Thus, the exterior inner wall $12c_3$ and the interior inner walls $12b_3$ and $12b_4$ form the groove part G3 that extends in the top-bottom direction, on the inner circumferential surface of the main body part 12. That is, the groove part G3 is adjacent to the second portion $12b_{42}$ of the interior inner wall $12b_4$. The position of the upper end of the exterior inner wall $12c_3$ is equivalent to the position of the upper end of the adjacent second portion $12b_{42}$ of the interior inner wall $12b_4$, in the top-bottom direction. That is, the upper end of the exterior inner wall $12c_3$ is located closer to the bottom wall 12d than the upper end of the outer wall 12a. The exterior inner wall $12c_3$ and the outer wall 12a are coupled to each other by a coupling wall $12g_7$, whereby the rigidities of the two walls are enhanced. The position of the upper end of the coupling wall $12g_7$ is located closer to the bottom wall 12d than the position of the upper end of the exterior inner wall $12c_3$. Accordingly, in a cross section of the exterior inner wall $12c_3$, the coupling wall $12g_7$, and the outer wall 12a, a portion of the coupling wall $12g_7$ is observed as a concave part. The exterior inner wall $12c_3$, the outer wall 12a, and the coupling wall $12g_7$ can be integrally shaped.

A lateral part of the exterior inner wall $12c_4$ is connected to lateral parts of the interior inner walls $12b_4$ and $12b_1$. The exterior inner wall $12c_4$ and the interior inner walls $12b_4$ and $12b_1$ can be integrally shaped. Thus, the exterior inner wall $12c_4$ and the interior inner walls $12b_4$ and $12b_1$ form the groove part G4 that extends in the top-bottom direction, on the inner circumferential surface of the main body part 12. That is, the groove part G4 is adjacent to the second portion $12b_{12}$ of the interior inner wall $12b_1$. The position of the upper end of the exterior inner wall $12c_4$ is equivalent to the position of the upper end of the adjacent second portion $12b_{12}$ of the interior inner wall $12b_1$, in the top-bottom direction. That is, the upper end of the exterior inner wall $12c_4$ is located closer to the bottom wall 12d than the upper end of the outer wall 12a. The exterior inner wall $12c_4$ and the outer wall 12a are coupled to each other by a coupling wall $12g_8$, whereby the rigidities of the two walls are enhanced. The position of the upper end of the coupling wall $12g_8$ is equivalent to the position of the upper end of the exterior inner wall $12c_4$. The exterior inner wall $12c_4$, the outer wall 12a, and the coupling wall $12g_8$ can be integrally shaped.

The bottom wall 12d is connected to the lower end of the outer wall 12a, the lower ends of the interior inner walls $12b_1$, $12b_2$, $12b_3$ and $12b_4$, the lower ends of the exterior inner walls $12c_1$, $12c_2$, $12c_3$ and $12c_4$, and the lower ends of the coupling walls $12g_1$, $12g_2$, $12g_3$, $12g_4$, $12g_5$, $12g_6$, $12g_7$ and $12g_8$. The outer diameter of the bottom wall 12d is equivalent to the diameter of the outer circumference of the outer wall 12a. The inner diameter of the bottom wall 12d is equivalent to the diameter of the circle formed by the inner circumferential surfaces of the interior inner walls $12b_1$, $12b_2$, $12b_3$ and $12b_4$. Thus, the lower ends of the groove parts G1, G2, G3 and G4 are closed by the bottom wall 12d (see FIG. 2 and FIG. 5).

As illustrated in FIG. 1 to FIG. 3, the cover part 14 includes a top plate 14a having a circular shape; and a cylindrical member 14b that extends downward from the periphery of the top plate 14a. The height of the cylindrical member 14b can be set to be equivalent to the length from the flange member 12e to the upper end on the outer wall 12a. The cylindrical member 14b is provided with a cutout part 14c that extends in the circumferential direction. The length of the cutout part 14c can be set to the same length as that of the cutout part 12f of the outer wall 12a.

In the completed state of the applicator A1, the cover part 14 is attached to the main body part 12. The cover part 14 is attached to the main body part 12 in the state where the cover part 14 is positioned with respect to the main body part 12 such that the cutout part 14c of the cover part 14 and the cutout part 12f of the outer wall 12a are coincident with each other. Thus, the cutout parts 12f and 14c form a through-hole 14 (see FIG. 3 and FIG. 5) that communicates the inside and the outside of the casing 10 with each other. Examples of the adoptable method of attaching the cover part 14 to the main body part 12 include: a method of adhering the cylindrical member 14b of the cover part 14 to the flange member 12e of the main body part 12 with the use of an adhesive, an adhesive sheet, and the like; a method of mechanically engaging the two parts (for example, providing an engagement claw in the cylindrical member $14b$, providing an engagement hole in the flange member $12e$, and fitting the engagement claw and the engagement hole to each other); a method of pressure-bonding the cover part 14 to the main body part 12 (for example, setting the diameter of the cylindrical member $14b$ of the cover part 14 to be smaller than the outer diameter of the main body part 12 and press-fitting the cover part 14 to the main body part 12); and a method of welding the cover part 14 to the main body part 12 (for example, heating and melting the cylindrical member $14b$ and the flange member $12e$ and then cooling and integrating the two members).

Figure 4:
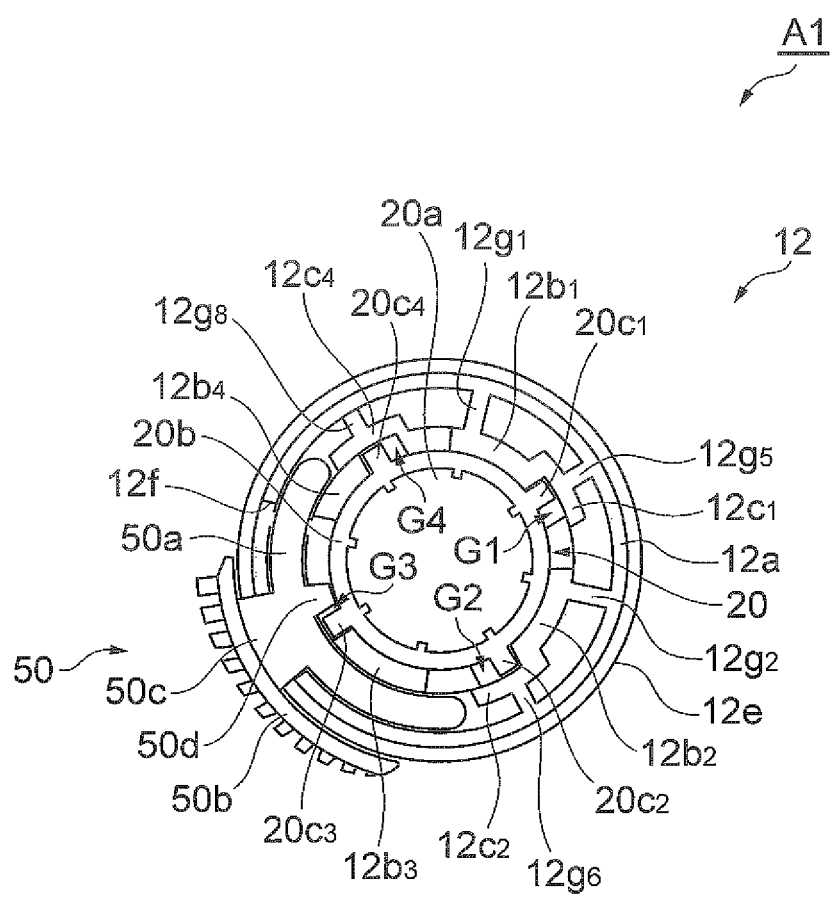
FIG. 4 is a top view illustrating the state after the operation of the applicator according to the first embodiment, from which a cover part is detached.
Figure 5:
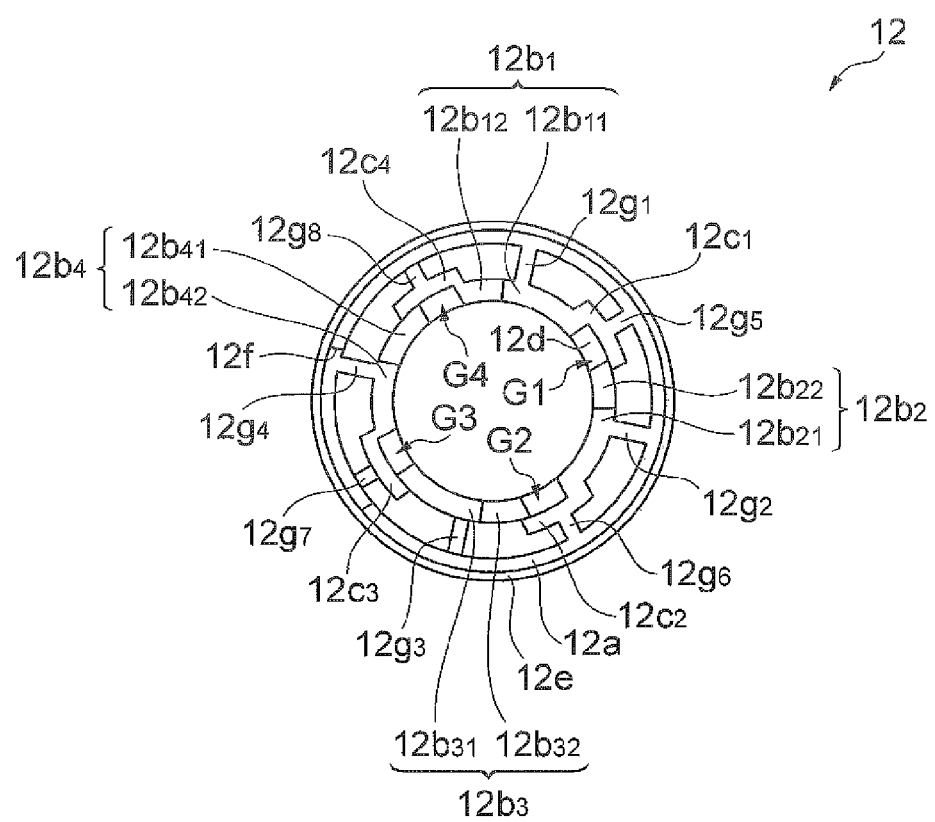
FIG. 5 is a top view illustrating a main body part.

The piston plate 20 is housed in the main body part 12, and is movable in the top-bottom direction along the central axis of the main body part 12 inside of the main body part 12. The material of the piston plate 20 may be the same as the material of the casing 10, and may be the same as the material (to be described later) of the microneedle array 30. As illustrated in FIG. 2 to FIG. 4, the piston plate 20 includes: a disc-like main body $20a$; and a cylindrical member $20b$ that extends upward from the periphery of the main body $20a$. An opening, a groove, a through-hole, or the like may be formed in the main body $20a$ for the purpose of reducing the air resistance and the weight of the piston plate 20. Further, an elongated protrusion or the like may be provided on the upper surface (the surface on which the conical coil spring 40 is arranged) of the main body $20a$ for the purpose of improving the rigidity of the piston plate 20. It is preferable that the lower surface (the surface opposite to the upper surface) of the main body $20a$ be planar, in consideration of causing the piston plate 20 to evenly act on the microneedle array 30. Alternatively, the lower surface of the main body $20a$ may have other shapes than the planar shape, and the shape of the lower surface of the main body $20a$ can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The inner diameter of the cylindrical member $20b$ is set to be larger than a maximum diameter D1 (to be described later) of the conical coil spring 40. The height of the cylindrical member $20b$ is not particularly limited as long as the cylindrical member $20b$ can function as such a stopper that prevents the conical coil spring 40 from dropping off the piston plate 20 during its movement in the radial direction. For example, in the case where the height of the applicator A1 is desired to be minimized, the height of the cylindrical member $20b$ can be set to be equivalent to the thickness of a metal wire that forms the conical coil spring 40. In the case where the stopper for the conical coil spring 40 is not necessary, the piston plate 20 does not need to include the cylindrical member $20b$. Even in the case where the piston plate 20 does not include the cylindrical member $20b$, if a ring-like groove in which the metal wire that forms the conical coil spring 40 can be fit is formed in the main body $20a$, the function as the stopper for the conical coil spring 40 can be fulfilled by the ring-like groove. In the case where such a stopper for the conical coil spring 40 is provided, a failure in positioning of the conical coil spring 40 with respect to the piston plate 20 can be prevented at the time of arranging the conical coil spring 40 on the upper surface of the piston plate 20 and then attaching the cover part 14 to the main body part 12 to thereby make the applicator A1.

The plurality of projections (in the first embodiment, four projections) $20c_1$, $20c_2$, $20c_3$ and $20c_4$ are provided in the periphery (on the outer circumferential surface) of the piston plate 20, and the projections $20c_1$, $20c_2$, $20c_3$ and $20c_4$ each protrude outward in the radial direction (the direction that intersects with the thickness direction of the piston plate). The projections $20c_1$, $20c_2$, $20c_3$ and $20c_4$ are arranged in the stated order in the clockwise direction when viewed from above (the upper surface side of the piston plate 20 on which the conical coil spring 40 is placed), with given intervals in the circumferential direction. In the first embodiment, the projections $20c_1$, $20c_2$, $20c_3$ and $20c_4$ each have a quadrangular prism shape. Alternatively, the projections $20c_1$, $20c_2$, $20c_3$ and $20c_4$ may have other shapes (for example, a columnar shape, a polygonal prism shape, a deformed pillar shape, a circular cone shape, a polygonal pyramid shape, a truncated circular cone shape, and a truncated polygonal pyramid shape) as long as locking with the second portions $12b_{12}$, $12b_{22}$, $12b_{32}$ and $12b_{42}$ of the interior inner walls $12b_1$, $12b_2$, $12b_3$ and $12b_4$ is possible and movement in the groove parts G1, G2, G3 and G4 is possible.

The projection $20c_1$ is movable along the extending direction of the groove part G1 inside of the groove part G1. The projection $20c_2$ is movable along the extending direction of the groove part G2 inside of the groove part G2. The projection $20c_3$ is movable along the extending direction of the groove part G3 inside of the groove part G3. The projection $20c_4$ is movable along the extending direction of the groove part G4 inside of the groove part G4. Thus, the piston plate 20 can be guided in the top-bottom direction along the extending directions of the groove parts G1, G2, G3 and G4 (the axial direction of the main body part 12).

In the state where the projection $20c_1$ is located on the upper end side of the groove part G1, the projection $20c_1$ is movable in the horizontal direction above the second portion $12b_{22}$ of the interior inner wall $12b_2$. Thus, the projection $20c_1$ can be placed on the upper end of the second portion $12b_{22}$ of the interior inner wall $12b_2$ adjacent to the groove part G1. In the state where the projection $20c_2$ is located on the upper end side of the groove part G2, the projection $20c_2$ is movable in the horizontal direction above the second portion $12b_{32}$ of the interior inner wall $12b_3$. Thus, the projection $20c_2$ can be placed on the upper end of the second portion $12b_{32}$ of the interior inner wall $12b_3$ adjacent to the groove part G2.

In the state where the projection $20c_3$ is located on the upper end side of the groove part G3, the projection $20c_3$ is movable in the horizontal direction above the second portion $12b_{42}$ of the interior inner wall $12b_4$. Thus, the projection $20c_3$ can be placed on the upper end of the second portion $12b_{42}$ of the interior inner wall $12b_4$ adjacent to the groove part G3. In the state where the projection $20c_4$ is located on the upper end side of the groove part G4, the projection $20c_4$ is movable in the horizontal direction above the second portion $12b_{12}$ of the interior inner wall $12b_1$. Thus, the projection $20c_4$ can be placed on the upper end of the second portion $12b_{12}$ of the interior inner wall $12b_1$ adjacent to the groove part G4.

The upper ends of the second portions $12b_{12}$, $12b_{22}$, $12b_{32}$ and $12b_{42}$ of the interior inner walls $12b_1$, $12b_2$, $12b_3$ and $12b_4$ may extend in the circumferential direction so as to be parallel to a horizontal plane, and may be inclined to the horizontal plane, in the circumferential direction. In particular, the upper ends of the second portions $12b_{12}$, $12b_{22}$, $12b_{32}$ and $12b_{42}$ may be inclined such that the heights thereof become larger toward the respective adjacent groove parts G1, G2, G3 and G4. In this case, when the projections $20c_1$, $20c_2$, $20c_3$ and $20c_4$ placed on the upper ends of the second portions $12b_{12}$, $12b_{22}$, $12b_{32}$ and $12b_{42}$ move toward the groove parts G1, G2, G3 and G4, the projections $20c_1$, $20c_2$, $20c_3$ and $20c_4$ need to climb the slopes of the upper ends of the second portions $12b_{12}$, $12b_{22}$, $12b_{32}$ and $12b_{42}$. Thus, even if an impact or the like is applied from the outside to the applicator A1, the projections $20c_1$, $20c_2$, $20c_3$ and $20c_4$ can be prevented from unintentionally moving into the groove parts G1 to G4.

As illustrated in FIG. 2, FIG. 3, FIG. 6, and FIG. 7, the microneedle array 30 includes: a disc-like substrate 31; and a plurality of microneedles 32 that are provided in a protruding manner on one main surface (lower surface) of the substrate 31. The substrate 31 is a foundation for supporting the microneedles 32. The area of the substrate 31 may be 0.5 cm$^2$ to 300 cm$^2$, may be 1 cm$^2$ to 100 cm$^2$, and may be 1 cm$^2$ to 50 cm$^2$. A substrate having a desired size may be formed by connecting a plurality of the substrates 31.

The substrate 31 has the other main surface (upper surface) attached to the lower surface of the main body 20a of the piston plate 20. That is, the microneedle array 30 is integrated with the piston plate 20. Examples of the adoptable method of attaching the substrate 31 to the piston plate 20 include: a method of mechanically integrating the substrate 31 with the piston plate 20 (for example, providing an engagement claw on the upper surface of the substrate 31, providing an engagement hole in the piston plate 20, and fitting the engagement claw and the engagement hole to each other); and a method of adhering the substrate 31 to the piston plate 20 with the use of an adhesive, an adhesive sheet, and the like.

Figure 6:
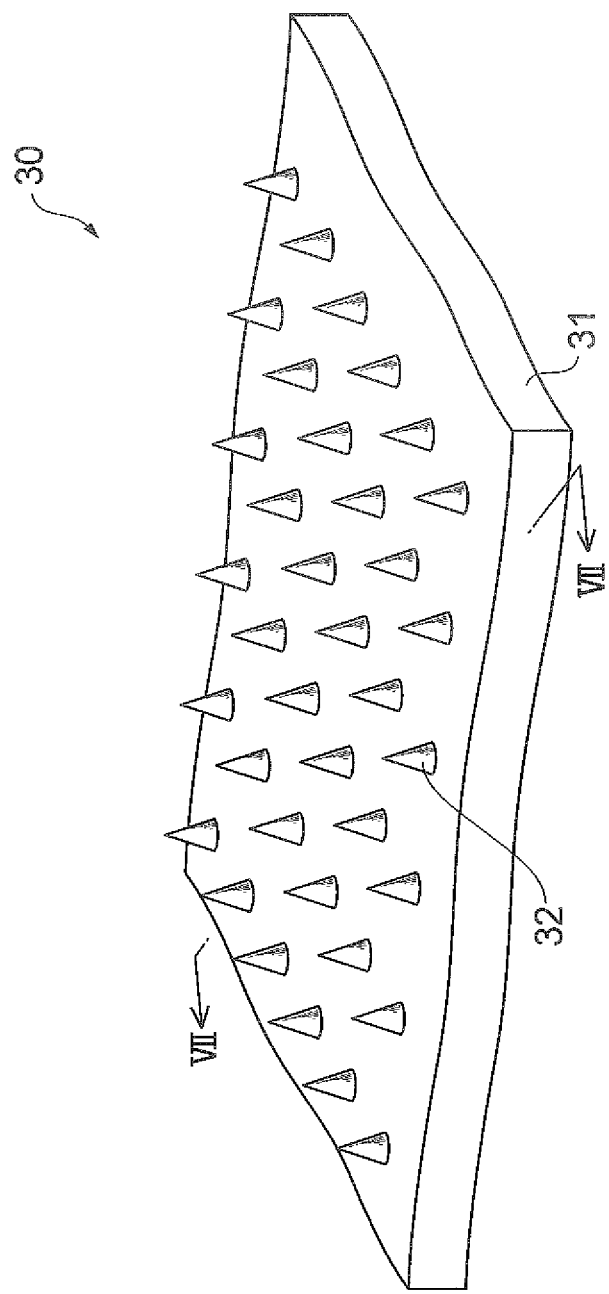
FIG. 6 is a perspective view partially illustrating a microneedle array.

As illustrated in FIG. 6, the microneedles 32 are arranged at substantially regular intervals in a zigzag (alternate) pattern on the surface of the substrate 31. The height (length) of the microneedles 32 may be 20 μm to 700 μm, and may be 50 μm to 700 μm. The reason why the height of the microneedles 32 is set to be equal to or more than 20 μm is to reliably transfer the medical agent or the like into the body. The reason why the height of the microneedles 32 is set to be equal to or less than 700 μm is to allow the microneedles 32 to be stuck up to only a horny layer of the skin and to prevent the microneedles 32 from reaching a dermic layer.

Each microneedle 32 is a tapered structure that becomes thinner toward its leading end part from its base end part connected to the substrate 31. That is, the microneedle 32 has a needle-like shape or a structure including a needle-like shape. The microneedle 32 may have a shape with a pointed tip, such as a circular cone shape and a polygonal pyramid shape, and may have a shape with an unpointed tip, such as a truncated circular cone shape and a truncated polygonal pyramid shape. In the case as illustrated in FIG. 6 where the microneedle 32 has a circular cone shape, the diameter of the base end part thereof may be 5 μm to 250 μm, and may be 10 μm to 200 μm.

In the case where the leading end of each microneedle 32 is rounded, the radius of curvature of the leading end part may be 2 μm to 100 μm, and may be 5 μm to 30 μm. In the case where the leading end of the microneedle 32 is flat, the area of the flat part may be 20 μm$^2$ to 600 μm$^2$, and may be 50 μm$^2$ to 250 μm$^2$.

With regard to the density of the microneedles 32 on the substrate 31, typically, one to ten microneedles 32 are arranged per 1 mm in one line. In general, adjacent rows are spaced apart from each other by a distance that is substantially equal to the space of the microneedles 32 in the rows. Thus, the lower limit of the density of the microneedles 32 may be 100 needles/cm$^2$, may be 200 needles/cm$^2$, may be 300 needles/cm$^2$, may be 400 needles/cm$^2$, and may be 500 needles/cm$^2$. The upper limit of the density of the microneedles 32 may be 10000 needles/cm$^2$, may be 5000 needles/cm$^2$, may be 2000 needles/cm$^2$, and may be 850 needles/cm$^2$.

The materials of the substrate 31 and the microneedles 32 may be the same and may be different. All the microneedles 32 may be made of the same material, and the microneedles 32 made of different materials may be mixedly provided. Examples of the materials of the substrate 31 and the microneedles 32 include silicon, silicon dioxide, ceramics, metal (such as stainless steel, titanium, nickel, molybdenum, chromium, and cobalt), and synthetic or natural resin materials. Examples of the resin materials include: biodegradable polymers such as polylactide, polyglycolide, polylactide-co-polyglycolide, pullulan, caprolactone, polyurethane, and polyanhydride; and undegradable polymers such as polycarbonate, polymethacrylate, ethylene vinyl acetate, polytetrafluoroethylene, and polyoxymethylene, in consideration of the antigenicity of the substrate 31 and the microneedles 32 and the unit prices of the materials. Examples of the materials of the substrate 31 and the microneedles 32 may also include polysaccharides such as hyaluronic acid, sodium hyaluronate, pullulan, dextran, dextrin, chondroitin sulfate, and cellulose derivatives. Further, in another embodiment, mixtures of the above-mentioned biodegradable resins and active ingredients may be used as the material(s) of the substrate 31 and/or the microneedles 32. Glass fiber may be added to the above-mentioned resin materials for the purpose of increasing the strength and the like.

The material of the microneedles 32 may be biodegradable resins such as polylactide, considering the case where the microneedles 32 break on the skin. Note that polylactide includes: polylactide homopolymers of poly-L-lactide, poly-D-lactide, and the like; poly-L/D-lactide copolymers; and mixtures thereof, and any of these substances may be used. The strength of polylactide is higher as the average molecular weight thereof is larger. Polylactide having a molecular weight of 40000 to 100000 can be used.

Examples of the method of manufacturing the substrate 31 and the microneedles 32 include: wet etching or dry etching using a silicon substrate; precision machining (such as electrical discharge machining, laser beam machining, dicing, hot embossing, and injection molding) using metal or resin; and mechanical cutting. According to these manufacturing methods, the substrate 31 and the microneedles 32 are integrally formed. Examples of the method of making the microneedles 32 hollow include secondarily processing the microneedles 32 through laser beam machining or the like after manufacture of the microneedles 32.

Figure 7:
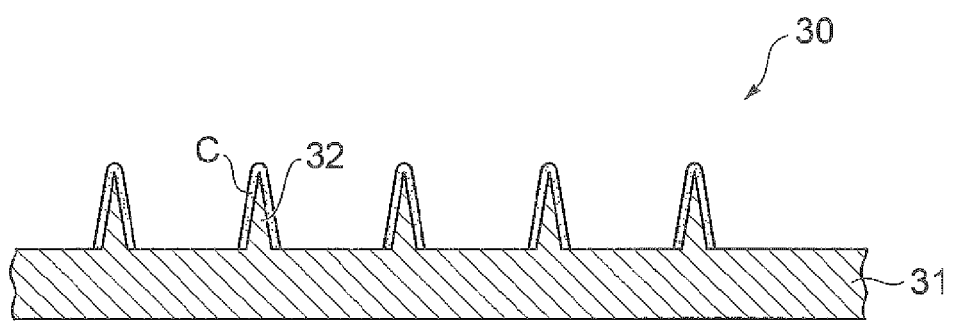
FIG. 7 is a cross sectional view taken along line VII-VII in FIG. 6.

As illustrated in FIG. 7, coating C with active ingredients may be applied to the substrate 31 and/or the microneedles 32. In the present exemplary embodiment, the coating C is obtained by firmly fixing a coating agent (coating liquid) containing active ingredients and purified water and/or coating carriers to the entirety or a part of the surface(s) of the substrate 31 and/or the microneedles 32. "Firmly fixing" here refers to maintaining the state where the coating liquid substantially uniformly adheres to a target. Immediately after the coating, the coating liquid is firmly fixed in a dried state according to a known drying method such as air drying, vacuum drying, freeze drying, and combinations thereof, but after dermal administration, the coating liquid is not necessarily firmly fixed in a dried state because the coating liquid may hold a moisture content in equilibrium with a surrounding atmosphere, an organic solvent, and the like.

The active ingredients used in the present exemplary embodiment are not particularly limited, and are selected from the group consisting of antioxidants, free radical scavengers, moisturizers, depigmentation agents, fat regulating agents, UV reflective agents, humectants, antibacterial agents, antiallergic drugs, anti-acne agents, anti-aging agents, anti-wrinkling agents, bactericides, analgesics, antitussives, antipruritics, local anesthetics, anti-hair loss agents, hair growth promoting agents, hair growth inhibitor agents, dandruff inhibitors, antihistamines, keratolytic agents, anti-inflammatory agents, anti-infectives, antiemetics, anticholinergics, vasoconstrictors, vasodilators, wound healing promoters, peptides, polypeptides, proteins, deodorants, antiperspirants, skin emollients, tanning agents, skin lightening agents, antifungals, hemorrhoidal preparations, make-up preparations, vitamins, amino acids, amino acid derivatives, cell turnover enhancers, immunostimulants, DNAs, RNAs, vaccines, low molecular peptides, sugar, nucleic acids, hypnotics/sedatives, antipyretic antiphlogistic analgetic agents, steroidal antiphlogistics, stimulants/psychostimulants, psychoneurotic drugs, hormone drugs, agents affecting urinary organs, skeletal muscle relaxants, agents affecting genital organs, antiepileptics, medicine for autonomic nerves, antiparkinsonism agents, diuretics, respiratory stimulants, antimigraine agents, bronchodilating preparations, cardiotonics, coronary vasodilators, peripheral vasodilators, smoking-cessation drugs, agents affecting circulatory organs, antiarrhythmic agents, antitherioma agents, antilipemic agents, hypoglycemic agents, antiulcer drugs, cholagogues, prokinetic agents, agents for liver diseases, antiviral drugs, antimotionsickness agents, antibiotics, agents for habitual intoxication, appetite suppressants, chemotherapeutic drugs, blood coagulation accelerants, anti-Alzheimer disease drugs, serotonin-receptor antagonist antiemetic drugs, gout treatment agents, and mixtures thereof.

Note that the active ingredients can be used alone or in combination of two or more kinds thereof and, as a matter of course, includes a pharmaceutically acceptable salt regardless of its form, i.e., either mineral salt or organic salt. Furthermore, although the active ingredients are basically included in the coating carrier, the active ingredients can be supplied later through a through-hole formed on the substrate 31 without allowing the coating carrier to include the active ingredients. In addition, the active ingredients can be directly applied onto the skin, and the microneedle array 30 can be applied later to the same portion of the skin. In this case, it is enabled to promote the penetration of the active ingredients into the skin due to the effect of stretching the skin and the occlusive dressing technique (ODT) effect on the skin.

Figure 8:
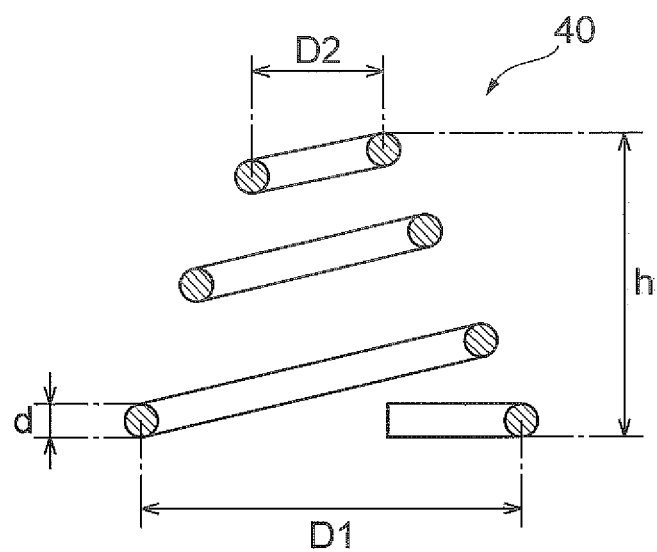
FIG. 8 is a cross sectional view illustrating a conical coil spring.

As illustrated in FIG. 2 and FIG. 3, the conical coil spring 40 is housed in the main body part 12. Specifically, the conical coil spring 40 is arranged between the piston plate 20 and the cover part 14, and is sandwiched between the upper surface of the piston plate 20 and the lower surface of the cover part 14. As illustrated in FIG. 2, FIG. 3, and FIG. 8, the conical coil spring 40 is formed by winding a metal wire circular in cross section in a spiral manner, and the conical coil spring 40 has a circular cone shape when viewed from its lateral. In the present exemplary embodiment, the conical coil spring 40 does not overlap when viewed from the central line direction of the conical coil spring 40. Examples of the metal wire include a stainless steel wire, a piano wire (iron wire), and a copper wire. Among these wires, particularly the stainless steel wire is extremely resistant to corrosion.

In the present exemplary embodiment, the smaller diameter side of the conical coil spring 40 abuts against the cover part 14, and the larger diameter side of the conical coil spring 40 abuts against the piston plate 20. Parameters concerning the energy of the piston plate 20 actuated by the biasing force of the conical coil spring 40 include: the modulus of transverse elasticity; the wire diameter (d in FIG. 8); the maximum diameter (D1 in FIG. 8); the minimum diameter (D2 in FIG. 8); the total number of coil turns; the weight of the conical coil spring 40; the total weight of the piston plate 20 and the microneedle array 30; the free height (h in FIG. 8); the height in a close contact state; the pitch angle; and the pitch.

The modulus of transverse elasticity is determined by the material of the conical coil spring 40. The modulus of transverse elasticity of the stainless steel wire is 68500 N/mm$^2$, the modulus of transverse elasticity of the piano wire (iron wire) is 78500 N/mm$^2$, and the modulus of transverse elasticity of the copper wire is $3.9 \times 10^4$ N/mm$^2$ to $4.4 \times 10^4$ N/mm$^2$. The wire diameter d of the conical coil spring may be 0.01 mm to 2 mm, may be 0.1 mm to 1.5 mm, and may be 0.3 mm to 1.3 mm. From one end to the other end of the metal wire that forms the conical coil spring 40, the wire diameter d may be constant, and may change like a tapered coil spring.

It is sufficient that the maximum diameter D1 be equal to or more than four times the wire diameter d. The maximum diameter D1 may be 1 mm to 100 mm, may be 1 mm to 50 mm, and may be 5 mm to 30 mm. If the maximum diameter D1 is less than 1 mm, the applicator A1 tends to be incapable of delivering satisfactory puncture performance. Because a region of the skin of the animal that can be regarded as being flat is limited, if the maximum diameter D1 exceeds 100 mm, stable attachment of the applicator A1 to the skin tends to be difficult.

The minimum diameter D2 may be equal to or more than 1/1000 times and less than one times the maximum diameter DE may be 1/100 times to 2/3 times the maximum diameter D1, and may be 1/10 times to 1/2 times the maximum diameter D1. The minimum diameter D2 may be, for example, 1 mm to 100 mm, may be 1 mm to 50 mm, may be 1 mm to 20 mm, and may be 1 mm to 10 mm. In particular, the minimum diameter D2 may be 0.33 times to 0.38 times the maximum diameter D1, and may be 0.34 times to 0.37 times the maximum diameter D1.

The total number of coil turns may be 1 to 100, may be 1 to 10, and may be 2 to 5. The weight of the conical coil spring 40 may be 0.01 g to 10 g, may be 0.1 g to 5 g, and may be 0.1 g to 3 g. The lower limit of the total weight of an actuation part including the piston plate 20, the microneedle array 30, and the conical coil spring 40 may be 0.1 g, may be 0.2 g, and may be 0.3 g. The upper limit of the total weight of the actuation part may be 20.0 g, may be 10.0 g, may be 1.5 g, and may be 0.6 g. The lower limit of the momentum of the actuation part may be 0.006 Ns, and may be 0.0083 Ns. The upper limit of the momentum of the actuation part may be 0.015 Ns, may be 0.012 Ns, and may be 0.010 Ns. Note that the momentum of the actuation part is obtained by multiplying the speed of the actuation part during actuation of the applicator A1 by the total weight of the actuation part.

The free height may be equal to or more than three times the wire diameter. For example, the free height may be 1 mm to 100 mm, may be 2 mm to 20 mm, and may be 2 mm to 10 mm. If the free height is less than 1 mm, the applicator A1 tends to be incapable of delivering satisfactory puncture performance. If the free height exceeds 100 mm, it tends to be difficult for a user to move with the applicator A1 being attached to the user.

As illustrated in FIG. 2 to FIG. 4 and FIG. 9, the release member 50 includes: an interior part 50a located inside of the main body part 12; an exterior part 50b located outside of the main body part 12; and a coupling part 50c that couples the interior part 50a and the exterior part 50b to each other. The interior part 50a is a flat plate having a circular arc-like shape. The diameter of the interior part 50a is larger than the diameter of the interior inner walls $12b_1$, $12b_2$, $12b_3$ and $12b_4$, and is smaller than the diameter of the outer wall 12a. In the completed state of the applicator A1, the interior part 50a is located between the outer wall 12a and the interior inner walls $12b_1$, $12b_2$, $12b_3$ and $12b_4$ (see FIG. 4). In the completed state of the applicator A1, the interior part 50a is placed above the exterior inner walls $12c_3$ and $12c_4$ each having a small height and the coupling walls $12g_3$, $12g_4$, $12g_7$, and $12g_8$ each having a small height (see the same drawing).

The interior part 50a is integrally provided with a protrusion part 50d that protrudes in the radial direction from the inner edge of the interior part 50a toward the central axis. The protrusion part 50d is a flat plate having a rectangular shape. In the completed state of the applicator A1, the protrusion part 50d is located on the circumference having the same radius as that of the interior inner walls $12b_1$, $12b_2$, $12b_3$ and $12b_4$ and between the first portion $12b_{31}$ of the interior inner wall $12b_3$ and the first portion $12b_{41}$ of the interior inner wall $12b_4$ (see FIG. 4).

Figure 9:
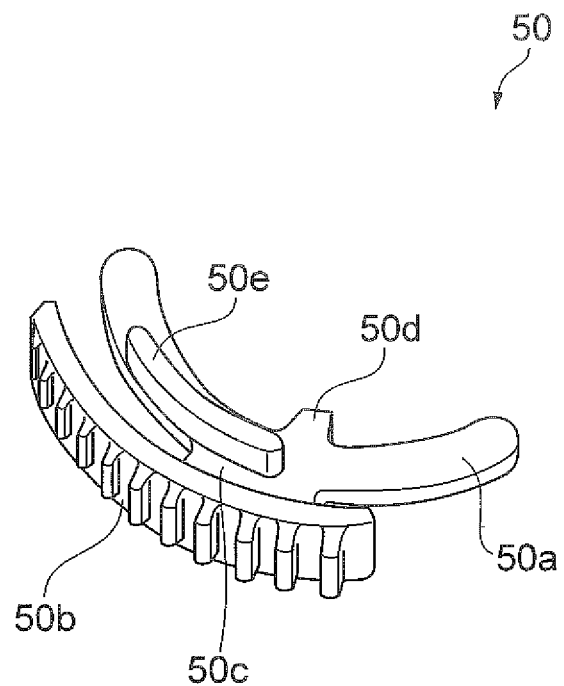
FIG. 9 is a perspective view illustrating the lower surface side of a release member.

As illustrated in FIG. 2 and FIG. 9, the interior part 50a is integrally provided with an elongated protrusion 50e that protrudes downward from the lower surface of the interior part 50a. The elongated protrusion 50e has a circular arc-like shape with a curvature equivalent to that of the interior part 50a, and extends along the interior part 50a. In the completed state of the applicator A1, the elongated protrusion 50e is located between the exterior inner wall $12c_3$ and the outer wall 12a. In order not to prevent movement in the circumferential direction of the release member 50 to be described later, it is preferable that the height of the elongated protrusion 50e be set to be smaller than the depth of a concave part formed by the exterior inner wall $12c_3$, the coupling wall $12g_7$, and the outer wall 12a.

As illustrated in FIG. 3, FIG. 4, and FIG. 9, the exterior part 50b is a curved plate that extends in the circumferential direction along the outer circumferential surface of the main body part 12, and has a circular arc-like shape in cross section. A plurality of elongated protrusions that extend along the top-bottom direction are provided on the outer surface of the exterior part 50b. The plurality of elongated protrusions are arranged side by side along the circumferential direction. Thus, the outer circumferential surface of the exterior part 50b has irregularities in the circumferential direction. Accordingly, when the user of the applicator A1 moves the release member 50 in the circumferential direction by touching the outer circumferential surface of the exterior part 50b with user's fingers, the fingers slip less easily on the outer circumferential surface of the exterior part 50b. In order to obtain such an antislip effect, for example, the outer circumferential surface of the exterior part 50b may be embossed or roughened instead of providing the plurality of elongated protrusions. The outer circumferential surface of the exterior part 50b does not particularly need to be processed.

The coupling part 50c is a flat plate having a rectangular shape. The coupling part 50c protrudes in the radial direction from the outer edge of the interior part 50a toward the opposite side to the central axis. In the completed state of the applicator A1, the coupling part 50c is exposed on the outer circumferential surface of the main body part 12 through the through-hole H. In order to make the coupling part 50c (release member 50) movable in the extending direction of the through-hole H, the width of the coupling part 50c is set to be smaller than the opening width of the through-hole H.

[1.2] Method of Manufacturing Applicator

Now, the method of manufacturing the applicator A1 is described.

(a) First Step

First, the respective components (the casing 10, the piston plate 20, the microneedle array 30, the conical coil spring 40, and the release member 50) of the applicator A1 described above are prepared. The coating C is applied in advance to the microneedles 32 of the prepared microneedle array 30. Next, the microneedle array 30 is attached to the lower surface of the piston plate 20.

(b) Second Step

Figure 10:
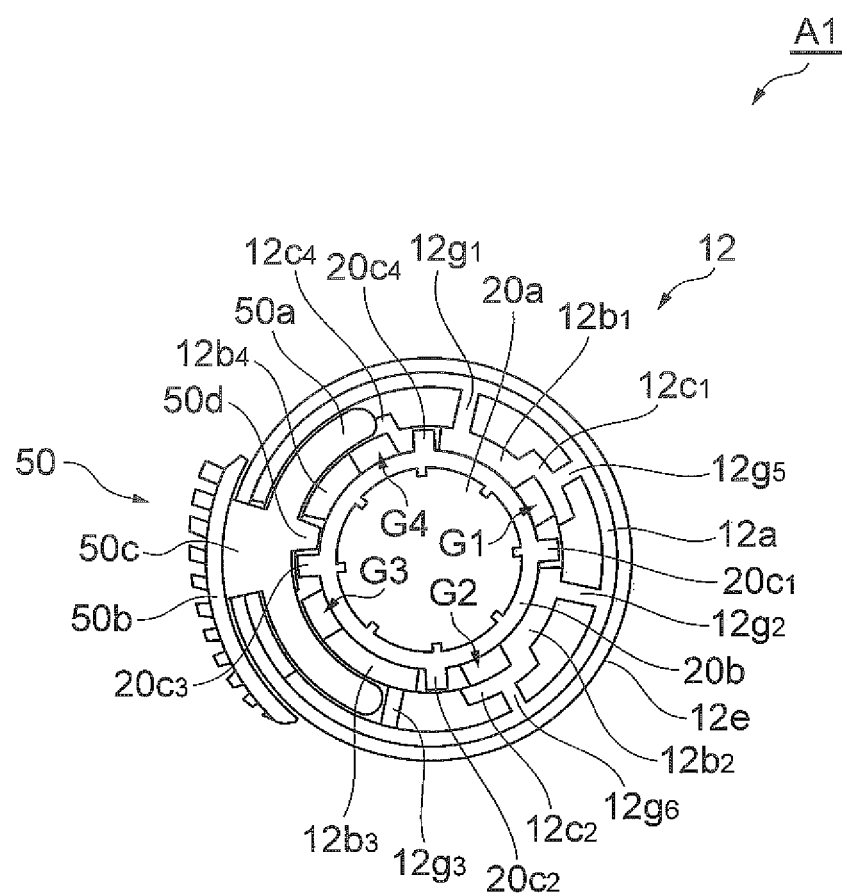
FIG. 10 is a top view illustrating a state before the operation of the applicator according to the first embodiment, from which the cover part is detached.

Subsequently, the interior part 50a of the release member 50 is placed above the exterior inner walls $12c_3$ and $12c_4$ and the coupling walls $12g_3$, $12g_4$, $12g_7$, and $12g_8$ such that the protrusion part 50d of the release member 50 is located above the first portion $12b_{41}$ of the interior inner wall $12b_4$ (see FIG. 10). Accordingly, the release member 50 (coupling part 50c) is located on one end side of the through-hole H.

(c) Third Step

Subsequently, the piston plate 20 is placed in the main body part 12 such that: the projection $20c_1$ of the piston plate 20 is located above the second portion $12b_{22}$ of the interior inner wall $12b_2$; the projection $20c_2$ of the piston plate 20 is located above the second portion $12b_{32}$ of the interior inner wall $12b_3$; the projection $20c_3$ of the piston plate 20 is located above the second portion $12b_{42}$ of the interior inner wall $12b_4$ and between the protrusion part 50d of the release member 50 and the groove part G3; and the projection $20c_4$ of the piston plate 20 is located above the second portion $12b_{12}$ of the interior inner wall $12b_1$ (see the same drawing). On this occasion, the protrusion part 50d of the release member 50 and the projection $20c_4$ of the piston plate 20 are placed above the second portion $12b_{42}$ of the interior inner wall $12b_4$, and hence it is preferable that the width of the second portion $12b_{42}$ be larger than the sum of the width of the protrusion part 50d and the width of the projection $20c_4$.

(d) Fourth Step

Subsequently, the conical coil spring 40 is placed on the upper surface of the piston plate 20 such that: the larger diameter side of the conical coil spring 40 faces downward; and the smaller diameter side thereof faces upward. In this way, the conical coil spring 40 stably stands up at the time of placing the conical coil spring 40 on the piston plate 20, and hence the applicator A1 can be manufactured more easily.

(e) Fifth Step

Figure 11:
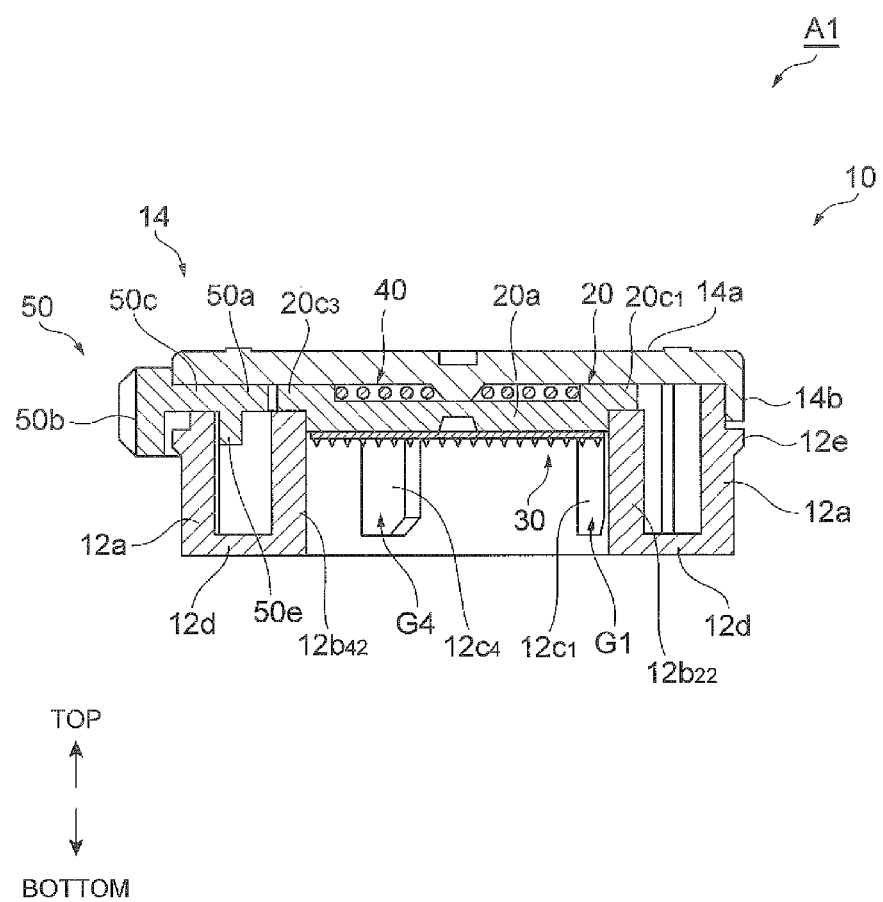
FIG. 11 is a cross sectional view illustrating the state before the operation of the applicator according to the first embodiment.

Subsequently, the cover part 14 is attached to the main body part 12 such that the cutout part 12f of the main body part 12 and the cutout part 14c of the cover part 14 coincide with each other. On this occasion, because the projections $20c_1$, $20c_2$, $20c_3$ and $20c_4$ are placed on the second portions $12b_{12}$, $12b_{22}$, $12b_{32}$ and $12b_{42}$ of the interior inner walls $12b_1$, $12b_2$, $12b_3$ and $12b_4$, respectively, even if the conical coil spring 40 is compressed by attaching the cover part 14 to the main body part 12, the piston plate 20 is not pushed out in the bottom direction by the conical coil spring 40. That is, the piston plate 20 is locked with the casing 10 (main body part 12). Accordingly, as illustrated in FIG. 11, the piston plate 20 is held at its retraction position on the cover part 14 side inside of the main body part 12, in the state where the cover part 14 and the piston plate 20 compress the conical coil spring 40. Such a state as described above where the piston plate 20 is locked with the casing 10 (main body part 12) and where the cover part 14 and the piston plate 20 compress the conical coil spring 40 is hereinafter referred to as "locked state".

Locking the piston plate 20 with the casing 10 (main body part 12) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the piston plate 20 and the cover part 14 becomes equivalent to the wire diameter, in the state where the piston plate 20 is locked (cocked) with the casing 10 (see FIG. 11).

Through the above-mentioned procedures, assembling of the applicator A1 is completed. Accordingly, the conical coil spring 40 remains in a compressed state until the applicator A1 is used by a user after manufacture and shipping thereof.

[1.3] Method of Using Applicator

Now, the method of using the applicator A1 is described. First, the applicator A1 is positioned with respect to a portion of a skin to which a medical agent or the like is desired to be applied, such that the microneedles 32 face the skin. The release member 50 is slid to the other end side of the through-hole H while the applicator A1 is kept positioned. As a result, the protrusion part 50$d$ of the release member 50 pushes the projection 20$c_3$ of the piston plate 20 toward the groove part G3. Consequently, the piston plate 20 turns.

The upper end of the second portion 12$b_{22}$ is adjacent to the end part on the cover part 14 side of the groove part G1 (the upper end part of the groove part G1). Hence, if the piston plate 20 turns, the projection 20$c_1$ slides on the upper end of the second portion 12$b_{22}$ to reach the groove part G1. The upper end of the second portion 12$b_{32}$ is adjacent to the end part on the cover part 14 side of the groove part G2 (the upper end part of the groove part G2). Hence, if the piston plate 20 turns, the projection 20$c_2$ slides on the upper end of the second portion 12$b_{32}$ to reach the groove part G2. The upper end of the second portion 12$b_{42}$ is adjacent to the end part on the cover part 14 side of the groove part G3 (the upper end part of the groove part G3). Hence, if the piston plate 20 turns, the projection 20$c_3$ slides on the upper end of the second portion 12$b_{32}$ to reach the groove part G3. The upper end of the second portion 12$b_{12}$ is adjacent to the end part on the cover part 14 side of the groove part G4 (the upper end part of the groove part G4). Hence, if the piston plate 20 turns, the projection 20$c_4$ slides on the upper end of the second portion 12$b_{12}$ to reach the groove part G4. As a result, the locking (cocking) of the piston plate 20 with the casing 10 (main body part 12) is released. Then, the piston plate 20 is moved, by the biasing force (elastic force) of the conical coil spring 40, outward (toward the skin) along the groove parts G1, G2, G3 and G4 (the central axis of the main body part 12) inside of the main body part 12, and the microneedle array 30 collides against the skin. At this time, the projections 20$c_1$, 20$c_2$, 20$c_3$ and 20$c_4$ abut against the bottom wall 12$d$, and hence the piston plate 20 is prevented from jumping out of the casing 10 (main body part 12).

When the microneedle array 30 collides against the skin, the microneedles 32 are stuck into the skin. The speed of the microneedles 32 (piston plate 20) on this occasion may be 4 m/s to 30 m/s, may be 4 m/s to 15 m/s, and may be 7 m/s to 15 m/s. In the configuration in which the microneedles 32 collide against the skin at a speed of 4 m/s to 30 m/s, the microneedles 32 can be appropriately stuck into the skin, whereby the medical agent or the like can be sufficiently transferred into the body of an animal.

[1.4] Actions

Actions of the applicator A1 according to the first embodiment are described.

(A) According to the first embodiment as described above, a user can make a puncture in a skin using the applicator A1 by simply sliding the release member 50. Accordingly, whoever may use the applicator A1, the biasing force of the conical coil spring 40 is transmitted to the microneedles 32 with the intermediation of the piston plate 20, and the microneedles 32 are stuck into the skin with a given impact force. Hence, the puncture in the skin can be reliably made (the reproducibility of the puncture is enhanced). When the microneedles 32 are stuck into the skin, active ingredients of the coating C that adhere to the microneedles 32 are delivered into the body, and the active ingredients are transferred into the body through the skin.

(B) In the applicator A1 according to the first embodiment, the locked state where the piston plate 20 is locked with the casing 10 is released by the release member 50. Consequently, the biasing force of the conical coil spring 40 acts on the piston plate 20, and the piston plate 20 moves along the groove parts G1, G2, G3 and G4 inside of the main body part 12 to reach a position for action on the skin. Thus, a member such as a shaft that extends in the axial direction of the main body part 12 (the height direction of the applicator A1) does not need to be attached to the piston plate 20. Further, in the applicator A1 according to the first embodiment, the conical coil spring 40 is used to exert a biasing force on the piston plate 20. When being compressed, the height of the conical coil spring 40 becomes extremely smaller compared with general cylindrical coil springs. In this way, the height of the applicator A1 itself can be made smaller, thus achieving a reduction in weight of the applicator A1.

(C) Depending on the type of a medical agent or the like, the applicator A1 needs to be held on the skin for a long time after a collision of the microneedles 32 against the skin. Even in such a case, with the use of the applicator A1 according to the first embodiment that can achieve a reduction in size and weight, the user can put on clothing and move without any restriction with the applicator A1 being attached to the skin. Moreover, because the applicator A1 according to the first embodiment is small, even in the case where the user freely moves in such a manner, the applicator A1 is extremely unlikely to collide against another object (obstacle) to thereby cause the microneedles 32 to come off the skin or to break and stay in the skin.

(D) In the case of using a conventional large-size applicator, the user may have trouble in handling, and the large exterior appearance thereof may bring about a feeling of fear. In contrast, the applicator A1 according to the first embodiment that can achieve a reduction in size and weight can be easily handled, and a feeling of fear that the user may develop can be significantly reduced.

(E) In the applicator A1 according to the first embodiment, the release member 50 is located lateral to (on the outer circumferential surface of) the casing 10 (main body part 12), and hence the release member 50 is suppressed from extending in the axial direction of the main body part 12 (the height direction of the applicator A1). Thus, the height of the applicator A1 itself can be made further smaller.

[2] Second Embodiment

Now, an applicator A2 according to a second embodiment is described with reference to FIG. 12 to FIG. 15. The applicator A2 according to the second embodiment is different from the applicator A1 according to the first embodiment mainly in that: the main body part 12 is not provided with the cutout part 12f; and the cover part 14 is not provided with the cutout part 14c but is provided with a through-hole 14d, as well as in the configuration of the release member 50. In the following, contents different from the applicator A1 according to the first embodiment are mainly described, and redundant description is omitted.

Figure 12:
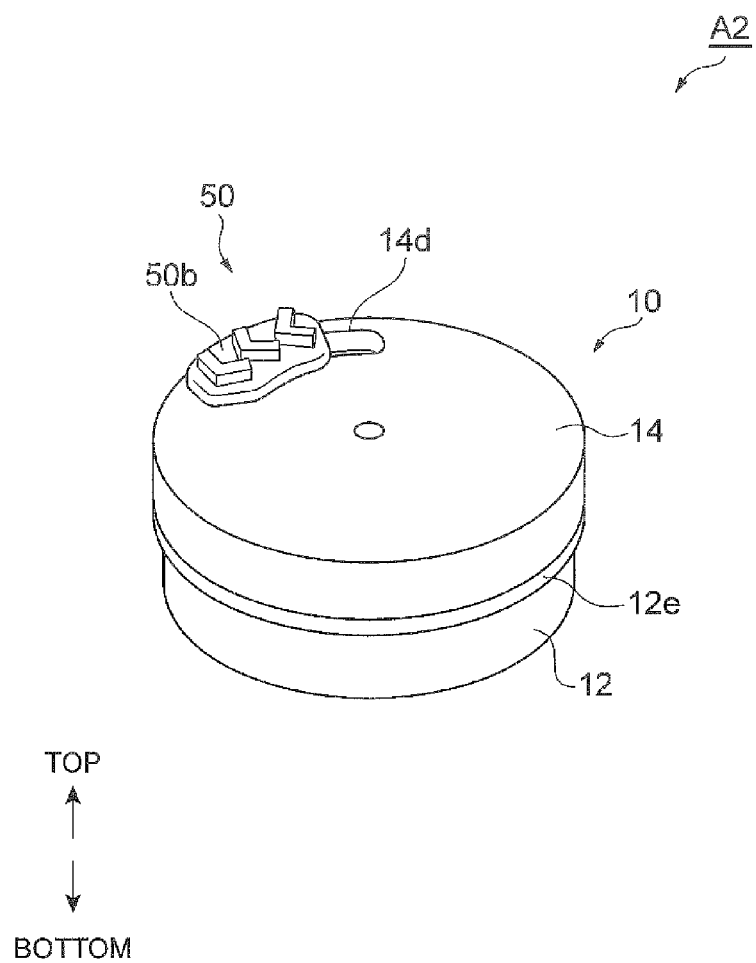
FIG. 12 is a perspective view of an applicator according to a second embodiment.
Figure 13:
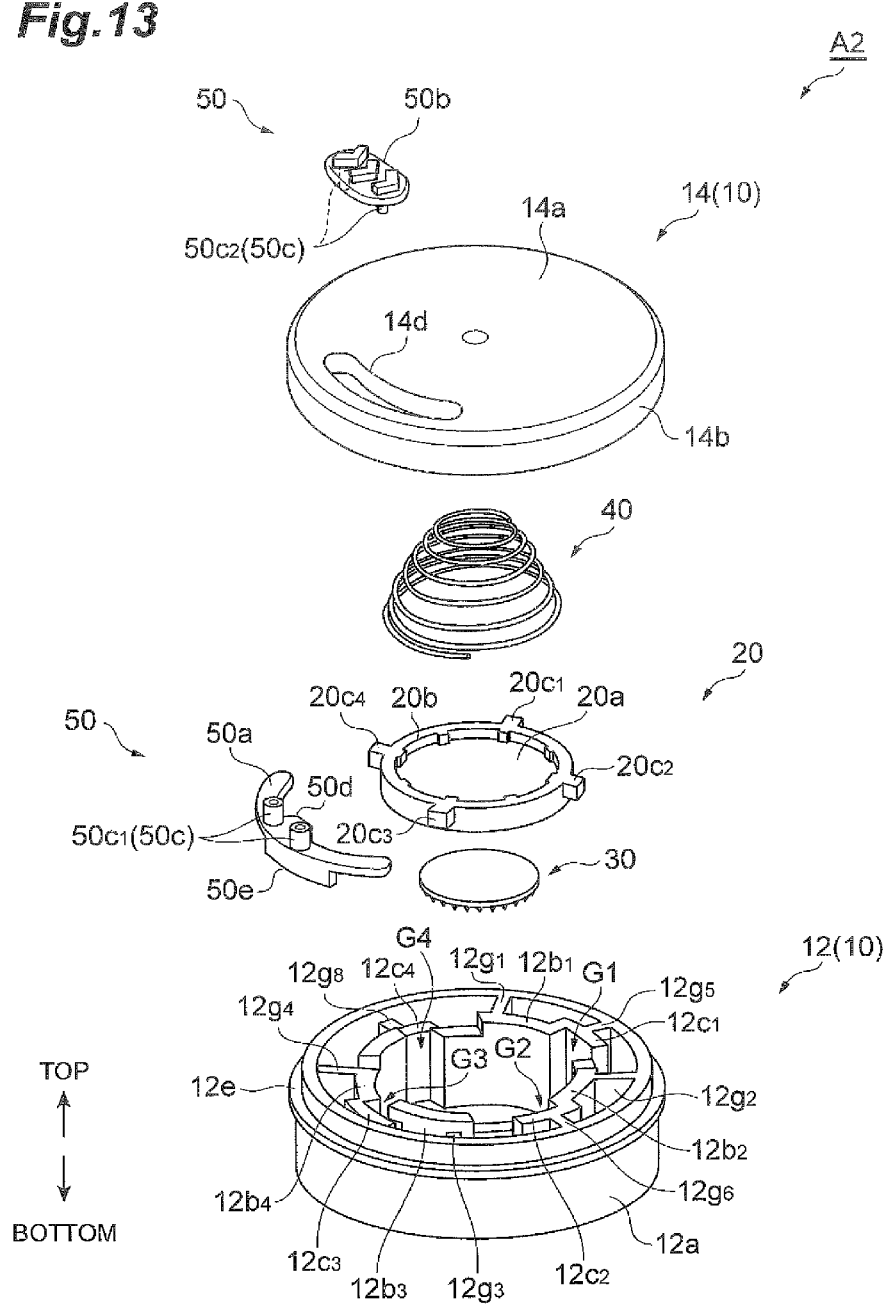
FIG. 13 is an exploded perspective view of the applicator according to the second embodiment.

As illustrated in FIG. 12 and FIG. 13, the through-hole 14d has a circular arc-like shape that extends along the periphery of the top plate 14a, and communicates the inside and the outside of the casing 10 with each other. The amount of movement and the movement position of the release member 50 are determined by the through-hole 14d. Thus, at the time of attaching the cover part 14 to the main body part 12, the cover part 14 is positioned with respect to the main body part 12 such that the release member 50 can move through a desired position. Note that the through-hole 14d does not necessarily need to have the circular arc-like shape, and may have other shapes such as a linear shape, as long as the locking of the piston plate 20 with the casing 10 (main body part 12) can be released by the movement of the release member 50.

As illustrated in FIG. 12 and FIG. 13, the release member 50 includes the interior part 50a, the exterior part 50b, and the coupling part 50c. The configuration of the interior part 50a is the same as that of the applicator A1 according to the first embodiment, and hence description thereof is omitted. The exterior part 50b is a flat plate having a circular arc-like shape, and is located on the upper surface of the cover part 14. A plurality of elongated protrusions each having a V shape are provided on the upper surface of the exterior part 50b. The elongated protrusions are arranged side by side along the circumferential direction of the exterior part 50b. The elongated protrusions enable a user to visually easily understand the sliding direction of the release member 50, and fulfill an antislip function when the user moves the release member 50 with user's fingers. The width of the exterior part 50b can be set to be larger than the width of the through-hole 14d in order to prevent the exterior part 50b from passing through the through-hole 14d.

The coupling part 50c includes: a pair of cylindrical bodies $50c_1$ that are erected on the upper surface of the interior part 50a; and a pair of round bars $50c_2$ that are erected on the lower surface of the exterior part 50b. The round bars $50c_2$ are respectively inserted into the corresponding cylindrical bodies $50c_1$ to be integrated therewith, whereby the coupling part 50c is configured. That is, the release member 50 of the applicator A2 according to the second embodiment is formed of the combination of: a first member including the interior part 50a provided with the cylindrical bodies $50c_1$ and the elongated protrusion 50e; and a second member including the exterior part 50b provided with the round bars $50c_2$ and the plurality of elongated protrusions. In order not to hinder the movement of the release member 50, the length of the coupling part 50c can be set to be larger than the length of the through-hole 14d (the thickness of the top plate 14a).

At the time of manufacturing the applicator A2, first, components other than the cover part 14 and the exterior part 50b of the release member 50 are assembled through procedures similar to the first to fourth steps in the method of manufacturing the applicator A1 according to the first embodiment.

Subsequently, in order to enable the protrusion part 50d of the release member 50 to move toward the groove part G3, the cover part 14 is positioned with respect to the main body part 12 such that the release member 50 is located on one end side of the through-hole 14d. In this state, the cylindrical bodies $50c_1$ are inserted into the through-hole 14d, and the cover part 14 is attached to the main body part 12. On this occasion, because the projections $20c_1$, $20c_2$, $20c_3$ and $20c_4$ are placed on the second portions $12b_{12}$ to $12b_{42}$ of the interior inner walls $12b_1$, $12b_2$, $12b_3$ and $12b_4$, even if the conical coil spring 40 is compressed by attaching the cover part 14 to the main body part 12, the piston plate 20 is not pushed out in the bottom direction by the conical coil spring 40. That is, the piston plate 20 is locked with the casing 10 (main body part 12). Accordingly, as illustrated in (b) of FIG. 14, the piston plate 20 is held at its retraction position on the cover part 14 side inside of the main body part 12, in the state where the cover part 14 and the piston plate 20 compress the conical coil spring 40. Next, the round bars $50c_2$ are respectively inserted into the corresponding cylindrical bodies $50c_1$ to be integrated therewith, whereby the coupling part 50c is configured.

Through the above-mentioned procedures, the applicator A2 is manufactured. Accordingly, the conical coil spring 40 remains in a compressed state until the applicator A2 is used by a user after manufacture and shipping thereof.

The method of using the applicator A2 is similar to the method of using the applicator A1 according to the first embodiment. That is, the release member 50 is slid to the other end side of the through-hole 14d, whereby the locking of the piston plate 20 with the casing 10 (main body part 12) is released. After that, similarly to the applicator A1 according to the first embodiment, the microneedle array 30 collides against the skin due to the biasing force (elastic force) of the conical coil spring 40 (see FIG. 15).

The second embodiment as described above produces actions and effects similar to the actions (A) to (D) of the applicator A1 according to the first embodiment.

[3] Third Embodiment

Figure 16:
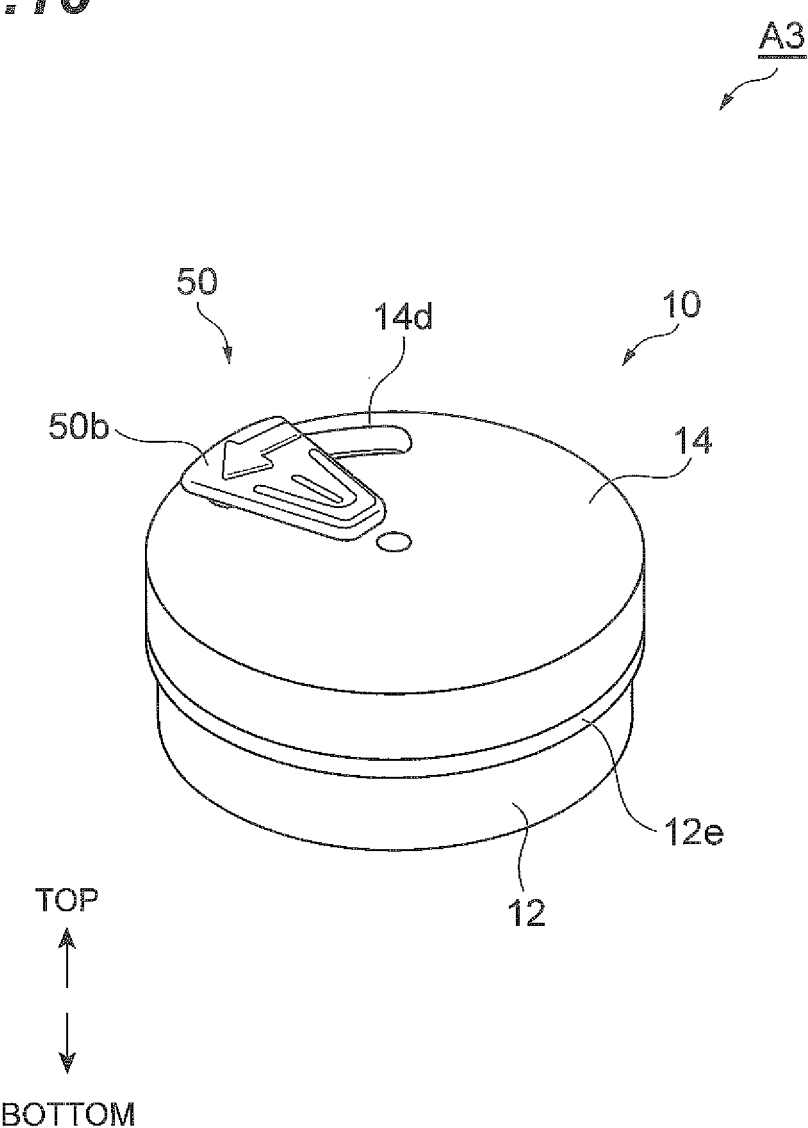
FIG. 16 is a perspective view of an applicator according to a third embodiment.

Now, an applicator A3 according to a third embodiment is described with reference to FIG. 16. The applicator A3 according to the third embodiment is different from the applicator A2 according to the second embodiment in the shape of the exterior part 50b of the release member 50. Specifically, the exterior part 50b is a flat plate having a trapezoidal shape. On the longer side of the upper surface of the exterior part 50b, an arrow-like body that extends along the longer side is provided so as to stand out. On the shorter side of the upper surface of the exterior part 50b, a first elongated protrusion and a second elongated protrusion are provided. The first elongated protrusion extends along the shorter side and the oblique sides of the exterior part 50b and has a C shape, and the second elongated protrusion extends from the shorter side to the longer side of the exterior part 50b inside of the first elongated protrusion. The elongated protrusions enable a user to visually easily understand the sliding direction of the release member 50, and fulfill an antislip function when the user moves the release member 50 with user's fingers. In the completed state of the applicator A3, the longer side of the exterior part 50b faces the periphery of the cover part 14, and the shorter side of the exterior part 50b faces the center of the cover part 14.

The applicator A3 according to the third embodiment as described above produces actions and effects similar to those of the applicator A2 according to the second embodiment.

[4] Fourth Embodiment

Figure 17:
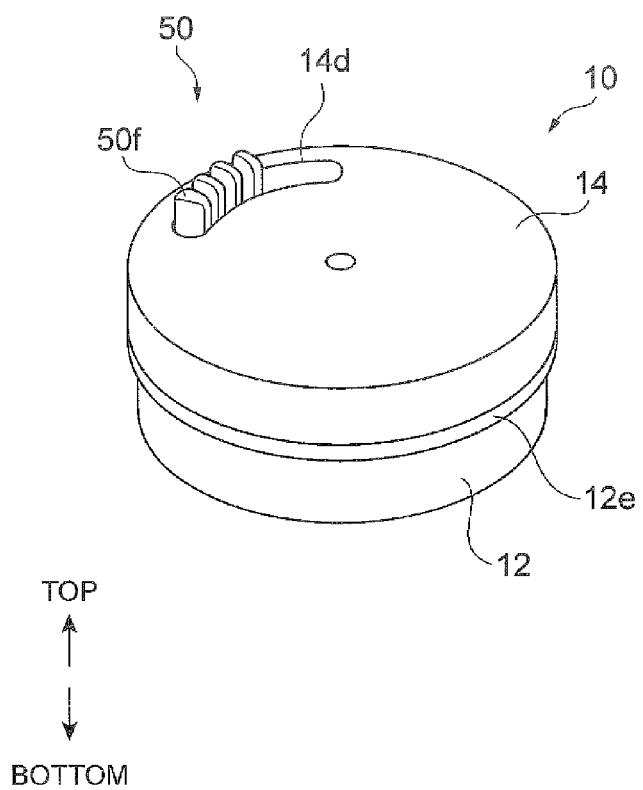
FIG. 17 is a perspective view of an applicator according to a fourth embodiment.
Figure 18:
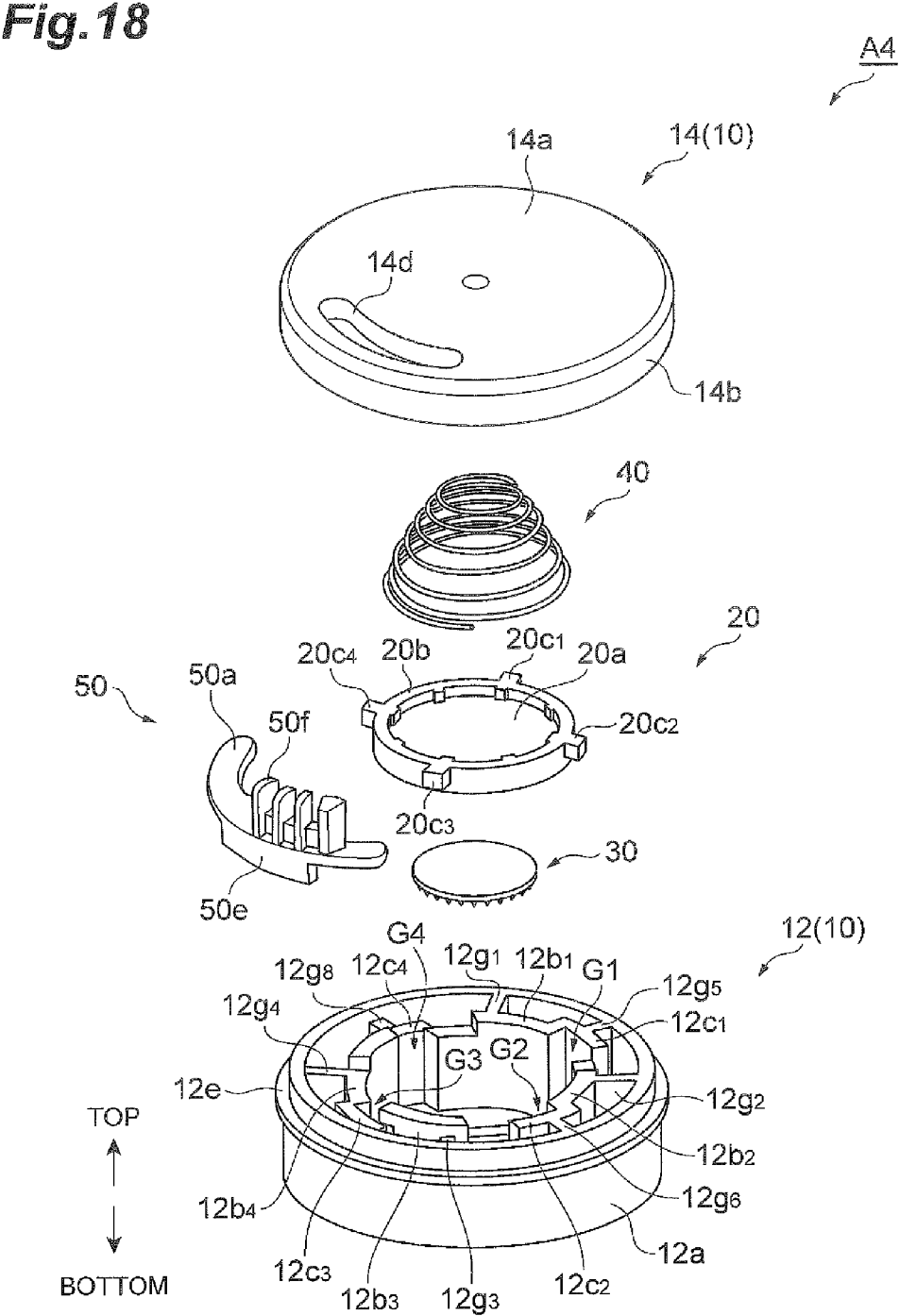
FIG. 18 is an exploded perspective view of the applicator according to the fourth embodiment.

Now, an applicator A4 according to a fourth embodiment is described with reference to FIG. 17 and FIG. 18. The applicator A4 according to the fourth embodiment is different from the applicator A2 according to the second embodiment in the shape of the release member 50. Specifically, instead of the exterior part 50b and the coupling part 50c, a plurality of plate-like bodies 50f each having a rectangular shape are provided in a protruding manner on the upper surface of the interior part 50a. The plate-like bodies 50f are spaced apart from each other with predetermined intervals, and are arranged side by side along the circumferential direction of the interior part 50a. The length of each plate-like body 50f is set such that the upper end thereof is located above the upper surface of the cover part 14 in the completed state of the applicator A4. That is, in the completed state of the applicator A4, the plate-like bodies 50f are inserted through the through-hole 14d, and the upper end parts thereof are exposed on the outer surface of the cover part 14. Thus, the upper end parts of the plate-like bodies 50f fulfill an antislip function when a user moves the release member 50 with user's fingers.

The applicator A4 according to the fourth embodiment is assembled through procedures similar to the first to fifth steps in the method of manufacturing the applicator A1 according to the first embodiment (see FIG. 19). Accordingly, the conical coil spring 40 remains in a compressed state until the applicator A4 is used by a user after manufacture and shipping thereof.

The method of using the applicator A4 is similar to the method of using the applicator A1 according to the first embodiment. That is, the release member 50 is slid to the other end side of the through-hole 14d, whereby the locking of the piston plate 20 with the casing 10 (main body part 12) is released. After that, similarly to the applicator A1 according to the first embodiment, the microneedle array 30 collides against the skin due to the biasing force (elastic force) of the conical coil spring 40 (see FIG. 20).

The applicator A4 according to the fourth embodiment as described above produces actions and effects similar to those of the applicator A2 according to the second embodiment.

[5] Fifth Embodiment

Figure 21:
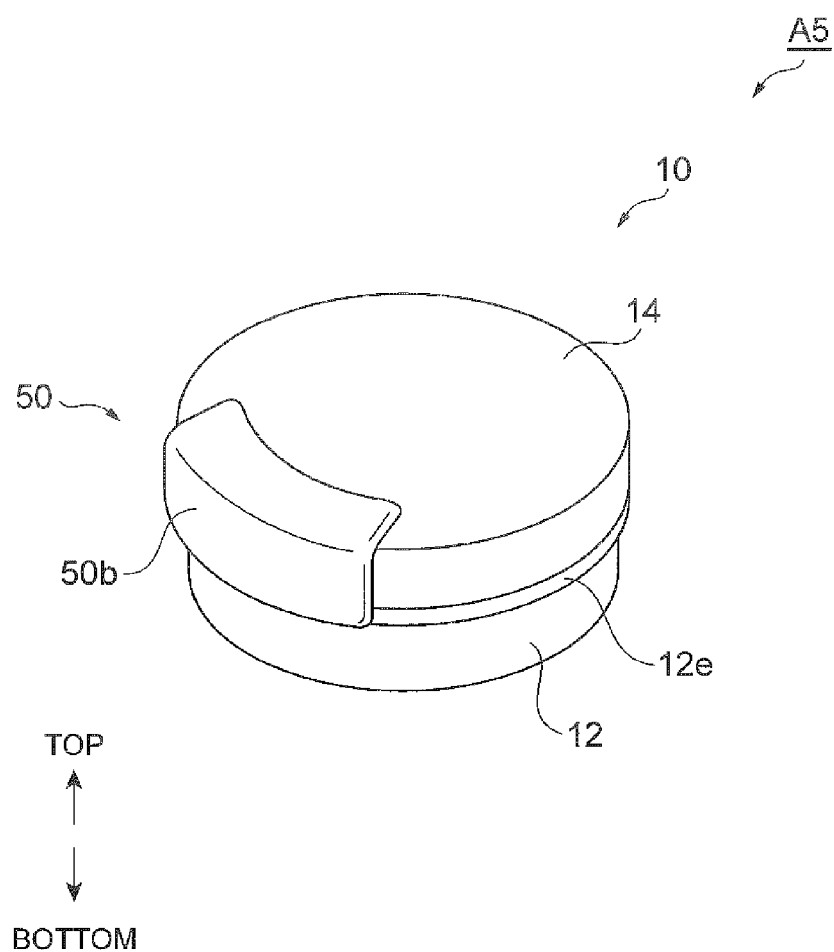
FIG. 21 is a perspective view of an applicator according to a fifth embodiment.
Figure 22:
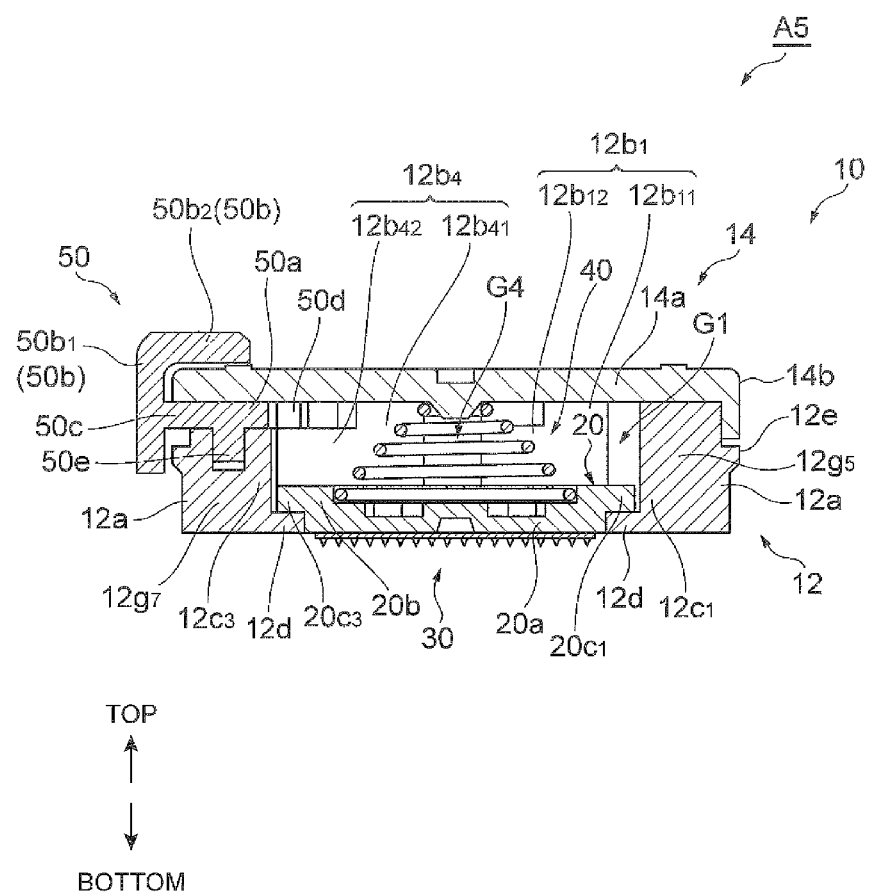
FIG. 22 is a cross sectional view of the applicator according to the fifth embodiment.
Figure 23:
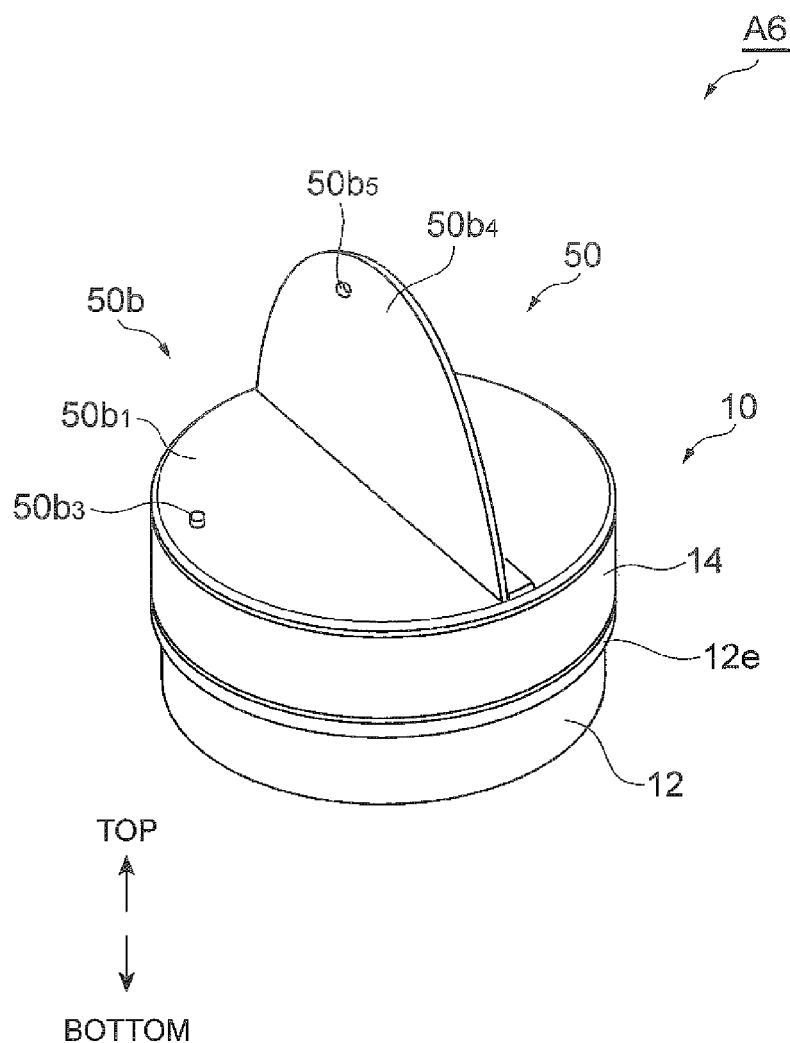
FIG. 23 is a perspective view of an applicator according to a sixth embodiment.
Figure 24:
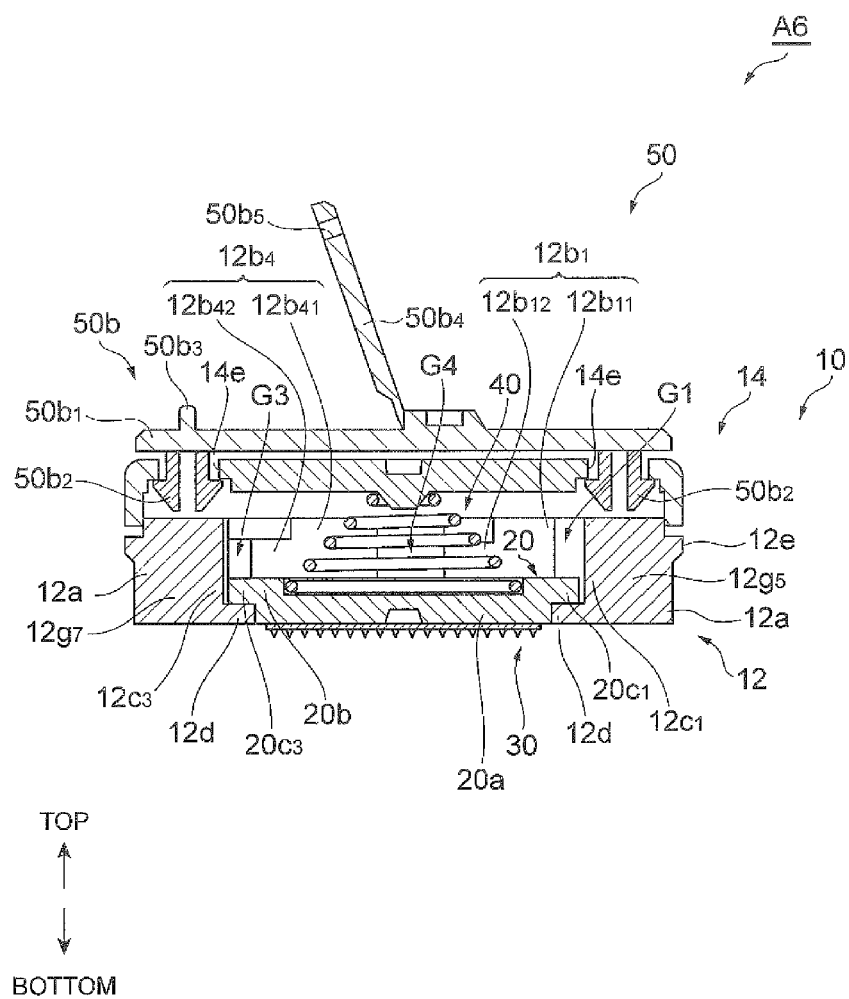
FIG. 24 is a cross sectional view illustrating a state after an operation of the applicator according to the sixth embodiment.
Figure 25:
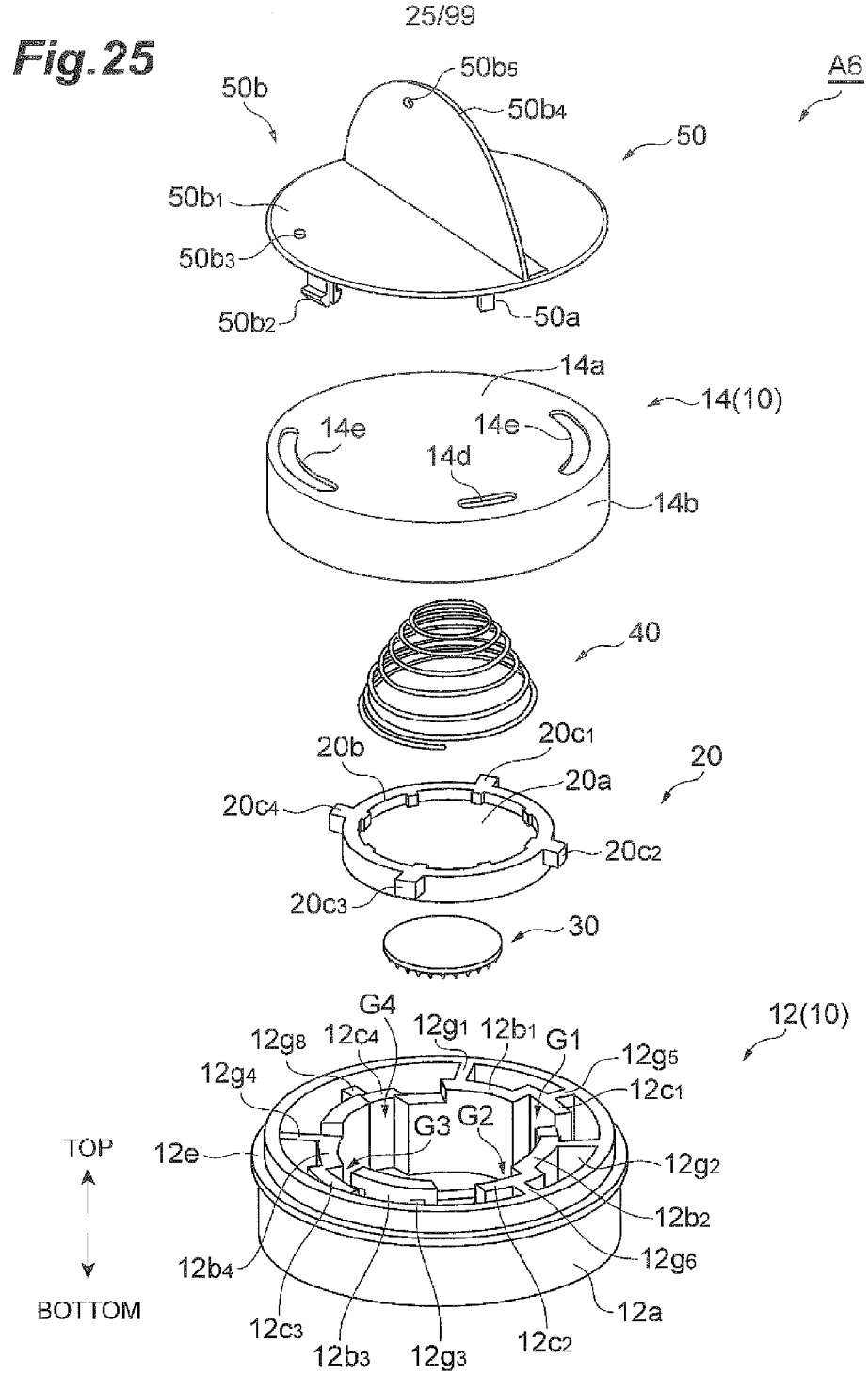
FIG. 25 is an exploded perspective view of the applicator according to the sixth embodiment.

Now, an applicator A5 according to a fifth embodiment is described with reference to FIG. 21 and FIG. 22. The applicator A5 according to the fifth embodiment is different from the applicator A1 according to the first embodiment in the shape of the exterior part 50b of the release member 50. Specifically, the exterior part 50b includes a first member $50b_1$ and a second member $50b_2$. The first member $50b_1$ is a curved plate that extends in the circumferential direction along the outer circumferential surface of the main body part 12, and has a circular arc-like shape in cross section. The second member $50b_2$ is a flat plate having a circular arc-like shape. The second member $50b_2$ horizontally extends from the upper end of the first member $50b_1$ toward the center of the casing 10 (main body part 12). That is, the exterior part 50b extends from the outer circumferential surface of the main body part 12 to the upper surface of the cover part 14. Thus, a cross section of the exterior part 50b has an L shape. In order to obtain an antislip function when a user moves the release member 50 with user's fingers, the surface of the exterior part 50b may have irregularities, and may be roughened.

The applicator A5 according to the fifth embodiment as described above produces actions and effects similar to those of the applicator A2 according to the second embodiment.

[6] Sixth Embodiment

Now, an applicator A6 according to a sixth embodiment is described with reference to FIG. 23 to FIG. 26. The applicator A6 according to the sixth embodiment is different from the applicator A1 according to the first embodiment mainly in that the main body part 12 is not provided with the cutout part 12f as well as in the configurations of the cover part 14 and the release member 50. In the following, differences between the applicator A6 according to the sixth embodiment and the applicator A1 according to the first embodiment are mainly described, and redundant description is omitted.

The cover part 14 is provided with one through-hole 14d and a pair of through-holes 14e. The through-holes 14d and 14e each have a circular arc-like shape that extends along the periphery of the top plate 14a, and communicate the inside and the outside of the casing 10 with each other. The pair of through-holes 14e are located so as to be point-symmetrical with respect to the center of the top plate 14a, and the through-hole 14d is located between the pair of through-holes 14e in the circumferential direction. The amount of movement and the movement position of the release member 50 are determined by the through-holes 14d and 14e. Thus, at the time of attaching the cover part 14 to the main body part 12, the cover part 14 is positioned with respect to the main body part 12 such that the release member 50 can move through a desired position.

The release member 50 includes the interior part 50a and the exterior part 50b. The interior part 50a has a quadrangular prism shape, and is inserted through the through-hole 14d. The interior part 50a is provided in a protruding manner on the lower surface of a base part $50b_1$ of the exterior part 50b to be described later, and is located between a pair of hooks $50b_2$ to be described later in the circumferential direction. The lower end of the interior part 50a is located below the lower surface of the top plate 14a. That is, the lower end part of the interior part 50a is located inside of the casing 10 (main body part 12).

The exterior part 50b includes: the base part $50b_1$ having a disc-like shape; the pair of hooks $50b_2$; a projection $50b_3$ that is provided on the base part $50b_1$ and has a columnar shape; a knob part $50b_4$; and a through-hole $50b_5$ provided in the knob part $50b_4$. The base part $50b_1$ is arranged on the upper surface (outer surface) of the cover part 14.

The pair of hooks $50b_2$ are provided in a protruding manner on the lower surface of the base part $50b_1$ so as to be point-symmetrical with respect to the central axis of the base part $50b_1$. Each hook $50b_2$ is formed of a pair of rods that are spaced apart from each other with a predetermined interval and are opposed to each other. The leading end (lower end) of each of the pair of rods includes a protrusion part that protrudes toward the opposite side to the paired rod. The protrusion part is tapered toward the leading end (lower end), and has a conical shape. The distance between the pair of rods that is defined by the leading ends of the protrusion parts is set to be smaller than the opening width of the through-hole 14e of the cover part 14. The distance between the pair of rods that is defined by the base ends of the protrusion parts is set to be larger than the opening width of the through-hole 14e of the cover part 14.

The pair of hooks $50b_2$ are respectively inserted through the pair of through-holes 14e of the cover part 14, whereby the exterior part 50b (base part $50b_1$) is attached to the cover part 14. At the time of attaching the exterior part 50b (base part $50b_1$) to the cover part 14, the leading ends of the pair of rods of each hook $50b_2$ abut against the corresponding through-hole 14e to approach each other. When the leading ends of the rods bend sufficiently enough to allow the protrusion parts of the rods to pass through the through-hole 14e, the protrusion parts of the rods move into the casing 10, and the bent rods return to their original shapes. As a result, the protrusion parts of the rods are engaged with the cover part 14, and the pair of hooks $50b_2$ become movable along the pair of through-holes 14e. The pair of through-holes 14e each have a circular arc-like shape that extends along the periphery of the top plate 14a, and hence the exterior part 50b (base part $50b_1$) becomes turnable about the center of the casing 10 (main body part 12).

At the time of attaching the exterior part 50b (base part $50b_1$) to the cover part 14, the interior part 50a is inserted through the through-hole 14d. When the exterior part 50b (base part $50b_1$) is turned about the center of the casing 10 (main body part 12), the interior part 50a is also turned to move inside of the through-hole 14d.

The projection $50b_3$ is arranged on the upper surface of the base part $50b_1$ and in the vicinity of the periphery thereof. The knob part $50b_4$ is a plate-like body having a semicircular shape. The knob part $50b_4$ is arranged on the base part $50b_1$. The knob part $50b_4$ has a base end having a linear shape, and the base end is pivotably attached to the base part $50b_1$. More specifically, the knob part $50b_4$ is pivotable about the direction that intersects with the axial direction of the casing 10 (main body part 12). Accordingly, the knob part $50b_4$ takes a lay-down state and a stand-up state. In the lay-down state, the knob part $50b_4$ overlaps with the base part $50b_1$, and covers a half of the upper surface of the base part $50b_1$. In the stand-up state, the knob part $50b_4$ is substantially erected with respect to the base part $50b_1$.

The through-hole $50b_5$ is arranged in the vicinity of the periphery of the knob part $50b_4$. The through-hole $50b_5$ is engaged with the projection $50b_3$ on the base part $50b_1$ when the knob part $50b_4$ is in the lay-down state. When the through-hole $50b_5$ is engaged with the projection $50b_3$, a user of the applicator A6 cannot pinch the knob part $50b_4$, and hence an unintentional operation of the applicator A6 can be prevented. Meanwhile, if the engagement of the through-hole $50b_5$ with the projection $50b_3$ is released, the knob part $50b_4$ can be pivoted to be brought into the stand-up state.

Figure 26:
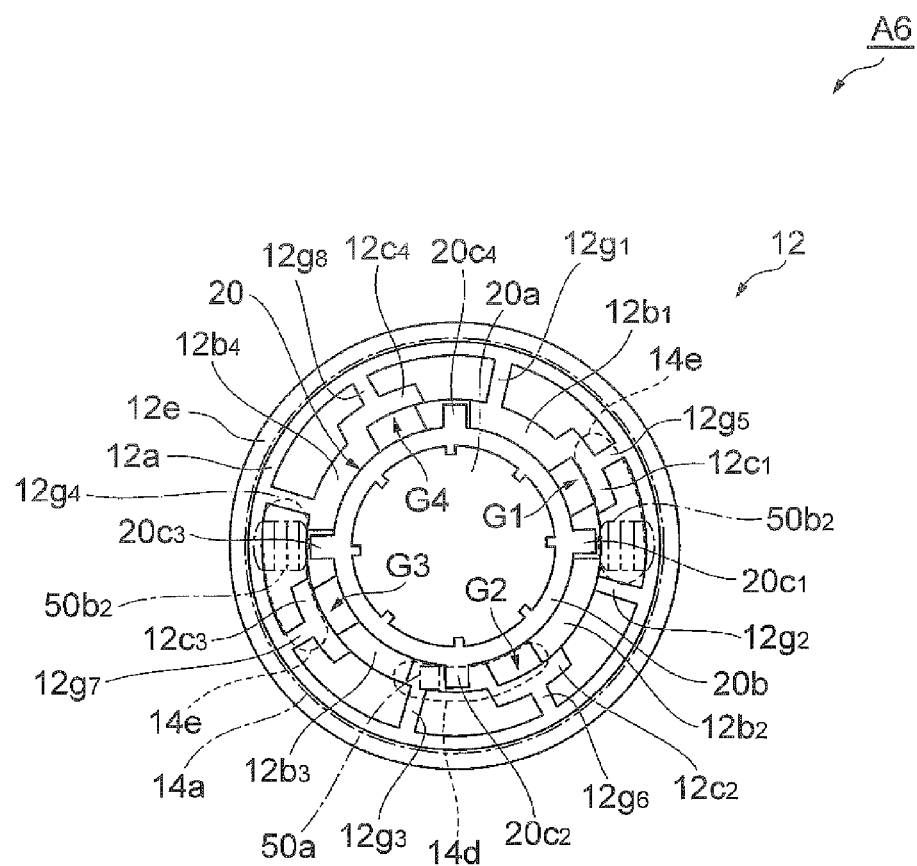
FIG. 26 is a top view illustrating a state before the operation of the applicator according to the sixth embodiment, from which a cover part is detached.

At the time of manufacturing the applicator A6 according to the sixth embodiment, first, the piston plate 20 is placed in the main body part 12 through procedures similar to the first and third steps in the method of manufacturing the applicator A1 according to the first embodiment (see FIG. 26). At this time, the projection $20c_2$ of the piston plate 20 and the first portion $12b_{31}$ of the interior inner wall $12b_3$ are spaced apart from each other.

Subsequently, the conical coil spring 40 is placed on the upper surface of the piston plate 20 through a procedure similar to the fourth step in the method of manufacturing the applicator A1 according to the first embodiment.

Subsequently, the cover part 14 is attached to the main body part 12 through a procedure similar to the fifth step in the method of manufacturing the applicator A1 according to the first embodiment. At this time, in order to enable the interior part 50a of the release member 50 to move toward the groove part G2, the cover part 14 is positioned with respect to the main body part 12 such that the through-hole 14d is located above the first portion $12b_{31}$ of the interior inner wall $12b_3$ and the groove part G2.

Subsequently, the interior part 50a is inserted through the through-hole 14d, and the pair of hooks $50b_2$ are respectively inserted through the pair of through-holes 14e of the cover part 14, whereby the release member 50 is attached to the cover part 14. At this time, the leading end part (lower end part) of the interior part 50a is located in a gap between the projection $20c_2$ of the piston plate 20 and the first portion $12b_{31}$ of the interior inner wall $12b_3$ (see FIG. 26).

Through the above-mentioned procedures, the applicator A6 is manufactured. Accordingly, the conical coil spring 40 remains in a compressed state until the applicator A6 is used by a user after manufacture and shipping thereof.

At the time of using the applicator A6, the applicator A6 is positioned with respect to a portion of a skin to which a medical agent or the like is desired to be applied, such that the microneedles 32 face the skin. Then, in the release member 50, the engagement of the through-hole $50b_5$ with the projection $50b_3$ is released, and the knob part $50b_4$ is pivoted to be brought into the stand-up state, while the applicator A6 is kept positioned. Next, the knob part $50b_4$ in the stand-up state is turned, whereby the release member 50 is turned about the axis of the casing 10 (main body part 12). As a result, the interior part 50a of the release member 50 moves from one end to the other end of the through-hole 14d, and pushes the projection $20c_2$ of the piston plate 20 toward the groove part G2. Consequently, the piston plate 20 turns. That is, the turning force of the release member 50 (base part $50b_1$) is transmitted to the piston plate 20 with the intermediation of the interior part 50a. After that, similarly to the applicator A1 according to the first embodiment, the locking of the piston plate 20 with the casing 10 (main body part 12) is released, the piston plate 20 is moved, by the biasing force (elastic force) of the conical coil spring 40, outward (toward the skin) along the groove parts G1, G2, G3 and G4 (the central axis of the main body part 12) inside of the main body part 12, and the microneedle array 30 collides against the skin.

According to the sixth embodiment as described above, a user can make a puncture in a skin using the applicator A6 by simply pivoting the knob part $50b_4$ of the release member 50 into the stand-up state and then turning the knob part $50b_4$. Accordingly, whoever may use the applicator A6, the biasing force of the conical coil spring 40 is transmitted to the microneedles 32 with the intermediation of the piston plate 20, and the microneedles 32 are stuck into the skin with a given impact force. Hence, the puncture in the skin can be reliably made (the reproducibility of the puncture is enhanced). When the microneedles 32 are stuck into the skin, active ingredients of the coating C that adhere to the microneedles 32 are delivered into the body, and the active ingredients are transferred into the body through the skin.

In the applicator A6 according to the sixth embodiment, the locked state where the piston plate 20 is locked with the casing 10 is released by the release member 50. Consequently, the biasing force of the conical coil spring 40 acts on the piston plate 20, and the piston plate 20 moves along the groove parts G1, G2, G3 and G4 inside of the main body part 12 to reach a position for action on the skin. Thus, a member such as a shaft that extends in the axial direction of the main body part 12 (the height direction of the applicator A6) does not need to be attached to the piston plate 20. Further, in the applicator A6 according to the sixth embodiment, the conical coil spring 40 is used to exert a biasing force on the piston plate 20. When being compressed, the height of the conical coil spring 40 becomes extremely smaller compared with general cylindrical coil springs. In this way, the height of the applicator A6 itself can be made smaller, thus achieving a reduction in weight of the applicator A6.

In the applicator A6 according to the sixth embodiment, the knob part $50b_4$ is attached to the base part $50b_1$ so as to be pivotable about the direction that intersects with the axial direction of the casing 10 (main body part 12). Thus, in this case, when the puncture in the skin is to be made using the applicator A6, it is sufficient to pivot the knob part $50b_4$ and cause the knob part $50b_4$ to stand up with respect to the base part $50b_1$ (stand-up state). On the other hand, when the applicator A6 is held on the skin, it is sufficient to lay down the knob part $50b_4$ on the base part $50b_1$ (lay-down state). Thus, the locked state can be easily released by the release member 50 by means of the knob part $50b_4$. Further, in the case where the applicator A6 is held on the skin, the height of the applicator A6 can be made smaller by bringing the knob part $50b_4$ into the lay-down state.

The applicator A6 according to the sixth embodiment produces actions and effects similar to the actions (C) and (D) of the applicator A1 according to the first embodiment.

[7] Seventh Embodiment

[7.1] Configuration of Applicator

Figure 27:
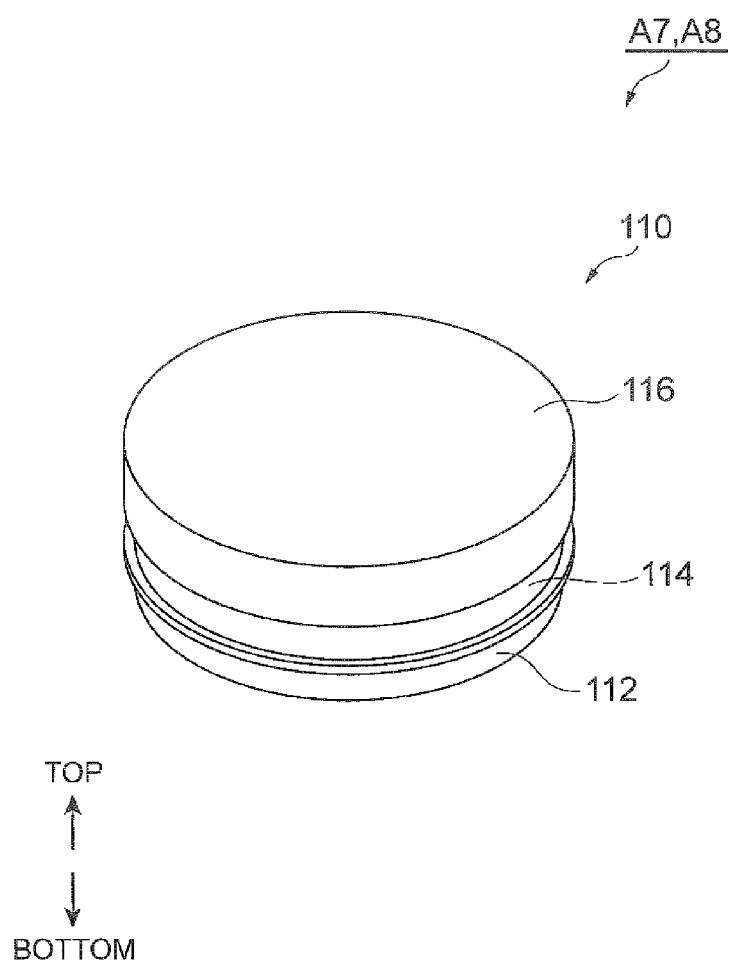
FIG. 27 is a perspective view of an applicator according to each of a seventh embodiment and an eighth embodiment.

Now, a configuration of an applicator A7 according to a seventh embodiment is described with reference to FIG. 27 to FIG. 29. In the following description, the term "top" corresponds to the top direction of FIG. 27 to FIG. 29, and the term "bottom" corresponds to the bottom direction of FIG. 27 to FIG. 29. That is, the top-bottom direction corresponds to the height direction of the applicator A7.

The applicator A7 is a device for transferring active ingredients of a medical agent or the like into the body of an animal such as a human through a skin of the animal. The applicator A7 includes a casing 110, a piston plate 120, the microneedle array 30, and the conical coil spring 40.

The casing 110 includes an interior main body part 112, an exterior main body part 114, and a cover part 116. The strength and the material of the casing 110 may be the same as those of the casing 10 of the applicator A1 according to the first embodiment.

Figure 28:
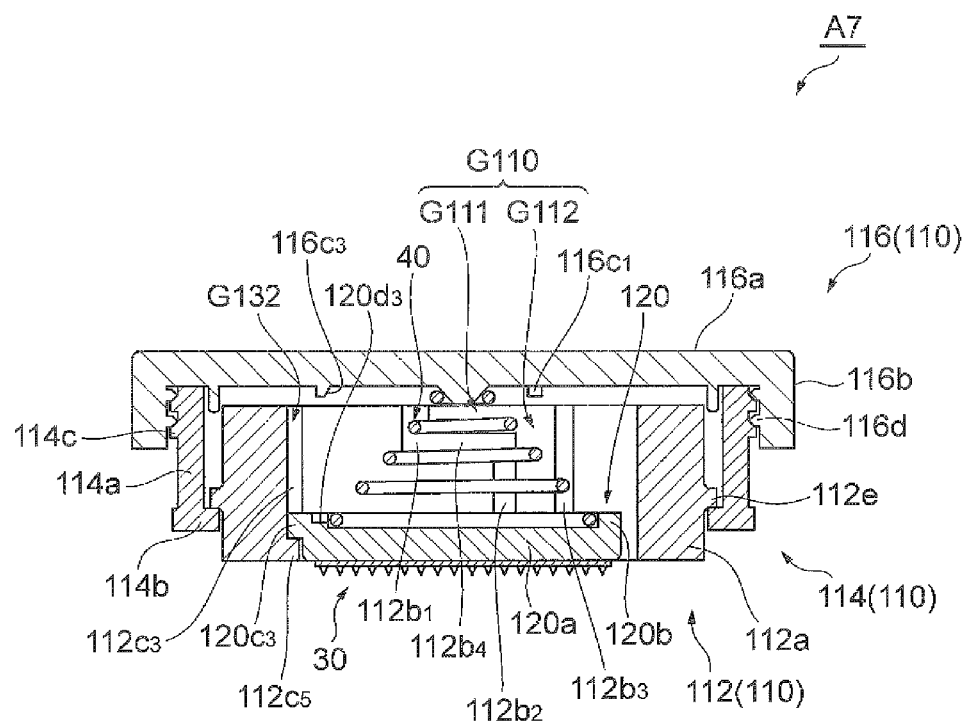
FIG. 28 is a cross sectional view illustrating a state after an operation of the applicator according to the seventh embodiment.
Figure 29:
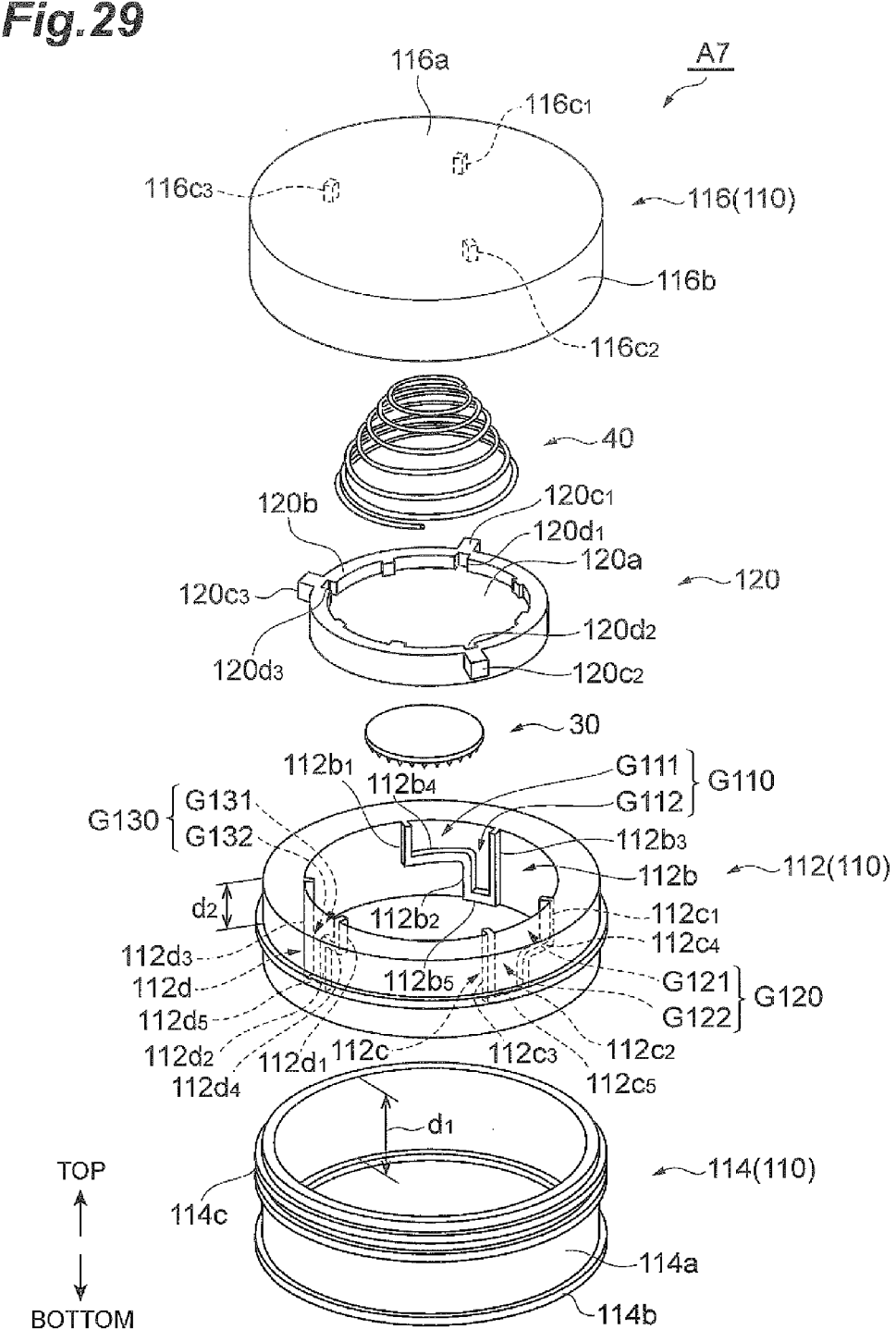
FIG. 29 is an exploded perspective view of the applicator according to the seventh embodiment.

As illustrated in FIG. 28 and FIG. 29, the interior main body part 112 has a cylindrical shape having a central axis that extends along the top-bottom direction. The interior main body part 112 includes: a cylindrical body 112a; guide parts 112b, 112c and 112d that are provided on the inner circumferential surface of the cylindrical body 112a; and a flange member 112e that is provided on the outer circumferential surface of the cylindrical body 112a and has a circular ring-like shape. The inner diameter of the cylindrical body 112a can be set to be equivalent to or slightly larger than the outer diameter of the piston plate 120 including projections $120c_1$, $120c_2$ and $120c_3$ to be described later, in order to enable the piston plate 120 to move in the top-bottom direction inside of the cylindrical body 112a.

The guide parts 112b, 112c and 112d are arranged in the stated order in the clockwise direction when viewed from the upper end side (cover part 116 side) of the interior main body part 112, with given intervals in the circumferential direction. That is, the guide part 112b and the guide part 112c are spaced apart from each other with a predetermined interval in the circumferential direction, the guide part 112c and the guide part 112d are spaced apart from each other with a predetermined interval in the circumferential direction, and the guide part 112d and the guide part 112b are spaced apart from each other with a predetermined interval in the circumferential direction. In order to enable the piston plate 120 to move in the top-bottom direction inside of the cylindrical body 112a, the protruding heights of the guide parts 112b, 112c and 112d can be set such that the diameter of a virtual circle that is circumscribed on the guide parts 112b, 112c and 112d when viewed from the top-bottom direction is equivalent to or slightly larger than the outer diameter of a main body 120a (to be described later) of the piston plate 120. Note that, in order to prevent the projections $120c_1$, $120c_2$ and $120c_3$ (to be described later) of the piston plate 120 from moving beyond the guide parts 112b, 112c and 112d, the protruding heights of the guide parts 112b, 112c and 112d can be set such that the diameter of the virtual circle that is circumscribed on the guide parts 112b, 112c and 112d when viewed from the top-bottom direction is smaller than the outer diameter of the piston plate 120 including the projections $120c_1$, $120c_2$ and $120c_3$ to be described later.

The guide part 112b includes: elongated protrusions $112b_1$, $112b_2$ and $112b_3$ that each linearly extend in the top-bottom direction; and elongated protrusions $112b_4$ and $112b_5$ that each linearly extend in the circumferential direction. The elongated protrusions $112b_1$, $112b_2$ and $112b_3$ are arranged in the stated order in the clockwise direction when viewed from the upper end side (cover part 116 side) of the interior main body part 112.

The upper end of the elongated protrusion $112b_1$ is substantially coincident with the upper end of the cylindrical body 112a. The lower end of the elongated protrusion $112b_1$ is located in the middle of the cylindrical body 112a in the top-bottom direction. The upper end of the elongated protrusion $112b_2$ is located in the middle of the cylindrical body 112a in the top-bottom direction and at a height equivalent to that of the lower end of the elongated protrusion $112b_1$. The lower end of the elongated protrusion $112b_2$ is substantially coincident with the lower end of the cylindrical body 112a. The upper end of the elongated protrusion $112b_3$ is substantially coincident with the upper end of the cylindrical body 112a. The lower end of the elongated protrusion $112b_3$ is substantially coincident with the lower end of the cylindrical body 112a.

The elongated protrusions $112b_4$ and $112b_5$ are arranged in the stated order in the clockwise direction when viewed from the upper end side (cover part 116 side) of the interior main body part 112. One end of the elongated protrusion $112b_4$ is integrally connected to the lower end of the elongated protrusion $112b_1$. The other end of the elongated protrusion $112b_4$ is integrally connected to the upper end of the elongated protrusion $112b_2$. One end of the elongated protrusion $112b_5$ is integrally connected to the lower end of the elongated protrusion $112b_2$. The other end of the elongated protrusion $112b_5$ is integrally connected to the lower end of the elongated protrusion $112b_3$.

By means of the elongated protrusions $112b_1$, $112b_2$, $112b_3$, $112b_4$ and $112b_5$ thus arranged, the guide part 112b forms a groove body G110 including: a linear groove part G111 that extends in the circumferential direction; and a linear groove part G112 that extends in the top-bottom direction, the groove parts G111 and G112 being orthogonal to each other. The groove body G110 has an L shape when viewed from the outer circumferential surface side of the interior main body part 112.

The guide part 112c includes: elongated protrusions $112c_1$, $112c_2$ and $112c_3$ that each linearly extend in the top-bottom direction; and elongated protrusions $112c_4$ and $112c_5$ that each linearly extend in the circumferential direction. The elongated protrusions $112c_1$, $112c_2$ and $112c_3$ are arranged in the stated order in the clockwise direction when viewed from the upper end side (cover part 116 side) of the interior main body part 112.

The upper end of the elongated protrusion $112c_1$ is substantially coincident with the upper end of the cylindrical body 112a. The lower end of the elongated protrusion $112c_1$ is located in the middle of the cylindrical body 112a in the top-bottom direction. The upper end of the elongated protrusion $112c_2$ is located in the middle of the cylindrical body 112a in the top-bottom direction and at a height equivalent to that of the lower end of the elongated protrusion $112c_1$. The lower end of the elongated protrusion $112c_2$ is substantially coincident with the lower end of the cylindrical body 112a. The upper end of the elongated protrusion $112c_3$ is substantially coincident with the upper end of the cylindrical body 112a. The lower end of the elongated protrusion $112c_3$ is substantially coincident with the lower end of the cylindrical body 112a.

The elongated protrusions $112c_4$ and $112c_5$ are arranged in the stated order in the clockwise direction when viewed from the upper end side (cover part 116 side) of the interior main body part 112. One end of the elongated protrusion $112c_4$ is integrally connected to the lower end of the elongated protrusion $112c_1$. The other end of the elongated protrusion $112c_4$ is integrally connected to the upper end of the elongated protrusion $112c_2$. One end of the elongated protrusion $112c_5$ is integrally connected to the lower end of the elongated protrusion $112c_2$. The other end of the elongated protrusion $112c_5$ is integrally connected to the lower end of the elongated protrusion $112c_3$.

By means of the elongated protrusions $112c_1$, $112c_2$, $112c_3$, $112c_4$ and $112c_5$ thus arranged, the guide part 112c forms a groove body G120 including: a linear groove part G121 that extends in the circumferential direction; and a linear groove part G122 that extends in the top-bottom direction, the groove parts G121 and G122 being orthogonal to each other. The groove body G120 has an L shape when viewed from the outer circumferential surface side of the interior main body part 112.

The guide part 112d includes: elongated protrusions $112d_1$, $112d_2$ and $112d_3$ that each linearly extend in the top-bottom direction; and elongated protrusions $112d_4$ and $112d_5$ that each linearly extend in the circumferential direction. The elongated protrusions $112d_1$, $112d_2$ and $112d_3$ are arranged in the stated order in the clockwise direction when viewed from the upper end side (cover part 116 side) of the interior main body part 112.

The upper end of the elongated protrusion $112d_1$ is substantially coincident with the upper end of the cylindrical body 112a. The lower end of the elongated protrusion $112d_1$ is located in the middle of the cylindrical body 112a in the top-bottom direction. The upper end of the elongated protrusion $112d_2$ is located in the middle of the cylindrical body 112a in the top-bottom direction and at a height equivalent to that of the lower end of the elongated protrusion $112d_1$. The lower end of the elongated protrusion $112d_2$ is substantially coincident with the lower end of the cylindrical body 112a. The upper end of the elongated protrusion $112d_3$ is substantially coincident with the upper end of the cylindrical body 112a. The lower end of the elongated protrusion $112d_3$ is substantially coincident with the lower end of the cylindrical body 112a.

The elongated protrusions $112d_4$ and $112d_5$ are arranged in the stated order in the clockwise direction when viewed from the upper end side (cover part 116 side) of the interior main body part 112. One end of the elongated protrusion $112d_4$ is integrally connected to the lower end of the elongated protrusion $112d_1$. The other end of the elongated protrusion $112d_4$ is integrally connected to the upper end of the elongated protrusion $112d_2$. One end of the elongated protrusion $112d_5$ is integrally connected to the lower end of the elongated protrusion $112d_2$. The other end of the elongated protrusion $112d_5$ is integrally connected to the lower end of the elongated protrusion $112d_3$.

By means of the elongated protrusions $112d_1$, $112d_2$, $112d_3$, $112d_4$ and $112d_5$ thus arranged, the guide part 112d forms a groove body G130 including: a linear groove part G131 that extends in the circumferential direction; and a linear groove part G132 that extends in the top-bottom direction, the groove parts G131 and G132 being orthogonal to each other. The groove body G130 has an L shape when viewed from the outer circumferential surface side of the interior main body part 112.

The flange member 112e is located in the middle of the cylindrical body 112a in the top-bottom direction.

The exterior main body part 114 has a cylindrical shape having a central axis that extends along the top-bottom direction. The exterior main body part 114 includes: a cylindrical body 114a; a circular ring-like flange member 114b located at the lower end of the cylindrical body 114a; and an elongated protrusion 114c. As illustrated in FIG. 29, a direct distance $d_1$ from the flange member 114b to the upper end of the exterior main body part 114 is set to be longer than a direct distance $d_2$ from the flange member 112e to the upper end of the interior main body part 112.

The inner edge of the flange member 114b protrudes inward from the inner circumferential surface of the cylindrical body 114a. The inner diameter of the flange member 114b is set to be equal to or more than the outer diameter of the cylindrical body 112a and less than the outer diameter of the flange member 112e. Thus, in the completed state of the applicator A7, the interior main body part 112 is movable in the top-bottom direction inside of the exterior main body part 114 through the flange member 114b unless the flange member 112e of the interior main body part 112 abuts against and is locked with the flange member 114b of the exterior main body part 114.

The elongated protrusion 114c is located on the outer circumferential surface of the cylindrical body 114a and on the upper end side thereof. The elongated protrusion 114c runs in a spiral manner on the outer circumferential surface of the cylindrical body 114a, and forms a male thread.

The cover part 116 includes: a top plate 116a having a circular shape; and a cylindrical member 116b that extends downward from the periphery of the top plate 116a. Projections $116c_1$, $116c_2$ and $116c_3$ that each protrude downward are provided on the lower surface of the top plate 116a. The projections $116c_1$, $116c_2$ and $116c_3$ are located on a circumference having the same radius, and are arranged in the stated order in the clockwise direction when viewed from above (the upper surface side of the cover part 116). In the seventh embodiment, the projections $116c_1$, $116c_2$ and $116c_3$ each have a quadrangular prism shape. Alternatively, the projections $116c_1$, $116c_2$ and $116c_3$ may have other shapes (for example, a columnar shape, a polygonal prism shape, a deformed pillar shape, a circular cone shape, a polygonal pyramid shape, a truncated circular cone shape, and a truncated polygonal pyramid shape) as long as engagement with recess parts $120d_1$, $120d_2$ and $120d_3$ to be described later is possible.

An elongated protrusion $116d$ that runs in a spiral manner is provided on the inner circumferential surface of the cylindrical member $116b$ (see FIG. 28). The elongated protrusion $116d$ forms a female thread, and is screwed with the elongated protrusion $114c$ (male thread) of the exterior main body part 114, whereby the cover part 116 is attached on the upper end side of the exterior main body part 114. Examples of the adoptable method of attaching the cover part 116 to the exterior main body part 114 include: a method of adhering the inner circumferential surface of the cover part 116 to the outer circumferential surface of the exterior main body part 114 with the use of an adhesive, an adhesive sheet, and the like; a method of mechanically engaging the two parts (for example, providing an engagement claw in the upper end part of the cylindrical body $114a$, providing an engagement hole in the cylindrical member $116b$, and fitting the engagement claw and the engagement hole to each other); a method of pressure-bonding the cover part 116 to the exterior main body part 114 (for example, setting the diameter of the cylindrical member $116b$ of the cover part 116 to be smaller than the outer diameter of the exterior main body part 114 and press-fitting the cover part 116 to the exterior main body part 114); and a method of welding the cover part 116 to the exterior main body part 114 (for example, heating and melting the cylindrical member $116b$ and the upper end part of the cylindrical body $114a$ and then cooling and integrating the two members).

It is desirable that the applicator A7 have a shape that enables easy hold and enables easy application (easy puncture) of the microneedles 32 to the skin of the animal (including a human). Thus, the outer shape of the exterior main body part 114 or the cover part 116 may be, for example, multangular or rounded. A recess or a step may be provided on the surface of the exterior main body part 114 or the cover part 116. A fine groove may be formed on the surface of the exterior main body part 114 or the cover part 116, or a non-slippery coating layer may be provided thereon, whereby the surface of the exterior main body part 114 or the cover part 116 may be roughened. A through-hole may be formed in the exterior main body part 114 or the cover part 116 for the purpose of reducing the air resistance and the weight.

The piston plate 120 is housed in the interior main body part 112, and is movable in the top-bottom direction along the central axis of the interior main body part 112 inside of the interior main body part 112. The material of the piston plate 120 may be the same as the material of the casing 110, and may be the same as the material of the microneedle array 30. As illustrated in FIG. 28 and FIG. 29, the piston plate 120 includes: the disc-like main body $120a$; and a cylindrical member $120b$ that extends upward from the periphery of the main body $120a$. An opening, a groove, a through-hole, or the like may be formed in the main body $120a$ for the purpose of reducing the air resistance and the weight of the piston plate 120. Further, an elongated protrusion or the like may be provided on the upper surface (the surface on which the conical coil spring 40 is arranged) of the main body $120a$ for the purpose of improving the rigidity of the piston plate 120. It is preferable that the lower surface (the surface opposite to the upper surface) of the main body $120a$ be planar, in consideration of causing the piston plate 120 to evenly act on the microneedle array 30. Alternatively, the lower surface of the main body $120a$ may have other shapes than the planar shape, and the shape of the lower surface of the main body $120a$ can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The inner diameter of the cylindrical member $120b$ is set to be larger than the maximum diameter D1 of the conical coil spring 40. The height of the cylindrical member $120b$ is not particularly limited as long as the cylindrical member $120b$ can function as such a stopper that prevents the conical coil spring 40 from dropping off the piston plate 120 during its movement in the radial direction. For example, in the case where the height of the applicator A7 is desired to be minimized, the height of the cylindrical member $120b$ can be set to be equivalent to the thickness of a metal wire that forms the conical coil spring 40. In the case where the stopper for the conical coil spring 40 is not necessary, the piston plate 120 does not need to include the cylindrical member $120b$. Even in the case where the piston plate 120 does not include the cylindrical member $120b$, if a ring-like groove in which the metal wire that forms the conical coil spring 40 can be fit is formed in the main body $120a$, the function as the stopper for the conical coil spring 40 can be fulfilled by the ring-like groove. In the case where such a stopper for the conical coil spring 40 is provided, a failure in positioning of the conical coil spring 40 with respect to the piston plate 120 can be prevented at the time of arranging the conical coil spring 40 on the upper surface of the piston plate 120 and then attaching the cover part 116 to the exterior main body part 114 to thereby make the applicator A7.

The plurality of projections (in the seventh embodiment, three projections) $120c_1$, $120c_2$ and $120c_3$ are provided in the periphery (on the outer circumferential surface) of the piston plate 120, and the projections $120c_1$, $120c_2$ and $120c_3$ protrude outward in the radial direction (the direction that intersects with the thickness direction of the piston plate). The projections $120c_1$, $120c_2$ and $120c_3$ are arranged in the stated order in the clockwise direction when viewed from above (the upper surface side of the piston plate 120 on which the conical coil spring 40 is placed), with given intervals in the circumferential direction. In the seventh embodiment, the projections $120c_1$, $120c_2$ and $120c_3$ each have a quadrangular prism shape. Alternatively, the projections $120c_1$, $120c_2$ and $120c_3$ may have other shapes (for example, a columnar shape, a polygonal prism shape, a deformed pillar shape, a circular cone shape, a polygonal pyramid shape, a truncated circular cone shape, and a truncated polygonal pyramid shape) as long as locking with the elongated protrusions $112b_4$, $112c_4$ and $112d_4$ is possible and movement in the groove parts G110, G120 and G130 is possible.

The projection $120c_1$ is movable along the extending direction of the groove body G110 inside of the groove body G110. Specifically, the projection $120c_1$ is movable in the horizontal direction (circumferential direction) along the groove part G111 that extends in the horizontal direction (circumferential direction), and is movable in the top-bottom direction along the groove part G112 that extends in the top-bottom direction. That is, the projection $120c_1$ is movable in the horizontal direction above the elongated protrusion $112b_4$ in the state where the projection $120c_1$ is located on the upper end side of the groove part G112. Thus, the projection $120c_1$ can be placed on the elongated protrusion $112b_4$ adjacent to the groove part G112.

The projection $120c_2$ is movable along the extending direction of the groove body G120 inside of the groove body G120. Specifically, the projection $120c_2$ is movable in the horizontal direction (circumferential direction) along the groove part G121 that extends in the horizontal direction (circumferential direction), and is movable in the top-bottom direction along the groove part G122 that extends in the top-bottom direction. That is, the projection $120c_2$ is movable in the horizontal direction above the elongated protrusion $112c_4$ in the state where the projection $120c_2$ is located on the upper end side of the groove part G122. Thus, the projection $120c_2$ can be placed on the elongated protrusion $112c_4$ adjacent to the groove part G122.

The projection $120c_3$ is movable along the extending direction of the groove body G130 inside of the groove body G130. Specifically, the projection $120c_3$ is movable in the horizontal direction (circumferential direction) along the groove part G131 that extends in the horizontal direction (circumferential direction), and is movable in the top-bottom direction along the groove part G132 that extends in the top-bottom direction. That is, the projection $120c_3$ is movable in the horizontal direction above the elongated protrusion $112d_4$ in the state where the projection $120c_3$ is located on the upper end side of the groove part G132. Thus, the projection $120c_3$ can be placed on the elongated protrusion $112d_4$ adjacent to the groove part G132.

As described above, as the projections $120c_1$, $120c_2$ and $120c_3$ are respectively guided inside of the groove bodies G110, G120 and G130, the piston plate 120 can be guided along the extending directions (circumferential directions) of the groove parts G111, G121 and G131 (can be turned about the axis of the interior main body part 112), and can be guided in the top-bottom direction along the extending directions of the groove parts G112, G122 and G132 (the axial direction of the interior main body part 112).

The elongated protrusions $112b_4$, $112c_4$ and $112d_4$ may extend in the circumferential direction so as to be parallel to a horizontal plane, and may be inclined to the horizontal plane, in the circumferential direction. In particular, the elongated protrusions $112b_4$, $112c_4$ and $112d_4$ may be inclined so as to gradually approach the upper end of the interior main body part 112 toward the respective adjacent groove parts G112, G122 and G132. In this case, when the projections $120c_1$, $120c_2$ and $120c_3$ respectively placed on the elongated protrusions $112b_4$ to $112d_4$ move toward the groove parts G112, G122 and G132, the projections $120c_1$, $120c_2$ and $120c_3$ need to climb the slopes of the elongated protrusions $112b_4$, $112c_4$ and $112d_4$. Thus, even if an impact or the like is applied from the outside to the applicator A7, the projections $120c_1$, $120c_2$ and $120c_3$ can be prevented from unintentionally moving into the groove parts G112, G122 and G132.

The cylindrical member 120b of the piston plate 120 is provided with recess parts $120d_1$, $120d_2$ and $120d_3$ that are concaved in the radial direction. The recess parts $120d_1$, $120d_2$ and $120d_3$ are located on a circumference having the same radius, and are arranged in the stated order in the clockwise direction when viewed from above (the cover part 116 side). At the time of operating the applicator A7, the projection $116c_1$ of the cover part 116 is engageable with the recess part $120d_1$ of the piston plate 120, the projection $116c_2$ of the cover part 116 is engageable with the recess part $120d_2$ of the piston plate 120, and the projection $116c_3$ of the cover part 116 is engageable with the recess part $120d_3$ of the piston plate 120.

The microneedle array 30 and the conical coil spring 40 are the same as those in the first embodiment, and hence description thereof is omitted.

[7.2] Method of Manufacturing Applicator

Now, the method of manufacturing the applicator A7 is described. First, the piston plate 120 is placed in the interior main body part 112 through procedures similar to the first and third steps in the method of manufacturing the applicator A1 according to the first embodiment (see FIG. 30).

Subsequently, the conical coil spring 40 is placed on the upper surface of the piston plate 120 through a procedure similar to the fourth step in the method of manufacturing the applicator A1 according to the first embodiment.

Subsequently, the elongated protrusion 116d (female thread) of the cover part 116 is screwed with the elongated protrusion 114c (male thread) of the exterior main body part 114, whereby the cover part 116 is attached on the upper end side of the exterior main body part 114. In the state where the cover part 116 is attached to the exterior main body part 114, the projection $116c_1$ of the cover part 116 is located so as to be opposed to the recess part $120d_1$ of the piston plate 120, the projection $116c_2$ of the cover part 116 is located so as to be opposed to the recess part $120d_2$ of the piston plate 120, and the projection $116c_3$ of the cover part 116 is located so as to be opposed to the recess part $120d_3$ of the piston plate 120, when viewed from the top-bottom direction.

Figure 30:
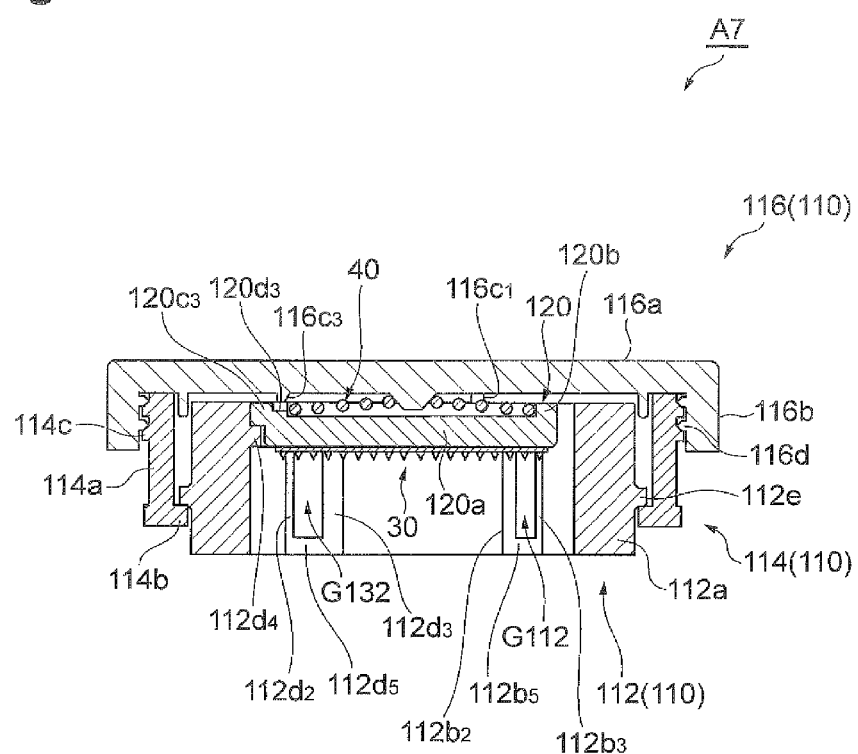
FIG. 30 is a cross sectional view illustrating a state before the operation of the applicator according to the seventh embodiment.

On this occasion, because the projections $120c_1$, $120c_2$ and $120c_3$ are respectively placed on the elongated protrusions $112b_4$, $112c_4$ and $112d_4$ of the guide parts 112b, 112c and 112d, even if the conical coil spring 40 is compressed by attaching the cover part 116 to the exterior main body part 114, the piston plate 120 is not pushed out in the bottom direction by the conical coil spring 40. That is, the piston plate 120 is locked with the casing 110 (interior main body part 112). Accordingly, as illustrated in FIG. 30, the piston plate 120 is held at its retraction position on the cover part 116 side inside of the interior main body part 112, in the state where the cover part 116 and the piston plate 120 compress the conical coil spring 40. Such a state as described above where the piston plate 120 is locked with the casing 110 (interior main body part 112) and where the cover part 116 and the piston plate 120 compress the conical coil spring 40 is hereinafter referred to as "locked state". Locking the piston plate 120 with the casing 110 (interior main body part 112) at its retraction position as described above is also referred to as cocking.

Because the direct distance $d_1$ from the flange member 114b to the upper end of the exterior main body part 114 is set to be longer than the direct distance $d_2$ from the flange member 112e to the upper end of the interior main body part 112, the interior main body part 112 is slightly movable in the top-bottom direction inside of the exterior main body part 114. Note that the piston plate 120 and the cover part 116 are biased by the conical coil spring 40 so as be spaced apart from each other, and the piston plate 120 causes the flange member 112e of the interior main body part 112 to abut against the flange member 114b of the exterior main body part 114. Hence, as illustrated in FIG. 30, a slight gap exists between the lower surface of the cover part 116 and the upper end of the interior main body part 112. That is, the cover part 116 is at a separate position at which the cover part 116 is spaced apart from the interior main body part 112 and the piston plate 120. In the case where the cover part 116 is at the separate position, the projections $116c_1$, $116c_2$ and $116c_3$ of the cover part 116 are outside of the recess parts $120d_1$, $120d_2$ and $120d_3$ of the piston plate 120, and are not engaged with the recess parts $120d_1$, $120d_2$ and $120d_3$ of the piston plate 120 (see FIG. 30). In the completed state of the applicator A7 (in the state where the cover part 116 is at the separate position), the conical coil spring 40 is not completely compressed, and has a height that is slightly larger than the wire diameter (see the same drawing).

Through the above-mentioned procedures, assembling of the applicator A7 is completed. Accordingly, the conical coil spring 40 remains in a compressed state until the applicator A7 is used by a user after manufacture and shipping thereof.

[7.3] Method of Using Applicator

Figure 31:
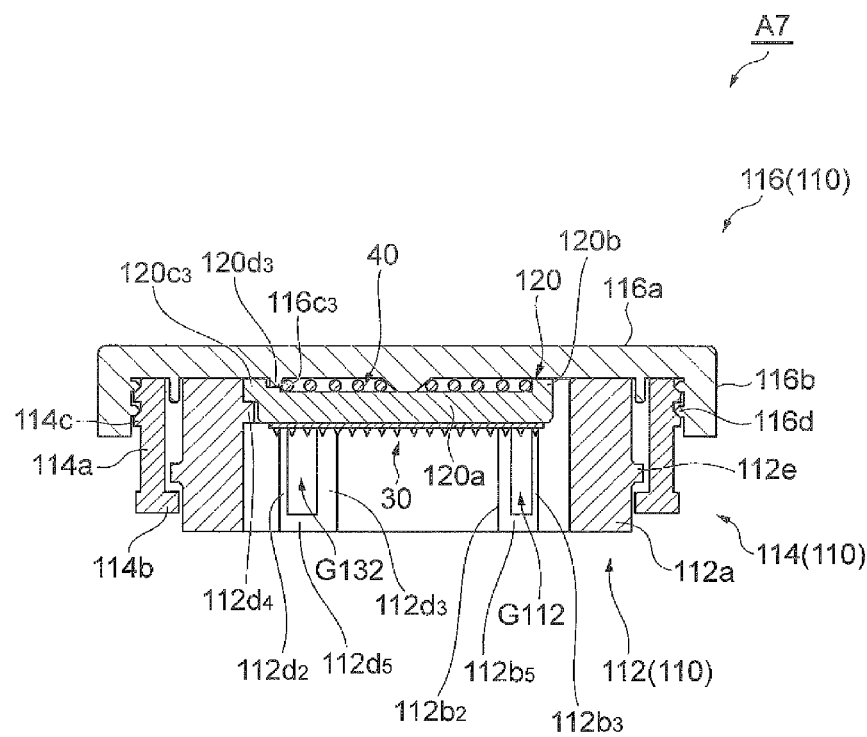
FIG. 31 is a cross sectional view illustrating the applicator according to the seventh embodiment, in which a cover part is pressed.

Now, the method of using the applicator A7 is described. First, the applicator A7 is positioned with respect to a portion of a skin to which a medical agent or the like is desired to be applied, such that the microneedles 32 face the skin. The cover part 116 is pushed toward the interior main body part 112 while the applicator A7 is kept positioned. As a result, the lower surface of the cover part 116 abuts against the upper end of the interior main body part 112. That is, the cover part 116 moves to a close position at which the cover part 116 is close to the interior main body part 112 and the piston plate 120. As illustrated in FIG. 31, in the state where the cover part 116 is at the close position, the projections $116c_1$, $116c_2$ and $116c_3$ of the cover part 116 are respectively engaged with the recess parts $120d_1$, $120d_2$ and $120d_3$ of the piston plate 120. In the present exemplary embodiment, the metal wire that forms the conical coil spring 40 does not overlap when viewed from the central line direction of the conical coil spring 40. Hence, as a result of the abutment of the lower surface of the cover part 116 against the upper end of the interior main body part 112, the height of the conical coil spring 40 sandwiched between the piston plate 120 and the cover part 116 becomes equivalent to the wire diameter (see FIG. 31).

Subsequently, the cover part 116 is turned in the circumferential direction while the cover part 116 is kept pushed toward the interior main body part 112. Because the projections $116c_1$, $116c_2$ and $116c_3$ of the cover part 116 are respectively engaged with the recess parts $120d_1$, $120d_2$ and $120d_3$ of the piston plate 120, the projections $116c_1$, $116c_2$ and $116c_3$ exert a turning force on the piston plate 120, with the result that the piston plate 120 turns. Accordingly, the locking (cocking) of the piston plate 120 with the casing 110 (interior main body part 112) is released. After that, similarly to the applicator A1 according to the first embodiment, the microneedle array 30 collides against the skin due to the biasing force (elastic force) of the conical coil spring 40 (see FIG. 28).

[7.4] Actions

The seventh embodiment as described above produces actions and effects similar to the actions (A) to (D) of the applicator A1 according to the first embodiment.

In the applicator A7 according to the seventh embodiment, the piston plate 120 is not turned by the projections $116c_1$, $116c_2$ and $116c_3$ unless the cover part 116 is turned while a pressing force against the biasing force of the conical coil spring 40 is exerted on the cover part 116. Thus, the applicator A7 can be prevented from malfunctioning.

[8] Eighth Embodiment

Now, an applicator A8 according to an eighth embodiment is described with reference to FIG. 27 and FIG. 32 to FIG. 34. The applicator A8 according to the eighth embodiment is different from the applicator A7 according to the seventh embodiment in that: the cover part 116 includes a mesh part 116e instead of the projections $116c_1$, $116c_2$ and $116c_3$; and the piston plate 120 includes a mesh part 120e instead of the recess parts $120d_1$, $120d_2$ and $120d_3$. In the following, differences between the applicator A8 according to the eighth embodiment and the applicator A7 according to the seventh embodiment are mainly described, and redundant description is omitted.

Figure 32:
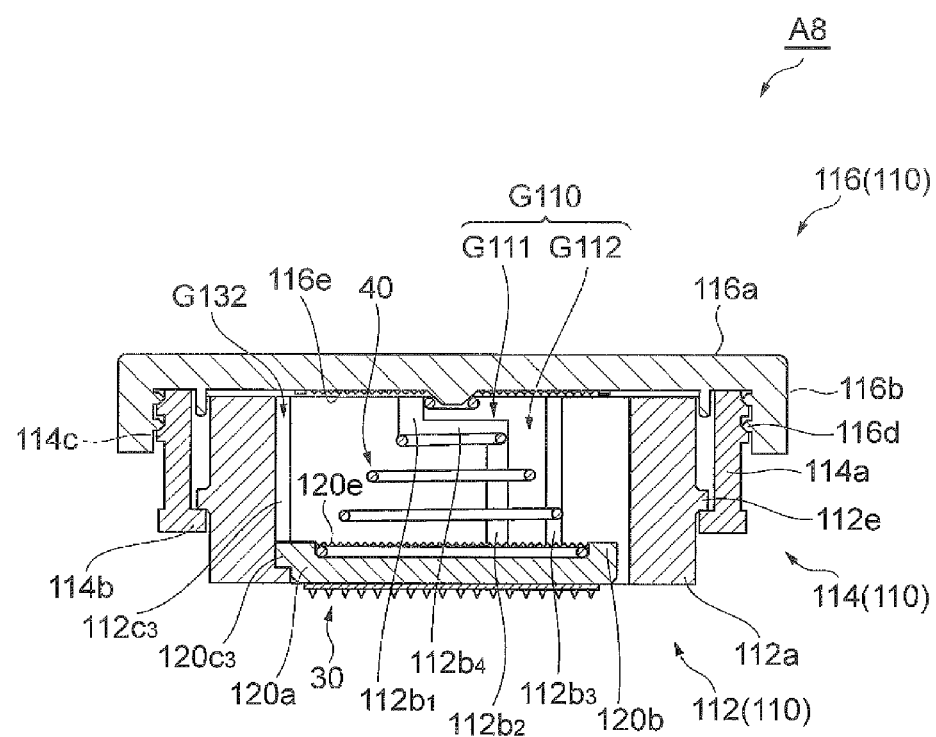
FIG. 32 is a cross sectional view illustrating a state after an operation of the applicator according to the eighth embodiment.
Figure 33:
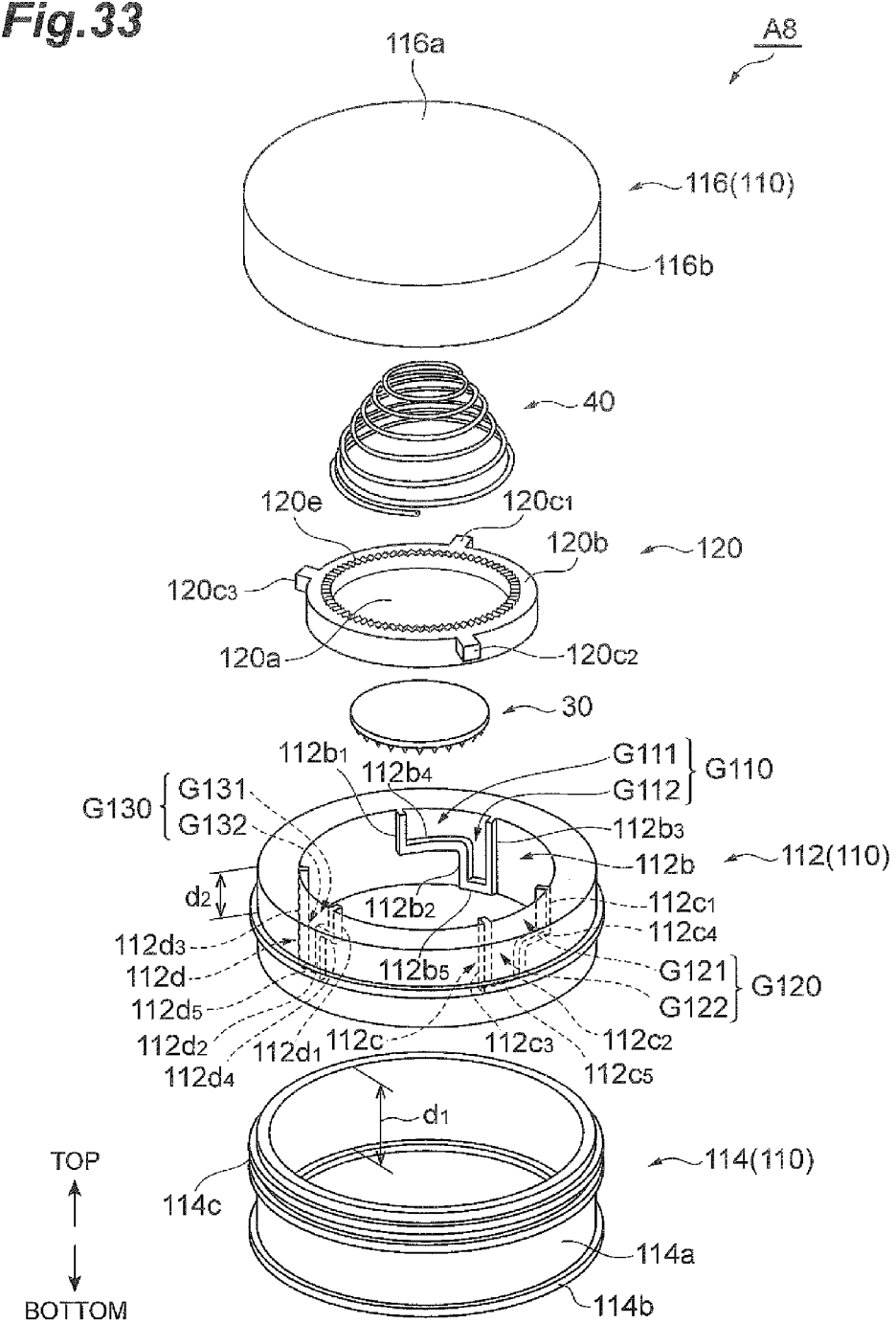
FIG. 33 is an exploded perspective view of the applicator according to the eighth embodiment.
Figure 34:
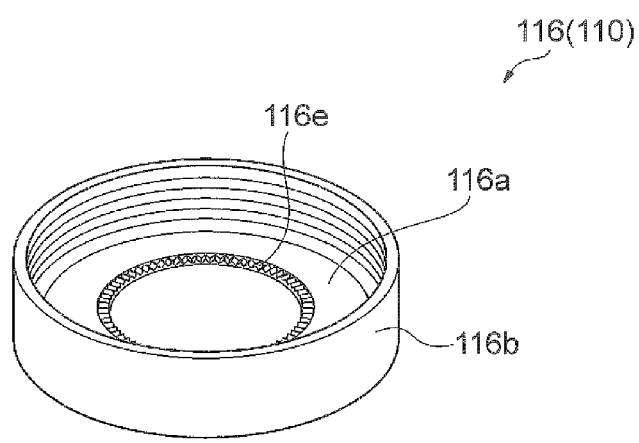
FIG. 34 is a perspective view illustrating the lower surface side of a cover part.

Specifically, as illustrated in FIG. 32 and FIG. 34, the mesh part 116e is formed on the lower surface of the cover part 116 (top plate 116a). The mesh part 116e has a circular ring-like shape, and is formed of sawtooth irregularities that are arranged side by side along the circumferential direction. As illustrated in FIG. 33, the mesh part 120e is formed at the upper end of the cylindrical member 120b of the piston plate 120. The mesh part 120e has a circular ring-like shape, and is formed of sawtooth irregularities that are arranged side by side along the circumferential direction. In the completed state of the applicator A8 (the state where the cover part 116 is attached to the exterior main body part 114), the mesh part 116e and the mesh part 120e are located so as to overlap with each other when viewed from above, and can be engaged (meshed) with each other.

Figure 35:
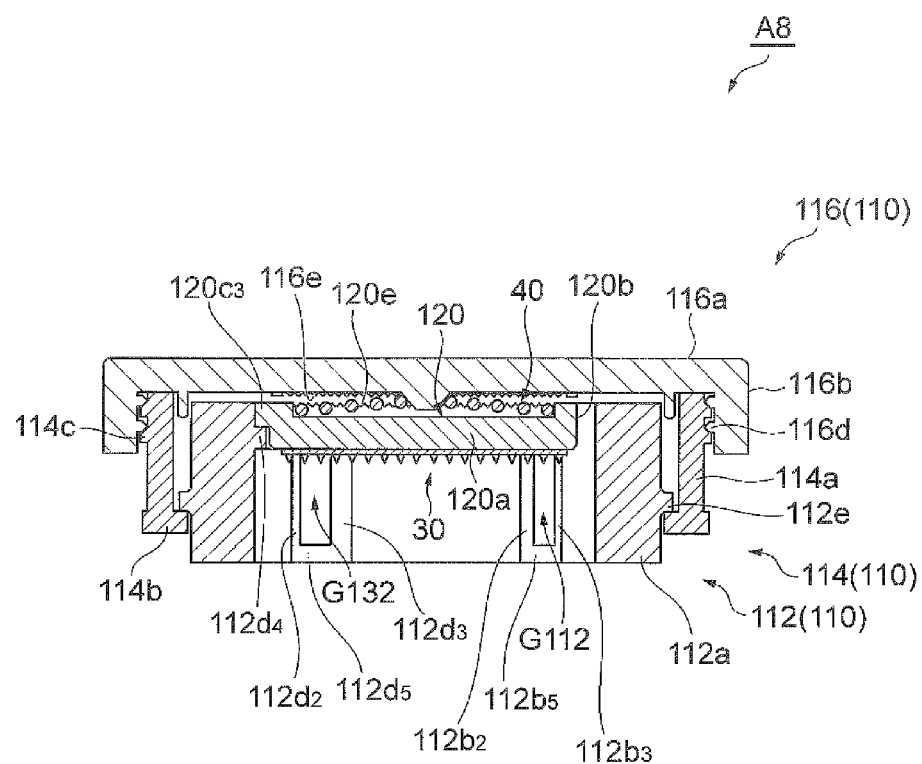
FIG. 35 is a cross sectional view illustrating a state before the operation of the applicator according to the eighth embodiment.

The applicator A8 according to the eighth embodiment can be manufactured through procedures similar to those for the applicator A7 according to the seventh embodiment. In the applicator A8 according to the eighth embodiment, similarly to the applicator A7 according to the seventh embodiment, a slight gap exists between the lower surface of the cover part 116 and the upper end of the interior main body part 112, in the state where the cover part 116 is attached to the exterior main body part 114 (see FIG. 35). That is, the cover part 116 is at a separate position at which the cover part 116 is spaced apart from the interior main body part 112 and the piston plate 120. In the case where the cover part 116 is at the separate position, the mesh part 116e of the cover part 116 is also spaced apart from the mesh part 120e of the piston plate 120, and thus is not meshed therewith (see the same drawing).

Figure 36:
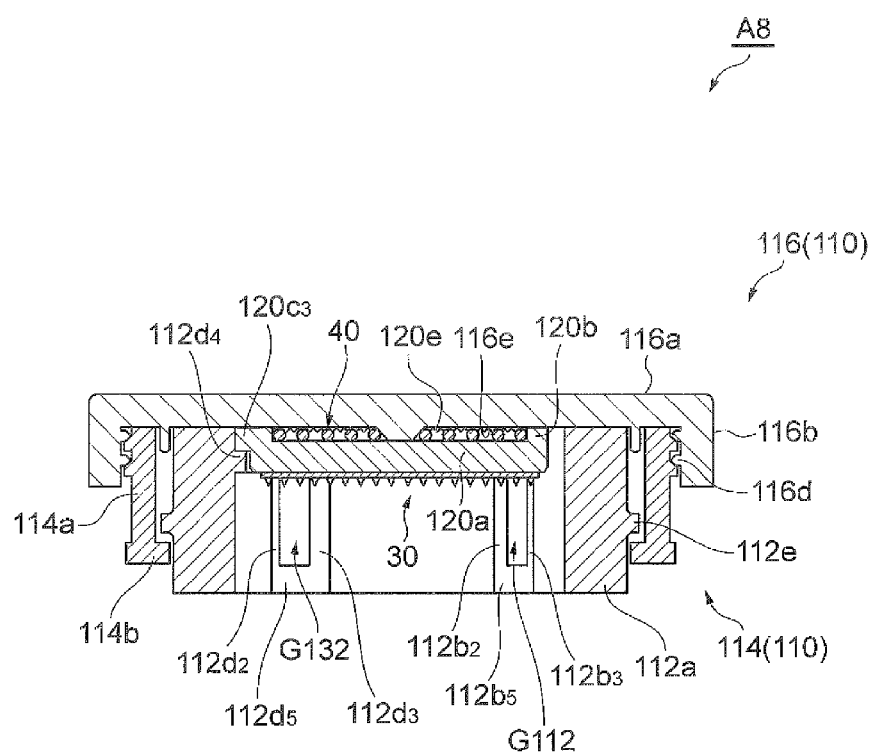
FIG. 36 is a cross sectional view illustrating the applicator according to the eighth embodiment, in which the cover part is pressed.
Figure 37:
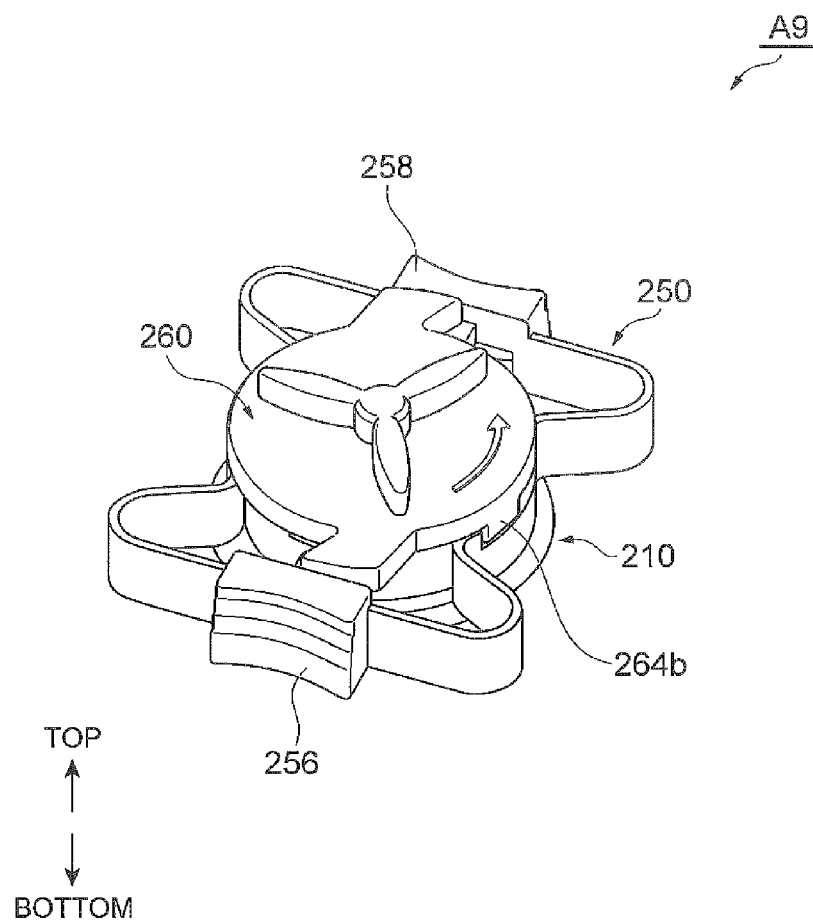
FIG. 37 is a perspective view of an applicator according to a ninth embodiment.
Figure 38:
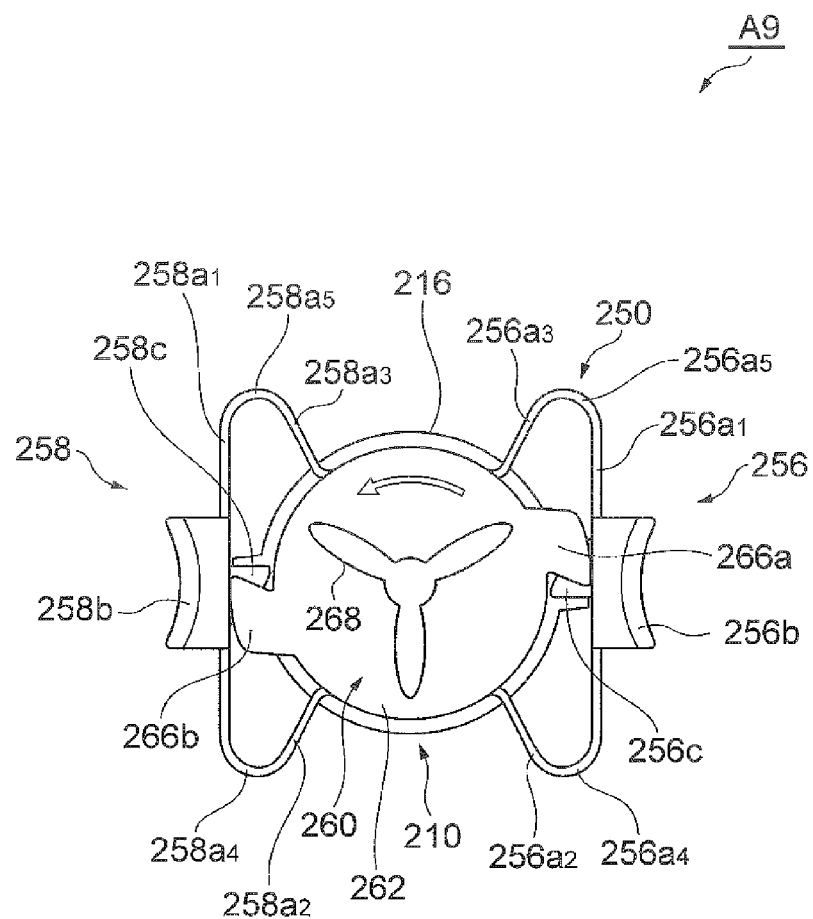
FIG. 38 is a top view of the applicator according to the ninth embodiment.
Figure 39:
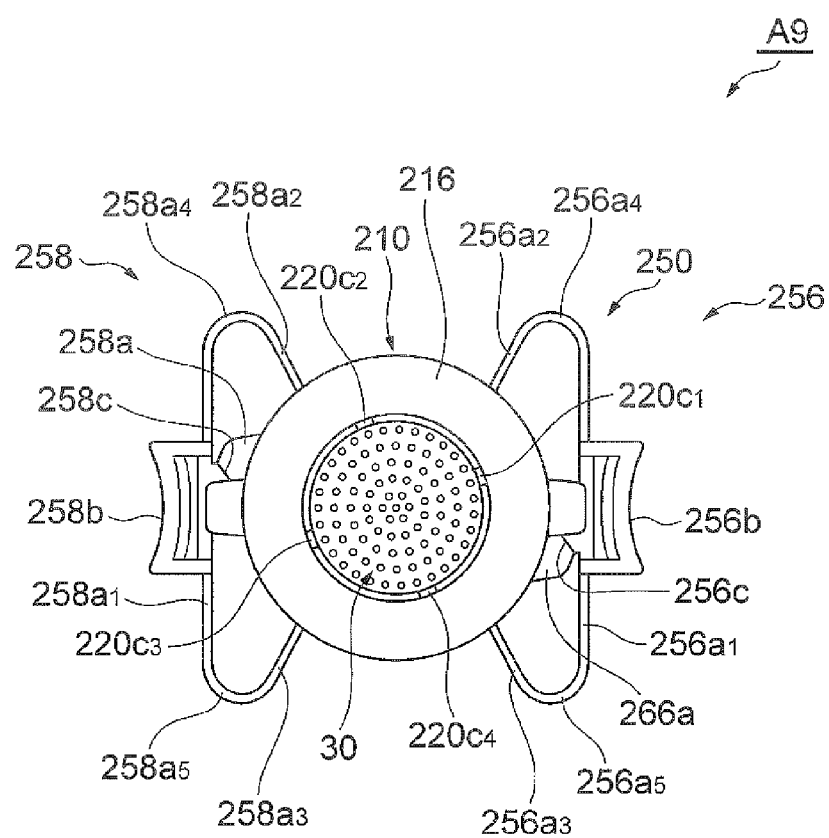
FIG. 39 is a bottom view of the applicator according to the ninth embodiment.
Figure 40:
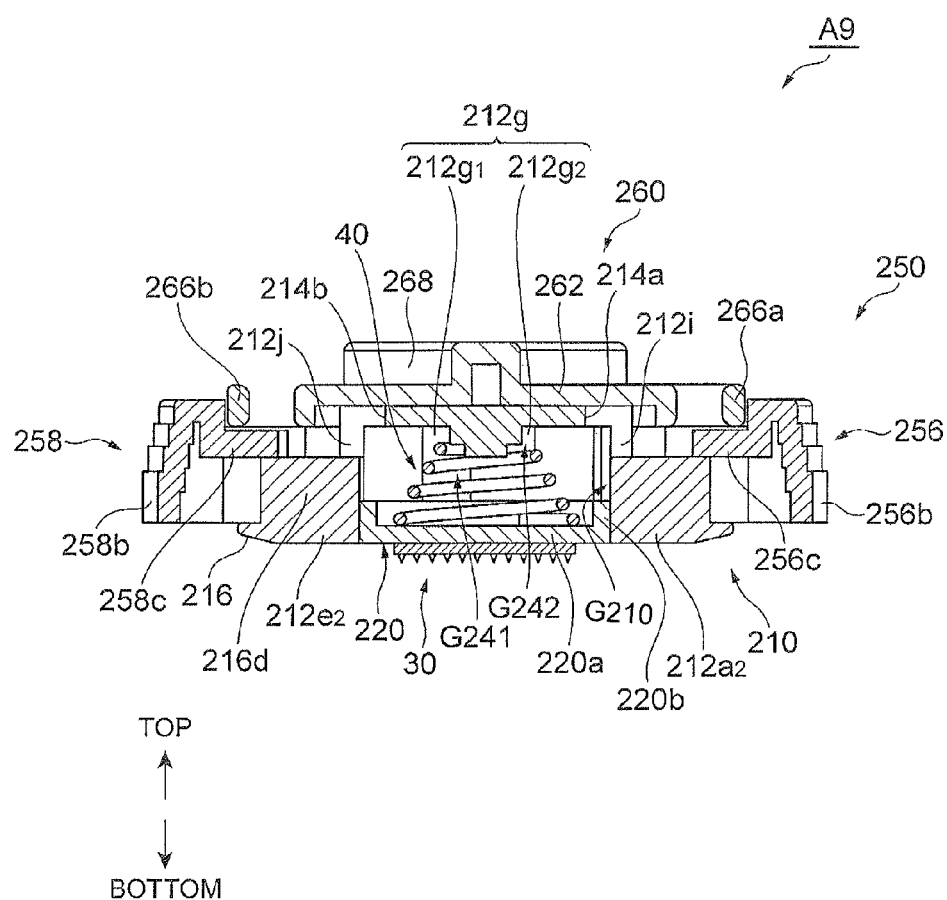
FIG. 40 is a cross sectional view of the applicator according to the ninth embodiment.

The applicator A8 according to the eighth embodiment can be used through an operation similar to that on the applicator A7 according to the seventh embodiment. Specifically, the applicator A8 is positioned with respect to a portion of a skin to which a medical agent or the like is desired to be applied, such that the microneedles 32 face the skin. The cover part 116 is pushed toward the interior main body part 112 while the applicator A8 is kept positioned. As a result, the lower surface of the cover part 116 abuts against the upper end of the interior main body part 112. That is, the cover part 116 moves to a close position at which the cover part 116 is close to the interior main body part 112 and the piston plate 120. As illustrated in FIG. 36, in the state where the cover part 116 is at the close position, the mesh part 116e of the cover part 116 is engaged (meshed) with the mesh part 120e of the piston plate 120.

Subsequently, the cover part 116 is turned in the circumferential direction while the cover part 116 is kept pushed toward the interior main body part 112. Because the mesh part 116e of the cover part 116 is engaged (meshed) with the mesh part 120e of the piston plate 120, a turning force is exerted on the piston plate 120 from the cover part 116 with the intermediation of the mesh parts 116e and 120e, with the result that the piston plate 120 turns. Accordingly, the locking (cocking) of the piston plate 120 with the casing 110 (interior main body part 112) is released. After that, similarly to the applicator A7 according to the seventh embodiment, the microneedle array 30 collides against the skin due to the biasing force (elastic force) of the conical coil spring 40 (see FIG. 32).

The applicator A8 according to the eighth embodiment as described above produces actions and effects similar to those of the applicator A7 according to the seventh embodiment.

[9] Ninth Embodiment

[9.1] Configuration of Applicator

Now, a configuration of an applicator A9 according to a ninth embodiment is described with reference to FIG. 37 to FIG. 43. In the following description, the term "top" corresponds to the top direction of FIG. 37, FIG. 40, FIG. 41, and FIG. 43, and the term "bottom" corresponds to the bottom direction of FIG. 37, FIG. 40, FIG. 41, and FIG. 43. That is, the top-bottom direction corresponds to the height direction of the applicator A9.

The applicator A9 is a device for transferring active ingredients of a medical agent or the like into the body of an animal such as a human through a skin of the animal. The applicator A9 includes a casing 210, a piston plate 220, the microneedle array 30, the conical coil spring 40, a release member 250, and a stopper 260.

Figure 41:
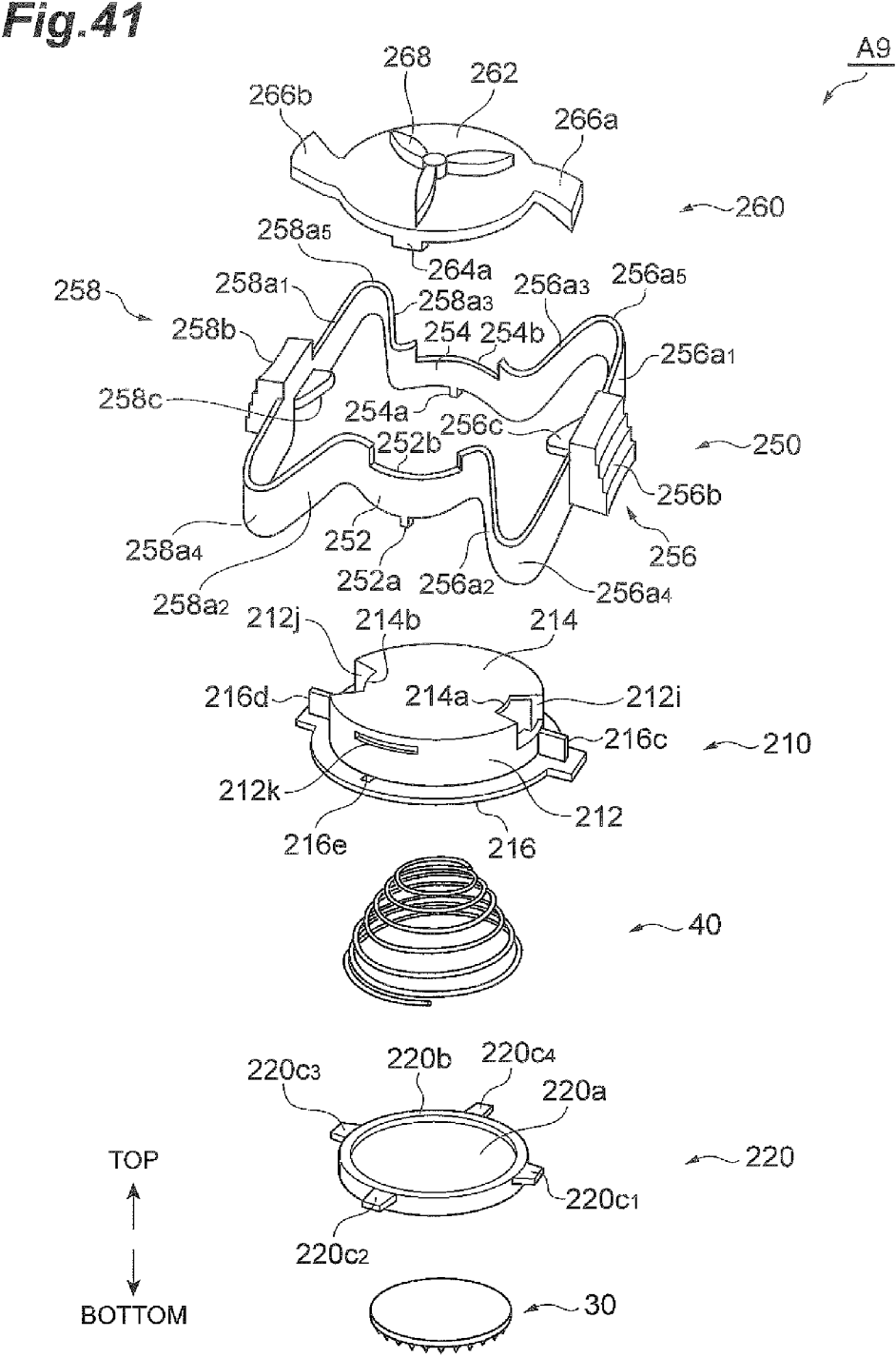
FIG. 41 is an exploded perspective view of the applicator according to the ninth embodiment.
Figure 42:
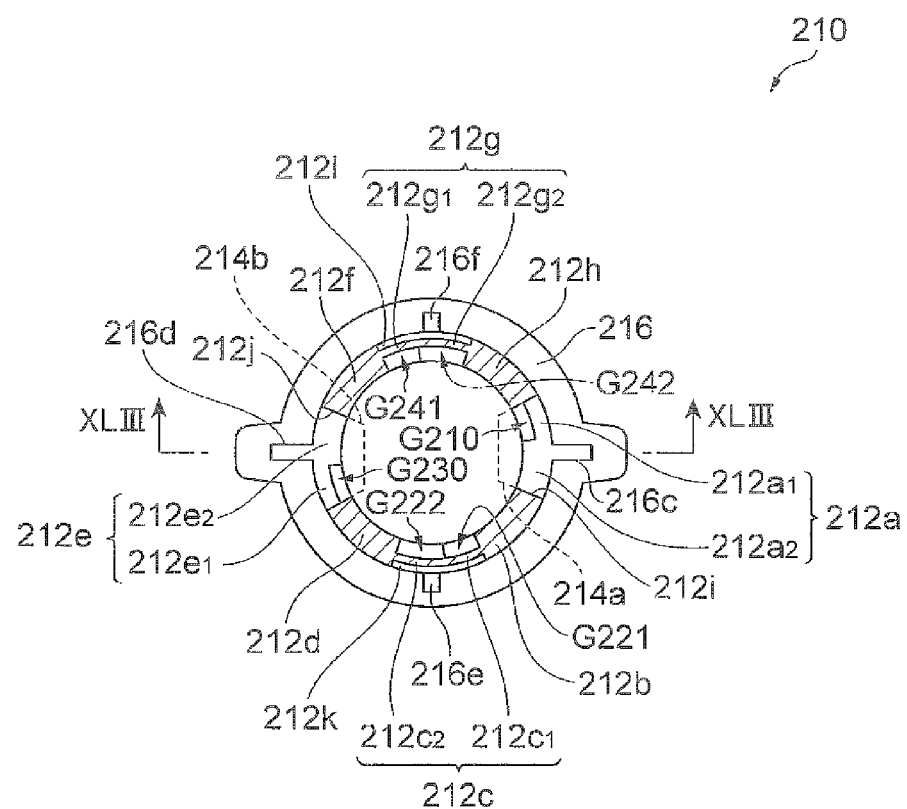
FIG. 42 is a top view of a casing, the upper end part (cover part) of which is cut away.
Figure 43:
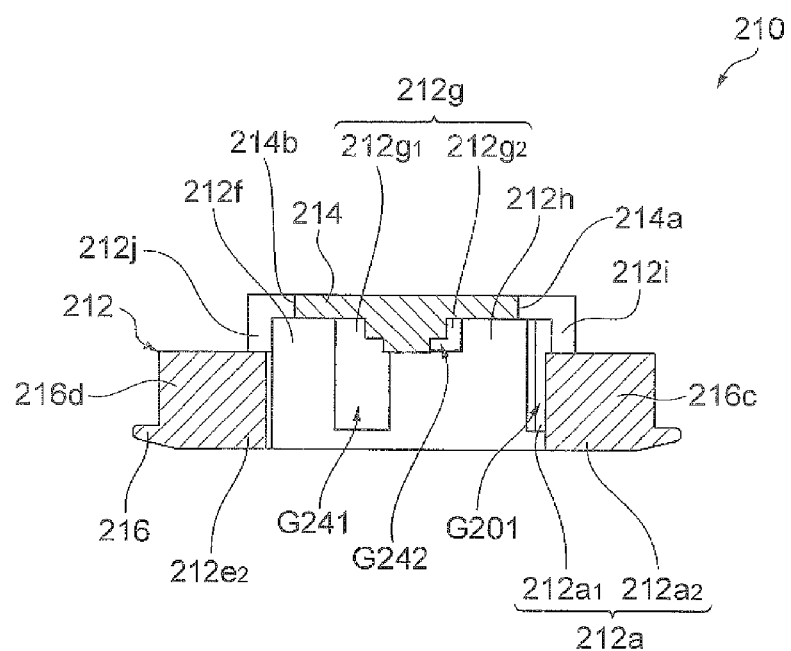
FIG. 43 is a cross sectional view taken along line XLIII-XLIII in FIG. 42.

As illustrated in FIG. 41 to FIG. 43, the casing 210 includes: a main body part 212 that has a cylindrical shape and has a central axis that extends along the top-bottom direction; a cover part 214 arranged on the upper end side of the main body part 212; and a circular ring-like flange part 216 arranged on the lower end side of the main body part 212. The strength and the material of the casing 210 may be the same as those of the casing 10 of the applicator A1 according to the first embodiment.

The main body part 212 includes wall parts 212a, 212b, 212c, 212d, 212e, 212f, 212g and 212h each having a circular arc-like shape when viewed from above. The wall parts 212a, 212b, 212c, 212d, 212e, 212f, 212g and 212h are arranged in the stated order in the clockwise direction when viewed from the upper end side (the cover part 214 side) of the main body part 212, and are integrated with the respective adjacent wall parts (see FIG. 42). The wall part 212a and the wall part 212e are opposed to each other with the axis of the main body part 212 being centered therebetween, when viewed from above. The wall part 212b and the wall part 212f are opposed to each other with the axis of the main body part 212 being centered therebetween, when viewed from above. The wall part 212c and the wall part 212g are opposed to each other with the axis of the main body part 212 being centered therebetween, when viewed from above. The wall part 212d and the wall part 212h are opposed to each other with the axis of the main body part 212 being centered therebetween, when viewed from above.

The main body part 212 is provided with cutout parts 212i and 212j at positions respectively corresponding to the wall parts 212a and 212e. The cutout parts 212i and 212j are opposed to each other with the axis of the main body part 212 being centered therebetween, when viewed from above. Thus, the height of the wall part 212a is made smaller by the existence of the cutout part 212i, and the upper end thereof does not reach the cover part 214. The height of the wall part 212e is made smaller by the existence of the cutout part 212j, and the upper end thereof does not reach the cover part 214.

Groove parts 212k and 212l are provided on the outer circumferential surface of the main body part 212 at positions respectively corresponding to the wall parts 212c and 212g. The groove parts 212k and 212l are located closer to the upper end of the main body part 212, and extend along the circumferential direction.

On the inner surface of the wall part 212a, a groove part G210 that extends in the top-bottom direction is provided closer to the wall part 212h. The groove part G210 extends from the vicinity of the lower end of the wall part 212a to the upper end thereof. That is, the wall part 212a includes: a first portion $212a_1$ that is made thinner by the existence of the groove part G210 except the lower end part thereof; and a second portion $212a_2$ that is thicker than the first portion $212a_1$ over the entire region in the top-bottom direction.

On the inner surface of the wall part 212c, a groove part G221 that extends in the top-bottom direction is provided closer to the wall part 212b, and a groove part G222 that extends in the circumferential direction is provided in the vicinity of the upper end of the wall part 212c. The groove part G221 extends from the vicinity of the lower end of the wall part 212c to the upper end thereof. The groove part G222 extends from the wall part 212b to the wall part 212d, and is communicated with the upper end of the groove part G221. Thus, the wall part 212c includes: a first portion $212c_1$ that is made thinner by the existence of the groove part G221 except the lower end part thereof; and a second portion $212c_2$ having an upper end part made thinner by the existence of the groove part G222 and a thicker portion below the groove part G222.

On the inner surface of the wall part 212e, a groove part G230 that extends in the top-bottom direction is provided closer to the wall part 212d. The groove part G230 extends from the vicinity of the lower end of the wall part 212e to the upper end thereof. That is, the wall part 212e includes: a first portion $212e_1$ that is made thinner by the existence of the groove part G230 except the lower end part thereof; and a second portion $212e_2$ that is thicker than the first portion $212e_1$ over the entire region in the top-bottom direction.

On the inner surface of the wall part 212g, a groove part G241 that extends in the top-bottom direction is provided closer to the wall part 212f, and a groove part G242 that extends in the circumferential direction is provided in the vicinity of the upper end of the wall part 212g. The groove part G241 extends from the vicinity of the lower end of the wall part 212g to the upper end thereof. The groove part G242 extends from the wall part 212f to the wall part 212h, and is communicated with the upper end of the groove part G241. Thus, the wall part 212g includes: a first portion $212g_1$ that is made thinner by the existence of the groove part G241 except the lower end part thereof; and a second portion $212g_2$ having an upper end part made thinner by the existence of the groove part G242 and a thicker portion below the groove part G242.

The wall parts 212b, 212d, 212f, and 212h each have a thickness equivalent to those of the second portion $212a_2$ of the wall part 212a and the second portion $212e_2$ of the wall part 212e.

The cover part 214 is a plate-like body having a circular shape. The peripheral part of the lower surface of the cover part 214 is integrated with the upper ends of the wall parts 212b, 212c, 212d, 212f, 212g and 212h. Thus, the cover part 214 closes the upper end of the main body part 212.

The cover part 214 is provided with cutout parts 214a and 214b at positions respectively corresponding to the wall parts 212a and 212e when viewed from above. The cutout parts 214a and 214b are opposed to each other with the axis of the cover part 214 being centered therebetween, when viewed from above. The cutout parts 214a and 214b are both concaved toward the center of the cover part 214.

The flange part 216 protrudes outward from the lower end of the main body part 212. At the time of using the applicator A9, the flange part 216 makes the contact area with the skin larger, and hence a pressure applied to the skin can be made smaller.

On the upper surface of the flange part 216, plate-like reinforcement members 216c and 216d each having a rectangular shape are erected at positions respectively adjacent to the wall parts 212a and 212e. The reinforcement members 216c and 216d are opposed to each other with the axis of the main body part 212 being centered therebetween, when viewed from above. The reinforcement member 216c is integrated with the upper surface of the flange part 216 and the outer surface of the wall part 212a. The reinforcement member 216d is integrated with the upper surface of the flange part 216 and the outer surface of the wall part 212e. The reinforcement members 216c and 216d enhance the rigidity between the main body part 212 and the flange part 216.

The flange part 216 is provided with through-holes 216e and 216f at positions respectively adjacent to the wall parts 212c and 212g. The through-holes 216e and 216f are opposed to each other with the axis of the main body part 212 being centered therebetween, when viewed from above.

The piston plate 220 is housed in the main body part 212, and is movable in the top-bottom direction along the central axis of the main body part 212 inside of the main body part 212. The material of the piston plate 220 may be the same as the material of the casing 210, and may be the same as the material of the microneedle array 30. As illustrated in FIG. 41, the piston plate 220 includes: a disc-like main body 220a; and a cylindrical member 220b that extends upward from the periphery of the main body 220a. An opening, a groove, a through-hole, or the like may be formed in the main body 220a for the purpose of reducing the air resistance and the weight of the piston plate 220. Further, an elongated protrusion or the like may be provided on the upper surface (the surface on which the conical coil spring 40 is arranged) of the main body 220a for the purpose of improving the rigidity of the piston plate 220. It is preferable that the lower surface (the surface opposite to the upper surface) of the main body 220a be planar, in consideration of causing the piston plate 220 to evenly act on the microneedle array 30. Alternatively, the lower surface of the main body 220a may have other shapes than the planar shape, and the shape of the lower surface of the main body 220a can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The inner diameter of the cylindrical member 220b is set to be larger than the maximum diameter D1 of the conical coil spring 40. The height of the cylindrical member 220b is not particularly limited as long as the cylindrical member 220b can function as such a stopper that prevents the conical coil spring 40 from dropping off the piston plate 220 during its movement in the radial direction. For example, in the case where the height of the applicator A9 is desired to be minimized, the height of the cylindrical member 220b can be set to be equivalent to the thickness of a metal wire that forms the conical coil spring 40. In the case where the stopper for the conical coil spring 40 is not necessary, the piston plate 220 does not need to include the cylindrical member 220b. Even in the case where the piston plate 220 does not include the cylindrical member 220b, if a ring-like groove in which the metal wire that forms the conical coil spring 40 can be fit is formed in the main body 220a, the function as the stopper for the conical coil spring 40 can be fulfilled by the ring-like groove. In the case where such a stopper for the conical coil spring 40 is provided, a failure in positioning of the conical coil spring 40 with respect to the piston plate 220 can be prevented at the time of arranging the conical coil spring 40 on the upper surface of the piston plate 220 and attaching the two to the inside of the casing 210.

A plurality of projections (in the ninth embodiment, four projections) $220c_1$, $220c_2$, $220c_3$ and $220c_4$ are provided in the periphery (on the outer circumferential surface) of the piston plate 220, and the projections $220c_1$, $220c_2$, $220c_3$ and $220c_4$ protrude outward in the radial direction (the direction that intersects with the thickness direction of the piston plate). The projections $220c_1$, $220c_2$, $220c_3$ and $220c_4$ are arranged in the stated order in the clockwise direction when viewed from above (the upper surface side of the piston plate 220 on which the conical coil spring 40 is placed), with given intervals in the circumferential direction. In the ninth embodiment, the projections $220c_1$, $220c_2$, $220c_3$ and $220c_4$ are plate-like bodies each having a trapezoidal shape. Alternatively, the projections $220c_1$, $220c_2$, $220c_3$ and $220c_4$ may have other shapes (for example, a columnar shape, a polygonal prism shape, a deformed pillar shape, a circular cone shape, a polygonal pyramid shape, a truncated circular cone shape, and a truncated polygonal pyramid shape) as long as locking with the second portions $212a_2$, $212c_2$, $212e_2$, and $212g_2$ of the wall parts 212a, 212c, 212e, and 212g is possible and movement in the groove parts G210, G221, G230, and G241 is possible.

The projection $220c_1$ is movable along the extending direction of the groove part G210 inside of the groove part G210. The projection $220c_2$ is movable along the extending direction of the groove part G221 inside of the groove part G221. The projection $220c_3$ is movable along the extending direction of the groove part G230 inside of the groove part G230. The projection $220c_4$ is movable along the extending direction of the groove part G241 inside of the groove part G241. Thus, the piston plate 220 can be guided in the top-bottom direction along the extending directions of the groove parts G210, G221, G230, and G241 (the axial direction of the main body part 212).

In the state where the projection $220c_1$ is located on the upper end side of the groove part G210, the projection $220c_1$ is movable in the horizontal direction inside of the cutout part 212i. Thus, the projection $220c_1$ can be placed on the upper end of the second portion $212a_2$ of the wall part 212a adjacent to the groove part G210. In the state where the projection $220c_2$ is located on the upper end side of the groove part G221, the projection $220c_2$ is movable in the horizontal direction inside of the groove part G222 communicated with the groove part G221. Thus, the projection $220c_2$ can be placed on the upper end of the second portion $212c_2$ of the wall part 212c adjacent to the groove part G221.

In the state where the projection $220c_3$ is located on the upper end side of the groove part G230, the projection $220c_3$ is movable in the horizontal direction inside of the cutout part 212j. Thus, the projection $220c_3$ can be placed on the upper end of the second portion $212e_2$ of the wall part 212e adjacent to the groove part G230. In the state where the projection $220c_4$ is located on the upper end side of the groove part G241, the projection $220c_4$ is movable in the horizontal direction inside of the groove part G242 communicated with the groove part G241. Thus, the projection $220c_4$ can be placed on the upper end of the second portion $212g_2$ of the wall part 212g adjacent to the groove part G241.

The upper ends of the second portions $212a_2$, $212c_2$, $212e_2$, and $212g_2$ of the wall parts 212a, 212c, 212e, and 212g may extend in the circumferential direction so as to be parallel to a horizontal plane, and may be inclined to the horizontal plane, in the circumferential direction. In particular, the upper ends of the second portions $212a_2$, $212c_2$, $212e_2$, and $212g_2$ may be inclined such that the heights thereof become larger toward the respective adjacent groove parts G210, G221, G230, and G241. In this case, when the projections $220c_1$, $220c_2$, $220c_3$ and $220c_4$ respectively placed on the upper ends of the second portions $212a_2$, $212c_2$, $212e_2$, and $212g_2$ move toward the groove parts G210, G221, G230, and G241, the projections $220c_1$, $220c_2$, $220c_3$ and $220c_4$ need to climb the slopes of the upper ends of the second portions $212a_2$, $212c_2$, $212e_2$, and $212g_2$. Thus, even if an impact or the like is applied from the outside to the applicator A9, the projections $220c_1$, $220c_2$, $220c_3$ and $220c_4$ can be prevented from unintentionally moving into the groove parts G210, G221, G230, and G241.

The microneedle array 30 and the conical coil spring 40 are the same as those in the first embodiment, and hence description thereof is omitted.

As illustrated in FIG. 41, the release member 250 is an open-end ring-like body. The release member 250 includes: a pair of arc-like parts 252 and 254 that extend along the outer circumferential surface of the main body part 212; and press parts 256 and 258 on which a user performs a pressing operation. The material of the release member 250 may be the same as the material of the casing 210, and may be the same as the material of the microneedle array 30. The material of the release member 250 may be flexible or elastic materials.

The arc-like part 252 is a belt-like plate member that extends along the outer circumferential surface of the wall part 212c of the main body part 212. A projection 252a that protrudes downward is provided at the lower end edge of the arc-like part 252. In the completed state of the applicator A9, the projection 252a is inserted through the through-hole 216e of the flange part 216. As a result, the arc-like part 252 is attached to the flange part 216, so that the release member 250 is positioned with respect to the casing 210.

The arc-like part 252 is provided with a cutout part 252b at a position corresponding to the groove part 212k of the main body part 212. Specifically, the cutout part 252b is located in the upper end part of the arc-like part 252, is concaved downward, and is opened upward. The groove part 212k is exposed to the outside through the cutout part 252b.

The arc-like part 254 is a belt-like plate member that extends along the outer circumferential surface of the wall part 212g of the main body part 212. A projection 254a that protrudes downward is provided at the lower end edge of the arc-like part 254. In the completed state of the applicator A9, the projection 254a is inserted through the through-hole 216f of the flange part 216. As a result, the arc-like part 254 is attached to the flange part 216, so that the release member 250 is positioned with respect to the casing 210.

The arc-like part 254 is provided with a cutout part 254b at a position corresponding to the groove part 212l of the main body part 212. Specifically, the cutout part 254b is located in the upper end part of the arc-like part 254, is concaved downward, and is opened upward. The groove part 212l is exposed to the outside through the cutout part 254b.

The press part 256 is a plate-like body having a C shape. The press part 256 includes: first to third portions $256a_1$, $256a_2$ and $256a_3$ each having a linear shape; and bend parts $256a_4$ and $256a_5$. One end of the first portion $256a_1$ is connected to one end of the second portion $256a_2$ with the intermediation of the bend part $256a_4$, and the other end of the first portion $256a_1$ is connected to one end of the third portion $256a_3$ with the intermediation of the bend part $256a_5$. The other end of the second portion $256a_2$ (one end of the press part 256) is integrally connected to one end of the arc-like part 252, and the other end of the third portion $256a_3$ (the other end of the press part 256) is integrally connected to one end of the arc-like part 254.

A grip member 256b to be gripped by the user is provided on the outer surface of the first portion $256a_1$. The grip member 256b has a block-like shape. A surface of the side surfaces of the grip member 256b is stepped, the surface being parallel to the first portion $256a_1$. A protrusion part 256c that protrudes inward (toward the main body part 212) is provided on the inner surface of the first portion $256a_1$. The protrusion part 256c is a plate-like body having a triangular shape when viewed from above. In the completed state of the applicator A9, the oblique side of the protrusion part 256c faces the cutout part 212i of the main body part 212, and the height thereof is larger from the bend part $256a_5$ toward the bend part $256a_4$.

The first portion $256a_1$ can take a first state and a second state. In the first state, a pressing force is not exerted on the grip member 256b, and the release member 250 is not deformed. The second state is a state after a pressing force is exerted on the grip member 256b and the release member 250 is thus deformed. In the second state after the deformation, the first portion $256a_1$ approaches the second and third portions $256a_2$ and $256a_3$, and the bend parts $256a_4$ and $256a_5$ are further bent. Thus, in the second state after the deformation, the first portion $256a_1$ comes close to the main body part 212, and the protrusion part 256c passes through the cutout part 212i of the main body part 212 to be inserted in the main body part 212.

The press part 258 is a plate-like body having a C shape. The press part 258 includes: first to third portions $258a_1$, $258a_2$ and $258a_3$ each having a linear shape; and bend parts $258a_4$ and $258a_5$. One end of the first portion $258a_1$ is connected to one end of the second portion $258a_2$ with the intermediation of the bend part $258a_4$, and the other end of the first portion $258a_1$ is connected to one end of the third portion $258a_3$ with the intermediation of the bend part $258a_5$. The other end of the second portion $258a_2$ (one end of the press part 258) is integrally connected to the other end of the arc-like part 252, and the other end of the third portion $258a_3$ (the other end of the press part 258) is integrally connected to the other end of the arc-like part 254.

A grip member 258b to be gripped by the user is provided on the outer surface of the first portion $258a_1$. The grip member 258b has a block-like shape. A surface of the side surfaces of the grip member 258b is stepped, the surface being parallel to the first portion $258a_1$. A protrusion part 258c that protrudes inward (toward the main body part 212) is provided on the inner surface of the first portion $258a_1$. The protrusion part 258c is a plate-like body having a triangular shape when viewed from above. In the completed state of the applicator A9, the oblique side of the protrusion part 258c faces the cutout part 212j of the main body part 212, and the height thereof is larger from the bend part $258a_4$ toward the bend part $258a_5$.

The first portion $258a_1$ can take a first state and a second state. In the first state, a pressing force is not exerted on the grip member 258b, and the release member 250 is not deformed. The second state is a state after a pressing force is exerted on the grip member 258b and the release member 250 is thus deformed. In the second state after the deformation, the first portion $258a_1$ approaches the second and third portions $258a_2$ and $258a_3$, and the bend parts $258a_4$ and $258a_5$ are further bent. Thus, in the second state after the deformation, the first portion $258a_1$ comes close to the main body part 212, and the protrusion part 258c passes through the cutout part 212j of the main body part 212 to be inserted in the main body part 212.

The stopper 260 includes: a base part 262 having a disc-like shape; a pair of hooks 264a and 264b; a pair of stopper members 266a and 266b; and a knob part 268. The base part 262 is arranged on the cover part 214 of the casing 210.

The pair of hooks 264a and 264b are provided in a protruding manner on the lower surface of the base part 262 so as to be point-symmetrical with respect to the central axis of the base part 262. The pair of hooks 264a and 264b each have a leading end bent inward, and have an L shape. In the completed state of the applicator A9, the leading end of the hook 264a is engaged with the groove part 212k of the main body part 212, and the leading end of the hook 264b is engaged with the groove part 212l of the main body part 212. The widths of the hooks 264a and 264b in the circumferential direction of the base part 262 are smaller than the widths of the groove parts 212k and 212l in the circumferential direction of the main body part 212. Thus, the hooks 264a and 264b are respectively movable in the circumferential direction inside of the groove parts 212k and 212l. As the hooks 264a and 264b respectively move inside of the groove parts 212k and 212l, the stopper 260 turns around the central axis of the base part 262 (main body part 212).

The pair of stopper members 266a and 266b are provided in a protruding manner in the periphery of the base part 262 so as to be point-symmetrical with respect to the central axis of the base part 262. The pair of stopper members 266a and 266b are located between the pair of hooks 264a and 264b in the circumferential direction of the base part 262. The pair of stopper members 266a and 266b extend outward from the periphery of the base part 262.

At a first position at which the hooks 264a and 264b are respectively located on one end sides of the groove parts 212k and 212l, the leading end of the stopper member 266a comes close to or abuts against the first portion $256a_1$ of the press part 256, and the leading end of the stopper member 266b comes close to or abuts against the first portion $258a_1$ of the press part 258. Thus, even if the press parts 256 and 258 are pressed, the stopper members 266a and 266b respectively prevent the press parts 256 and 258 (first portions $256a_1$ and $258a_1$) from approaching the casing 210 (main body part 212), and the first state of the release member 250 is maintained. In contrast, at a second position at which the hooks 264a and 264b are respectively located on the other end sides of the groove parts 212k and 212l, the leading end of the stopper member 266a is spaced apart from the first portion $256a_1$ of the press part 256, and the leading end of the stopper member 266b is spaced apart from the first portion $258a_1$ of the press part 258. Thus, if the press parts 256 and 258 are pressed, the stopper members 266a and 266b do not prevent the press parts 256 and 258 (first portions $256a_1$ and $258a_1$) from approaching the casing 210 (main body part 212), and the release member 250 is deformed into the second state.

The knob part 268 is provided on the upper surface of the base part 262. In the ninth embodiment, the knob part 268 is formed of three elongated protrusions that radially extend from the central axis of the base part 262, but may have other configurations as long as the user can catch the knob part 268 with user's fingers to turn the stopper 260. For example, the knob part 268 may be one or more elongated protrusions, may be one or more concave parts provided on the upper surface of the base part 262, may be one or more through-holes that pass through the base part 262, and may be combinations thereof.

It is desirable that the applicator A9 have a shape that enables easy hold and enables easy application (easy puncture) of the microneedles 32 to the skin of the animal (including a human). Thus, a recess or a step may be provided on the surface of the release member 250 or the surface of the stopper 260. A fine groove may be formed on the surface of the release member 250 or the surface of the stopper 260, or a non-slippery coating layer may be provided thereon, whereby the surfaces thereof may be roughened. A through-hole may be formed in the casing 210, the release member 250, or the stopper 260 for the purpose of reducing the air resistance and the weight.

[9.2] Method of Manufacturing Applicator

Now, the method of manufacturing the applicator A9 is described. First, the piston plate 220 is placed in the main body part 212 through procedures similar to the first, fourth, and third steps in the method of manufacturing the applicator A1 according to the first embodiment, which are performed in the stated order (see FIG. 44).

Figure 44:
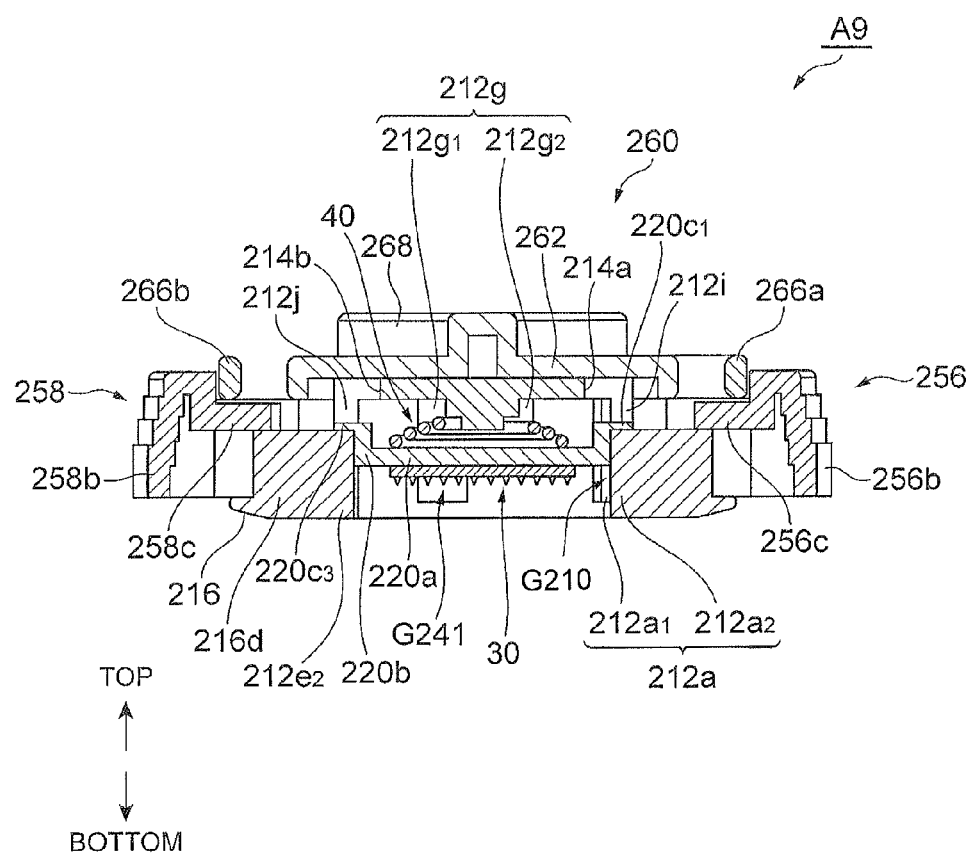
FIG. 44 is a cross sectional view illustrating a state before an operation of the applicator according to the ninth embodiment.

On this occasion, because the projections $220c_1$, $220c_2$, $220c_3$ and $220c_4$ are respectively placed on the second portions $212a_2$, $212c_2$, $212e_2$, and $212g_2$ of the wall parts 212a, 212c, 212e, and 212g, even if the cover part 214 and the piston plate 220 compress the conical coil spring 40, the piston plate 220 is not pushed out in the bottom direction by the conical coil spring 40. That is, the piston plate 220 is locked with the casing 210 (main body part 212). Accordingly, as illustrated in FIG. 44, the piston plate 220 is held at its retraction position on the cover part 214 side inside of the main body part 212, in the state where the cover part 214 and the piston plate 220 compress the conical coil spring 40. Such a state as described above where the piston plate 220 is locked with the casing 210 (main body part 212) and where the cover part 214 and the piston plate 220 compress the conical coil spring 40 is hereinafter referred to as "locked state".

Locking the piston plate 220 with the casing 210 (main body part 212) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the piston plate 220 and the cover part 214 becomes slightly larger than the wire diameter, in the state where the piston plate 220 is locked (cocked) with the casing 210 (see FIG. 44). Note that, depending on the configuration of the piston plate 220, the piston plate 220 can come extremely close to the cover part 214, and the height of the conical coil spring 40 sandwiched between the piston plate 220 and the cover part 214 can become equivalent to the wire diameter, in the state where the piston plate 220 is locked (cocked) with the casing 210.

Subsequently, the release member 250 is attached to the casing 210 (main body part 212) such that the projections 252a and 254a are respectively inserted through the through-holes 216e and 216f. Subsequently, the hooks 264a and 264b are respectively engaged with the groove parts 212k and 212l, and the stopper 260 is thus attached to the casing 210 (main body part 212) such that the hooks 264a and 264b are respectively located on one end sides of the groove parts 212k and 212l.

Through the above-mentioned procedures, assembling of the applicator A9 is completed. Accordingly, the conical coil spring 40 remains in a compressed state until the applicator A9 is used by a user after manufacture and shipping thereof. Further, the stopper members 266a and 266b respectively prevent the press parts 256 and 258 (first portions $256a_1$ and $258a_1$) from approaching the casing 210 (main body part 212), and hence the first state of the release member 250 is maintained (see FIG. 38) until the applicator A9 is used by the user after manufacture and shipping thereof. That is, the stopper members 266a and 266b prevent the protrusion part 256c from coming into contact with the projection $220c_1$, and prevent the protrusion part 258c from coming into contact with the projection $220c_3$.

[9.3] Method of Using Applicator

Figure 45:
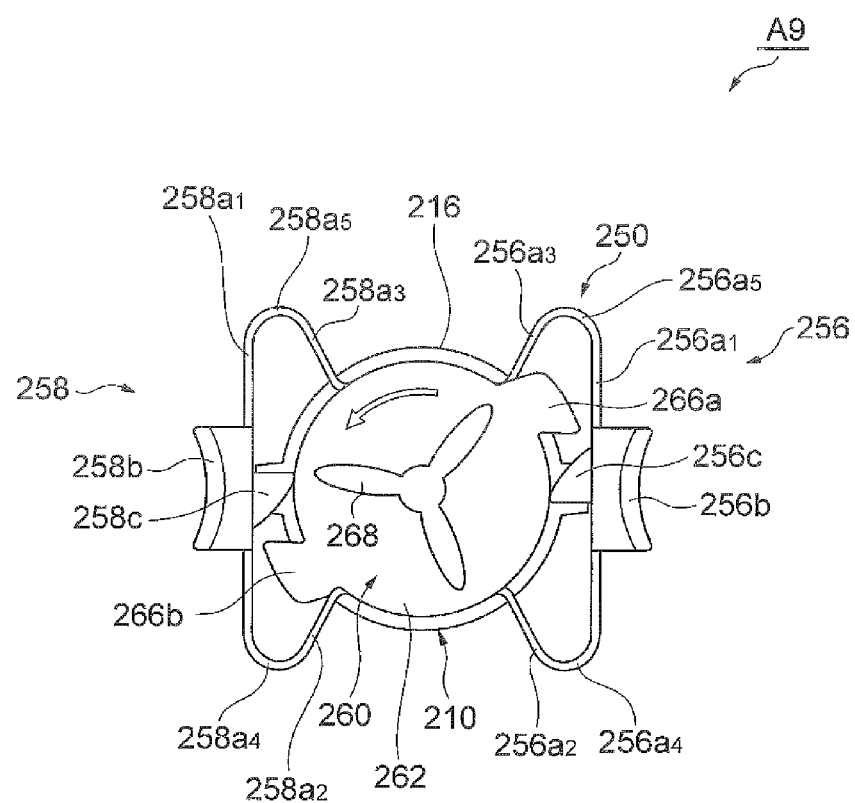
FIG. 45 is a top view of the applicator according to the ninth embodiment, for describing a turning state of a stopper.
Figure 46:
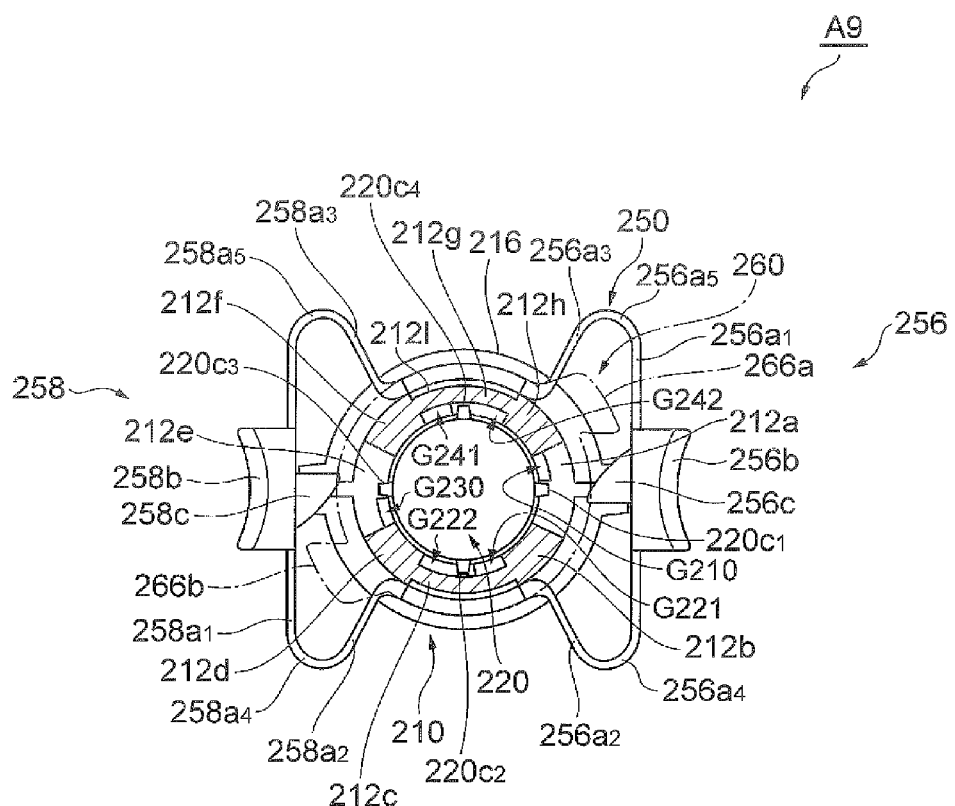
FIG. 46 is a top view illustrating the state before the operation of the applicator according to the ninth embodiment, in which the stopper and the cover part of the casing are cut away.

Now, the method of using the applicator A9 is described. First, the hooks 264a and 264b are respectively moved to the other end sides of the groove parts 212k and 212l by pinching the knob part 268 and turning the stopper 260 (see FIG. 45). This enables the press parts 256 and 258 to move toward the casing 210 (main body part 212). At this time, as illustrated in FIG. 46, the oblique side of the protrusion part 256c is opposed to the projection $220c_1$, and the oblique side of the protrusion part 258c is opposed to the projection $220c_3$.

Figure 47:
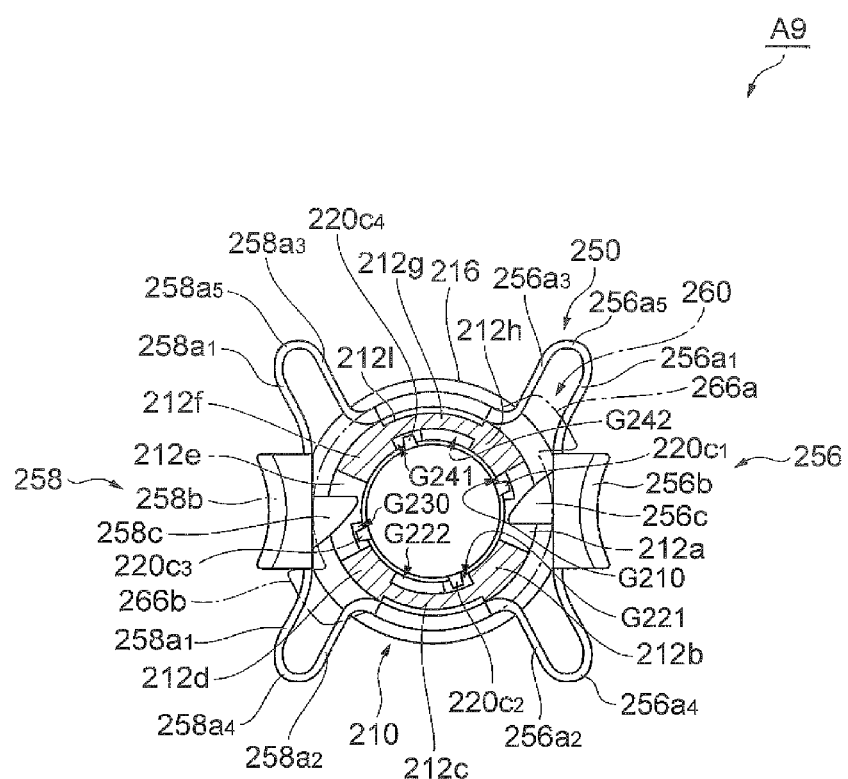
FIG. 47 is a top view illustrating a state during the operation of the applicator according to the ninth embodiment, in which the stopper and the cover part of the casing are cut away.

Subsequently, the applicator A9 is positioned with respect to a portion of a skin to which a medical agent or the like is desired to be applied, such that the microneedles 32 face the skin. The press parts 256 and 258 are pushed toward the casing 210 (main body part 212) while the applicator A9 is kept positioned. Consequently, the oblique side of the protrusion part 256c abuts against the projection $220c_1$, and the oblique side of the protrusion part 258c abuts against the projection $220c_3$. If the press parts 256 and 258 are further pushed toward the casing 210 (main body part 212), the projection $220c_1$ is pushed out in the direction normal to the oblique side of the protrusion part 256c while sliding on the oblique side thereof, and the projection $220c_3$ is pushed out in the direction normal to the oblique side of the protrusion part 258c while sliding on the oblique side thereof. Consequently, as illustrated in FIG. 47, a turning force is exerted on the piston plate 220, with the result that the piston plate 220 turns. Accordingly, the locking (cocking) of the piston plate 220 with the casing 210 (main body part 212) is released. After that, similarly to the applicator A1 according to the first embodiment, the microneedle array 30 collides against the skin due to the biasing force (elastic force) of the conical coil spring 40 (see FIG. 40).

[9.4] Actions

The ninth embodiment as described above produces actions and effects similar to the actions (A) to (D) of the applicator A1 according to the first embodiment.

In the applicator A9 according to the ninth embodiment, the stopper members 266a and 266b of the stopper 260 restrict the drive of the release member 250 (press parts 256 and 258), to thereby prevent the press parts 256 and 258 from passing through the cutout parts 212i and 212j and coming into contact with the projections $220c_1$, $220c_2$, $220c_3$ to $220c_4$ in the locked state. Thus, the stopper 260 can prevent the applicator A9 from malfunctioning. Further, at the time of use, it is only necessary to turn the stopper 260, and hence preparation for the use can be completed through a simple operation.

[10] Tenth Embodiment

[10.1] Configuration of Applicator

Now, a configuration of an applicator A10 according to a tenth embodiment is described with reference to FIG. 48 to FIG. 50. In the following description, the term "top" corresponds to the top direction of FIG. 48 to FIG. 50, and the term "bottom" corresponds to the bottom direction of FIG. 48 to FIG. 50. That is, the top-bottom direction corresponds to the height direction of the applicator A10.

The applicator A10 is a device for transferring active ingredients of a medical agent or the like into the body of an animal such as a human through a skin of the animal. The applicator A10 includes a casing 310, a piston plate 320, the microneedle array 30, the conical coil spring 40, and a release member 350.

Figure 48:
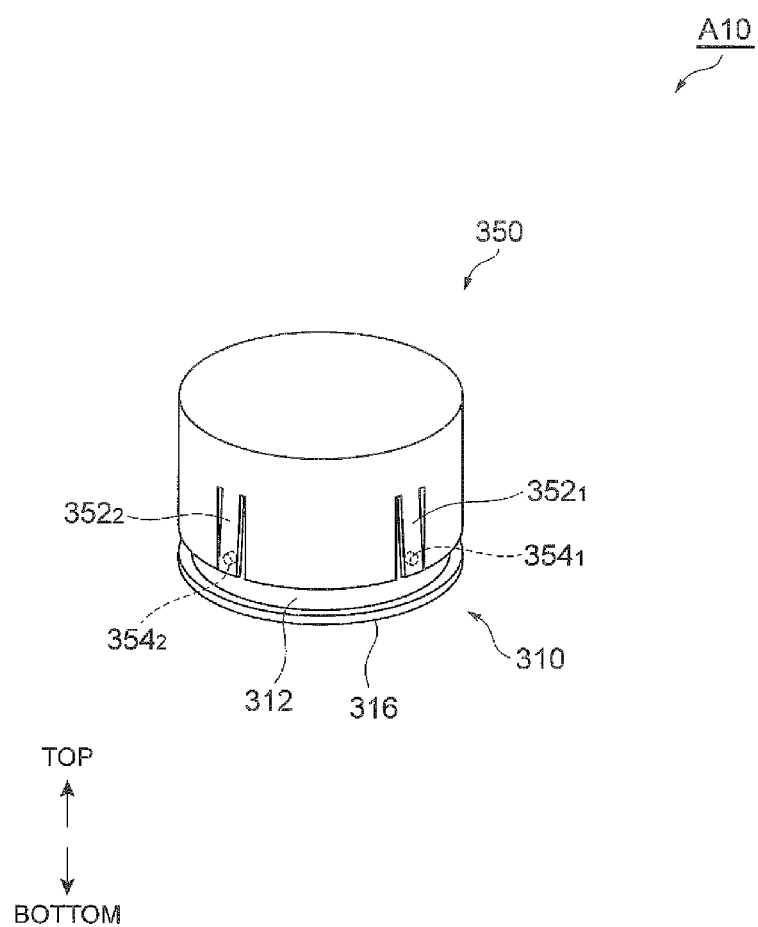
FIG. 48 is a perspective view illustrating a state after an operation of an applicator according to a tenth embodiment.
Figure 49:
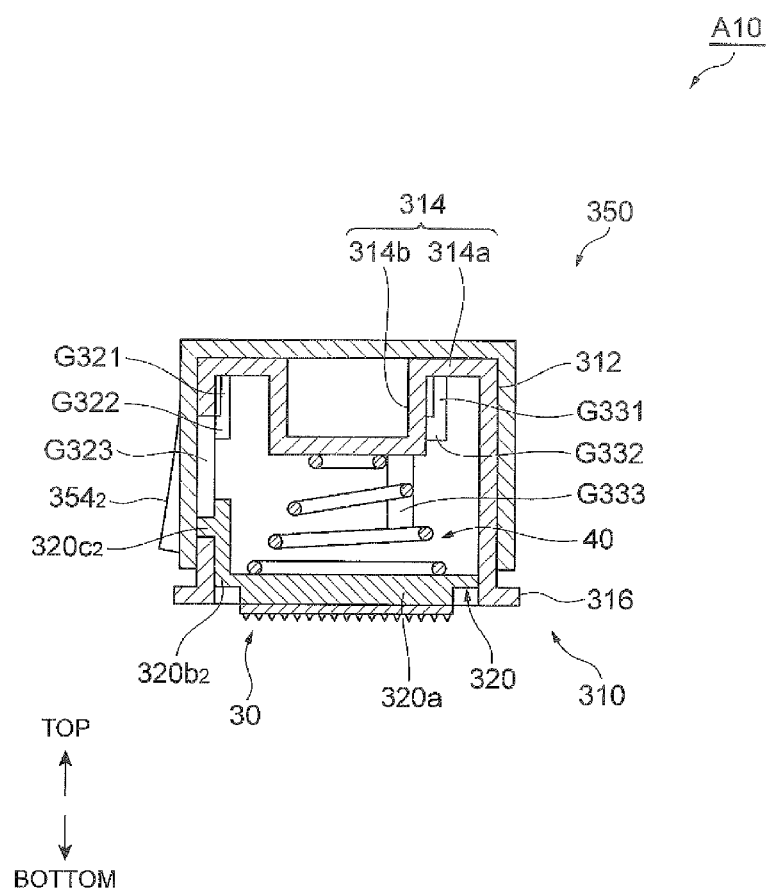
FIG. 49 is a cross sectional view illustrating the state after the operation of the applicator according to the tenth embodiment.
Figure 50:
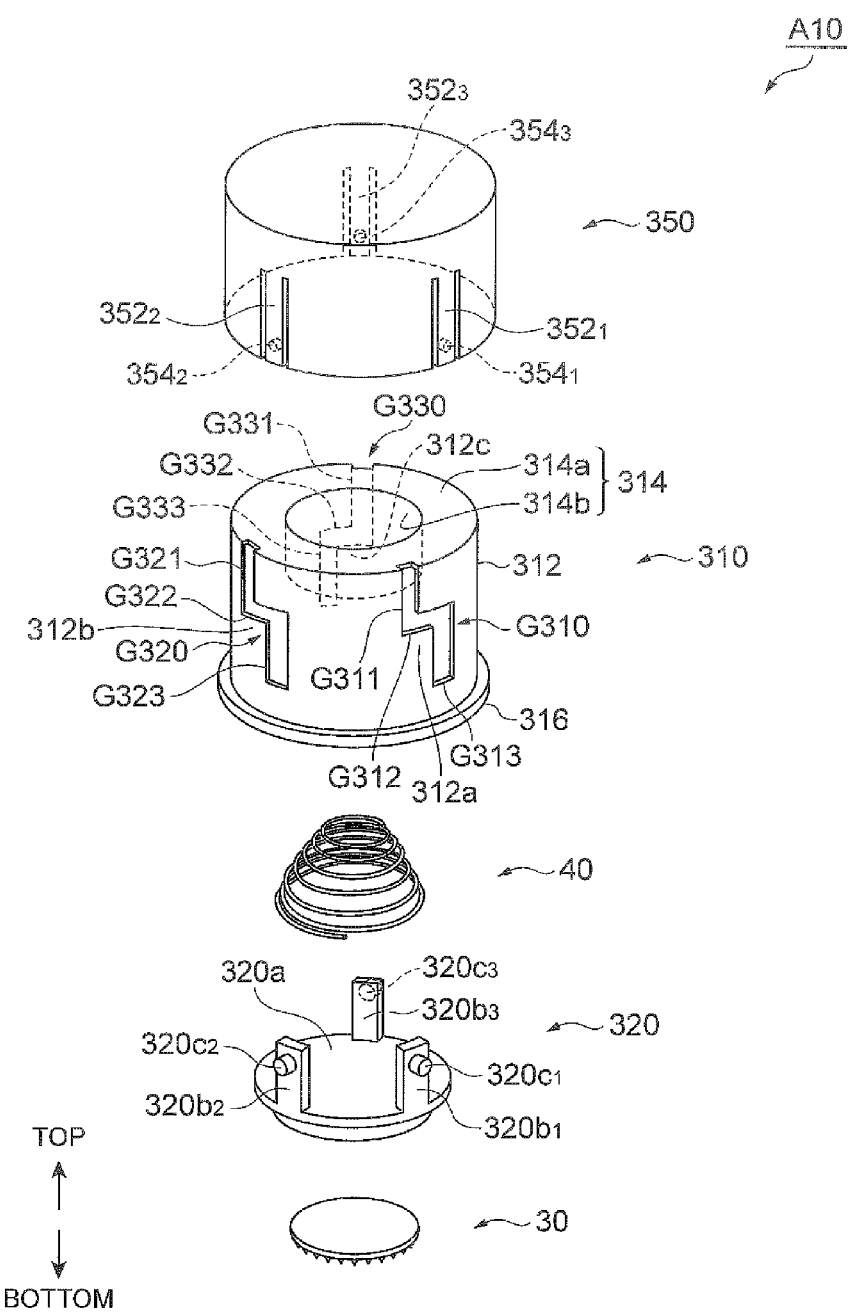
FIG. 50 is an exploded perspective view of the applicator according to the tenth embodiment.

As illustrated in FIG. 48 to FIG. 50, the casing 310 includes: a main body part 312 that has a cylindrical shape and has a central axis that extends along the top-bottom direction; a cover part 314 arranged on the upper end side of the main body part 312; and a circular ring-like flange part 316 arranged on the lower end side of the main body part 312. The strength and the material of the casing 310 may be the same as those of the casing 10 of the applicator A1 according to the first embodiment.

Three groove bodies G310, G320 and G330 are formed in the circumferential surface of the main body part 312. The groove bodies G310, G320 and G330 pass through the main body part 312 in the thickness direction thereof, and communicate the inside and the outside of the main body part 312 with each other. The groove bodies G310, G320 and G330 are arranged in the stated order in the clockwise direction when viewed from above, with given intervals in the circumferential direction.

The groove body G310 includes first to third portions G311, G312 and G313. The first portion G311 extends in the top-bottom direction from the upper end of the main body part 312 to the vicinity of the center thereof. The second portion G312 extends in the horizontal direction (circumferential direction). One end of the second portion G312 is communicated with the lower end of the first portion G311. The other of the second portion G312 extends toward the groove body G330. The third portion G313 extends in the top-bottom direction. The upper end of the third portion G313 is communicated with the the other end of the second portion G312. The lower end of the third portion G313 extends toward the vicinity of the lower end of the main body part 312. That is, the groove body G310 has a crank-like shape.

A projection $354_1$ of the release member 350 is inserted in the first portion G311, and the projection $354_1$ is guided along the first portion G311. A projection $320c_1$ of the piston plate 320 is inserted in the second and third portions G312 and G313, and the projection $320c_1$ is guided along the second and third portions G312 and G313. The width of the first portion G311 may be equivalent to the widths of the second and third portions G312 and G313, and may be larger or smaller than the widths of the second and third portions G312 and G313.

The groove body G320 includes first to third portions G321, G322 and G323. The first portion G321 extends in the top-bottom direction from the upper end of the main body part 312 to the vicinity of the center thereof. The second portion G322 extends in the horizontal direction (circumferential direction). One end of the second portion G322 is communicated with the lower end of the first portion G321. The other end of the second portion G322 extends toward the groove body G310. The third portion G323 extends in the top-bottom direction. The upper end of the third portion G323 is communicated with the the other end of the second portion G322. The lower end of the third portion G323 extends toward the vicinity of the lower end of the main body part 312. That is, the groove body G320 has a crank-like shape.

A projection $354_2$ of the release member 350 is inserted in the first portion G321, and the projection $354_2$ is guided along the first portion G321. A projection $320c_2$ of the piston plate 320 is inserted in the second and third portions G322 and G323, and the projection $320c_2$ is guided along the second and third portions G322 and G323. The width of the first portion G321 may be equivalent to the widths of the second and third portions G322 and G323, and may be larger or smaller than the widths of the second and third portions G322 and G323.

The groove body G330 includes first to third portions G331, G332 and G333. The first portion G331 extends in the top-bottom direction from the upper end of the main body part 312 to the vicinity of the center thereof. The second portion G332 extends in the horizontal direction (circumferential direction). One end of the second portion G332 is communicated with the lower end of the first portion G331. The other end of the second portion G332 extends toward the groove body G320. The third portion G333 extends in the top-bottom direction. The upper end of the third portion G333 is communicated with the other end of the second portion G332. The lower end of the third portion G333 extends toward the vicinity of the lower end of the main body part 312. That is, the groove body G330 has a crank-like shape.

A projection $354_3$ of the release member 350 is inserted in the first portion G331, and the projection $354_3$ is guided along the first portion G331. A projection $320c_3$ of the piston plate 320 is inserted in the second and third portions G332 and G333, and the projection $320c_3$ is guided along the second and third portions G332 and G333. The width of the first portion G331 may be equivalent to the widths of the second and third portions G332 and G333, and may be larger or smaller than the widths of the second and third portions G332 and G333.

The cover part 314 includes: a first portion 314a having a circular ring-like shape; and a second portion 314b having a bottomed cylindrical shape. The outer edge of the first portion 314a is integrated with the upper end of the main body part 312. The opened end (upper end) of the second portion 314b is integrated with the inner edge of the first portion 314a. The second portion 314b is arranged at a position lower than that of the first portion 314a. Thus, the bottom plate of the second portion 314b is located inside of the main body part 312.

The flange part 316 protrudes outward from the outer circumferential surface of the main body part 312. At the time of using the applicator A10, the flange part 316 makes the contact area with the skin larger, and hence a pressure applied to the skin can be made smaller.

The piston plate 320 is housed in the main body part 312, and is movable in the top-bottom direction along the central axis of the main body part 312 inside of the main body part 312. The material of the piston plate 320 may be the same as the material of the casing 310, and may be the same as the material of the microneedle array 30. As illustrated in FIG. 50, the piston plate 320 includes: a disc-like main body 320a; plate-like members $320b_1$, $320b_2$ and $320b_3$ that extend upward from the periphery of the upper surface of the main body 320a; and the projections $320c_1$, $320c_2$ and $320c_3$ that are respectively provided in the leading end parts (upper end parts) of the plate-like members $320b_1$, $320b_2$ and $320b_3$.

An opening, a groove, a through-hole, or the like may be formed in the main body 320a for the purpose of reducing the air resistance and the weight of the piston plate 320. Further, an elongated protrusion or the like may be provided on the upper surface (the surface on which the conical coil spring 40 is arranged) of the main body 320a for the purpose of improving the rigidity of the piston plate 320. It is preferable that the lower surface (the surface opposite to the upper surface) of the main body 320a be planar, in consideration of causing the piston plate 320 to evenly act on the microneedle array 30. Alternatively, the lower surface of the main body 320a may have other shapes than the planar shape, and the shape of the lower surface of the main body 320a can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The plate-like members $320b_1$, $320b_2$ and $320b_3$ each have a rectangular shape. The plate-like members $320b_1$, $320b_2$ and $320b_3$ are arranged in the stated order in the clockwise direction when viewed from above, with given intervals in the circumferential direction. The diameter of a virtual circle that is circumscribed on the plate-like members $320b_1$, $320b_2$ and $320b_3$ when viewed from above is set to be larger than the maximum diameter D1 of the conical coil spring 40. Thus, the plate-like members $320b_1$, $320b_2$ and $320b_3$ function as such a stopper that prevents the conical coil spring 40 from dropping off the piston plate 320 during its movement in the radial direction. The heights of the plate-like members $320b_1$, $320b_2$ and $320b_3$ may be changed as appropriate in accordance with the design of the applicator A10. For example, in the case where the height of the applicator A10 is desired to be minimized, the heights of the plate-like members $320b_1$, $320b_2$ and $320b_3$ can be set to be equivalent to the thickness of a metal wire that forms the conical coil spring 40. Note that, if a ring-like groove in which the metal wire that forms the conical coil spring 40 can be fit is formed in the main body 320a, the function as the stopper for the conical coil spring 40 can be fulfilled by the ring-like groove. In the case where such a stopper for the conical coil spring 40 is provided, a failure in positioning of the conical coil spring 40 with respect to the piston plate 320 can be prevented at the time of arranging the conical coil spring 40 on the upper surface of the piston plate 320 and attaching the two to the inside of the casing 310.

The projections $320c_1$, $320c_2$ and $320c_3$ each protrude outward in the radial direction (the direction that intersects with the thickness direction of the piston plate). In the tenth embodiment, the projections $320c_1$, $320c_2$ and $320c_3$ each have a columnar shape. Alternatively, the projections $320c_1$, $320c_2$ and $320c_3$ may have other shapes (for example, a polygonal prism shape, a deformed pillar shape, a circular cone shape, a polygonal pyramid shape, a truncated circular cone shape, and a truncated polygonal pyramid shape) as long as the projections $320c_1$, $320c_2$ and $320c_3$ are movable in the circumferential direction when being pushed by the projections $354_1$, $354_2$ and $354_3$ of the release member 350 to be described later.

The projection $320c_1$ is movable in the horizontal direction (circumferential direction) along the second portion G312 that extends in the horizontal direction (circumferential direction), and is movable in the top-bottom direction along the third portion G313 that extends in the top-bottom direction. That is, in the state where the projection $320c_1$ is located on the upper end side of the third portion G313, the projection $320c_1$ is movable in the horizontal direction above a wall part $312a$ of the main body part 312, the wall part $312a$ forming the second portion G312. Thus, the projection $320c_1$ can be placed on the wall part $312a$ adjacent to the third portion G313.

The projection $320c_2$ is movable in the horizontal direction (circumferential direction) along the second portion G322 that extends in the horizontal direction (circumferential direction), and is movable in the top-bottom direction along the third portion G323 that extends in the top-bottom direction. That is, in the state where the projection $320c_2$ is located on the upper end side of the third portion G323, the projection $320c_2$ is movable in the horizontal direction above a wall part $312b$ of the main body part 312, the wall part $312b$ forming the second portion G322. Thus, the projection $320c_2$ can be placed on the wall part $312b$ adjacent to the third portion G323.

The projection $320c_3$ is movable in the horizontal direction (circumferential direction) along the second portion G332 that extends in the horizontal direction (circumferential direction), and is movable in the top-bottom direction along the third portion G333 that extends in the top-bottom direction. That is, in the state where the projection $320c_3$ is located on the upper end side of the third portion G333, the projection $320c_3$ is movable in the horizontal direction above a wall part $312c$ of the main body part 312, the wall part $312c$ forming the second portion G332. Thus, the projection $320c_3$ can be placed on the wall part $312c$ adjacent to the third portion G333.

As described above, as the projections $320c_1$, $320c_2$ and $320c_3$ are guided inside of the second portions G312, G322 and G332, the piston plate 320 can be guided along the extending directions (circumferential directions) of the second portions G312, G322 and G332 (can be turned about the axis of the main body part 312). Further, as the projections $320c_1$, $320c_2$ and $320c_3$ are guided inside of the third portions G313 to G333, the piston plate 320 can be guided in the top-bottom direction along the extending directions of the third portions G313, G323 and G333 (the axial direction of the main body part 312).

The upper ends of the wall parts $312a$, $312b$ and $312c$ may extend in the circumferential direction so as to be parallel to a horizontal plane, and may be inclined to the horizontal plane, in the circumferential direction. In the tenth embodiment, the heights of the wall parts $312a$, $312b$ and $312c$ become larger toward the respective adjacent third portions G313, G323 and G333 (see FIG. 53). In this case, when the projections $320c_1$, $320c_2$ and $320c_3$ respectively placed on the upper ends of the wall parts $312a$, $312b$ and $312c$ move toward the third portions G313, G323 and G333, the projections $320c_1$, $320c_2$ and $320c_3$ need to climb the slopes of the upper ends of the wall parts $312a$, $312b$ and $312c$. Thus, even if an impact or the like is applied from the outside to the applicator A10, the projections $320c_1$, $320c_2$ and $320c_3$ can be prevented from unintentionally moving into the third portions G313, G323 and G333.

The microneedle array 30 and the conical coil spring 40 are the same as those in the first embodiment, and hence description thereof is omitted.

As illustrated in FIG. 48 to FIG. 50, the release member 350 has a bottomed cylindrical shape. A pair of slits that extend in the top-bottom direction are formed at three portions on the opened end side (lower end side) of the release member 350. The paired slits form cantilevered plate-like bodies $352_1$, $352_2$ and $352_3$ each having a rectangular shape.

The projections $354_1$, $354_2$ and $354_3$ that protrude inward in the radial direction (the direction that intersects with the thickness direction of the piston plate) are respectively provided on the leading end sides (lower end sides) of the plate-like bodies $352_1$, $352_2$ and $352_3$. In the tenth embodiment, the projections $354_1$, $354_2$ and $354_3$ each have a columnar shape. Alternatively, the projections $354_1$, $354_2$ and $354_3$ may have other shapes (for example, a polygonal prism shape, a deformed pillar shape, a circular cone shape, a polygonal pyramid shape, a truncated circular cone shape, and a truncated polygonal pyramid shape) as long as the projections $354_1$, $354_2$ and $354_3$ can push and move the projections $320c_1$, $320c_2$ and $320c_3$ of the piston plate 320 in the circumferential direction.

The projection $354_1$ is movable in the top-bottom direction along the first portion G311 that extends in the top-bottom direction. The projection $354_2$ is movable in the top-bottom direction along the first portion G321 that extends in the top-bottom direction. The projection $354_3$ is movable in the top-bottom direction along the first portion G331 that extends in the top-bottom direction. Accordingly, as the projections $354_1$, $354_2$ and $354_3$ are guided inside of the first portions G311, G321 and G331, the release member 350 can be guided in the top-bottom direction along the extending directions of the first portions G311, G321 and G331 (the axial direction of the main body part 312).

[10.2] Method of Manufacturing Applicator

Figure 51:
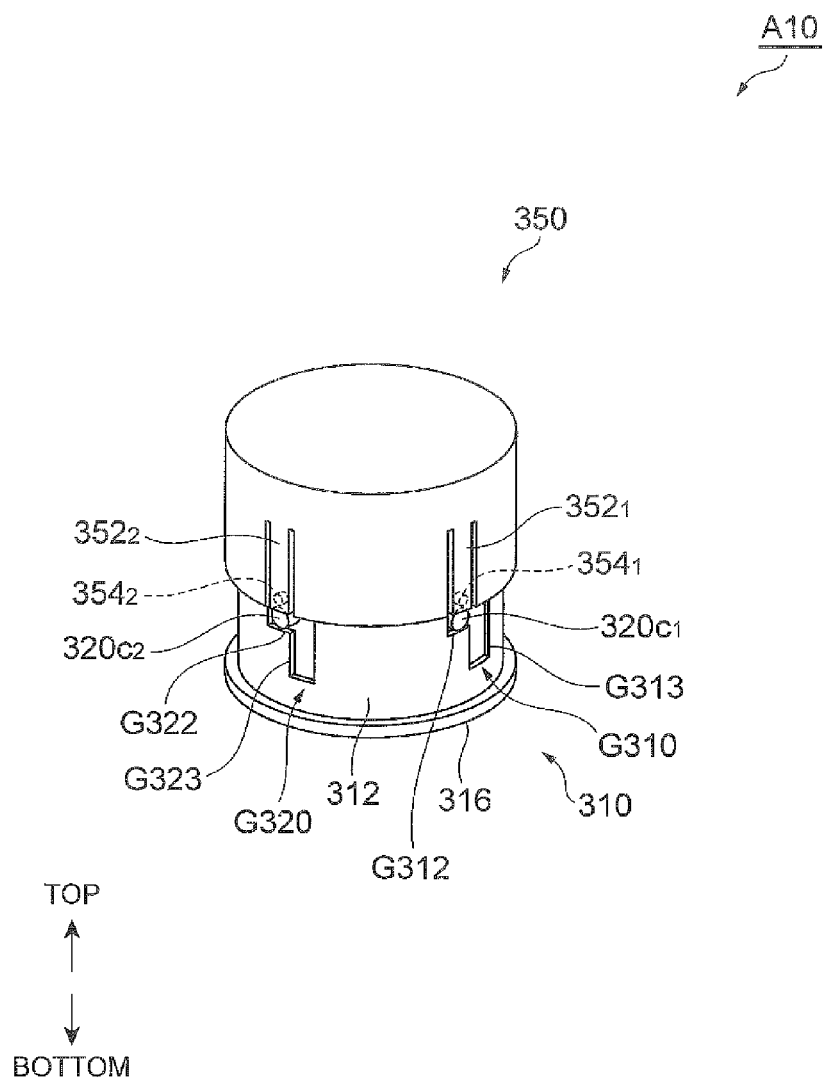
FIG. 51 is a perspective view illustrating a state before the operation of the applicator according to the tenth embodiment.

Now, the method of manufacturing the applicator A10 is described. First, the microneedle array 30 is attached to the lower surface of the piston plate 320, and the conical coil spring 40 is placed on the upper surface of the piston plate 320, through procedures similar to the first and fourth steps in the method of manufacturing the applicator A1 according to the first embodiment. Subsequently, the piston plate 320 is placed in the main body part 312 such that: the projection $320c_1$ of the piston plate 320 is located at the upper end of the wall part $312a$ and in a lower portion of the first portion G311; the projection $320c_2$ of the piston plate 320 is located at the upper end of the wall part $312b$ and in a lower portion of the first portion G321; and the projection $320c_3$ of the piston plate 320 is located at the upper end of the wall part $312c$ and in a lower portion of the first portion G331 (see FIG. 51 and FIG. 52).

Figure 52:
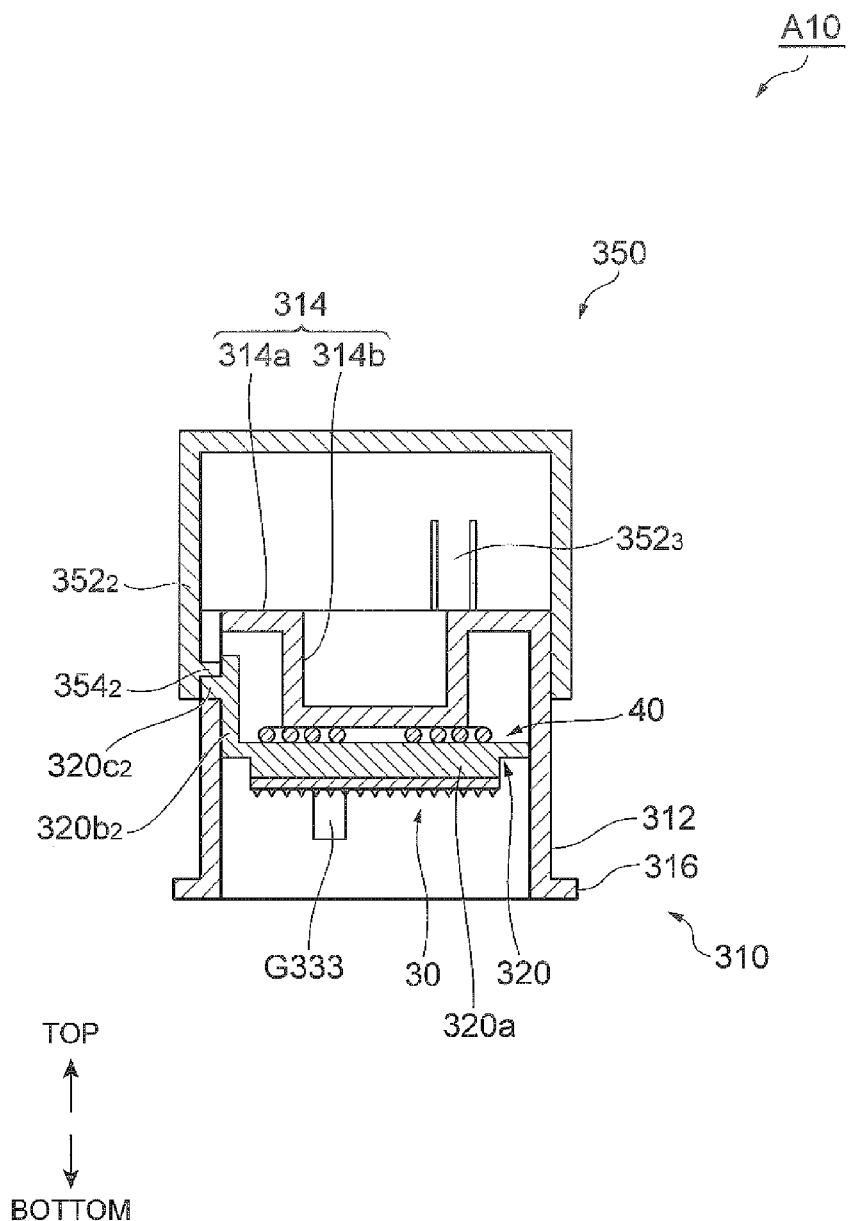
FIG. 52 is a cross sectional view illustrating the state before the operation of the applicator according to the tenth embodiment.

On this occasion, because the projections $320c_1$, $320c_2$ and $320c_3$ are respectively placed on the wall parts $312a$, $312b$ and $312c$, even if the second portion $314b$ of the cover part 314 and the piston plate 320 compress the conical coil spring 40, the piston plate 320 is not pushed out in the bottom direction by the conical coil spring 40. That is, the piston plate 320 is locked with the casing 310 (main body part 312). Accordingly, as illustrated in FIG. 52, the piston plate 320 is held at its retraction position on the cover part 314 side inside of the main body part 312, in the state where the second portion $314b$ of the cover part 314 and the piston plate 320 compress the conical coil spring 40. Such a state as described above where the piston plate 320 is locked with the casing 310 (main body part 312) and where the cover part 314 and the piston plate 320 compress the conical coil spring 40 is hereinafter referred to as "locked state".

Locking the piston plate 320 with the casing 310 (main body part 312) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the piston plate 320 and the second portion $314b$ of the cover part 314 becomes equivalent to the wire diameter, in the state where the piston plate 320 is locked (cocked) with the casing 310 (see FIG. 52).

Subsequently, the projections $354_1$, $354_2$ and $354_3$ are respectively arranged in the first portions G311, G321 and G331. As a result, the projections $354_1$, $354_2$ and $354_3$ respectively abut against the upper parts of the projections $320c_1$, $320c_2$ and $320c_3$ (see FIG. 51 and FIG. 52).

Through the above-mentioned procedures, assembling of the applicator A10 is completed. Accordingly, the conical coil spring 40 remains in a compressed state until the applicator A10 is used by a user after manufacture and shipping thereof.

[10.3] Method of Using Applicator

Now, the method of using the applicator A10 is described. First, the applicator A10 is positioned with respect to a portion of a skin to which a medical agent or the like is desired to be applied, such that the microneedles 32 face the skin. The release member 350 is pushed toward the casing 310 (cover part 314) while the applicator A10 is kept positioned. As a result, the projection $354_1$ is pushed against the projection $320c_1$ (see (a) of FIG. 53). Consequently, the projection $320c_1$ is pushed by the projection $354_1$, and thus moves in the horizontal direction (circumferential direction) along the second portion G312 so as to escape from the projection $354_1$ (see (b) of FIG. 53). Similarly, the projection $354_2$ is pushed against the projection $320c_2$. Consequently, the projection $320c_2$ is pushed by the projection $354_2$, and thus moves in the horizontal direction (circumferential direction) along the second portion G322 so as to escape from the projection $354_2$. Similarly, the projection $354_3$ is pushed against the projection $320c_3$. Consequently, the projection $320c_3$ is pushed by the projection $354_3$, and thus moves in the horizontal direction (circumferential direction) along the second portion G332 so as to escape from the projection $354_3$. In this way, a turning force is exerted on the piston plate 320, with the result that the piston plate 320 turns. Accordingly, the locking (cocking) of the piston plate 320 with the casing 310 (main body part 312) is released. After that, similarly to the applicator A1 according to the first embodiment, the microneedle array 30 collides against the skin due to the biasing force (elastic force) of the conical coil spring 40 (see FIG. 48 and FIG. 49). Note that, if the release member 350 is pushed until the release member 350 comes into contact with the first portion 314a of the casing 310, as illustrated in FIG. 48 and FIG. 49, the projections $354_1$, $354_2$ and $354_3$ respectively come out of the first portions G311, G321 and G331, and abut against the outer circumferential surface of the main body part 312, so that the plate-like bodies $352_1$, $352_2$ and $352_3$ are warped outward.

[10.4] Actions

The tenth embodiment as described above produces actions and effects similar to the actions (A) to (D) of the applicator A1 according to the first embodiment.

[11] Eleventh Embodiment

[11.1] Configuration of Applicator

Now, a configuration of an applicator A11 according to an eleventh embodiment is described with reference to FIG. 54 to FIG. 57. In the following description, the term "top" corresponds to the top direction of FIG. 54 to FIG. 56, and the term "bottom" corresponds to the bottom direction of FIG. 54 to FIG. 56. That is, the top-bottom direction corresponds to the height direction of the applicator A11.

The applicator A11 is a device for transferring active ingredients of a medical agent or the like into the body of an animal such as a human through a skin of the animal. The applicator A11 includes a casing 410, a piston plate 420, the microneedle array 30, the conical coil spring 40, and a release member 450.

Figure 54:
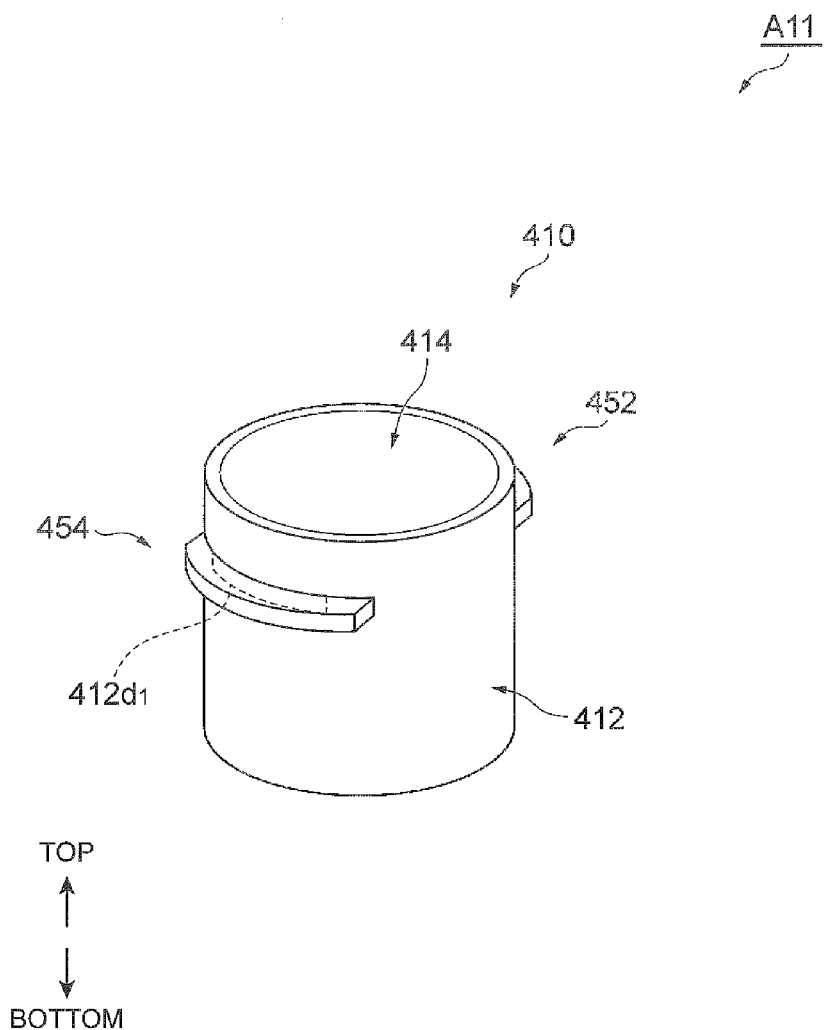
FIG. 54 is a perspective view illustrating a state after an operation of an applicator according to an eleventh embodiment.
Figure 55:
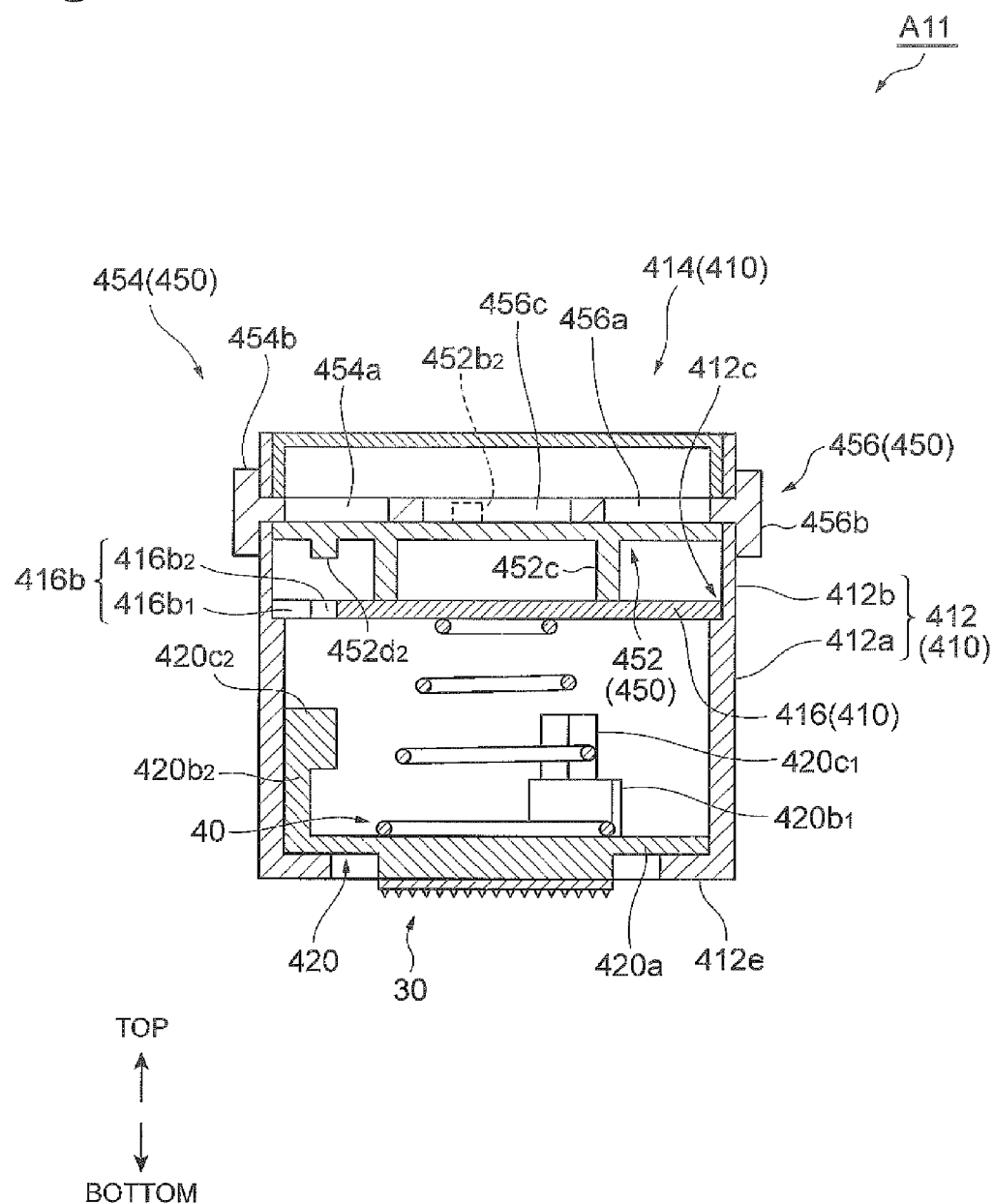
FIG. 55 is a cross sectional view illustrating the state after the operation of the applicator according to the eleventh embodiment.
Figure 56:
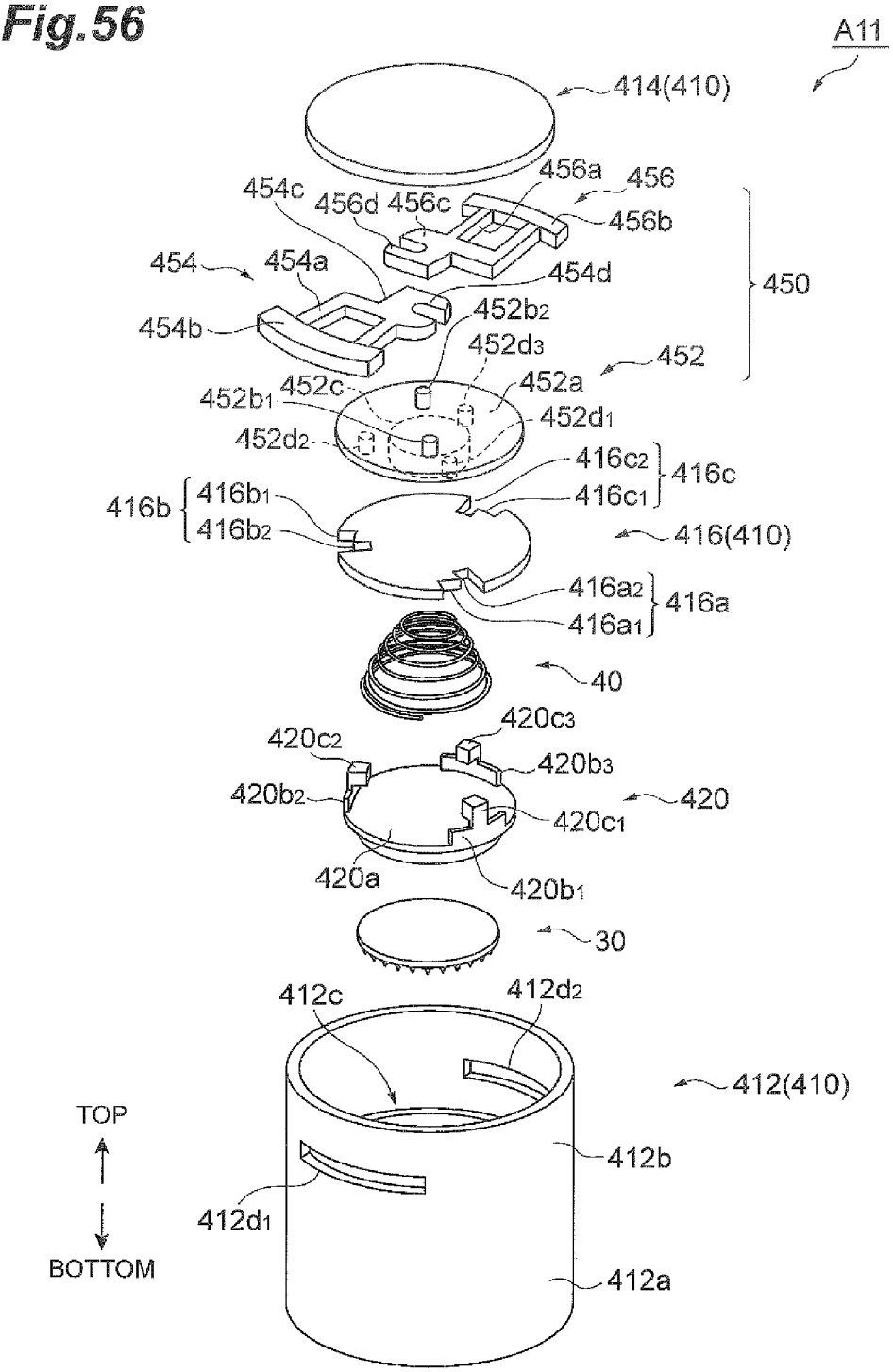
FIG. 56 is an exploded perspective view of the applicator according to the eleventh embodiment.
Figure 57:
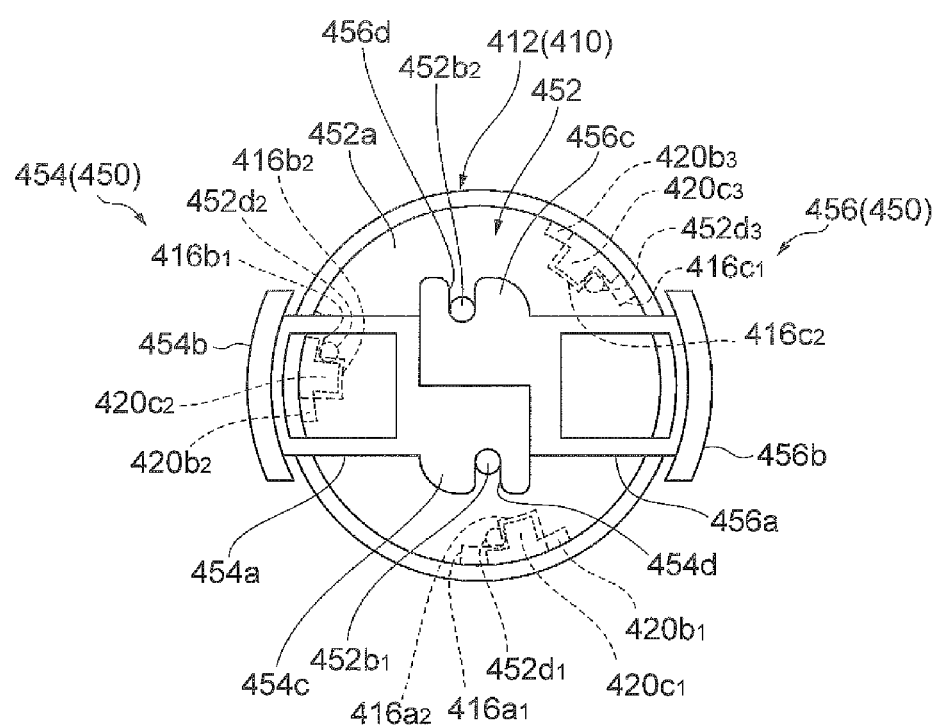
FIG. 57 is a top view illustrating the state after the operation of the applicator according to the eleventh embodiment, from which a cover part is detached.
Figure 58:
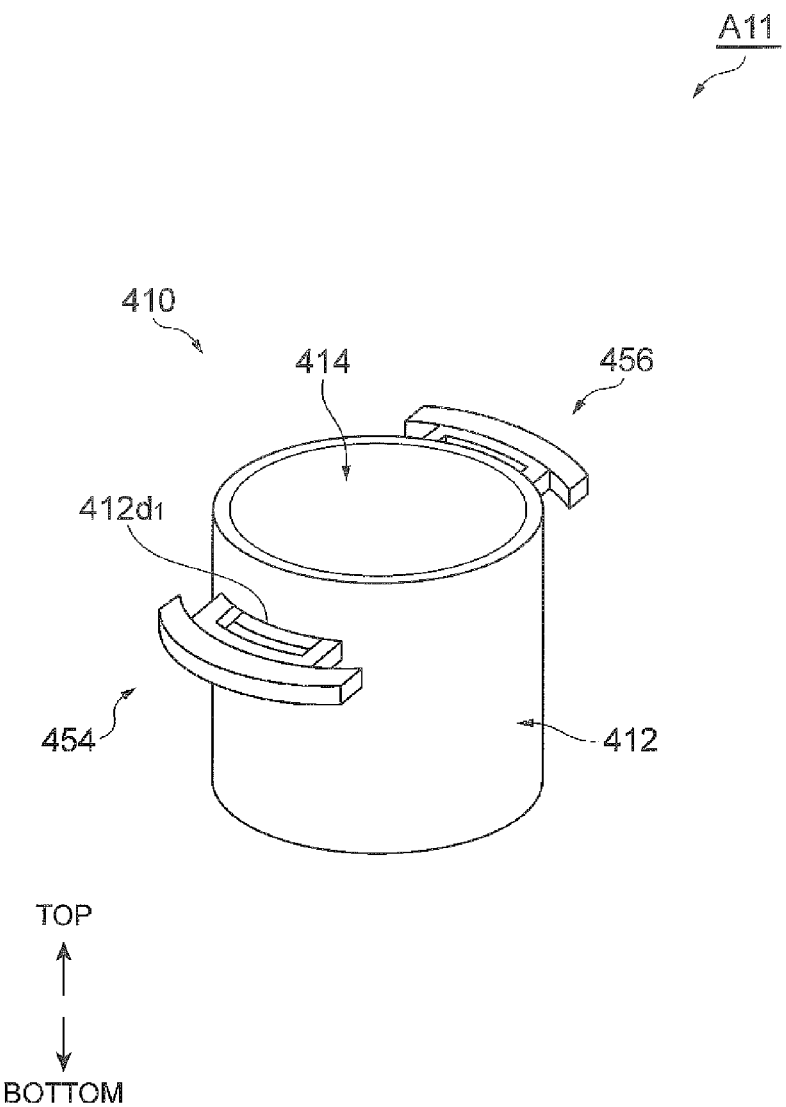
FIG. 58 is a perspective view illustrating a state before the operation of the applicator according to the eleventh embodiment.

As illustrated in FIG. 54 to FIG. 56, the casing 410 includes: a main body part 412 that has a cylindrical shape and has a central axis that extends along the top-bottom direction; an outer cover part 414 arranged on the upper end side of the main body part 412; and an inner cover part 416 arranged in the main body part 412. The strength and the material of the casing 410 may be the same as those of the casing 10 of the applicator A1 according to the first embodiment.

It is desirable that the applicator A11 have a shape that enables easy hold and enables easy application (easy puncture) of the microneedles 32 to the skin of the animal (including a human). Thus, the outer shape of the main body part 412 may be, for example, multangular or rounded. A recess or a step may be provided on the surface of the main body part 412. A fine groove may be formed on the surface of the main body part 412, or a non-slippery coating layer may be provided thereon, whereby the surface of the main body part 412 may be roughened. A through-hole may be formed in the main body part 412 for the purpose of reducing the air resistance and the weight.

The main body part 412 has a cylindrical shape. As illustrated in FIG. 55, the main body part 412 includes: a thick first portion 412a; and a second portion 412b thinner than the first portion 412a. The first portion 412a forms a lower part of the main body part 412, and the second portion 412b forms an upper part of the main body part 412. The upper end of the first portion 412a is integrated with the lower end of the second portion 412b. The inner diameter of the first portion 412a is set to be smaller than the inner diameter of the second portion 412b. Thus, a boundary portion between the first portion 412a and the second portion 412b forms a step part 412c.

A pair of groove parts $412d_1$ and $412d_2$ are formed in the circumferential surface of the main body part 412. The groove parts $412d_1$ and $412d_2$ pass through the main body part 412 in the thickness direction thereof, and communicate the inside and the outside of the main body part 412 with each other. The groove parts $412d_1$ and $412d_2$ are located closer to the upper end of the main body part 412, and linearly extend along the circumferential direction of the main body part 412. The groove parts $412d_1$ and $412d_2$ are opposed to each other with the axis of the main body part 412 being centered therebetween, when viewed from above.

As illustrated in FIG. 55, a circular ring-like member 412e is provided at the lower end of the main body part 412. The outer periphery of the circular ring-like member 412e is integrated with the lower end of the main body part 412. The inner diameter of the circular ring-like member 412e is set such that the piston plate 420 cannot pass through the circular ring-like member 412e and that the microneedle array 30 can pass therethrough.

The outer cover part 414 has a bottomed cylindrical shape, and is attached to the upper end part of the main body part 412 (second portion 412b). As illustrated in FIG. 55, the outer circumferential surface of the outer cover part 414 is fitted to the inner circumferential surface of the main body part 412 (second portion 412b) such that the closed end thereof faces upward. That is, the outer diameter of the outer cover part 414 is set to be equivalent to or slightly larger than the inner diameter of the main body part 412 (second portion 412b).

The inner cover part 416 has a disc-like shape. The inner cover part 416 is placed on the step part 412c of the main body part 412, and is fixed to the inner circumferential surface of the main body part 412. The outer diameter of the inner cover part 416 is equivalent to the inner diameter of the second portion 412b of the main body part 412. Cutout parts 416a, 416b and 416c are formed in the periphery of the inner cover part 416. The cutout parts 416a, 416b and 416c are arranged in the stated order in the clockwise direction when viewed from above, with given intervals in the circumferential direction.

The cutout part 416a includes: a first portion $416a_1$ having a small cutout depth; and a second portion $416a_2$ having a cutout depth larger than that of the first portion $416a_1$. The second portion $416a_2$ is adjacently integrated with the first portion $416a_1$, and is located between the first portion $416a_1$ and the cutout part 416c.

The cutout part 416b includes: a first portion $416b_1$ having a small cutout depth; and a second portion $416b_2$ having a cutout depth larger than that of the first portion $416b_1$. The second portion $416b_2$ is adjacently integrated with the first portion $416b_1$, and is located between the first portion $416b_1$ and the cutout part 416a.

The cutout part 416c includes: a first portion $416c_1$ having a small cutout depth; and a second portion $416c_2$ having a cutout depth larger than that of the first portion $416c_1$. The second portion $416c_2$ is adjacently integrated with the first portion $416c_1$, and is located between the first portion $416c_1$ and the cutout part 416b.

The piston plate 420 is housed in the main body part 412, and is movable in the top-bottom direction along the central axis of the main body part 412 inside of the main body part 412. The material of the piston plate 420 may be the same as the material of the casing 410, and may be the same as the material of the microneedle array 30. As illustrated in FIG. 56, the piston plate 420 includes: a disc-like main body 420a; plate-like members $420b_1$, $420b_3$ and $420b_3$ that extend upward from the periphery of the upper surface of the main body 420a; and projections $420c_1$, $420c_3$ and $420c_3$ that are respectively provided at the leading ends (upper ends) of the plate-like members $420b_1$, $420b_3$ and $420b_3$.

An opening, a groove, a through-hole, or the like may be formed in the main body 420a for the purpose of reducing the air resistance and the weight of the piston plate 420. Further, an elongated protrusion or the like may be provided on the upper surface (the surface on which the conical coil spring 40 is arranged) of the main body 420a for the purpose of improving the rigidity of the piston plate 420. It is preferable that the lower surface (the surface opposite to the upper surface) of the main body 420a be planar, in consideration of causing the piston plate 420 to evenly act on the microneedle array 30. Alternatively, the lower surface of the main body 420a may have other shapes than the planar shape, and the shape of the lower surface of the main body 420a can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The plate-like members $420b_1$, $420b_2$ and $420b_3$ each have a circular arc-like shape. The plate-like members $420b_1$, $420b_2$ and $420b_3$ are arranged in the stated order in the clockwise direction when viewed from above, with given intervals in the circumferential direction. The diameter of a virtual circle that is circumscribed on the plate-like members $420b_1$, $420b_2$ and $420b_3$ when viewed from above is set to be larger than the maximum diameter D1 of the conical coil spring 40. Thus, the plate-like members $420b_1$, $420b_2$ and $420b_3$ function as such a stopper that prevents the conical coil spring 40 from dropping off the piston plate 420 during its movement in the radial direction. The heights of the plate-like members $420b_1$, $420b_2$ and $420b_3$ may be changed as appropriate in accordance with the design of the applicator A11. For example, in the case where the height of the applicator A11 is desired to be minimized, the heights of the plate-like members $420b_1$, $420b_2$ and $420b_3$ can be set to be equivalent to the thickness of a metal wire that forms the conical coil spring 40. Note that, if a ring-like groove in which the metal wire that forms the conical coil spring 40 can be fit is formed in the main body 420a, the function as the stopper for the conical coil spring 40 can be fulfilled by the ring-like groove. In the case where such a stopper for the conical coil spring 40 is provided, a failure in positioning of the conical coil spring 40 with respect to the piston plate 420 can be prevented at the time of arranging the conical coil spring 40 on the upper surface of the piston plate 420 and attaching the two to the inside of the casing 410.

The projections $420c_1$, $420c_2$ and $420c_3$ each protrude inward in the radial direction (the direction that intersects with the thickness direction of the piston plate). In the eleventh embodiment, the projections $420c_1$, $420c_2$ and $420c_3$ each have a quadrangular prism shape. Alternatively, the projections $420c_1$, $420c_2$ and $420c_3$ may have other shapes (for example, a polygonal prism shape, a deformed pillar shape, a circular cone shape, a polygonal pyramid shape, a truncated circular cone shape, and a truncated polygonal pyramid shape) as long as locking with the inner cover part 416 by means of the cutout parts 416a, 416b and 416c is possible.

The plate-like member $420b_1$ can pass through both of the first and second portions $416a_1$ and $416a_2$ of the cutout part 416a. Meanwhile, the projection $420c_1$ can pass through the second portion $416a_2$ of the cutout part 416a, but cannot pass through the first portion $416a_1$ of the cutout part 416a. Thus, if the piston plate 420 is turned in the circumferential direction toward the first portion $416a_1$ after the projection $420c_1$ passes through the second portion $416a_2$, the projection $420c_1$ can be placed on the inner cover part 416.

The plate-like member $420b_2$ can pass through both of the first and second portions $416b_1$ and $416b_2$ of the cutout part 416b. Meanwhile, the projection $420c_2$ can pass through the second portion $416b_2$ of the cutout part 416b, but cannot pass through the first portion $416b_1$ of the cutout part 416b. Thus, if the piston plate 420 is turned in the circumferential direction toward the first portion $416b_1$ after the projection $420c_2$ passes through the second portion $416b_2$, the projection $420c_2$ can be placed on the inner cover part 416.

The plate-like member $420b_3$ can pass through both of the first and second portions $416c_1$ and $416c_2$ of the cutout part 416c. Meanwhile, the projection $420c_3$ can pass through the second portion $416c_2$ of the cutout part 416c, but cannot pass through the first portion $416c_1$ of the cutout part 416c. Thus, if the piston plate 420 is turned in the circumferential direction toward the first portion $416c_1$ after the projection $420c_3$ passes through the second portion $416c_2$, the projection $420c_3$ can be placed on the inner cover part 416.

As described above, as the plate-like members $420b_1$, $420b_2$ and $420b_3$ are guided inside of the cutout parts 416a, 416b and 416c, the piston plate 420 can be guided along the extending directions (circumferential directions) of the cutout parts 416a, 416b and 416c (can be turned about the axis of the main body part 412). Further, in the case where the projections $420c_1$, $420c_2$ and $420c_3$ respectively pass through the second portions $416a_2$, $416b_2$ and $416c_2$, the piston plate 420 can be guided in the top-bottom direction along the axial direction of the main body part 412. In order to guide the piston plate 420 inside of the main body part 412 with the lower surface of the piston plate 420 being kept horizontal, it is preferable that the outer circumferential surfaces of the plate-like members $420b_1$, $420b_2$ and $420b_3$ and the projections $420c_1$, $420c_2$ and $420c_3$ abut against the main body part 412. That is, the diameter of a circle circumscribed on the plate-like members $420b_1$, $420b_2$ and $420b_3$ and the projections $420c_1$, $420c_2$ and $420c_3$ is set to be equivalent to the inner diameter of the first portion 412a of the main body part 412.

The upper surface of the inner cover part 416 may be a horizontal plane. Alternatively, a region of the upper surface of the inner cover part 416 may be convex so as to gradually swell up toward the second portion $416a_2$, the region corresponding to the first portion $416a_1$ of the cutout part 416a. A region of the upper surface of the inner cover part 416 may be convex so as to gradually swell up toward the second portion $416b_2$, the region corresponding to the first portion $416b_1$ of the cutout part 416b. A region of the upper surface of the inner cover part 416 may be convex so as to gradually swell up toward the second portion $416c_2$, the region corresponding to the first portion $416c_1$ of the cutout part 416c. In this case, when the projections $420c_1$, $420c_2$ and $420c_3$ placed on the upper surface of the inner cover part 416 move toward the second portions $416a_2$, $416b_2$ and $416c_2$, the projections $420c_1$, $420c_2$ and $420c_3$ need to climb the slopes of the convex portions of the inner cover part 416. Thus, even if an impact or the like is applied from the outside to the applicator A11, the projections $420c_1$, $420c_2$ and $420c_3$ can be prevented from unintentionally moving into the second portions $416a_2$, $416b_2$ and $416c_2$.

The microneedle array 30 and the conical coil spring 40 are the same as those in the first embodiment, and hence description thereof is omitted.

The release member 450 includes a turning plate 452 and a pair of switch members 454 and 456.

The turning plate 452 includes: a disc-like base part 452a; a pair of projections $452b_1$ and $452b_2$ that are provided in a protruding manner on the upper surface of the base part 452a; a cylindrical member 452c that is provided in a protruding manner on the lower surface of the base part 452a; and projections $452d_1$, $452d_2$ and $452d_3$ that are provided in a protruding manner on the lower surface of the base part 452a. The outer diameter of the base part 452a is set to be equivalent to the inner diameter of the second portion 412b of the main body part 412. The outer edge of the base part 452a is not connected to the inner circumferential surface of the main body part 412 (second portion 412b).

The projections $452b_1$ and $452b_2$ each have a columnar shape. The projections $452b_1$ and $452b_2$ are opposed to each other with the axis of the base part 452a being centered therebetween, when viewed from above. The projections $452b_1$ and $452b_2$ are located on the circumference of the same circle having its center on the axis of the base part 452a. In order to enable the projections $452b_1$ and $452b_2$ to exert a couple on the turning plate 452 (base part 452a) when the projections $452b_1$ and $452b_2$ are respectively pushed by the switch members 454 and 456, it is preferable that the projections $452b_1$ and $452b_2$ be not arranged in a line in the opposing direction of the switch members 454 and 456 in the completed state of the applicator A11.

The cylindrical member 452c is placed on the upper surface of the inner cover part 416. The lower end of the cylindrical member 452c is not connected to the inner cover part 416. Thus, coupled with the fact that the outer edge of the base part 452a is not connected to the inner circumferential surface of the main body part 412 (second portion 412b), the turning plate 452 is turnable about the axis of the base part 452a inside of the main body part 412 (second portion 412b). The cylindrical member 452c is located between the base part 452a and the inner cover part 416, and functions as a spacer that makes the base part 452a and the inner cover part 416 spaced apart from each other with a predetermined interval. In order to enable the projections $420c_1$, $420c_2$ and $420c_3$ to move between the base part 452a and the inner cover part 416, the height of the cylindrical member 452c (the interval between the base part 452a and the inner cover part 416) is set to be equivalent to or larger than the heights of the projections $420c_1$, $420c_2$ and $420c_3$.

The projections $452d_1$, $452d_2$ and $452d_3$ each have a columnar shape. The projections $452d_1$, $452d_2$ and $452d_3$ are arranged in the stated order in the clockwise direction when viewed from above, with given intervals in the circumferential direction. The projections $452d_1$, $452d_2$ and $452d_3$ are located outside of the cylindrical member 452c and on the circumference of the same circle having its center on the axis of the base part 452a. The circle on which the projections $452d_1$, $452d_2$ and $452d_3$ are located overlaps with the cutout parts 416a, 416b and 416c of the inner cover part 416, when viewed from above.

The switch member 454 has a plate-like shape as a whole. The switch member 454 includes: a base part 454a; a press part 454b provided on the base end side of the base part 454a; and a leading end part 454c provided on the leading end side of the base part 454a. The base part 454a has a size that allows the base part 454a to pass through the groove part $412d_1$ of the main body part 412. The outer shape of the press part 454b is larger than the groove part $412d_1$ of the main body part 412. Thus, the press part 454b cannot pass through the groove part $412d_1$, and is located outside of the main body part 412 before and after the operation of the applicator A11.

In order to prevent a leading end part 456c of the switch member 456 from hindering movement of the switch member 454 when the switch members 454 and 456 are pushed toward the main body part 412 to approach each other, the leading end part 454c is located closer to the projection $452b_1$ when viewed from above. A linear cutout part 454d is formed in the leading end part 454c, and the cutout part 454d extends in a direction that intersects with (for example, the direction orthogonal to) the opposing direction of the switch members 454 and 456. The opened end of the cutout part 454d faces the projection $452b_1$ when viewed from above. In the completed state of the applicator A11, the projection $452b_1$ is arranged in the cutout part 454d, and the cutout part 454d and the projection $452b_1$ are engaged with each other. Thus, if the switch member 454 is moved in the opposing direction of the switch members 454 and 456, the projection $452b_1$ slides inside of the cutout part 454d.

The switch member 456 has a plate-like shape as a whole. The switch member 456 includes: a base part 456a; a press part 456b provided on the base end side of the base part 456a; and the leading end part 456c provided on the leading end side of the base part 456a. The base part 456a has a size that allows the base part 456a to pass through the groove part $412d_2$ of the main body part 412. The outer shape of the press part 456b is larger than the groove part $412d_2$ of the main body part 412. Thus, the press part 456b cannot pass through the groove part $412d_2$, and is located outside of the main body part 412 before and after the operation of the applicator A11.

In order to prevent the leading end part 454c of the switch member 454 from hindering movement of the switch member 456 when the switch members 454 and 456 are pushed toward the main body part 412 to approach each other, the leading end part 456c is located closer to the projection $452b_2$ when viewed from above. A linear cutout part 456d is formed in the leading end part 456c, and the cutout part 456d extends in a direction that intersects with (for example, the direction orthogonal to) the opposing direction of the switch members 454 and 456. The opened end of the cutout part 456d faces the projection $452b_2$ when viewed from above. In the completed state of the applicator A11, the projection $452b_2$ is arranged in the cutout part 456d, and the cutout part 456d and the projection $452b_2$ are engaged with each other. Thus, if the switch member 456 is moved in the opposing direction of the switch members 454 and 456, the projection $452b_2$ slides inside of the cutout part 456d.

[11.2] Method of Manufacturing Applicator

Now, the method of manufacturing the applicator A11 is described. First, the microneedle array 30 is attached to the lower surface of the piston plate 420, and the conical coil spring 40 is placed on the upper surface of the piston plate 420, through procedures similar to the first and fourth steps in the method of manufacturing the applicator A1 according to the first embodiment. Subsequently, the piston plate 420 is placed in the main body part 412 such that: the projection $420c_1$ of the piston plate 420 is located above the region of the upper surface of the inner cover part 416, the region corresponding to the first portion $416a_1$ of the cutout part 416a; the projection $420c_2$ of the piston plate 420 is located above the region of the upper surface of the inner cover part 416, the region corresponding to the first portion $416b_1$ of the cutout part 416b; and the projection $420c_3$ of the piston plate 420 is located above the region of the upper surface of the inner cover part 416, the region corresponding to the first portion $416c_1$ of the cutout part 416c (see FIG. 59 and FIG. 60).

Figure 59:
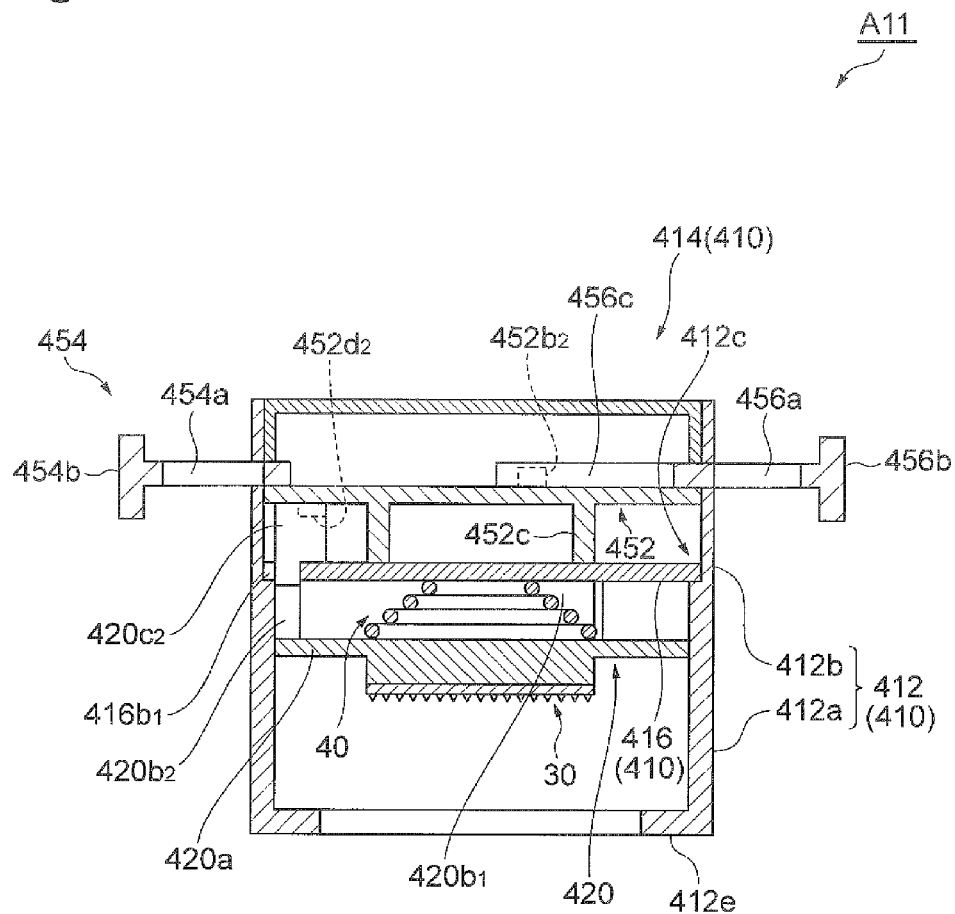
FIG. 59 is a cross sectional view illustrating the state before the operation of the applicator according to the eleventh embodiment.

On this occasion, because the projections $420c_1$, $420c_2$ and $420c_3$ are placed on the inner cover part 416, even if the inner cover part 416 and the piston plate 420 compress the conical coil spring 40, the piston plate 420 is not pushed out in the bottom direction by the conical coil spring 40. That is, the piston plate 420 is locked with the casing 410 (inner cover part 416). Accordingly, as illustrated in FIG. 59, the piston plate 420 is held at its retraction position on the inner cover part 416 side inside of the main body part 412, in the state where the inner cover part 416 and the piston plate 420 compress the conical coil spring 40. Such a state as described above where the piston plate 420 is locked with the casing 410 (inner cover part 416) and where the inner cover part 416 and the piston plate 420 compress the conical coil spring 40 is hereinafter referred to as "locked state".

Locking the piston plate 420 with the casing 410 (inner cover part 416) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the piston plate 420 and the inner cover part 416 becomes slightly larger than the wire diameter, in the state where the piston plate 420 is locked (cocked) with the casing 410 (see FIG. 59). Note that, depending on the configuration of the piston plate 420, the piston plate 420 can come extremely close to the inner cover part 416, and the height of the conical coil spring 40 sandwiched between the piston plate 420 and the inner cover part 416 can become equivalent to the wire diameter, in the state where the piston plate 420 is locked (cocked) with the casing 410.

Subsequently, the turning plate 452 is placed on the inner cover part 416. At this time, the projection $452d_1$ is arranged so as to abut against a side surface of the projection $420c_1$, the side surface being opposite to the second portion $416a_2$ of the cutout part 416a. The projection $452d_2$ is arranged so as to abut against a side surface of the projection $420c_2$, the side surface being opposite to the second portion $416b_2$ of the cutout part 416b. The projection $452d_3$ is arranged so as to abut against a side surface of the projection $420c_3$, the side surface being opposite to the second portion $416c_2$ of the cutout part 416c. Accordingly, the projection $420c_1$ is located between the projection $452d_1$ and the second portion $416a_2$ of the cutout part 416a, the projection $420c_2$ is located between the projection $452d_2$ and the second portion $416b_2$ of the cutout part 416b, and the projection $420c_3$ is located between the projection $452d_3$ and the second portion $416c_2$ of the cutout part 416c, when viewed from above.

Subsequently, the base part 454a and the leading end part 454c of the switch member 454 are inserted into the groove part $412d_1$ from the outside of the main body part 412, while the cutout part 454d of the leading end part 454c is engaged with the projection $452b_1$. Further, the base part 456a and the leading end part 456c of the switch member 456 are inserted into the groove part $412d_2$ from the outside of the main body part 412, while the cutout part 456d of the leading end part 456c is engaged with the projection $452b_2$. Subsequently, the outer cover part 414 is attached to the upper end of the main body part 412 (second portion 412b).

Figure 60:
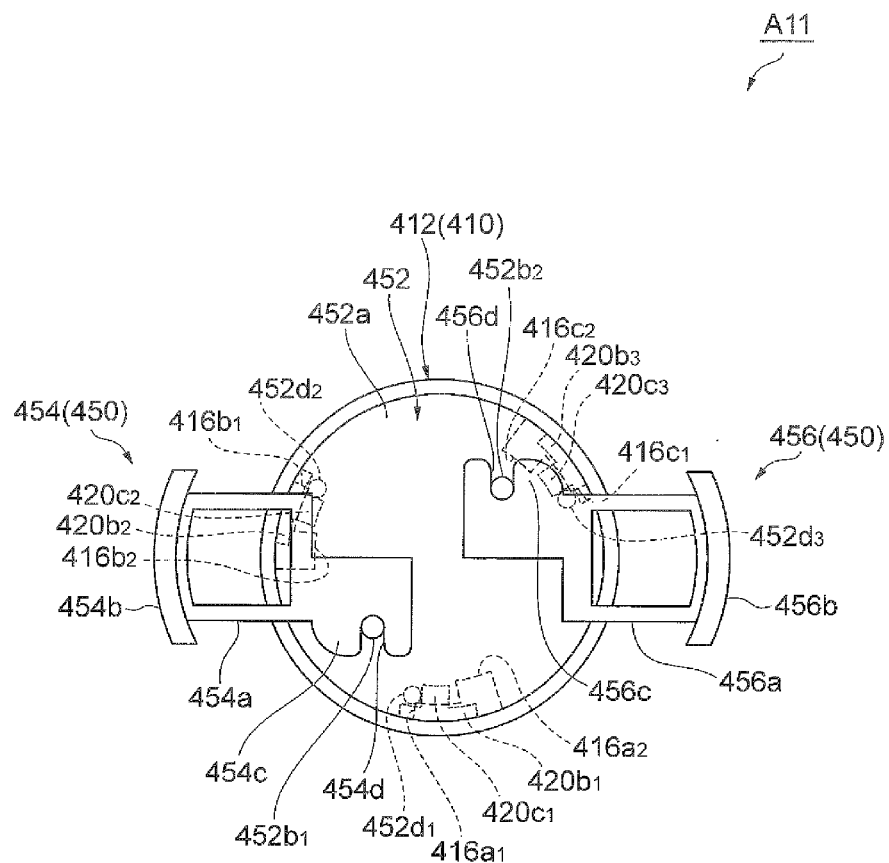
FIG. 60 is a top view illustrating the state before the operation of the applicator according to the eleventh embodiment, from which the cover part is detached.

Through the above-mentioned procedures, assembling of the applicator A11 is completed (see FIG. 59 and FIG. 60). Accordingly, the conical coil spring 40 remains in a compressed state until the applicator A11 is used by a user after manufacture and shipping thereof.

[11.3] Method of Using Applicator

Now, the method of using the applicator A11 is described. First, the applicator A11 is positioned with respect to a portion of a skin to which a medical agent or the like is desired to be applied, such that the microneedles 32 face the skin. The switch members 454 and 456 are pushed so as to approach each other (are pushed toward the main body part 412) by pinching the respective press parts 454b and 456b thereof, while the applicator A11 is kept positioned. As a result, the projections $452b_1$ and $452b_2$ respectively slide inside of the cutout parts 454d and 456d while exerting a couple on the turning plate 452 (base part 452a). Consequently, the turning plate 452 (base part 452a) turns, the projection $452d_1$ pushes the projection $420c_1$ toward the second portion $416a_2$ of the cutout part 416a, the projection $452d_2$ pushes the projection $420c_2$ toward the second portion $416b_2$ of the cutout part 416b, and the projection $452d_3$ pushes the projection $420c_3$ toward the second portion $416c_2$ of the cutout part 416c. In this way, a turning force is exerted on the piston plate 420, with the result that the piston plate 420 turns. Accordingly, the locking (cocking) of the piston plate 420 with the casing 410 (inner cover part 416) is released (see FIG. 57). After that, similarly to the applicator A1 according to the first embodiment, the microneedle array 30 collides against the skin due to the biasing force (elastic force) of the conical coil spring 40 (see FIG. 54 and FIG. 55).

[11.4] Actions

The eleventh embodiment as described above produces actions and effects similar to the actions (A) to (D) of the applicator A1 according to the first embodiment.

In the applicator A11 according to the eleventh embodiment, the switch members 454 and 456 are located lateral to (on the outer circumferential surface of) the casing 410 (main body part 412), and hence the switch members 454 and 456 are suppressed from extending in the axial direction of the main body part 412 (the height direction of the applicator A11). Thus, the height of the applicator A11 itself can be made further smaller.

[12] Twelfth Embodiment

[12.1] Configuration of Applicator

Now, a configuration of an applicator A12 according to a twelfth embodiment is described with reference to FIG. 61 to FIG. 68. In the following description, the term "top" corresponds to the top direction of FIG. 61, FIG. 63, and FIG. 65 to FIG. 67, and the term "bottom" corresponds to the bottom direction of FIG. 61, FIG. 63, and FIG. 65 to FIG. 67. That is, the top-bottom direction corresponds to the height direction of the applicator A12.

The applicator A12 is a device for transferring active ingredients of a medical agent or the like into the body of an animal such as a human through a skin of the animal. The applicator A12 includes a casing 510, a piston plate 520, the microneedle array 30, the conical coil spring 40, and a release member 550.

Figure 63:
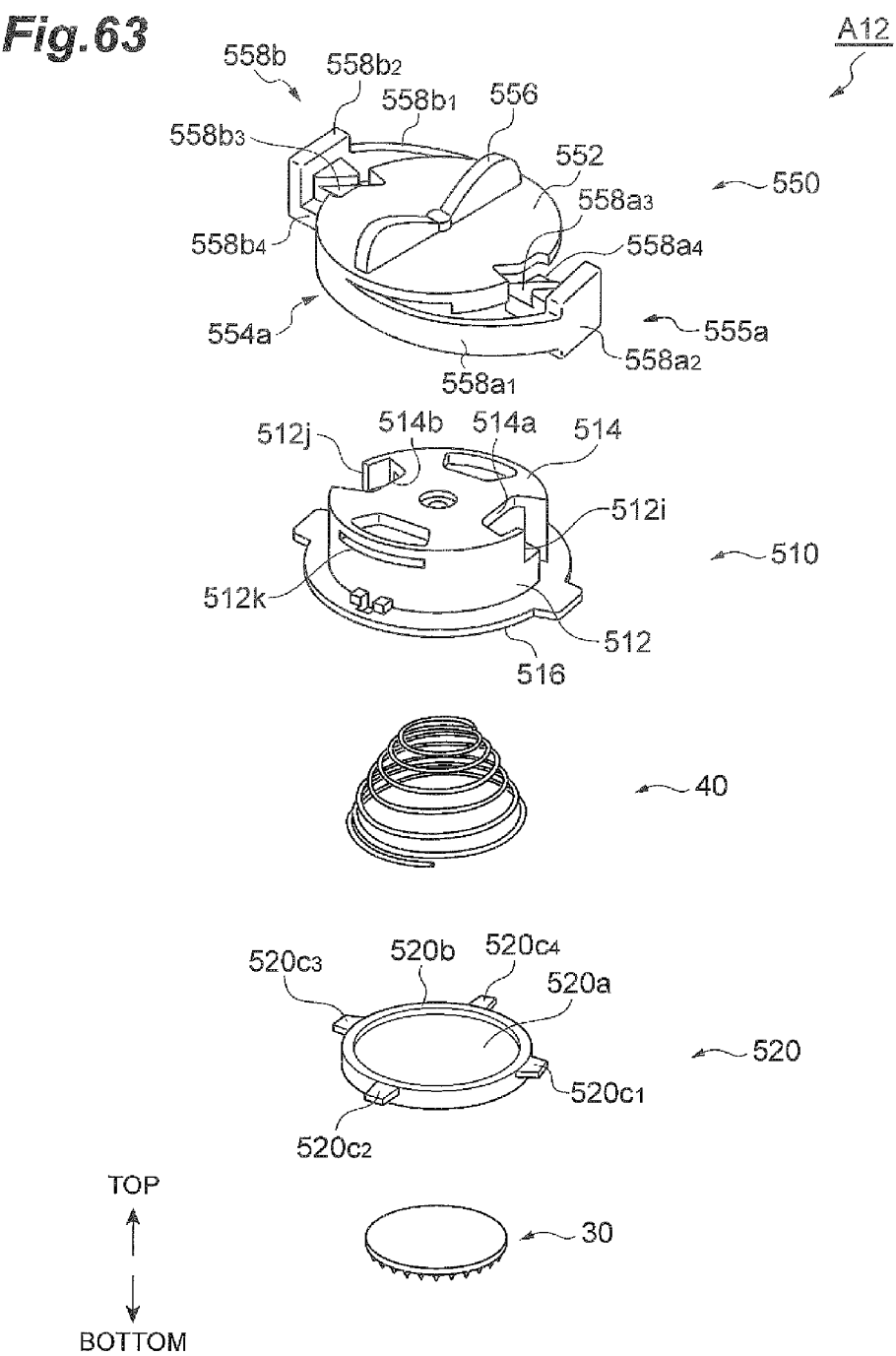
FIG. 63 is an exploded perspective view of the applicator according to the twelfth embodiment.
Figure 64:
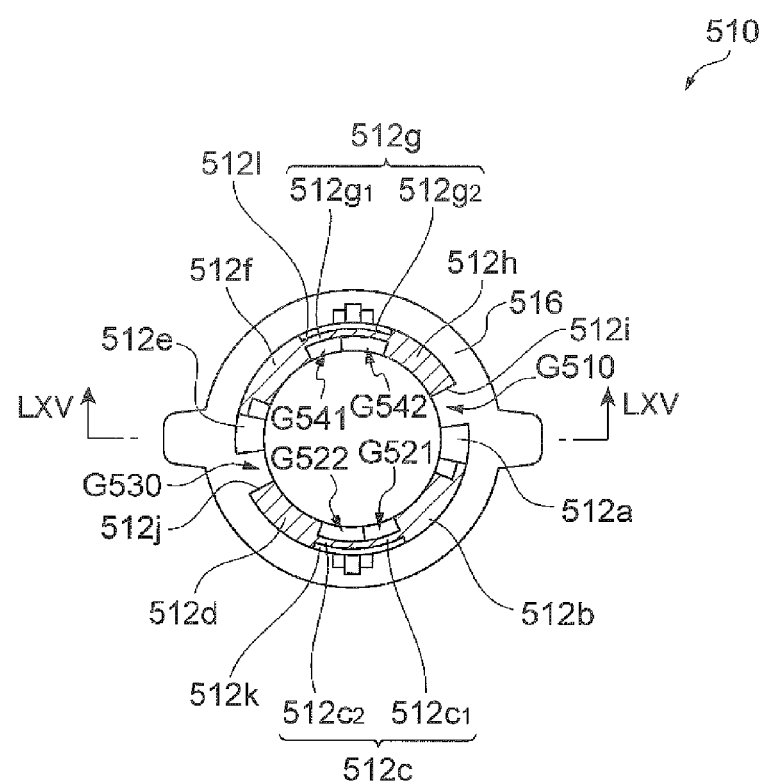
FIG. 64 is a top view of a casing, the upper end part (cover part) of which is cut away.
Figure 65:
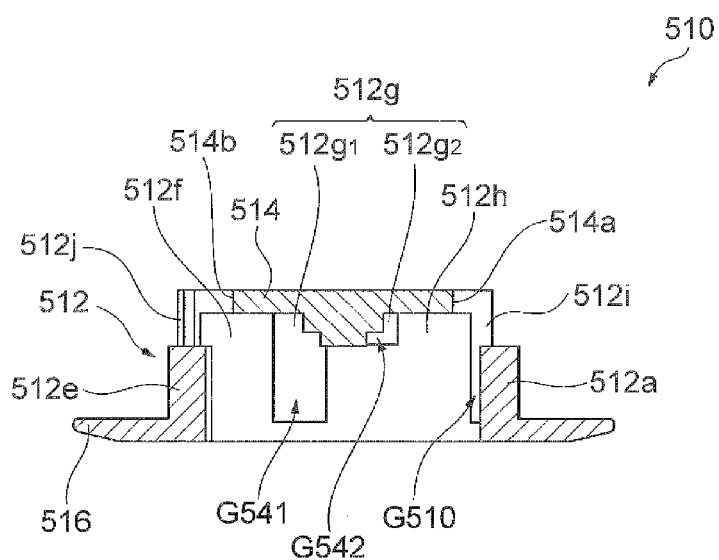
FIG. 65 is a cross sectional view taken along line LXV-LXV in FIG. 64.
Figure 66:
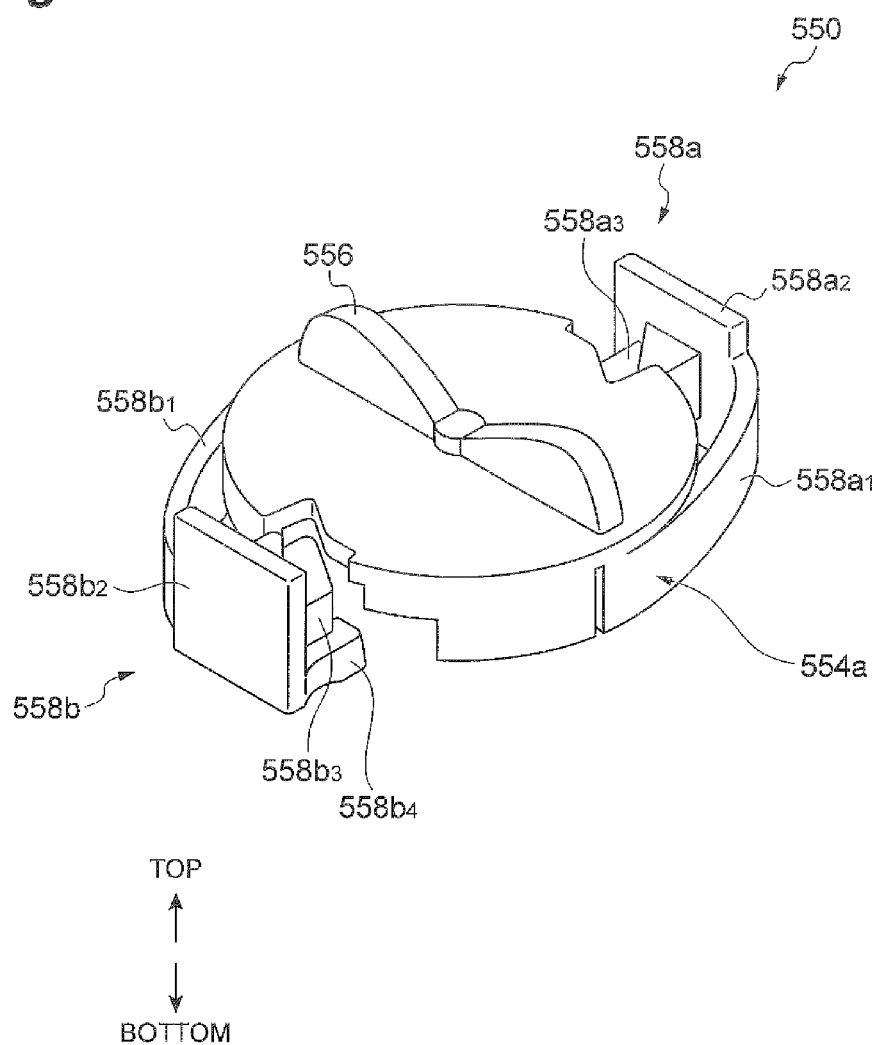
FIG. 66 is a perspective view illustrating the upper surface side of a release member.
Figure 67:
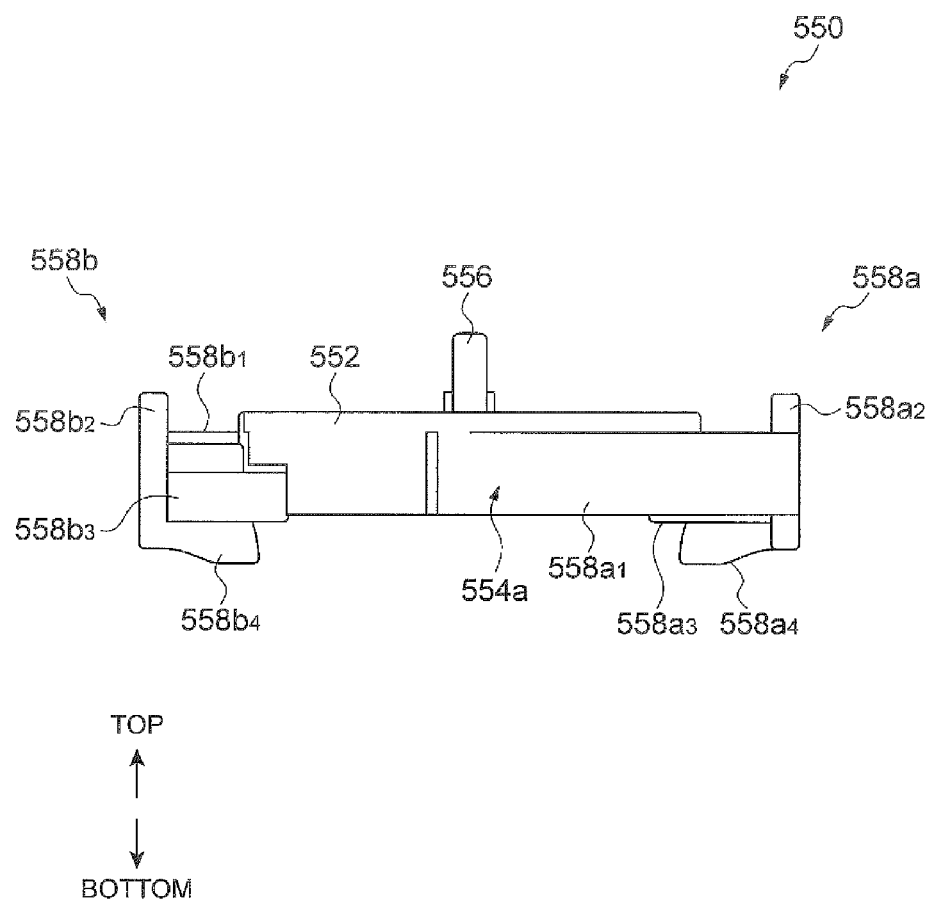
FIG. 67 is a side view of the release member.
Figure 68:
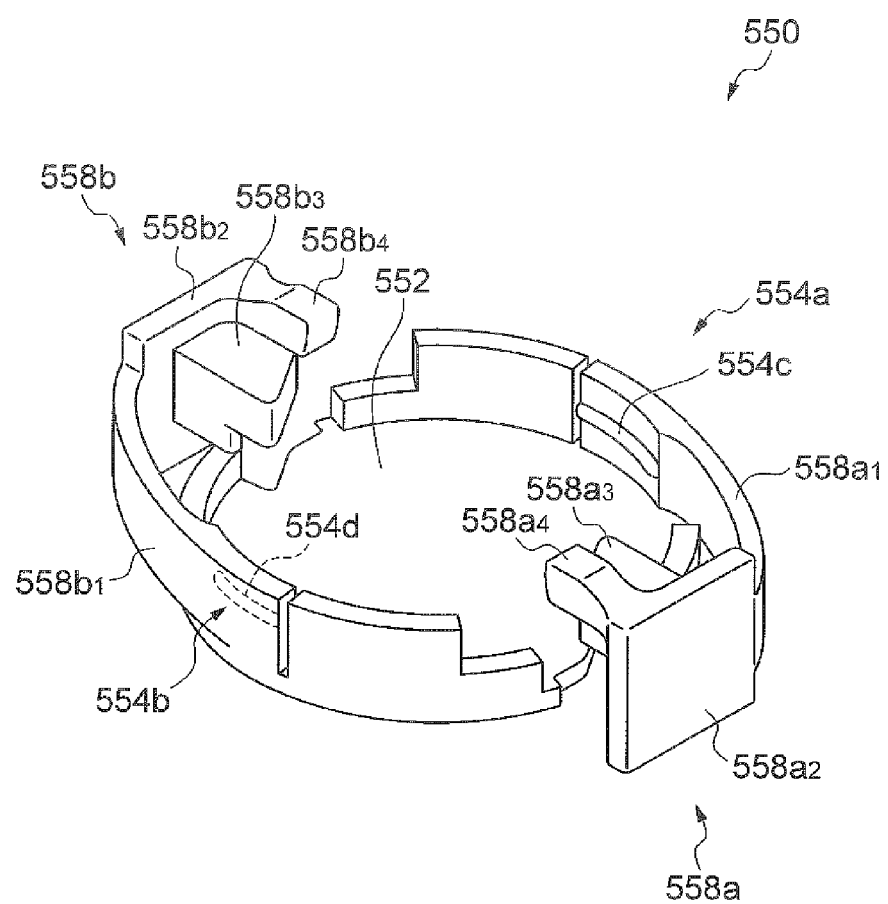
FIG. 68 is a perspective view illustrating the lower surface side of the release member.

As illustrated in FIG. 63 to FIG. 65, the casing 510 includes: a main body part 512 having the central axis that extends along the top-bottom direction and having a cylindrical shape; a cover part 514 arranged on the upper end side of the main body part 512; and a circular ring-like flange part 516 arranged on the lower end side of the main body part 512. The strength and the material of the casing 510 may be the same as those of the casing 10 of the applicator A1 according to the first embodiment.

The main body part 512 includes wall parts 512a, 512b, 512c, 512d, 512e, 512f, 512g and 512h each having a circular arc-like shape when viewed from above. The wall parts 512a, 512b, 512c, 512d, 512e, 512f, 512g and 512h are arranged in the stated order in the clockwise direction when viewed from the upper end side (the cover part 514 side) of the main body part 512. Respective adjacent wall parts of the wall parts 512a, 512b, 512c and 512d are integrated with each other (see FIG. 64). Respective adjacent wall parts of the wall parts 512e, 512f, 512g and 512h are integrated with each other (see the same drawing). The wall part 512a and the wall part 512e are opposed to each other with the central axis of the main body part 512 being centered therebetween, when viewed from above. The wall part 512b and the wall part 512f are opposed to each other with the central axis of the main body part 512 being centered therebetween, when viewed from above. The wall part 512c and the wall part 512g are opposed to each other with the central axis of the main body part 512 being centered therebetween, when viewed from above. The wall part 512d and the wall part 512h are opposed to each other with the central axis of the main body part 512 being centered therebetween, when viewed from above.

The main body part 512 is provided with cutout parts 512i and 512j at positions respectively corresponding to the wall parts 512a and 512e. The cutout parts 512i and 512j are opposed to each other with the central axis of the main body part 512 being centered therebetween, when viewed from above. Thus, the height of the wall part 512a is made smaller by the existence of the cutout part 512i, and the upper end thereof does not reach the cover part 514. The height of the wall part 512e is made smaller by the existence of the cutout part 512j, and the upper end thereof does not reach the cover part 514.

Groove parts 512k and 512l are provided on the outer circumferential surface of the main body part 512 at positions respectively corresponding to the wall parts 512c and 512g. The groove parts 512k and 512l are located closer to the upper end of the main body part 512, and extend along the circumferential direction.

The wall part 512a and the wall part 512h are spaced apart from each other with a predetermined interval. Thus, a groove body G510 that passes through the main body part 512 in the thickness direction thereof is formed on the circumferential surface of the main body part 512, by a gap between the wall part 512a and the wall part 512h. The wall part 512d and the wall part 512e are spaced apart from each other with a predetermined interval. Thus, a groove body G530 that passes through the main body part 512 in the thickness direction thereof is formed on the circumferential surface of the main body part 512, by a gap between the wall part 512d and the wall part 512e.

On the inner surface of the wall part 512c, a groove part G521 that extends in the top-bottom direction is provided closer to the wall part 512b, and a groove part G522 that extends in the circumferential direction is provided in the vicinity of the upper end of the wall part 512c. The groove part G521 extends from the vicinity of the lower end of the wall part 512c to the upper end thereof. The groove part G522 extends from the wall part 512b to the wall part 512d, and is communicated with the upper end of the groove part G521. Thus, the wall part 512c includes: a first portion $512c_1$ that is made thinner by the existence of the groove part G521 except the lower end part thereof; and a second portion $512c_2$ having an upper end part made thinner by the existence of the groove part G522 and a thicker portion below the groove part G522.

On the inner surface of the wall part 512g, a groove part G541 that extends in the top-bottom direction is provided closer to the wall part 512f, and a groove part G542 that extends in the circumferential direction is provided in the vicinity of the upper end of the wall part 512g. The groove part G541 extends from the vicinity of the lower end of the wall part 512g to the upper end thereof. The groove part G542 extends from the wall part 512f to the wall part 512h, and is communicated with the upper end of the groove part G541. Thus, the wall part 512g includes: a first portion $512g_1$ that is made thinner by the existence of the groove part G541 except the lower end part thereof; and a second portion $512g_2$ having an upper end part made thinner by the existence of the groove part G542 and a thicker portion below the groove part G542.

The cover part 514 is a plate-like body having a circular shape. The peripheral part of the lower surface of the cover part 514 is integrated with the upper ends of the wall parts 512b, 512c, 512d, 512f, 512g and 512h. Thus, the cover part 514 closes the upper end of the main body part 512.

The cover part 514 is provided with cutout parts 514a and 514b at positions respectively corresponding to the wall parts 512a and 512e when viewed from above. The cutout parts 514a and 514b are opposed to each other with the axis of the cover part 514 being centered therebetween, when viewed from above. The cutout parts 514a and 514b are both concaved toward the center of the cover part 514.

The flange part 516 protrudes outward from the outer circumferential surface of the main body part 512. At the time of using the applicator A12, the flange part 516 makes the contact area with the skin larger, and hence a pressure applied to the skin can be made smaller.

The piston plate 520 is housed in the main body part 512, and is movable in the top-bottom direction along the central axis of the main body part 512 inside of the main body part 512. The material of the piston plate 520 may be the same as the material of the casing 510, and may be the same as the material of the microneedle array 30. As illustrated in FIG. 63, the piston plate 520 includes: a disc-like main body 520a; and a cylindrical member 520b that extends upward from the periphery of the main body 520a. An opening, a groove, a through-hole, or the like may be formed in the main body 520a for the purpose of reducing the air resistance and the weight of the piston plate 520. Further, an elongated protrusion or the like may be provided on the upper surface (the surface on which the conical coil spring 40 is arranged) of the main body 520a for the purpose of improving the rigidity of the piston plate 520. It is preferable that the lower surface (the surface opposite to the upper surface) of the main body 520a be planar, in consideration of causing the piston plate 520 to evenly act on the microneedle array 30. Alternatively, the lower surface of the main body 520a may have other shapes than the planar shape, and the shape of the lower surface of the main body 520a can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The inner diameter of the cylindrical member 520b is set to be larger than the maximum diameter D1 of the conical coil spring 40. The height of the cylindrical member 520b is not particularly limited as long as the cylindrical member 520b can function as such a stopper that prevents the conical coil spring 40 from dropping off the piston plate 520 during its movement in the radial direction. For example, in the case where the height of the applicator A12 is desired to be minimized, the height of the cylindrical member 520b can be set to be equivalent to the thickness of a metal wire that forms the conical coil spring 40. In the case where the stopper for the conical coil spring 40 is not necessary, the piston plate 520 does not need to include the cylindrical member 520b. Even in the case where the piston plate 520 does not include the cylindrical member 520b, if a ring-like groove in which the metal wire that forms the conical coil spring 40 can be fit is formed in the main body 520a, the function as the stopper for the conical coil spring 40 can be fulfilled by the ring-like groove. In the case where such a stopper for the conical coil spring 40 is provided, a failure in positioning of the conical coil spring 40 with respect to the piston plate 520 can be prevented at the time of arranging the conical coil spring 40 on the upper surface of the piston plate 520 and attaching the two to the inside of the casing 510.

A plurality of projections (in the twelfth embodiment, four projections) $520c_1$, $520c_2$, $520c_3$ and $520c_4$ are provided in the periphery (on the outer circumferential surface) of the piston plate 520, and the projections $520c_1$, $520c_2$, $520c_3$ and $520c_4$ protrude outward in the radial direction (the direction that intersects with the thickness direction of the piston plate). The projections $520c_1$, $520c_2$, $520c_3$ and $520c_4$ are arranged in the stated order in the clockwise direction when viewed from above (the upper surface side of the piston plate 520 on which the conical coil spring 40 is placed), with given intervals in the circumferential direction. In the twelfth embodiment, the projections $520c_1$, $520c_2$, $520c_3$ and $520c_4$ are plate-like bodies each having a trapezoidal shape. Alternatively, the projections $520c_1$, $520c_2$, $520c_3$ and $520c_4$ may have other shapes (for example, a columnar shape, a polygonal prism shape, a deformed pillar shape, a circular cone shape, a polygonal pyramid shape, a truncated circular cone shape, and a truncated polygonal pyramid shape) as long as locking with the wall parts 512a and 512e and the second portions $512c_2$ and $512g_2$ of the wall parts 512c and 512g is possible and movement in the groove bodies G510 and G530 and the groove parts G521 and G541 is possible.

The projection $520c_1$ is movable along the extending direction of the groove body G510 inside of the groove body G510. The projection $520c_2$ is movable along the extending direction of the groove part G521 inside of the groove part G521. The projection $520c_3$ is movable along the extending direction of the groove body G530 inside of the groove body G530. The projection $520c_4$ is movable along the extending direction of the groove part G541 inside of the groove part G541. Thus, the piston plate 520 can be guided in the top-bottom direction along the extending directions of the groove bodies G510 and G530 and the groove parts G521 and G541 (the central axis direction of the main body part 512).

In the state where the projection $520c_1$ is located on the upper end side of the groove body G510, the projection $520c_1$ is movable in the horizontal direction inside of the cutout part 512i. Thus, the projection $520c_1$ can be placed on the upper end of the wall part 512a adjacent to the groove body G510. In the state where the projection $520c_2$ is located on the upper end side of the groove part G521, the projection $520c_2$ is movable in the horizontal direction inside of the groove part G522 communicated with the groove part G521. Thus, the projection $520c_2$ can be placed on the upper end of the second portion $512c_2$ of the wall part 512c adjacent to the groove part G521.

In the state where the projection $520c_3$ is located on the upper end side of the groove body G530, the projection $520c_3$ is movable in the horizontal direction inside of the cutout part 512j. Thus, the projection $520c_3$ can be placed on the upper end of the wall part 512e adjacent to the groove body G530. In the state where the projection $520c_4$ is located on the upper end side of the groove part G541, the projection $520c_4$ is movable in the horizontal direction inside of the groove part G542 communicated with the groove part G541. Thus, the projection $520c_4$ can be placed on the upper end of the second portion $512g_2$ of the wall part 512g adjacent to the groove part G541.

The upper ends of the wall parts 512a and 512e and the upper ends of the second portions $512c_2$ and $512g_2$ of the wall parts 512c and 512g may extend in the circumferential direction so as to be parallel to a horizontal plane, and may be inclined to the horizontal plane, in the circumferential direction. In particular, the upper ends of the wall parts 512a and 512e may be inclined such that the heights thereof become larger toward the respective adjacent groove bodies G510 and G530, and the upper ends of the second portions $512c_2$ and $512g_2$ of the wall parts 512c and 512g may be inclined such that the heights thereof become larger toward the respective adjacent groove parts G521 and G541. In this case, when the projections $520c_1$, $520c_2$, $520c_3$ and $520c_4$ respectively placed on the upper ends of the wall parts 512a and 512e and the upper ends of the second portions $512c_2$ and $512g_2$ move toward the groove bodies G510 and G530 and the groove parts G521 and G541, the projections $520c_1$, $520c_2$, $520c_3$ and $520c_4$ need to climb the slopes of the upper ends of the wall parts $512a$ and $512e$ and the upper ends of the second portions $512c_2$ and $512g_2$. Thus, even if an impact or the like is applied from the outside to the applicator A12, the projections $520c_1$, $520c_2$, $520c_3$ and $520c_4$ can be prevented from unintentionally moving into the groove bodies G510 and G530 and the groove parts G521 and G541.

The microneedle array 30 and the conical coil spring 40 are the same as those in the first embodiment, and hence description thereof is omitted.

As illustrated in FIG. 61 to FIG. 63 and FIG. 66 to FIG. 68, the release member 550 includes: a base part 552 having a disc-like shape; a pair of hook parts 554a and 554b; a knob part 556; and a pair of press parts 558a and 558b on which a user performs a pressing operation. The material of the release member 550 may be the same as the material of the casing 510, and may be the same as the material of the microneedle array 30. The release member 550 may be made of a flexible or elastic material.

The pair of hook parts 554a and 554b are provided in a protruding manner on the lower surface of the base part 552 so as to be point-symmetrical with respect to the central axis of the base part 552. The hook parts 554a and 554b each have a circular arc-like shape that extends along the periphery of the base part 552 when viewed from the central axis direction of the base part 552. The inner circumferential surfaces of the hook parts 554a and 554b are surfaces facing the central axis of the base part 552. Elongated protrusions 554c and 554d are respectively provided on the inner circumferential surfaces of the hook parts 554a and 554b (see FIG. 68). The elongated protrusions 554c and 554d protrude toward the central axis of the base part 552, and extend along the circumferential directions of the hook parts 554a and 554b (the circumferential direction of the base part 552).

In the completed state of the applicator A12, the elongated protrusion 554c is engaged with the groove part 512k of the main body part 512, and the elongated protrusion 554d is engaged with the groove part 512l of the main body part 512. The lengths of the elongated protrusions 554c and 554d in the circumferential direction of the base part 552 are smaller than the widths of the groove parts 512k and 512l in the circumferential direction of the main body part 512. Thus, the elongated protrusions 554c and 554d are respectively movable in the circumferential direction inside of the groove parts 512k and 512l. As the elongated protrusions 554c and 554d respectively move inside of the groove parts 512k and 512l, the release member 550 turns around the central axis of the base part 552 (main body part 512) by means of the hook parts 554a and 554b.

The knob part 556 is provided on the upper surface of the base part 552. In the twelfth embodiment, the knob part 556 is formed of two elongated protrusions that extend in the radial direction from the center of the base part 552, but may have other configurations as long as the user can catch the knob part 556 with user's fingers to turn the release member 550. For example, the knob part 556 may be one or more elongated protrusions, may be one or more concave parts provided on the upper surface of the base part 552, may be one or more through-holes that pass through the base part 552, and may be combinations thereof.

The press part 558a includes first and second plate-like bodies $558a_1$ and $558a_2$ and first and second protrusion parts $558a_3$ and $558a_4$. The first plate-like body $558a_1$ has a circular arc-like shape that extends along the periphery of the base part 552. One end of the first plate-like body $558a_1$ is integrally connected to the hook part 554a. The other end of the first plate-like body $558a_1$ extends toward the opposite side to the press part 558b and up to the vicinity of the cutout part 514a of the main body part 512. The other end of the first plate-like body $558a_1$ is more spaced outward apart from the base part 552 with increasing distance from the hook part 554a. The second plate-like body $558a_2$ has a rectangular shape. One main surface of the second plate-like body $558a_2$ is opposed to the periphery of the base part 552 and the outer circumferential surface of the main body part 512.

The first and second protrusion parts $558a_3$ and $558a_4$ extend from the one main surface of the second plate-like body $558a_2$ toward the outer circumferential surface of the main body part 512. The first protrusion part $558a_3$ is a plate-like body having a triangular shape when viewed from above. In the completed state of the applicator A12, the oblique side of the first protrusion part $558a_3$ faces the cutout part 512i of the main body part 512, and the height thereof is larger toward the first plate-like body 558m. The second protrusion part $558a_4$ is located below the first protrusion part $558a_3$ and closer to the side edge opposite to the first plate-like body $558a_1$, of the second plate-like body $558a_2$.

The press part 558a can take a first state and a second state. In the first state, a pressing force is not exerted on the second plate-like body $558a_2$, and the press part 558a is not deformed. The second state is a state after a pressing force is exerted on the second plate-like body $558a_2$ and the press part 558a is thus deformed. In the second state after the deformation, the second plate-like body $558a_2$ comes close to the periphery of the base part 552 and the outer circumferential surface of the main body part 512, and the first protrusion part $558a_3$ is inserted in the main body part 512 through a region above the wall part 512a, of the cutout part 512i, while the second protrusion part $558a_4$ is inserted in the main body part 512 through the groove body G510.

The press part 558b includes first and second plate-like bodies $558b_1$ and $558b_2$ and first and second protrusion parts $558b_3$ and $558b_4$. The first plate-like body $558b_1$ has a circular arc-like shape that extends along the periphery of the base part 552. One end of the first plate-like body $558b_1$ is integrally connected to the hook part 554b. The other end of the first plate-like body $558b_1$ extends toward the opposite side to the press part 558a and up to the vicinity of the cutout part 514b of the main body part 512. The other end of the first plate-like body $558b_1$ is more spaced outward apart from the base part 552 with increasing distance from the hook part 554b. The second plate-like body $558b_2$ has a rectangular shape. One main surface of the second plate-like body $558b_2$ is opposed to the periphery of the base part 552 and the outer circumferential surface of the main body part 512.

The first and second protrusion parts $558b_3$ and $558b_4$ extend from the one main surface of the second plate-like body $558b_2$ toward the outer circumferential surface of the main body part 512. The first protrusion part $558b_3$ is a plate-like body having a triangular shape when viewed from above. In the completed state of the applicator A12, the oblique side of the first protrusion part $558b_3$ faces the cutout part 512j of the main body part 512, and the height thereof is larger toward the first plate-like body $558b_1$. The second protrusion part $558b_4$ is located below the first protrusion part $558b_3$ and closer to the side edge opposite to the first plate-like body $558b_1$, of the second plate-like body $558b_2$.

The press part 558b can take a first state and a second state. In the first state, a pressing force is not exerted on the second plate-like body $558b_2$, and the press part $558b$ is not deformed. The second state is a state after a pressing force is exerted on the second plate-like body $558b_2$ and the press part $558b$ is thus deformed. In the second state after the deformation, the second plate-like body $558b_2$ comes close to the periphery of the base part 552 and the outer circumferential surface of the main body part 512, and the first protrusion part $558b_3$ is inserted in the main body part 512 through a region above the wall part $512e$, of the cutout part $512j$, while the second protrusion part $558b_4$ is inserted in the main body part 512 through the groove body G530.

It is desirable that the applicator A12 have a shape that enables easy hold and enables easy application (easy puncture) of the microneedles 32 to the skin of the animal (including a human). Thus, a recess or a step may be provided on the surface of the release member 550. A fine groove may be formed on the surface of the release member 550, or a non-slippery coating layer may be provided thereon, whereby the surface of the release member 550 may be roughened. A through-hole may be formed in the casing 510 or the release member 550 for the purpose of reducing the air resistance and the weight.

[12.2] Method of Manufacturing Applicator

Now, the method of manufacturing the applicator A12 is described. First, the piston plate 520 is placed in the main body part 512 through procedures similar to the first, fourth, and the third steps in the method of manufacturing the applicator A1 according to the first embodiment, which are performed in the stated order (see FIG. 70 to be described later).

Figure 71:
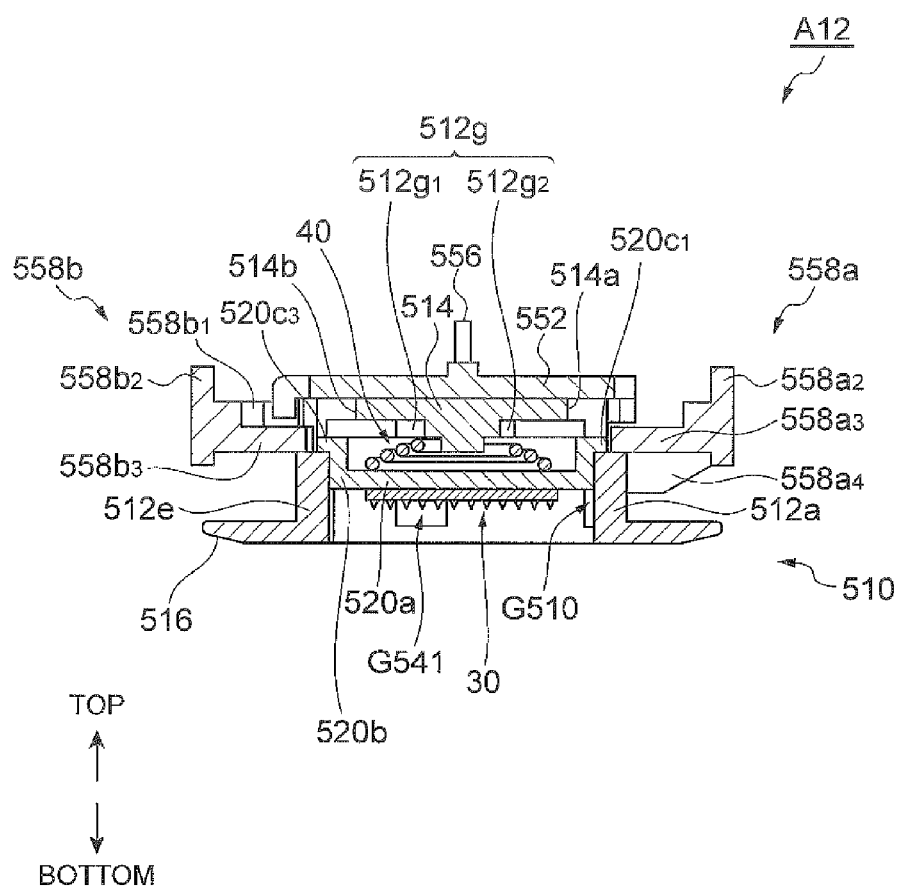
FIG. 71 is a cross sectional view taken along line LXXI-LXXI in FIG. 70.

On this occasion, because the projections $520c_1$, $520c_2$, $520c_3$ and $520c_4$ are respectively placed on the wall parts $512a$ and $512e$ and the second portions $512c_2$ and $512g_2$ of the wall parts $512c$ and $512g$, even if the cover part 514 and the piston plate 520 compress the conical coil spring 40, the piston plate 520 is not pushed out in the bottom direction by the conical coil spring 40. That is, the piston plate 520 is locked with the casing 510 (main body part 512). Accordingly, as illustrated in FIG. 71 to be described later, the piston plate 520 is held at its retraction position on the cover part 514 side inside of the main body part 512, in the state where the cover part 514 and the piston plate 520 compress the conical coil spring 40. Such a state as described above where the piston plate 520 is locked with the casing 510 (main body part 512) and where the cover part 514 and the piston plate 520 compress the conical coil spring 40 is hereinafter referred to as "locked state".

Locking the piston plate 520 with the casing 510 (main body part 512) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the piston plate 520 and the cover part 514 becomes slightly larger than the wire diameter, in the state where the piston plate 520 is locked (cocked) with the casing 510 (see FIG. 71). Note that, depending on the configuration of the piston plate 520, the piston plate 520 can come extremely close to the cover part 514, and the height of the conical coil spring 40 sandwiched between the piston plate 520 and the cover part 514 can become equivalent to the wire diameter, in the state where the piston plate 520 is locked (cocked) with the casing 510.

Figure 61:
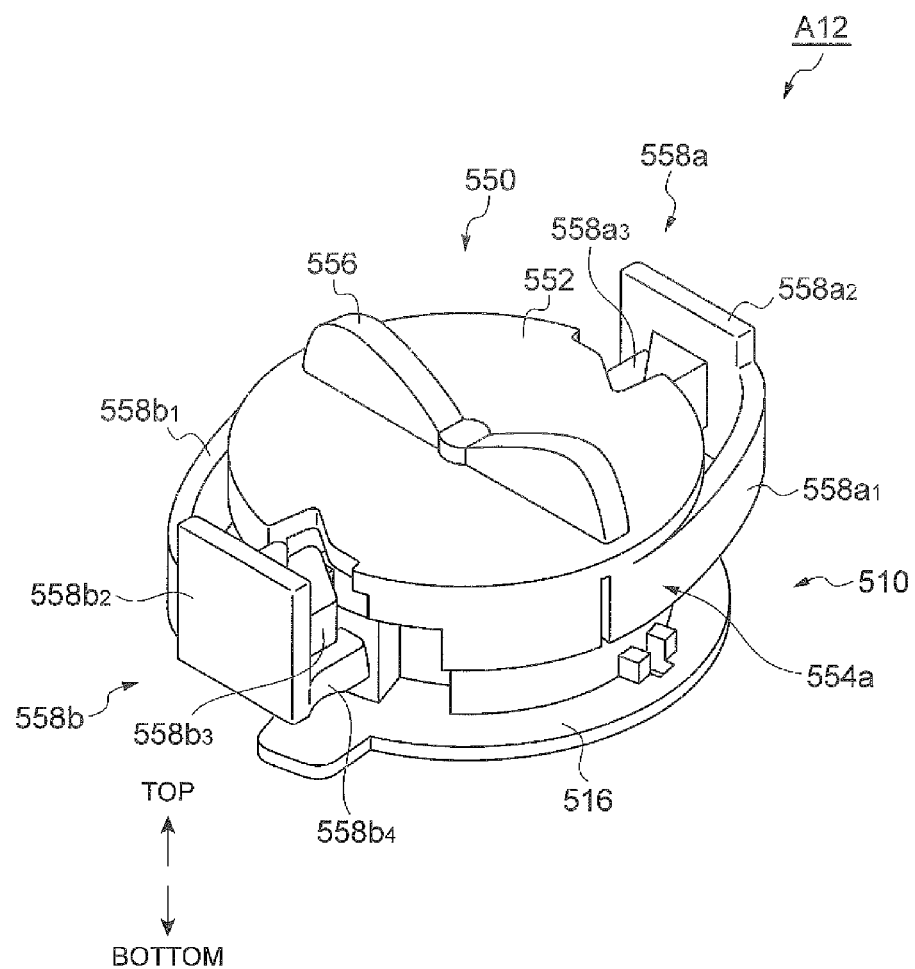
FIG. 61 is a perspective view of an applicator according to a twelfth embodiment.
Figure 62:
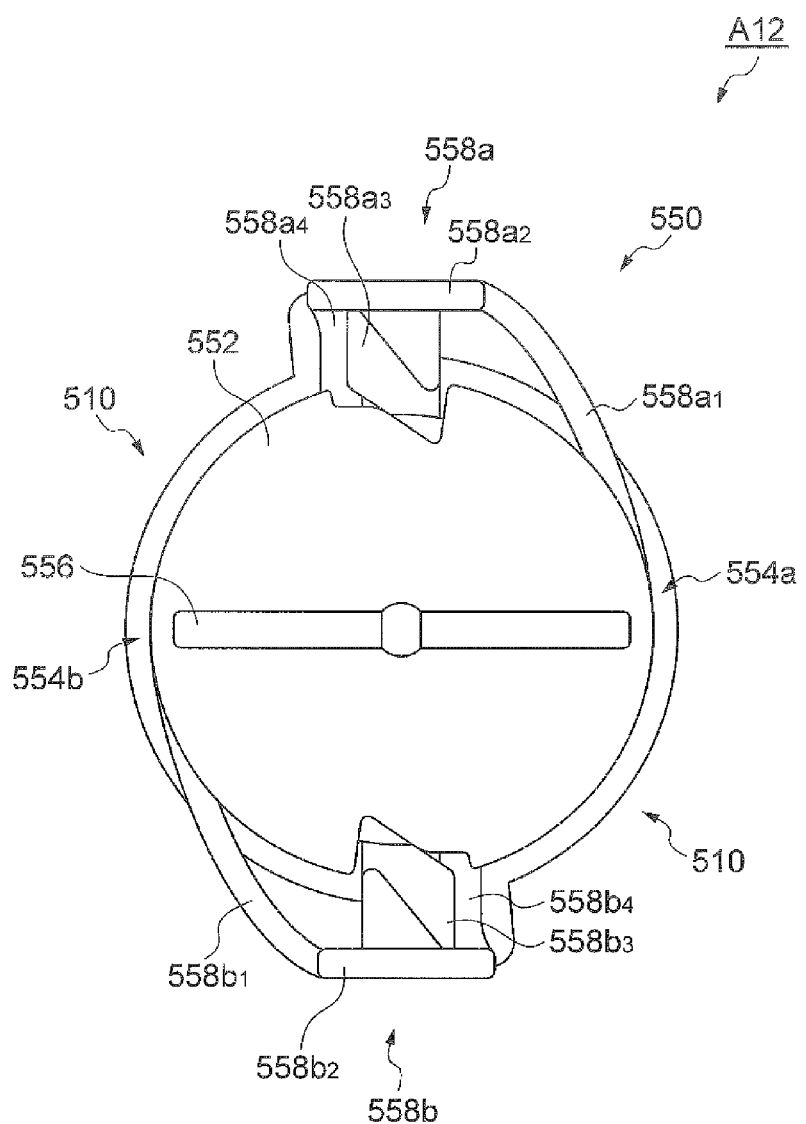
FIG. 62 is a top view of the applicator according to the twelfth embodiment.

Subsequently, the elongated protrusions $554c$ and $554d$ of the hook parts $554a$ and $554b$ are respectively engaged with the groove parts $512k$ and $512l$, and the release member 550 is thus attached to the casing 510 (main body part 512) such that the elongated protrusions $554c$ and $554d$ are respectively located on one end sides of the groove parts $512k$ and $512l$. At this time, as illustrated in FIG. 61 and FIG. 62, the first protrusion part $558a_3$ is not opposed to the cutout part $512i$ but is opposed to the outer circumferential surface of the wall part $512b$, and the second protrusion part $558a_4$ is not opposed to the groove body G510 but is opposed to the outer circumferential surface of the wall part $512a$. Similarly, the first protrusion part $558b_3$ is not opposed to the cutout part $512j$ but is opposed to the outer circumferential surface of the wall part $512f$, and the second protrusion part $558b_4$ is not opposed to the groove body G530 but is opposed to the outer circumferential surface of the wall part $512e$.

Through the above-mentioned procedures, assembling of the applicator A12 is completed. Accordingly, the conical coil spring 40 remains in a compressed state until the applicator A12 is used by a user after manufacture and shipping thereof. In addition, even if the user presses the press parts $558a$ and $558b$, the press parts $558a$ and $558b$ are not inserted into the main body part 512, and hence the first states of the press parts $558a$ and $558b$ are maintained (see FIG. 61 and FIG. 62). That is, the first protrusion parts $558a_3$ and $558b_3$ are prevented from coming into contact with the projections $520c_1$ and $520c_3$.

[12.3] Method of Using Applicator

Figure 69:
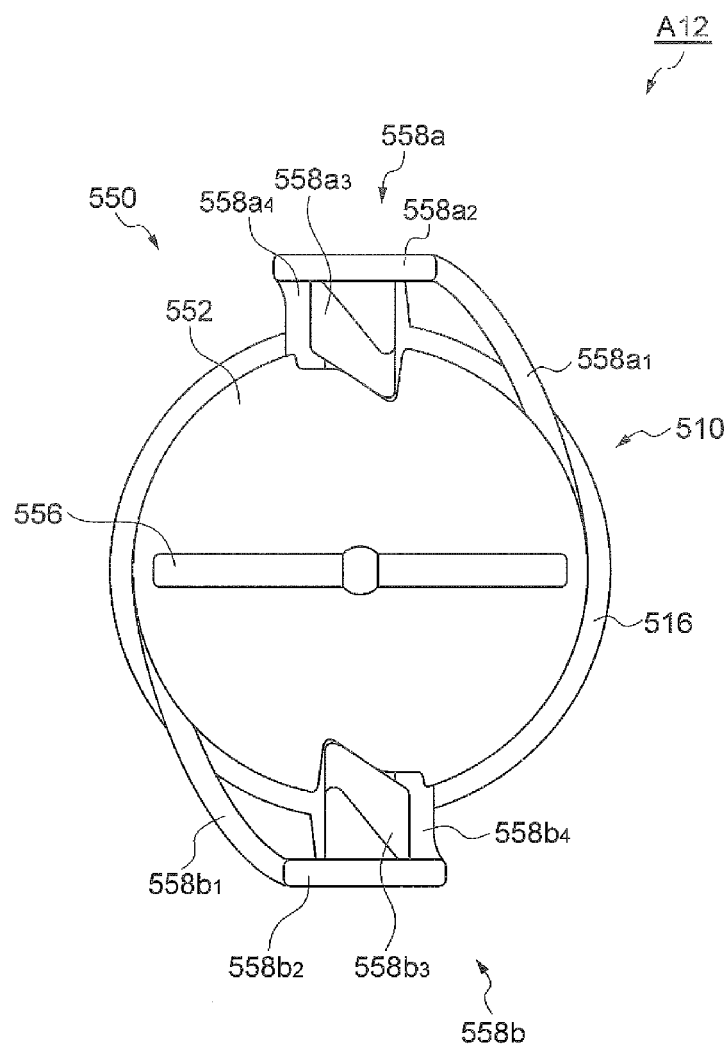
FIG. 69 is a top view of the applicator according to the twelfth embodiment, for describing a turning state of the release member.
Figure 70:
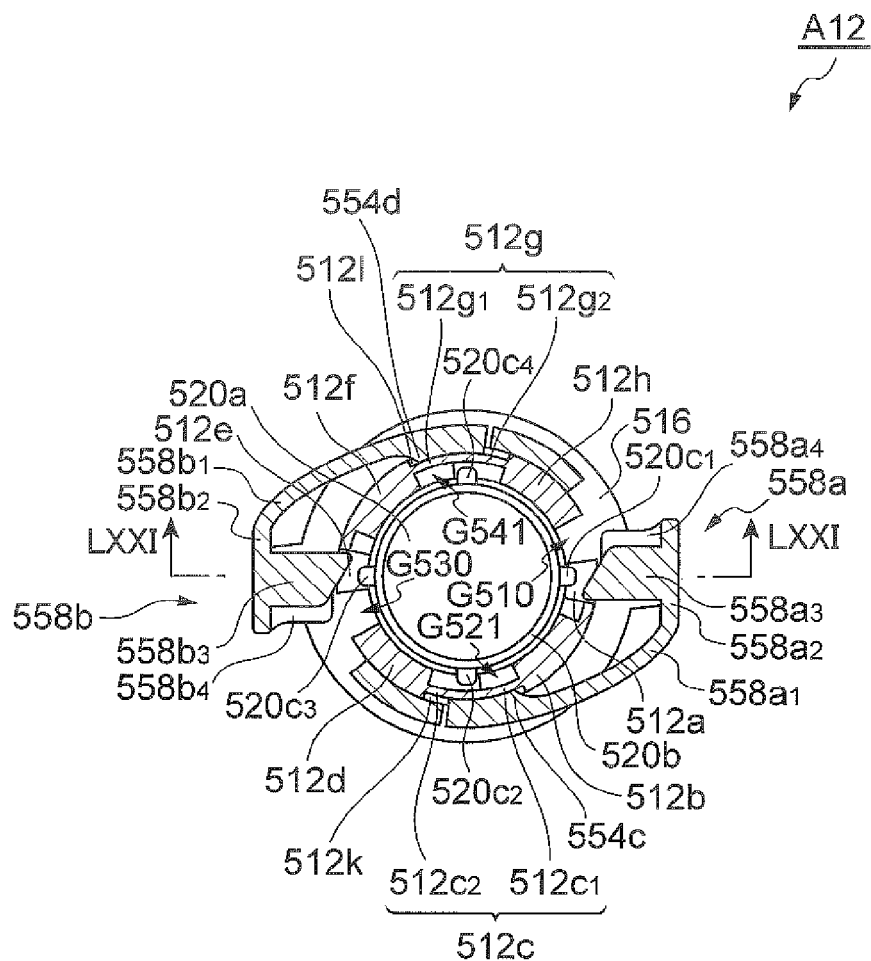
FIG. 70 is a top view illustrating a state before an operation of the applicator according to the twelfth embodiment, in which the release member and the cover part of the casing are cut away.

Now, the method of using the applicator A12 is described. First, the user respectively moves the elongated protrusions $554c$ and $554d$ to the other end sides of the groove parts $512k$ and $512l$ by pinching the knob part 556 and turning the release member 550 (see FIG. 69 to FIG. 71). This unlocks the release member 550 and enables the press parts $558a$ and $558b$ to move toward the casing 510 (main body part 512). At this time, as illustrated in FIG. 70 and FIG. 71, the oblique side of the first protrusion part $558a_3$ is opposed to the projection $520c_1$, and the oblique side of the first protrusion part $558b_3$ is opposed to the projection $520c_3$.

Figure 72:
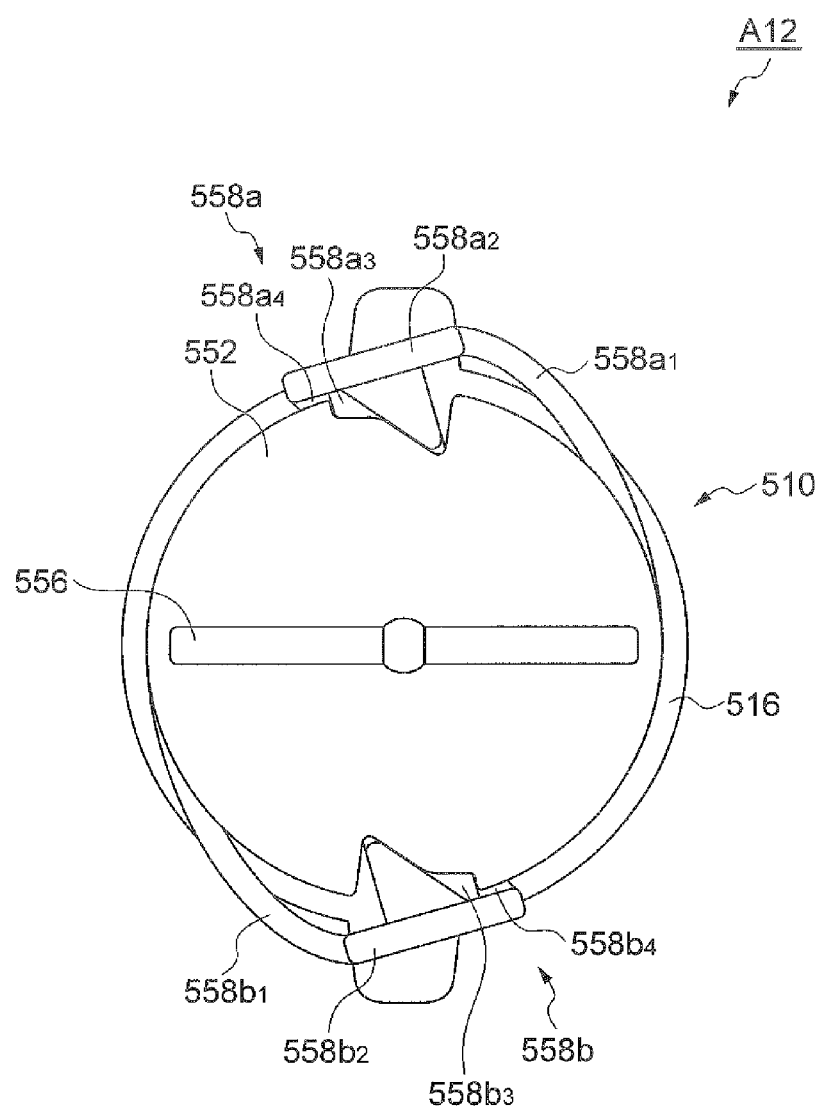
FIG. 72 is a top view illustrating a state after the operation of the applicator according to the twelfth embodiment.
Figure 73:
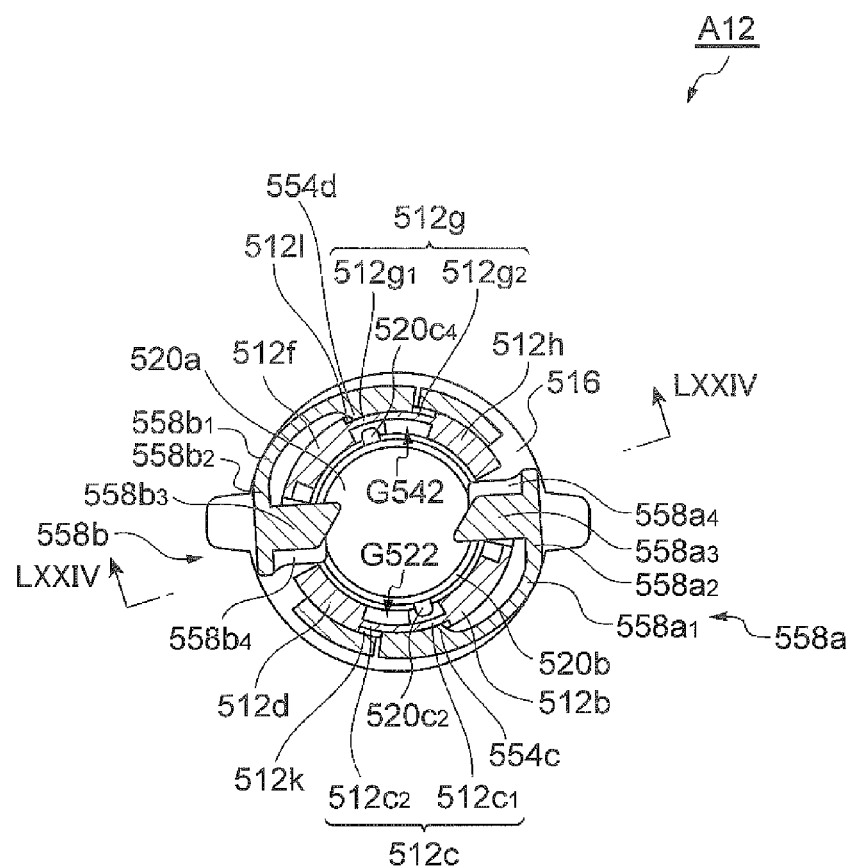
FIG. 73 is a top view illustrating the state after the operation of the applicator according to the twelfth embodiment, in which the release member and the cover part of the casing are cut away.
Figure 74:
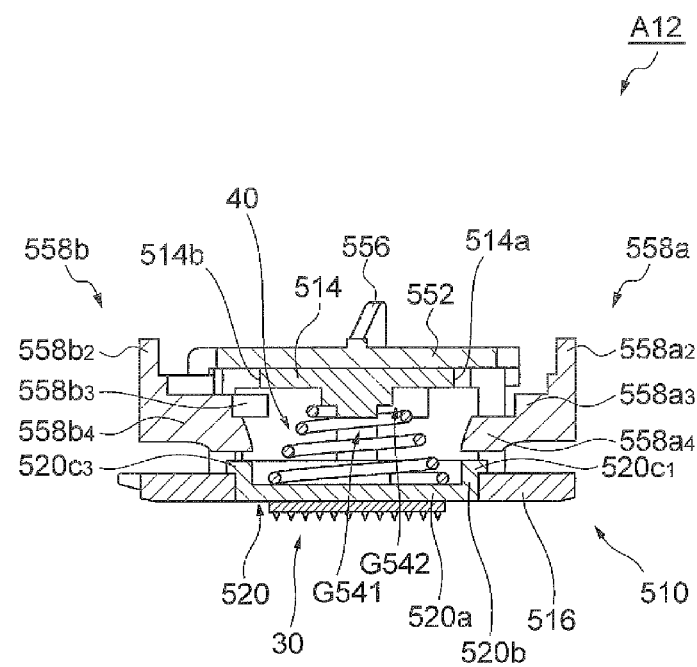
FIG. 74 is a cross sectional view taken along line LXXIV-LXXIV in FIG. 73.

Subsequently, the user positions the applicator A12 with respect to a portion of a skin to which a medical agent or the like is desired to be applied, such that the microneedles 32 face the skin. The user pushes the press parts $558a$ and $558b$ toward the casing 510 (main body part 512) while the applicator A12 is kept positioned. Consequently, the oblique side of the first protrusion part $558a_3$ abuts against the projection $520c_1$, and the oblique side of the first protrusion part $558b_3$ abuts against the projection $520c_3$. If the user further pushes the press parts $558a$ and $558b$ toward the casing 510 (main body part 512), the projection $520c_1$ is pushed out in the direction normal to the oblique side of the first protrusion part $558a_3$ while sliding on the oblique side thereof, and the projection $520c_3$ is pushed out in the direction normal to the oblique side of the first protrusion part $558b_3$ while sliding on the oblique side thereof. Consequently, a turning force is exerted on the piston plate 520, with the result that the piston plate 520 turns (see FIG. 72 to FIG. 74). Accordingly, the locking (cocking) of the piston plate 520 with the casing 510 (main body part 512) is released. After that, similarly to the applicator A1 according to the first embodiment, the microneedle array 30 collides against the skin due to the biasing force (elastic force) of the conical coil spring 40 (see FIG. 74).

If the user pushes the press parts $558a$ and $558b$ toward the casing 510 (main body part 512), the second protrusion part $558a_4$ is inserted in the main body part 512 through the groove body G510, and the second protrusion part $558b_4$ is inserted in the main body part 512 through the groove body G530. Because the second protrusion part $558a_4$ is located below the first protrusion part $558a_3$ and the second protrusion part $558b_4$ is located below the first protrusion part $558b_3$, the insertion states of the second protrusion parts $558a_4$ and $558b_4$ in the main body part 512 are achieved after the piston plate 520 passes by the second protrusion parts $558a_4$ and $558b_4$. Thus, after the piston plate 520 reaches a position for action on the skin, movement of the piston plate 520 is restricted by the second protrusion parts $558a_4$ and $558b_4$.

[12.4] Actions

The twelfth embodiment as described above produces actions and effects similar to the actions (A) to (D) of the applicator A1 according to the first embodiment.

Before the use of the applicator A12 according to the twelfth embodiment, the elongated protrusions 554c and 554d are respectively located on one end sides of the groove parts 512k and 512l, and the release member 550 is locked. Thus, even if the user presses the press parts 558a and 558b, the press parts 558a and 558b are not inserted into the main body part 512, and hence the first states of the press parts 558a and 558b are maintained. That is, the first protrusion parts $558a_3$ and $558b_3$ are prevented from coming into contact with the projections $520c_1$ and $520c_3$. Thus, the release member 550 can prevent the applicator A12 from malfunctioning. Further, at the time of the use, it is only necessary to turn the release member 550, and hence preparation for the use can be completed through a simple operation.

In the applicator A12 according to the twelfth embodiment, the release member 550 is provided with the second protrusion parts (engagement pieces) $558a_4$ and $558b_4$ to be engaged with the piston plate 520 that has reached the position for action on the skin. Thus, after the piston plate 520 reaches the position for action on the skin, movement of the piston plate 520 is restricted by the second protrusion parts $558a_4$ and $558b_4$. Thus, a bounce of the piston plate 520 toward the cover part 514 is suppressed by the second protrusion parts $558a_4$ and $558b_4$. As a result, the certainty of a puncture in the skin with the microneedles 32 can be enhanced.

[13] Thirteenth Embodiment

[13.1] Configuration of Applicator

Now, a configuration of an applicator A13 according to a thirteenth embodiment is described with reference to FIG. 75 to FIG. 78. In the following description, the term "top" corresponds to the top direction of FIG. 75, FIG. 76, and FIG. 78, and the term "bottom" corresponds to the bottom direction of FIG. 75, FIG. 76, and FIG. 78. That is, the top-bottom direction corresponds to the height direction of the applicator A13.

The applicator A13 is a device for transferring active ingredients of a medical agent or the like into the body of an animal such as a human through a skin of the animal. The applicator A13 includes a casing 610, a piston plate 620, the microneedle array 30, the conical coil spring 40, a first release member 650, and a second release member 660.

Figure 76:
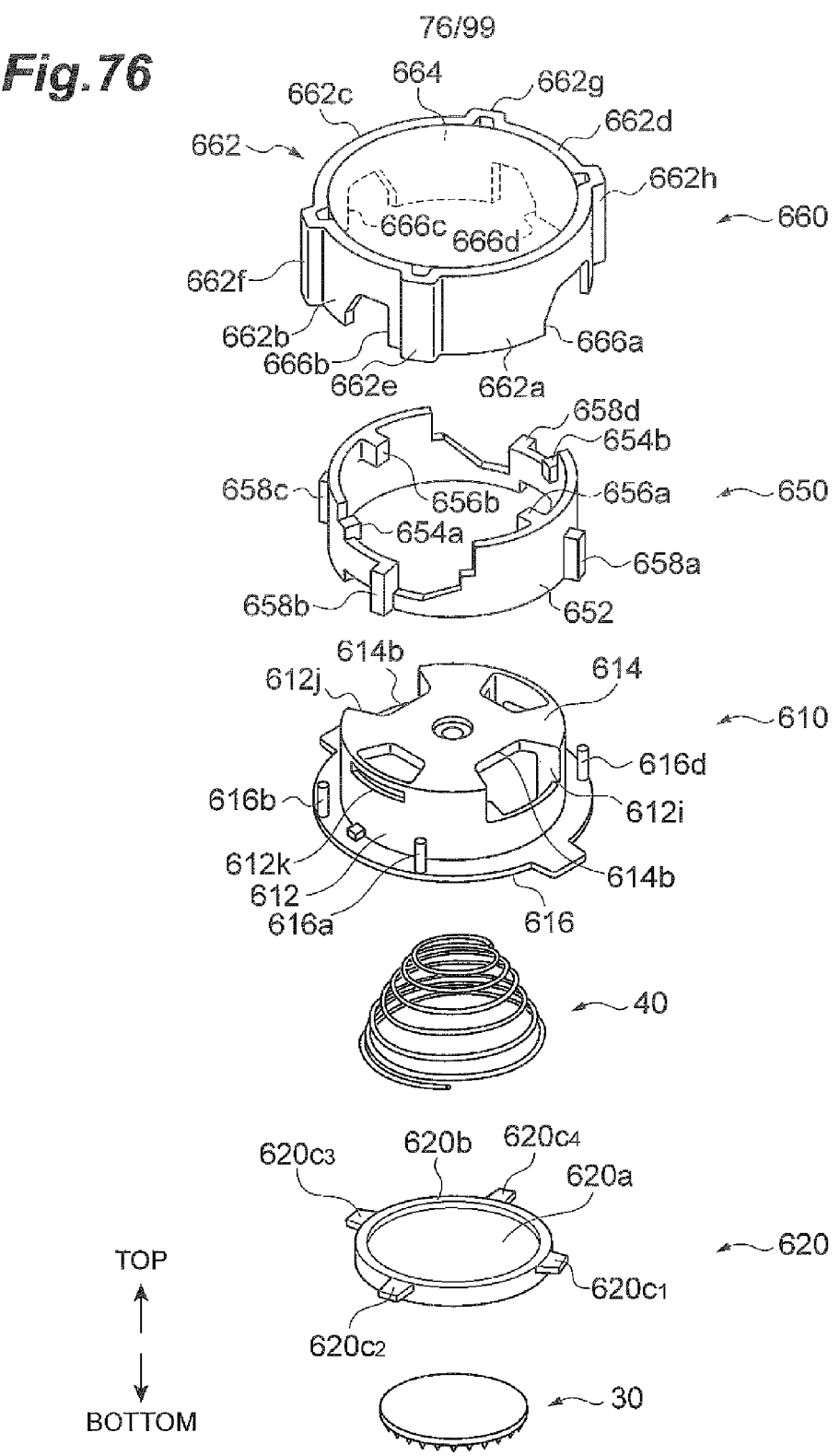
FIG. 76 is an exploded perspective view of the applicator according to the thirteenth embodiment.
Figure 77:
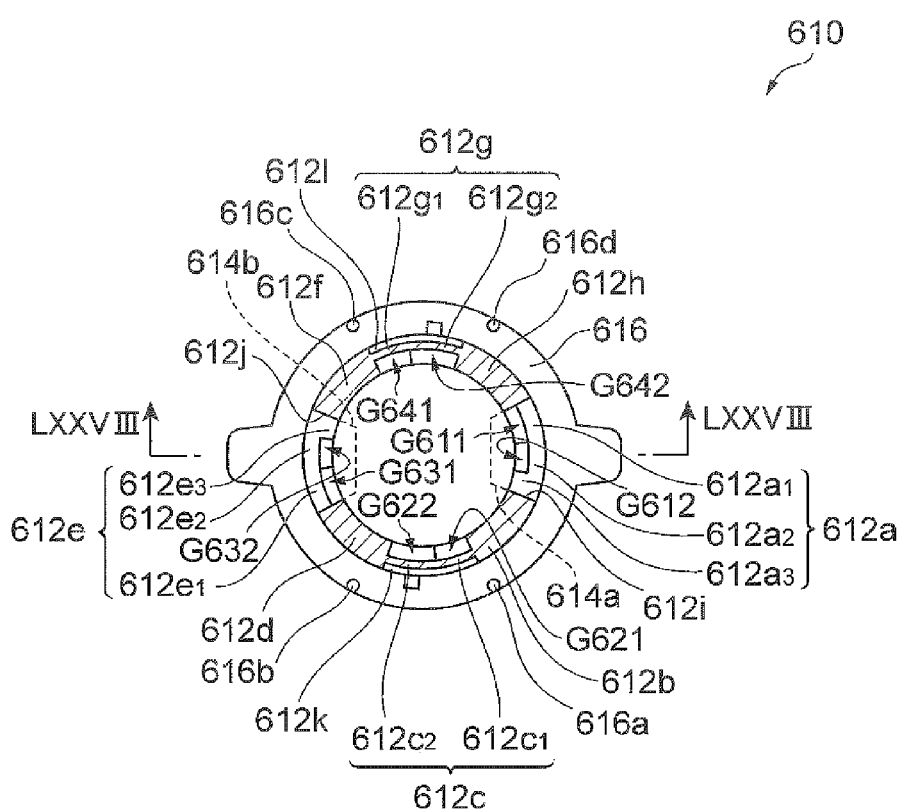
FIG. 77 is a top view of a casing, the upper end part (cover part) of which is cut away.
Figure 78:
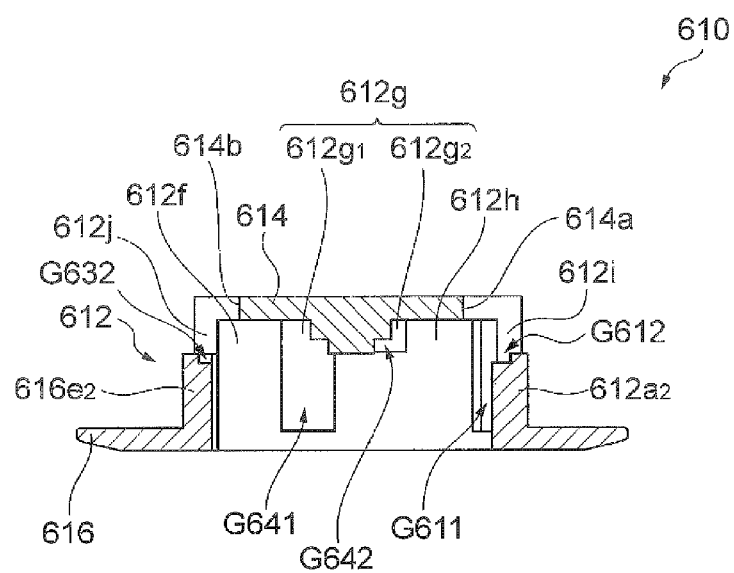
FIG. 78 is a cross sectional view taken along line LXXVIII-LXXVIII in FIG. 77.

As illustrated in FIG. 76 to FIG. 78, the casing 610 includes: a main body part 612 having the central axis that extends along the top-bottom direction and having a cylindrical shape; a cover part 614 arranged on the upper end side of the main body part 612; and a circular ring-like flange part 616 arranged on the lower end side of the main body part 612. The strength and the material of the casing 610 may be the same as those of the casing 10 of the applicator A1 according to the first embodiment.

The main body part 612 includes wall parts 612a, 612b, 612c, 612d, 612e, 612f, 612g and 612h each having a circular arc-like shape when viewed from above. The wall parts 612a, 612b, 612c, 612d, 612e, 612f, 612g and 612h are arranged in the stated order in the clockwise direction when viewed from the upper end side (the cover part 614 side) of the main body part 612. Respective adjacent wall parts of the wall parts 612a, 612b, 612c, 612d, 612e, 612f, 612g and 612h are integrated with each other (see FIG. 77). The wall part 612a and the wall part 612e are opposed to each other with the axis of the main body part 612 being centered therebetween, when viewed from above. The wall part 612b and the wall part 612f are opposed to each other with the axis of the main body part 612 being centered therebetween, when viewed from above. The wall part 612c and the wall part 612g are opposed to each other with the axis of the main body part 612 being centered therebetween, when viewed from above. The wall part 612d and the wall part 612h are opposed to each other with the axis of the main body part 612 being centered therebetween, when viewed from above.

The main body part 612 is provided with cutout parts 612i and 612j at positions respectively corresponding to the wall parts 612a and 612e. The cutout parts 612i and 612j are opposed to each other with the central axis of the main body part 612 being centered therebetween, when viewed from above. Thus, the height of the wall part 612a is made smaller by the existence of the cutout part 612i, and the upper end thereof does not reach the cover part 614. The height of the wall part 612e is made smaller by the existence of the cutout part 612j, and the upper end thereof does not reach the cover part 614.

Groove parts 612k and 612l are provided on the outer circumferential surface of the main body part 612 at positions respectively corresponding to the wall parts 612c and 612g. The groove parts 612k and 612l are located closer to the upper end of the main body part 612, and extend along the circumferential direction.

On the inner surface of the wall part 612a, a groove part G611 that extends in the top-bottom direction is provided closer to the wall part 612h, and a groove part G612 that extends in the circumferential direction is provided in the vicinity of the upper end of the wall part 612a. The groove part G611 extends from the vicinity of the lower end of the wall part 612a to the upper end thereof. The groove part G612 extends in the circumferential direction of the main body part 612 from the wall part 612h, and does not reach the wall part 612b. The groove part G612 is communicated with the upper end of the groove part G611. Thus, the wall part 612a includes: a first portion $612a_1$ that is made thinner by the existence of the groove part G611 except the lower end part thereof; a second portion $612a_2$ having an upper end part made thinner by the existence of the groove part G612 and a thicker portion below the groove part G612; and a third portion $612a_3$ that is thicker than the first portion $612a_1$ over the entire region in the top-bottom direction.

On the inner surface of the wall part 612c, a groove part G621 that extends in the top-bottom direction is provided closer to the wall part 612b, and a groove part G622 that extends in the circumferential direction is provided in the vicinity of the upper end of the wall part 612c. The groove part G621 extends from the vicinity of the lower end of the wall part 612c to the upper end thereof. The groove part G622 extends from the wall part 612b to the wall part 612d, and is communicated with the upper end of the groove part G621. Thus, the wall part 612c includes: a first portion $612c_1$ that is made thinner by the existence of the groove part G621 except the lower end part thereof; and a second portion $612c_2$ having an upper end part made thinner by the existence of the groove part G622 and a thicker portion below the groove part G622.

On the inner surface of the wall part 612e, a groove part G631 that extends in the top-bottom direction is provided closer to the wall part 612d, and a groove part G632 that extends in the circumferential direction is provided in the vicinity of the upper end of the wall part 612e. The groove part G631 extends from the vicinity of the lower end of the wall part 612e to the upper end thereof. The groove part G632 extends in the circumferential direction of the main body part 612 from the wall part 612d, and does not reach the wall part 612f. The groove part G632 is communicated with the upper end of the groove part G631. Thus, the wall part 612e includes: a first portion $612e_1$ that is made thinner by the existence of the groove part G631 except the lower end part thereof; a second portion $612e_2$ having an upper end part made thinner by the existence of the groove part G632 and a thicker portion below the groove part G632; and a third portion $612e_3$ that is thicker than the first portion $612e_1$ over the entire region in the top-bottom direction.

On the inner surface of the wall part 612g, a groove part G641 that extends in the top-bottom direction is provided closer to the wall part 612f, and a groove part G642 that extends in the circumferential direction is provided in the vicinity of the upper end of the wall part 612g. The groove part G641 extends from the vicinity of the lower end of the wall part 612g to the upper end thereof. The groove part G642 extends from the wall part 612f to the wall part 612h, and is communicated with the upper end of the groove part G641. Thus, the wall part 612g includes: a first portion $612g_1$ that is made thinner by the existence of the groove part G641 except the lower end part thereof; and a second portion $612g_2$ having an upper end part made thinner by the existence of the groove part G642 and a thicker portion below the groove part G642.

The cover part 614 is a plate-like body having a circular shape. The peripheral part of the lower surface of the cover part 614 is integrated with the upper ends of the wall parts 612b, 612c, 612d and 612f, 612g and 612h. Thus, the cover part 614 closes the upper end of the main body part 612.

The cover part 614 is provided with cutout parts 614a and 614b at positions respectively corresponding to the wall parts 612a and 612e when viewed from above. The cutout parts 614a and 614b are opposed to each other with the axis of the cover part 614 being centered therebetween, when viewed from above. The cutout parts 614a and 614b are both concaved toward the center of the cover part 614.

The flange part 616 protrudes outward from the lower end of the main body part 612. At the time of using the applicator A13, the flange part 616 makes the contact area with the skin larger, and hence a pressure applied to the skin can be made smaller. Four pin members 616a, 616b, 616c and 616d are erected on the upper surface of the flange part 616. The pin members 616a, 616b, 616c and 616d function as guide means for guiding the second release member 660 in the central axis direction of the main body part 612. The pin member 616a is opposed to the outer circumferential surface of the wall part 612b. The pin member 616b is opposed to the outer circumferential surface of the wall part 612d. The pin member 616c is opposed to the outer circumferential surface of the wall part 612f. The pin member 616d is opposed to the outer circumferential surface of the wall part 612h.

The piston plate 620 is housed in the main body part 612, and is movable in the top-bottom direction along the central axis of the main body part 612 inside of the main body part 612. The material of the piston plate 620 may be the same as the material of the casing 610, and may be the same as the material of the microneedle array 30. As illustrated in FIG. 76, the piston plate 620 includes: a disc-like main body 620a; and a cylindrical member 620b that extends upward from the periphery of the main body 620a. An opening, a groove, a through-hole, or the like may be formed in the main body 620a for the purpose of reducing the air resistance and the weight of the piston plate 620. Further, an elongated protrusion or the like may be provided on the upper surface (the surface on which the conical coil spring 40 is arranged) of the main body 620a for the purpose of improving the rigidity of the piston plate 620. It is preferable that the lower surface (the surface opposite to the upper surface) of the main body 620a be planar, in consideration of causing the piston plate 620 to evenly act on the microneedle array 30. Alternatively, the lower surface of the main body 620a may have other shapes than the planar shape, and the shape of the lower surface of the main body 620a can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The inner diameter of the cylindrical member 620b is set to be larger than the maximum diameter D1 of the conical coil spring 40. The height of the cylindrical member 620b is not particularly limited as long as the cylindrical member 620b can function as such a stopper that prevents the conical coil spring 40 from dropping off the piston plate 620 during its movement in the radial direction. For example, in the case where the height of the applicator A13 is desired to be minimized, the height of the cylindrical member 620b can be set to be equivalent to the thickness of a metal wire that forms the conical coil spring 40. In the case where the stopper for the conical coil spring 40 is not necessary, the piston plate 620 does not need to include the cylindrical member 620b. Even in the case where the piston plate 620 does not include the cylindrical member 620b, if a ring-like groove in which the metal wire that forms the conical coil spring 40 can be fit is formed in the main body 620a, the function as the stopper for the conical coil spring 40 can be fulfilled by the ring-like groove. In the case where such a stopper for the conical coil spring 40 is provided, a failure in positioning of the conical coil spring 40 with respect to the piston plate 620 can be prevented at the time of arranging the conical coil spring 40 on the upper surface of the piston plate 620 and attaching the two to the inside of the casing 610.

A plurality of projections (in the thirteenth embodiment, four projections) $620c_1$, $620c_2$, $620c_3$ and $620c_4$ are provided in the periphery (on the outer circumferential surface) of the piston plate 620, and the projections $620c_1$, $620c_2$, $620c_3$ and $620c_4$ protrude outward in the radial direction (the direction that intersects with the thickness direction of the piston plate). The projections $620c_1$, $620c_2$, $620c_3$ and $620c_4$ are arranged in the stated order in the clockwise direction when viewed from above (the upper surface side of the piston plate 620 on which the conical coil spring 40 is placed), with given intervals in the circumferential direction. In the thirteenth embodiment, the projections $620c_1$, $620c_2$, $620c_3$ and $620c_4$ are plate-like bodies each having a trapezoidal shape. Alternatively, the projections $620c_1$, $620c_2$, $620c_3$ and $620c_4$ may have other shapes (for example, a columnar shape, a polygonal prism shape, a deformed pillar shape, a circular cone shape, a polygonal pyramid shape, a truncated circular cone shape, and a truncated polygonal pyramid shape) as long as locking with the second portions $612a_2$, $612c_2$, $612e_2$, and $612g_2$ of the wall parts $612a$, $612c$, $612e$, and $612g$ is possible and movement in the groove parts G611, G621, G631, and G641 is possible.

The projection $620c_1$ is movable along the extending direction of the groove part G611 inside of the groove part G611. The projection $620c_2$ is movable along the extending direction of the groove part G621 inside of the groove part G621. The projection $620c_3$ is movable along the extending direction of the groove part G631 inside of the groove part G631. The projection $620c_4$ is movable along the extending direction of the groove part G641 inside of the groove part G641. Thus, the piston plate 620 can be guided in the top-bottom direction along the extending directions of the groove parts G611, G621, G631, and G641 (the central axis direction of the main body part 612).

In the state where the projection $620c_1$ is located on the upper end side of the groove part G611, the projection $620c_1$ is movable in the horizontal direction inside of the groove part G612 communicated with the groove part G611. Thus, the projection $620c_1$ can be placed on the upper end of the second portion $612a_2$ of the wall part $612a$ adjacent to the groove part G611. In the state where the projection $620c_2$ is located on the upper end side of the groove part G621, the projection $620c_2$ is movable in the horizontal direction inside of the groove part G622 communicated with the groove part G621. Thus, the projection $620c_2$ can be placed on the upper end of the second portion $612c_2$ of the wall part $612c$ adjacent to the groove part G621.

In the state where the projection $620c_3$ is located on the upper end side of the groove part G631, the projection $620c_3$ is movable in the horizontal direction inside of the groove part G632 communicated with the groove part G631. Thus, the projection $620c_3$ can be placed on the upper end of the wall part $612e$ adjacent to the groove part G631. In the state where the projection $620c_4$ is located on the upper end side of the groove part G641, the projection $620c_4$ is movable in the horizontal direction inside of the groove part G642 communicated with the groove part G641. Thus, the projection $620c_4$ can be placed on the upper end of the second portion $612g_2$ of the wall part $612g$ adjacent to the groove part G641.

The upper ends of the second portions $612a_2$, $612c_2$, $612e_2$, and $612g_2$ of the wall parts $612a$, $612c$, $612e$, and $612g$ may extend in the circumferential direction so as to be parallel to a horizontal plane, and may be inclined to the horizontal plane, in the circumferential direction. In particular, the upper ends of the second portions $612a_2$, $612c_2$, $612e_2$, and $612g_2$ may be inclined such that the heights thereof become larger toward the respective adjacent groove parts G611, G621, G631, and G641. In this case, when the projections $620c_1$, $620c_2$, $620c_3$ and $620c_4$ respectively placed on the upper ends of the second portions $612a_2$, $612c_2$, $612e_2$, and $612g_2$ move toward the groove parts G611, G621, G631, and G641, the projections $620c_1$, $620c_2$, $620c_3$ and $620c_4$ need to climb the slopes of the upper ends of the second portions $612a_2$, $612c_2$, $612e_2$, and $612g_2$. Thus, even if an impact or the like is applied from the outside to the applicator A13, the projections $620c_1$, $620c_2$, $620c_3$ and $620c_4$ can be prevented from unintentionally moving into the groove parts G611, G621, G631, and G641.

The microneedle array 30 and the conical coil spring 40 are the same as those in the first embodiment, and hence description thereof is omitted.

As illustrated in FIG. 76, the first release member 650 includes a main body 652 having a cylindrical shape, a pair of projections 654a and 654b, a pair of protrusion parts 656a and 656b, and four elongated protrusions 658a, 658b, 658c and 658d. The material of the first release member 650 may be the same as the material of the casing 610, and may be the same as the material of the microneedle array 30. The first release member 650 may be made of a flexible or elastic material.

In the completed state of the applicator A13, the main body 652 is inserted around the outer circumferential surface of the main body part 612 of the casing 610, and covers the outer circumferential surface. The inner diameter of the main body 652 is set to be equivalent to or slightly larger than the outer diameter of the main body part 612. Thus, the main body 652 is relatively turnable with respect to the main body part 612.

The pair of projections 654a and 654b are provided in a protruding manner on the inner circumferential surface of the main body 652 so as to face the central axis of the main body 652. The projections 654a and 654b are located so as to be opposed to each other on the inner circumferential surface of the main body 652. In the completed state of the applicator A13, the projection 654a is inserted in the groove part 612k of the main body part 612, and is engaged with the groove part 612k. In the completed state of the applicator A13, the projection 654b is inserted in the groove part 612l of the main body part 612, and is engaged with the groove part 612l. Thus, the projections 654a and 654b are respectively movable inside of the groove parts 612k and 612l.

The pair of protrusion parts 656a and 656b are provided in a protruding manner on the inner circumferential surface of the main body 652 so as to face the central axis of the main body 652. The protrusion parts 656a and 656b are located so as to be opposed to each other on the inner circumferential surface of the main body 652. In the completed state of the applicator A13, the protrusion part 656a is inserted in the cutout part 612i of the main body part 612. In the completed state of the applicator A13, the protrusion part 656b is inserted in the cutout part 612j of the main body part 612.

The four elongated protrusions 658a, 658b, 658c and 658d are provided on the outer circumferential surface of the main body 652. The elongated protrusions 658a, 658b, 658c and 658d extend from the lower end part of the main body 652 to the central part thereof along the central axis direction of the main body part 612 (the central axis direction of the main body 652). In the completed state of the applicator A13, the elongated protrusion 658a is opposed to the wall part 612a of the main body part 612, the elongated protrusion 658b is opposed to the wall part 612c of the main body part 612, the elongated protrusion 658c is opposed to the wall part 612e of the main body part 612, and the elongated protrusion 658d is opposed to the wall part 612g of the main body part 612.

Figure 75:
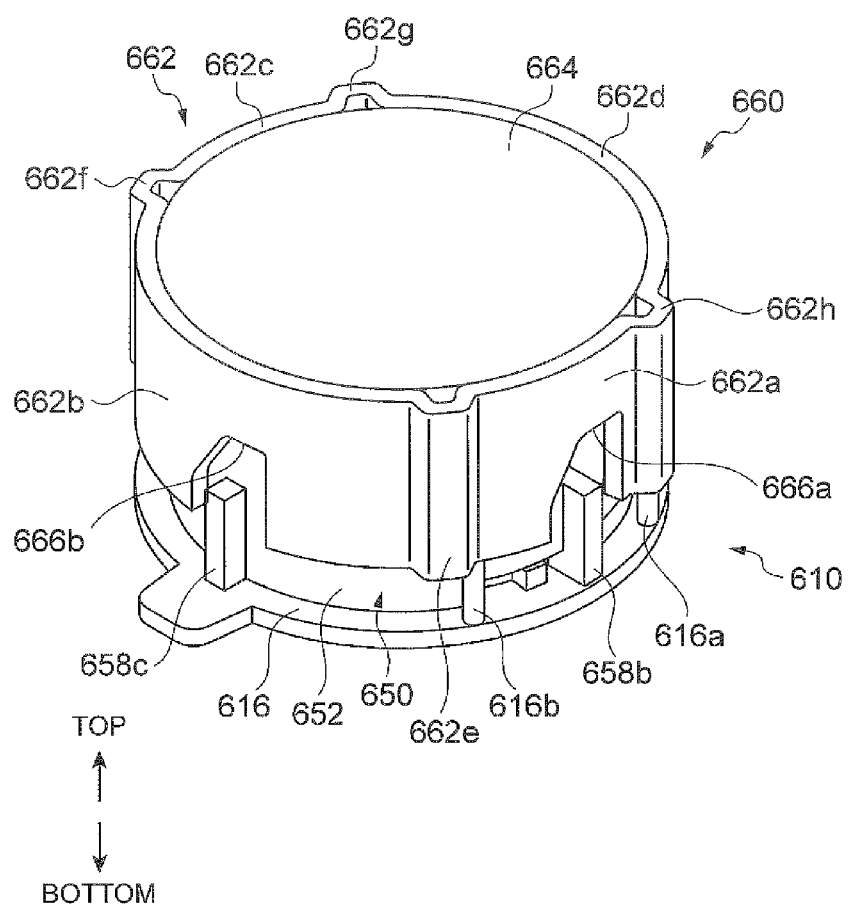
FIG. 75 is a perspective view of the applicator according to a thirteenth embodiment.

As illustrated in FIG. 75 and FIG. 76, the second release member 660 includes: a side wall part 662 having a tubular shape; and a disc-like top plate part 664 arranged in the upper end part of the side wall part 662. The material of the second release member 660 may be the same as the material of the casing 610, and may be the same as the material of the microneedle array 30. The second release member 660 may be made of a flexible or elastic material.

The side wall part 662 includes first to fourth portions 662a. 662b, 662c and 662d each having a circular arc-like shape and fifth to eighth portions 662e. 662f, 662g and 662h each having a C shape when viewed from the central axis direction of the main body part 612. The first to fourth portions 662a. 662b, 662c and 662d are located on a circumference having the same radius. Cutout parts 666a, 666b, 666c and 666d are respectively formed in the lower end parts of the first to fourth portions 662a. 662b, 662c and 662d. In the completed state of the applicator A13, the second release member 660 is attached to the casing 610 such that the cutout parts 666a, 666b, 666c and 666d respectively surround the elongated protrusions 658a. 658b, 658c and 658d.

The cutout part 666a has: a pair of first and second sides that extend substantially parallel to each other along the central axis direction of the main body part 612; a third side that extends along the circumferential direction of the first portion 662a; and a fourth side that extends so as to intersect with both the central axis direction of the main body part 612 and the circumferential direction of the first portion 662a. The first side is located closer to the fifth portion 662e, and the second side is located closer to the eighth portion 662h. The length of the first side is smaller than the length of the second side. One end of the third side is connected to the upper end of the second side, and the other end of the third side extends toward the fifth portion 662e. The length of the third side is smaller than the distance between the first and second sides. One end of the fourth side is connected to the upper end of the first side, and the other end of the fourth side is connected to the other end of the third side. Accordingly, the fourth side is inclined from the lower end side of the first portion 662a to the upper end side thereof from the first side toward the second side when viewed from lateral. The shapes of the cutout parts 666a, 666b, 666c and 666d are similar to that of the cutout part 666a, and hence description thereof is omitted.

The fifth portion 662e integrally couples the first and second portions 662a and 662b to each other. The sixth portion 662f integrally couples the second and third portions 662b and 662c to each other. The seventh portion 662g integrally couples the third and fourth portions 662c and 662d to each other. The eighth portion 662h integrally couples the fourth and first portions 662d and 662a to each other. That is, the first portion 662a, the fifth portion 662e, the second portion 662b, the sixth portion 662f, the third portion 662c, the seventh portion 662g, the fourth portion 662d, and the eighth portion 662h are arranged in the stated order in the clockwise direction when viewed from above. The fifth to eighth portions 662e. 662f, 662g and 662h each have a half-split tubular shape. Thus, in the case where concave parts of the fifth to eighth portions 662e. 662f, 662g and 662h are respectively opposed to the pin members 616a, 616b, 616c and 616d, the pin members 616a, 616b, 616c and 616d can be respectively inserted through the fifth to eighth portions 662e. 662f, 662g and 662h. Accordingly, the pin members 616a, 616b, 616c and 616d function as guide means for guiding the second release member 660 in the extending directions thereof.

In the completed state of the applicator A13, the side wall part 662 is inserted around the outer circumferential surface of the main body 652 of the first release member 650, and covers the outer circumferential surface. The inner diameter of the side wall part 662 is set to be equivalent to or slightly larger than the outer diameter of the main body 652.

[13.2] Method of Manufacturing Applicator

Now, the method of manufacturing the applicator A13 is described. First, the piston plate 620 is placed in the main body part 612 through procedures similar to the first, fourth, and third steps in the method of manufacturing the applicator A1 according to the first embodiment, which are performed in the stated order (see FIG. 81 to be described later).

On this occasion, because the projections $620c_1$, $620c_2$, $620c_3$ and $620c_4$ are respectively placed on the second portions $612a_2$, $612c_2$, $612e_2$, and $612g_2$ of the wall parts 612a, 612c, 612e, and 612g, even if the cover part 614 and the piston plate 620 compress the conical coil spring 40, the piston plate 620 is not pushed out in the bottom direction by the conical coil spring 40. That is, the piston plate 620 is locked with the casing 610 (main body part 612). Accordingly, the piston plate 620 is held at its retraction position on the cover part 614 side inside of the main body part 612, in the state where the cover part 614 and the piston plate 620 compress the conical coil spring 40. Such a state as described above where the piston plate 620 is locked with the casing 610 (main body part 612) and where the cover part 614 and the piston plate 620 compress the conical coil spring 40 is hereinafter referred to as "locked state".

Locking the piston plate 620 with the casing 610 (main body part 612) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the piston plate 620 and the cover part 614 becomes slightly larger than the wire diameter, in the state where the piston plate 620 is locked (cocked) with the casing 610. Note that, depending on the configuration of the piston plate 620, the piston plate 620 can come extremely close to the cover part 614, and the height of the conical coil spring 40 sandwiched between the piston plate 620 and the cover part 614 can become equivalent to the wire diameter, in the state where the piston plate 620 is locked (cocked) with the casing 610.

Figure 81:
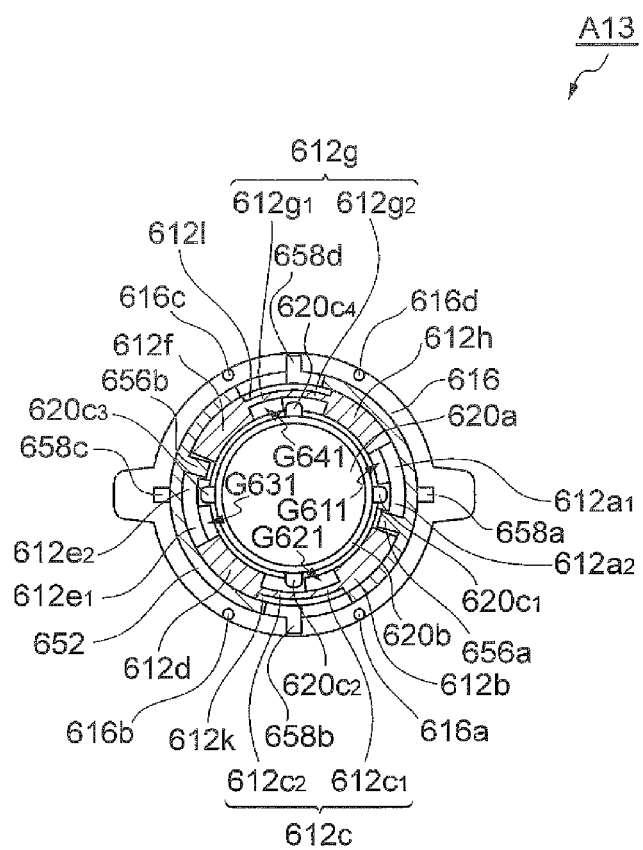
FIG. 81 is a top view illustrating the state during the operation of the applicator according to the thirteenth embodiment, from which a second release member is detached and in which a first release member and the cover part of the casing are cut away.

Subsequently, the projections 654a and 654b of the first release member 650 are respectively engaged with the groove parts 612k and 612l, and the first release member 650 is thus attached to the casing 610 (main body part 612) such that the elongated protrusions 654a and 654b are respectively located on one end sides of the groove parts 612k and 612l. At this time, as illustrated in FIG. 81, the protrusion part 656a of the first release member 650 is located on the third portion $612a_3$ of the wall part 612a and lateral to the projection $620c_1$ of the piston plate 620. Similarly, the protrusion part 656b of the first release member 650 is located on the third portion $612e_3$ of the wall part 612e and lateral to the projection $620c_3$ of the piston plate 620.

Subsequently, the second release member 660 is attached to the casing 610 so as to cover the first release member 650. At this time, the cutout parts 666a, 666b, 666c and 666d respectively surround the elongated protrusions 658a, 658b, 658c and 658d. At this time, the leading ends of the pin members 616a, 616b, 616c and 616d are not respectively opposed to the concave parts of the fifth to eighth portions 662e, 662f, 662g and 662h, but are respectively opposed to the first to fourth portions 662a, 662b, 662c and 662d. Accordingly, the pin members 616a, 616b, 616c and 616d are not respectively inserted in the fifth to eighth portions 662e, 662f, 662g and 662h, and the second release member 660 cannot move to below the pin members 616a, 616b, 616c and 616d. That is, the pin members 616a, 616b, 616c and 616*d* function as stoppers for restricting movement of the second release member 660.

Through the above-mentioned procedures, assembling of the applicator A13 is completed. Accordingly, the conical coil spring 40 remains in a compressed state until the applicator A13 is used by a user after manufacture and shipping thereof.

[13.3] Method of Using Applicator

Figure 79:
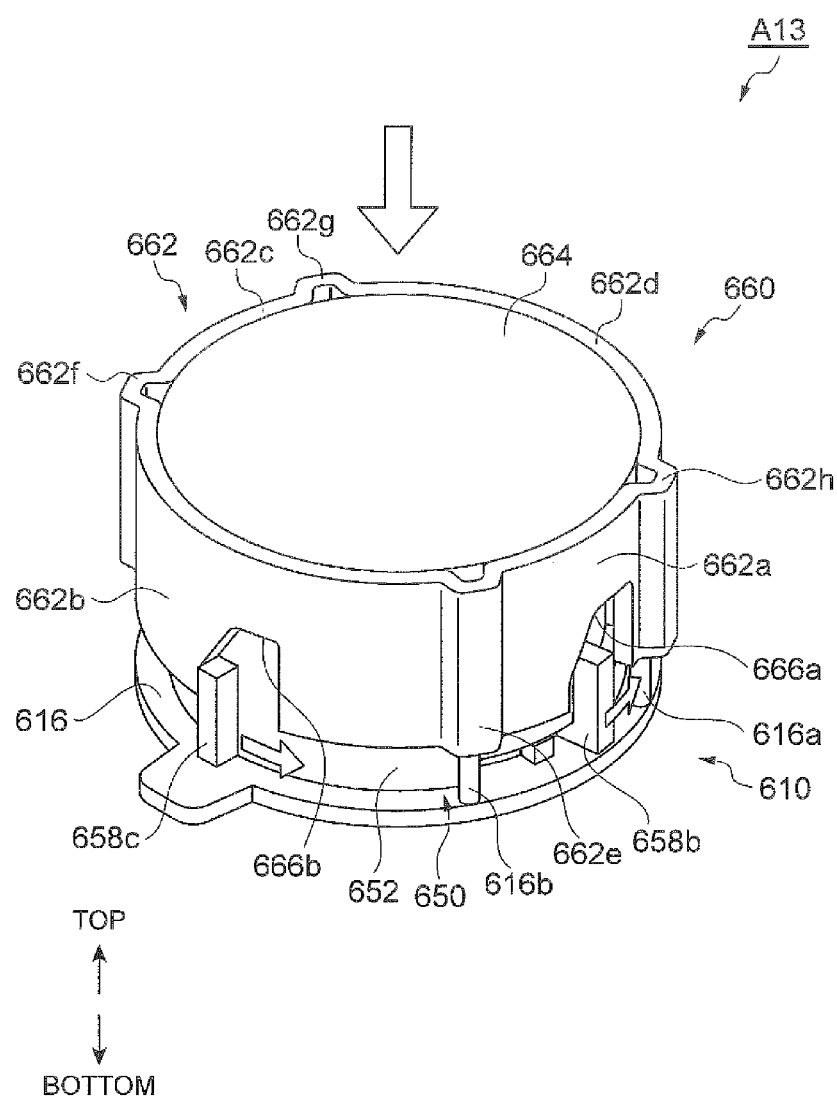
FIG. 79 is a perspective view illustrating a state during an operation of the applicator according to the thirteenth embodiment.
Figure 80:
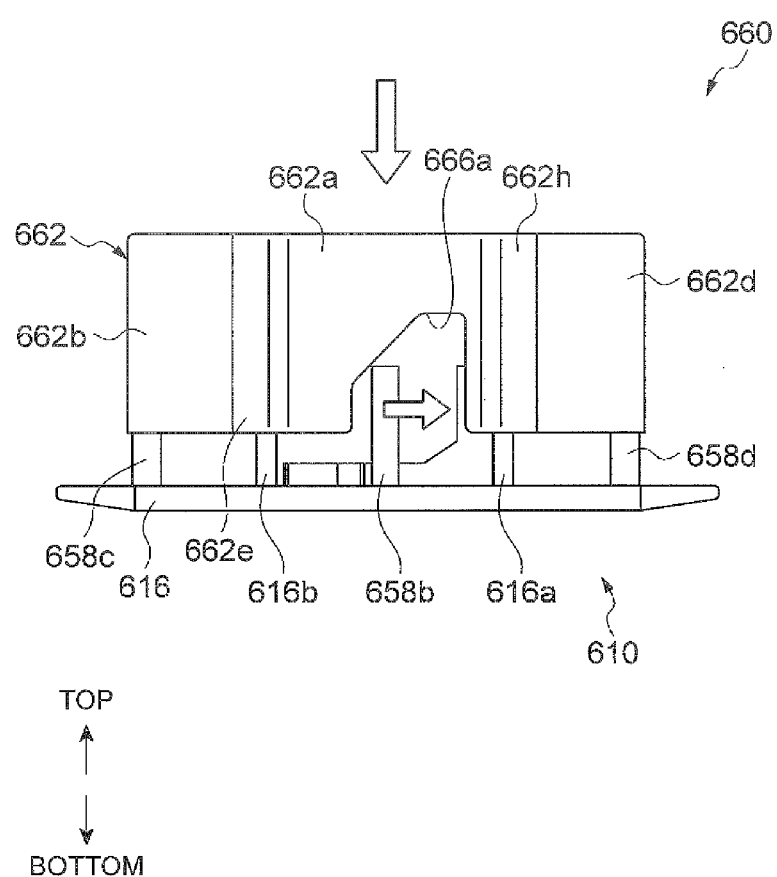
FIG. 80 is a side view illustrating the state during the operation of the applicator according to the thirteenth embodiment.

Now, the method of using the applicator A13 is described. First, the user respectively opposes the leading ends of the pin members 616*a*, 616*b*, 616*c* and 616*d* to the concave parts of the fifth to eighth portions 662*e*, 662*f*, 662*g* and 662*h* by pinching the second release member 660 and turning the second release member 660 (see FIG. 79 and FIG. 80). This unlocks the second release member 660 and enables the second release member 660 to move toward the flange part 616. At this time, as illustrated in FIG. 79 and FIG. 80, the fourth sides (oblique sides) of the cutout parts 666*a*, 666*b*, 666*c* and 666*d* are respectively opposed to the leading ends of the elongated protrusions 658*a*, 658*b*, 658*c* and 658*d*.

Figure 82:
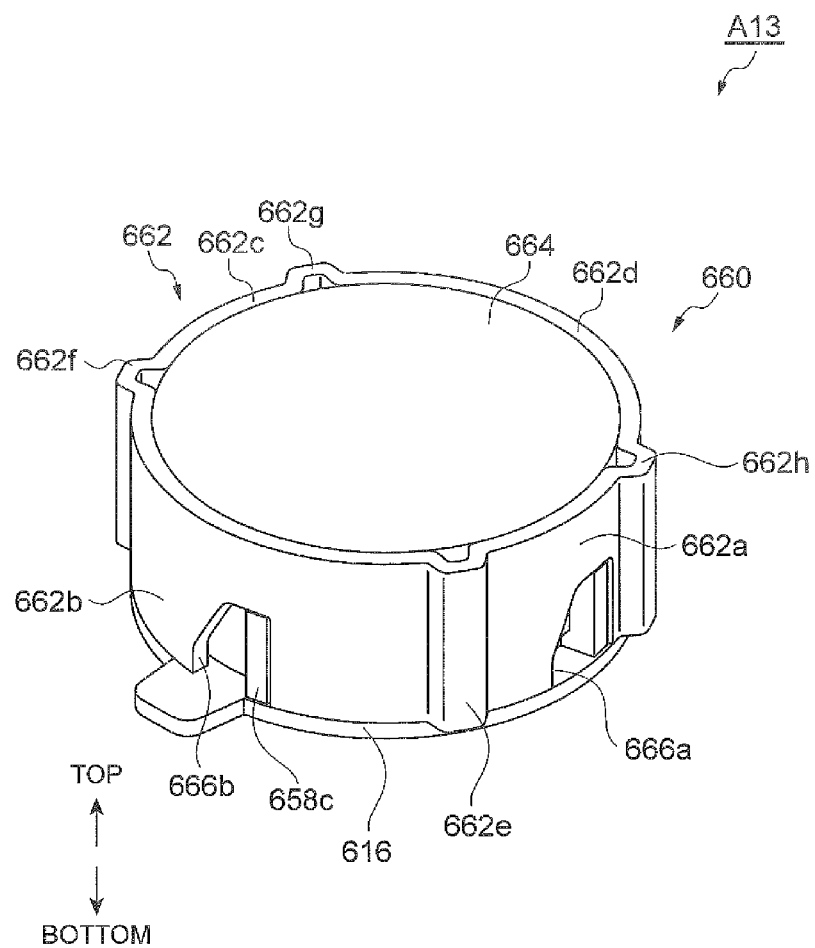
FIG. 82 is a perspective view illustrating a state after the operation of the applicator according to the thirteenth embodiment.
Figure 83:
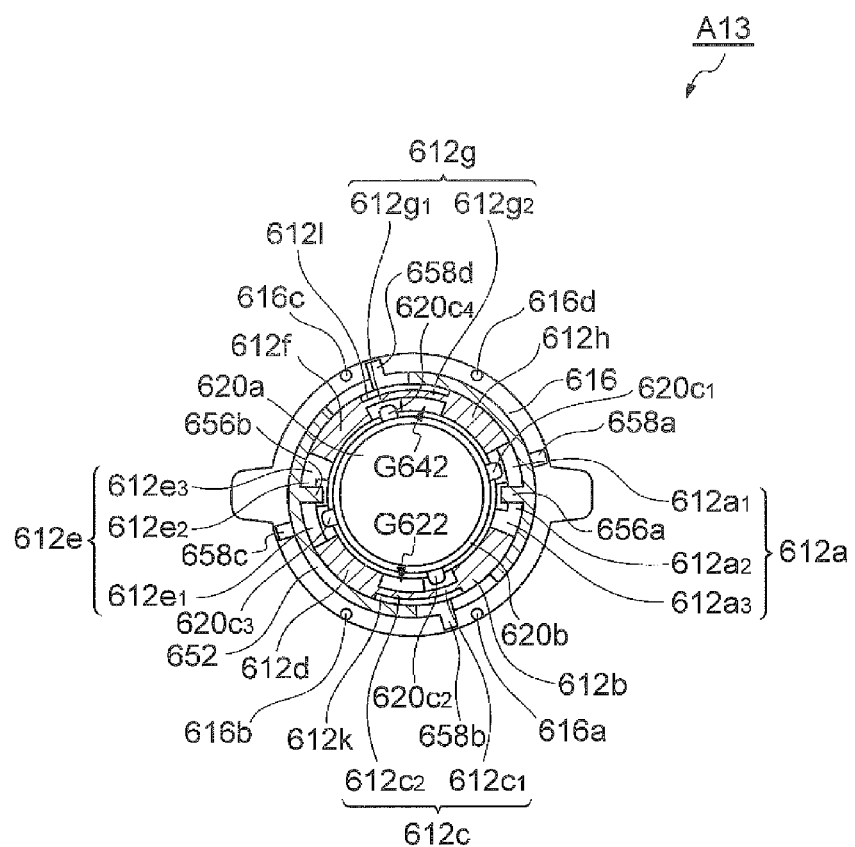
FIG. 83 is a top view illustrating the state after the operation of the applicator according to the thirteenth embodiment, from which the second release member is detached and in which the first release member and the cover part of the casing are cut away.

Subsequently, the user positions the applicator A13 with respect to a portion of a skin to which a medical agent or the like is desired to be applied, such that the microneedles 32 face the skin. The user pushes the second release member 660 toward the casing 610 (main body part 612) while the applicator A13 is kept positioned. Consequently, the second release member 660 is guided so as to approach the flange part 616 along the extending directions of the pin members 616*a*, 616*b*, 616*c* and 616*d*. At this time, the fourth sides (oblique sides) of the cutout parts 666*a*, 666*b*, 666*c* and 666*d* respectively abut against the leading ends of the elongated protrusions 658*a*, 658*b*, 658*c* and 658*d*. If the user further pushes the second release member 660 toward the casing 610 (main body part 612), the elongated protrusions 658*a*, 658*b*, 658*c* and 658*d* are pushed out in the circumferential direction of the main body 652 while respectively sliding on the fourth sides (oblique sides) of the cutout parts 666*a*, 666*b*, 666*c* and 666*d*. Consequently, a turning force is exerted on the first release member 650, with the result that the projections 654*a* and 654*b* are respectively guided to the other ends of the groove parts 612*k* and 612*l* and that the projections $620c_1$ and $620c_3$ are respectively pushed out by the protrusion parts 656*a* and 656*b*. In this way, the piston plate 620 turns (see FIG. 82 and FIG. 83). Accordingly, the locking (cocking) of the piston plate 620 with the casing 610 (main body part 612) is released. After that, similarly to the applicator A1 according to the first embodiment, the microneedle array 30 collides against the skin due to the biasing force (elastic force) of the conical coil spring 40.

[13.4] Actions

The thirteenth embodiment as described above produces actions and effects similar to the actions (A) to (D) of the applicator A1 according to the first embodiment.

Before the use of the applicator A13 according to the thirteenth embodiment, the leading ends of the pin members 616*a* to 616*d* are not respectively opposed to the concave parts of the fifth to eighth portions 662*e*, 662*f*, 662*g* and 662*h*, but are respectively opposed to the first to fourth portions 662*a*, 662*b*, 662*c* and 662*d*, and the second release member 660 is locked. Thus, even if the user presses the second release member 660, the pin members 616*a*, 616*b*, 616*c* and 616*d* are not inserted into the concave parts of the fifth to eighth portions 662*e*, 662*f*, 662*g* and 662*h*. Accordingly, the second release member 660 and the pin members 616*a*, 616*b*, 616*c* and 616*d* can prevent the applicator A13 from malfunctioning. Further, at the time of the use, it is only necessary to turn the second release member 660, and hence preparation for the use can be completed through a simple operation.

In the applicator A13 according to the thirteenth embodiment, the second release member 660 is attached to the outside of the main body part 612 so as to be movable in the central axis direction of the main body part 612. If a pressing force is exerted on the second release member 660, the second release member 660 moves from one end side (the cover part 614 side) of the main body part 612 to the other end side (the flange part 616 side) thereof. Consequently, the first release member 650 exerts a turning force on the piston plate 620. As a result, the locked state of the piston plate 620 is released, and the piston plate 620 reaches a position for action on the skin. Thus, in the state where the applicator A13 is pushed against the skin by means of the second release member 660, a puncture in the skin with the microneedles 32 is made. Accordingly, when the applicator A13 is pushed against the skin, the skin is stretched by the applicator A13. As a result, at the time of the puncture, a tensile force can be applied to the surface of the skin, and hence the microneedles 32 can be more easily stuck into the skin.

[14] Fourteenth Embodiment

[14.1] Configuration of Applicator

Now, a configuration of an applicator A14 according to a fourteenth embodiment is described with reference to FIG. 84 to FIG. 86. In the following description, the term "top" corresponds to the top direction of FIG. 84 and FIG. 85, and the term "bottom" corresponds to the bottom direction of FIG. 84 and FIG. 85. That is, the top-bottom direction corresponds to the height direction of the applicator A14.

The applicator A14 is a device for transferring active ingredients of a medical agent or the like into the body of an animal such as a human through a skin of the animal. The applicator A14 includes a casing 710, a piston member 720, the microneedle array 30, the conical coil spring 40, and a pair of release members 750*a* and 750*b*.

The casing 710 includes a main body part 712 and a cover part 716. The strength and the material of the casing 710 may be the same as those of the casing 10 of the applicator A1 according to the first embodiment.

Figure 84:
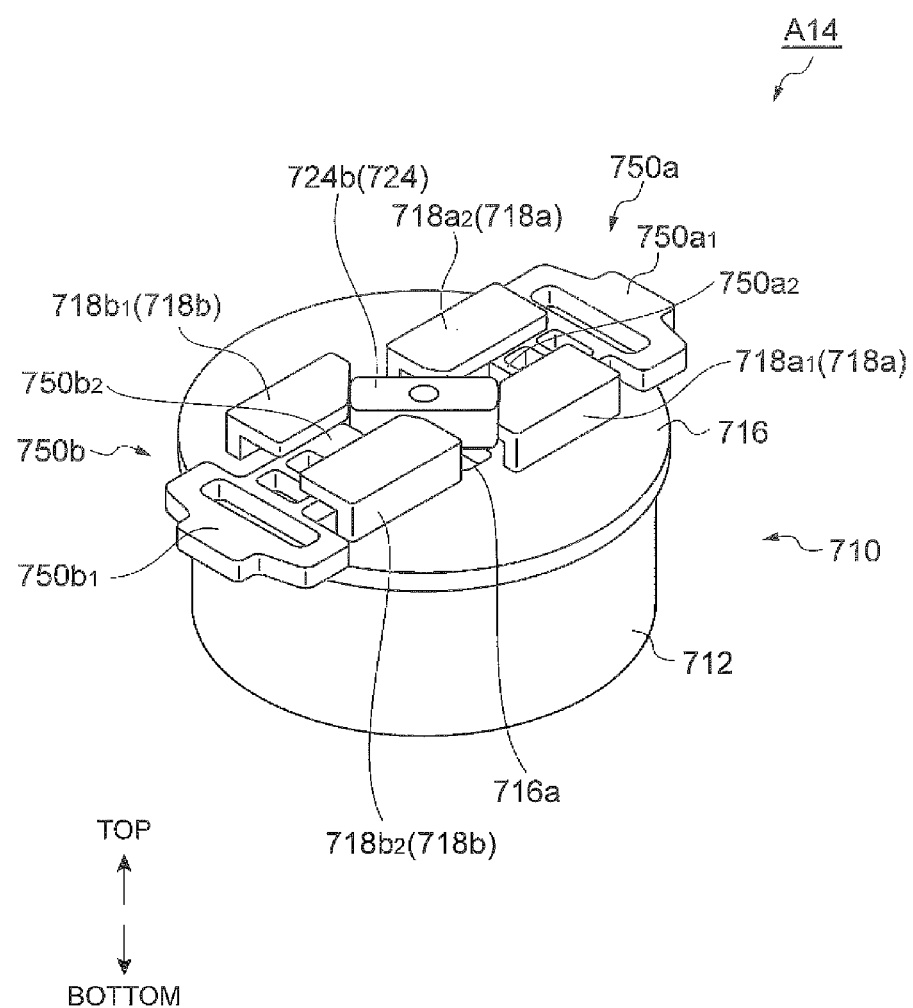
FIG. 84 is a perspective view of an applicator according to a fourteenth embodiment.
Figure 85:
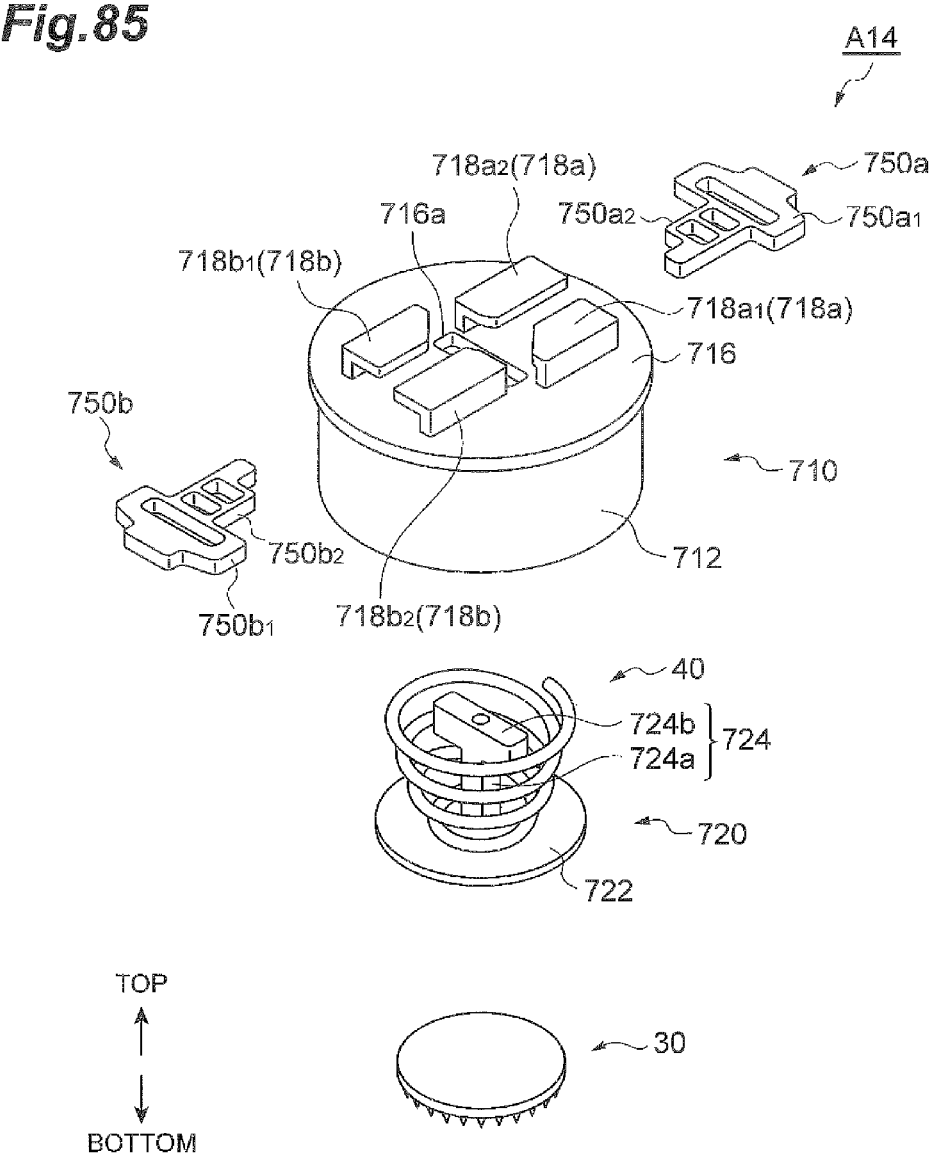
FIG. 85 is an exploded perspective view of the applicator according to the fourteenth embodiment.
Figure 86:
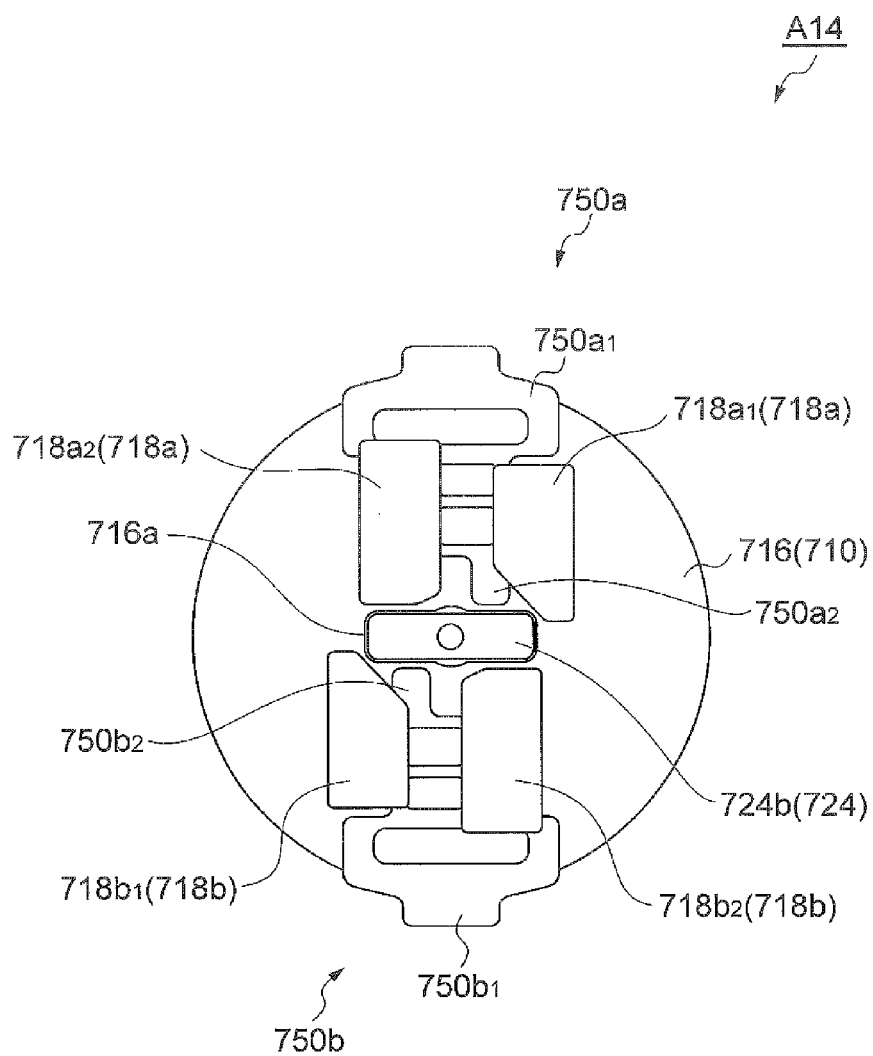
FIG. 86 is a top view illustrating a state after an operation of the applicator according to the fourteenth embodiment.

As illustrated in FIG. 84 and FIG. 85, the main body part 712 has the central axis that extends along the top-bottom direction and has a cylindrical shape. The cover part 716 has a disc-like shape, and is attached to the upper end part of the main body part 712. A rectangular through-hole 716*a* through which an arm member 724 to be described later can pass is formed in the central part of the cover part 716. Guide parts 718*a* and 718*b* that respectively guide the release members 750*a* and 750*b* are provided on the upper surface of the cover part 716.

The guide part 718*a* extends in the radial direction of the cover part 716 from one longer side of the through-hole 716*a* toward the outer periphery of the cover part 716. The guide part 718*a* includes a pair of guide members $718a_1$ and $718a_2$ each having an L shape in cross section. The guide member $718a_1$ includes: an elongated protrusion erected on the upper surface of the cover part 716; and a rectangular plate that extends from the leading end of the elongated protrusion toward the guide member $718a_2$. The guide member $718a_2$ includes: an elongated protrusion erected on the upper surface of the cover part 716; and a rectangular plate that extends from the leading end of the elongated protrusion toward the guide member $718a_1$. The direct distance between the elongated protrusions of the guide members $718a_1$ and $718a_2$ is set to be equivalent to or slightly larger than the width of the release member 750a. The direct distance between each of the rectangular plates of the guide members $718a_1$ and $718a_2$ and the cover part 716 is set to be equivalent to or slightly larger than the thickness of the release member 750a.

The guide part 718b extends in the radial direction of the cover part 716 from the other longer side of the through-hole 716a toward the outer periphery of the cover part 716. The guide part 718b includes a pair of guide members $718b_1$ and $718b_2$ each having an L shape in cross section. The guide member $718b_1$ includes: an elongated protrusion erected on the upper surface of the cover part 716; and a rectangular plate that extends from the leading end of the elongated protrusion toward the guide member $718b_2$. The guide member $718b_2$ includes: an elongated protrusion erected on the upper surface of the cover part 716; and a rectangular plate that extends from the leading end of the elongated protrusion toward the guide member $718b_1$. The direct distance between the elongated protrusions of the guide members $718b_1$ and $718b_2$ is set to be equivalent to or slightly larger than the width of the release member 750b. The direct distance between each of the rectangular plates of the guide members $718b_1$ and $718b_2$ and the cover part 716 is set to be equivalent to or slightly larger than the thickness of the release member 750b.

The piston member 720 is housed in the main body part 712, and is movable in the top-bottom direction along the central axis of the main body part 712 inside of the main body part 712. The material of the piston member 720 may be the same as the material of the casing 710, and may be the same as the material of the microneedle array 30. As illustrated in FIG. 85, the piston member 720 includes a disc-like main body (piston plate) 722 and the arm member 724 provided on the upper surface (the surface on which the conical coil spring 40 is arranged) of the main body 722. An opening, a groove, a through-hole, or the like may be formed in the main body 722 for the purpose of reducing the air resistance and the weight of the piston member 720. Further, an elongated protrusion or the like may be provided on the upper surface of the main body 722 for the purpose of improving the rigidity of the piston member 720. It is preferable that the lower surface (the surface opposite to the upper surface) of the main body 722 be planar, in consideration of causing the piston member 720 to evenly act on the microneedle array 30. Alternatively, the lower surface of the main body 722 may have other shapes than the planar shape, and the shape of the lower surface of the main body 722 can be appropriately selected, in consideration of various conditions for a puncture in the skin (for example, the medical agent, the shape of the microneedle array 30, the height of the microneedles 32, the density of the microneedles 32, the puncture speed, and the impact force to the skin).

The arm member 724 includes first and second portions 724a and 724b each having a quadrangular prism shape. The first portion 724a is erected on the upper surface of the main body 722. The second portion 724b extends in the direction parallel to the upper surface of the main body 722. The central part of the second portion 724b is connected to the leading end of the first portion 724a. Accordingly, the arm member 724 has a T shape formed by the first and second portions 724a and 724b.

The microneedle array 30 and the conical coil spring 40 are the same as those in the first embodiment, and hence description thereof is omitted. The conical coil spring 40 is attached around the arm member 724 such that: the smaller diameter side of the conical coil spring 40 faces downward (the main body 722 side); and the larger diameter side thereof faces upward (the second portion 724b side).

The pair of release members 750a and 750b each have a flat plate-like shape. The release member 750a includes a first portion $750a_1$ to be operated by the user and a second portion $750a_2$ to be guided by the guide part 718a. The release member 750b includes a first portion $750b_1$ to be operated by the user and a second portion $750b_2$ to be guided by the guide part 718b.

[14.2] Method of Manufacturing Applicator

Now, the method of manufacturing the applicator A14 is described. First, the respective components (the casing 710, the piston member 720, the microneedle array 30, the conical coil spring 40, and the release members 750a and 750b) of the applicator A14 described above are prepared. The coating C is applied in advance to the microneedles 32 of the prepared microneedle array 30. Next, the microneedle array 30 is attached to the lower surface of the main body 722 of the piston member 720.

Subsequently, the conical coil spring 40 is attached around the arm member 724 such that: the smaller diameter side of the conical coil spring 40 faces downward (the main body 722 side); and the larger diameter side thereof faces upward (the second portion 724b side). Subsequently, the arm member 724 is inserted through the through-hole 716a, while the conical coil spring 40 is compressed between the cover part 716 and the main body 722. Subsequently, after the second portion 724b completely passes through the through-hole 716a, the piston member 720 is turned until the second portion 724b moves to a position at which the second portion 724b does not coincide with the through-hole 716a, whereby the second portion 724b (piston member 720) is locked with the cover part 716 (see FIG. 84). Accordingly, the main body 722 is held at its retraction position on the cover part 716 side inside of the main body 722, in the state where the cover part 716 and the main body 722 compress the conical coil spring 40. Such a state as described above where the piston member 720 is locked with the casing 710 (cover part 716) and where the cover part 716 and the main body 722 compress the conical coil spring 40 is hereinafter referred to as "locked state".

Locking the piston member 720 with the casing 710 (cover part 716) at its retraction position as described above is also referred to as cocking. In the present exemplary embodiment, the metal wire that forms the conical coil spring 40 does not overlap when viewed from the central line direction of the conical coil spring 40, and hence the height of the conical coil spring 40 sandwiched between the main body 722 and the cover part 716 becomes slightly larger than the wire diameter, in the state where the piston member 720 is locked (cocked) with the casing 710. Note that, depending on the configuration of the piston member 720, the main body 722 can come extremely close to the cover part 716, and the height of the conical coil spring 40 sandwiched between the main body 722 and the cover part 716 can become equivalent to the wire diameter, in the state where the piston member 720 is locked (cocked) with the casing 710.

Subsequently, the release members 750a and 750b are respectively attached to the guide parts 718a and 718b such that the second portions $750a_2$ and $750b_2$ of the release members 750a and 750b are respectively inserted through the guide parts 718a and 718b.

Through the above-mentioned procedures, assembling of the applicator A14 is completed. Accordingly, the conical coil spring 40 remains in a compressed state until the applicator A14 is used by a user after manufacture and shipping thereof.

[14.3] Method of Using Applicator

Now, the method of using the applicator A14 is described. First, the applicator A14 is positioned with respect to a portion of a skin to which a medical agent or the like is desired to be applied, such that the microneedles 32 face the skin. The first portions $750a_1$ and $750b_1$ of the release members 750a and 750b are pushed so as to come close to each other while the applicator A14 is kept positioned. Consequently, the second portions $750a_2$ and $750b_2$ are respectively guided by the guide parts 718a and 718b, and the leading ends of the second portions $750a_2$ and $750b_2$ abut against the second portion 724b of the piston member 720. If the first portions $750a_1$ and $750b_1$ are further pushed, the second portion 724b of the piston member 720 turns until the second portion 724b coincides with the through-hole 716a. Consequently, a turning force is exerted on the piston member 720, with the result that the piston member 720 turns. As a result, the locking (cocking) of the piston member 720 with the casing 710 (cover part 716) is released. Then, the piston member 720 is moved, by the biasing force (elastic force) of the conical coil spring 40, outward (toward the skin) inside of the main body part 712, and the microneedle array 30 collides against the skin.

[14.4] Actions

The fourteenth embodiment as described above produces actions and effects similar to the actions (A) to (D) of the applicator A1 according to the first embodiment.

[15] Fifteenth Embodiment

Now, an applicator A15 according to a fifteenth embodiment is described with reference to FIG. 87 to FIG. 89. The applicator A15 according to the fifteenth embodiment is different from the applicator A14 according to the fourteenth embodiment in the configurations of a casing 810 and a release member 850. In the following, differences between the applicator A15 according to the fifteenth embodiment and the applicator A14 according to the fourteenth embodiment are mainly described, and redundant description is omitted.

Specifically, the casing 810 includes a main body part 812 and a cover part 816. As illustrated in FIG. 87 and FIG. 88, the main body part 812 has the central axis that extends along the top-bottom direction and has a cylindrical shape. The cover part 816 has a disc-like shape, and is attached closer to the upper end of the main body part 812. A rectangular through-hole 816a through which the arm member 724 can pass is formed in the central part of the cover part 816. A pair of projections 818a and 818b each having a columnar shape are provided on the upper surface of the cover part 816. The projections 818a and 818b are arranged at positions at which the projections 818a and 818b are respectively opposed to longer sides of the through-hole 816a, with the through-hole 816a being interposed therebetween. The projections 818a and 818b restrict movement (turn) of the second portion 724b of the arm member 724 on the upper surface of the cover part 816.

Figure 87:
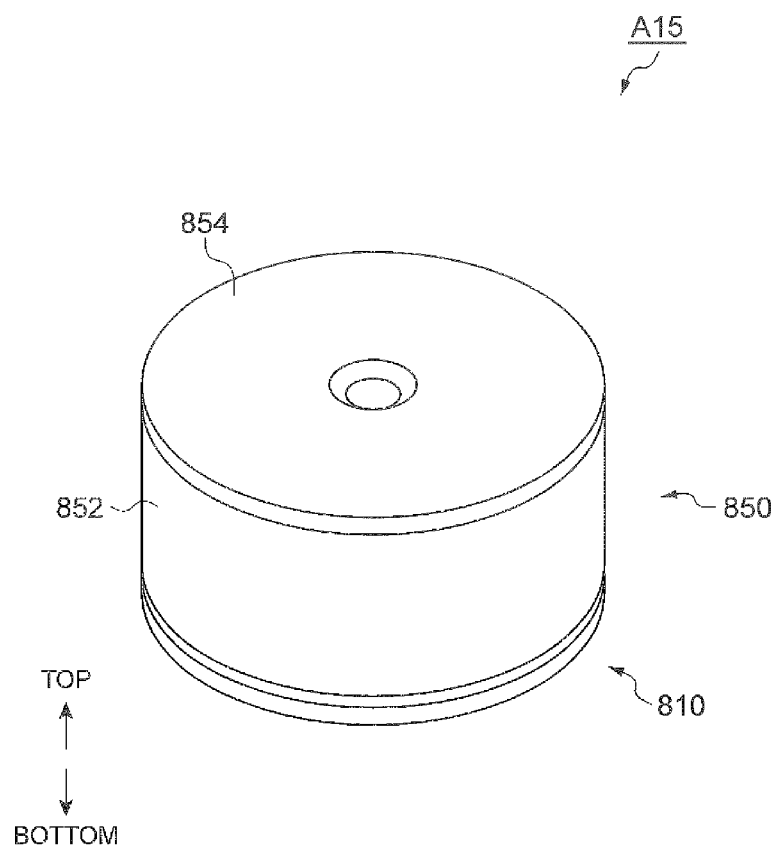
FIG. 87 is a perspective view of an applicator according to a fifteenth embodiment.
Figure 88:
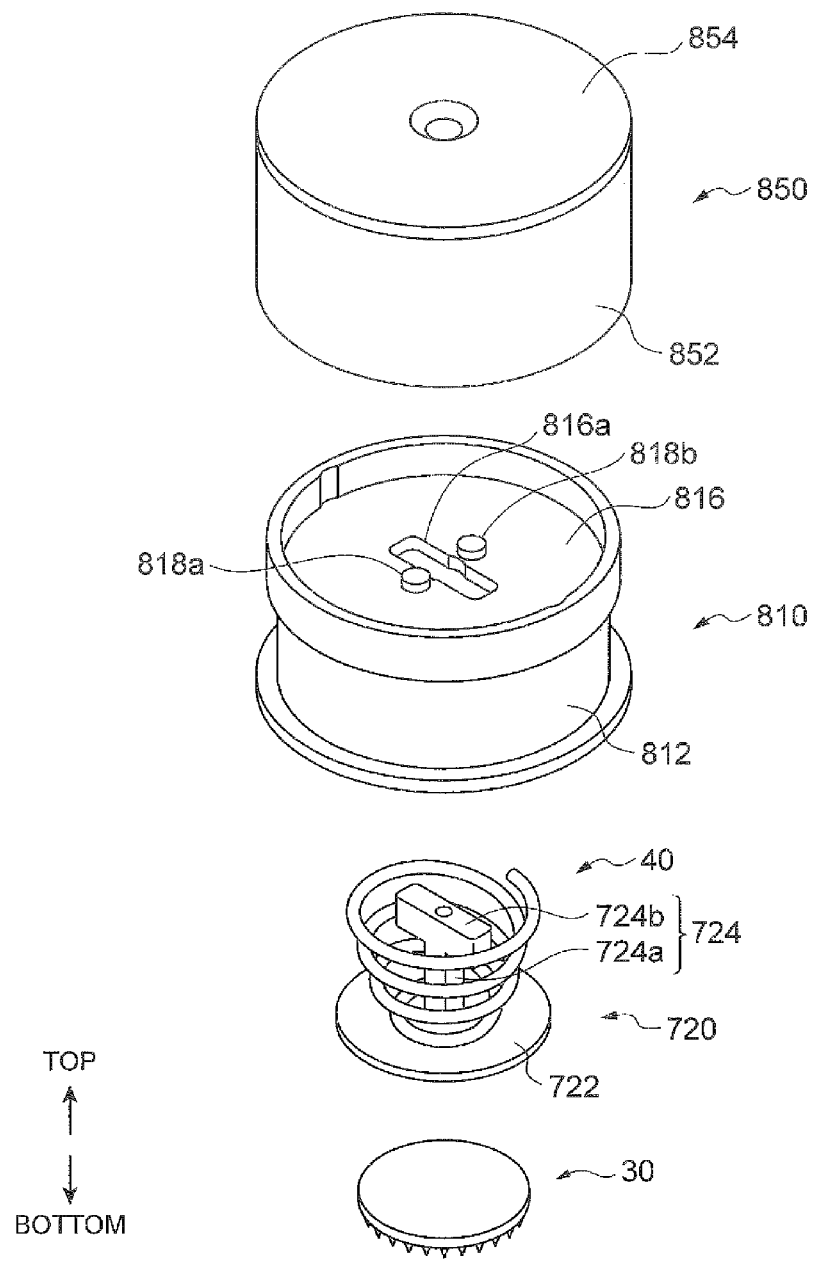
FIG. 88 is an exploded perspective view of the applicator according to the fifteenth embodiment.
Figure 89:
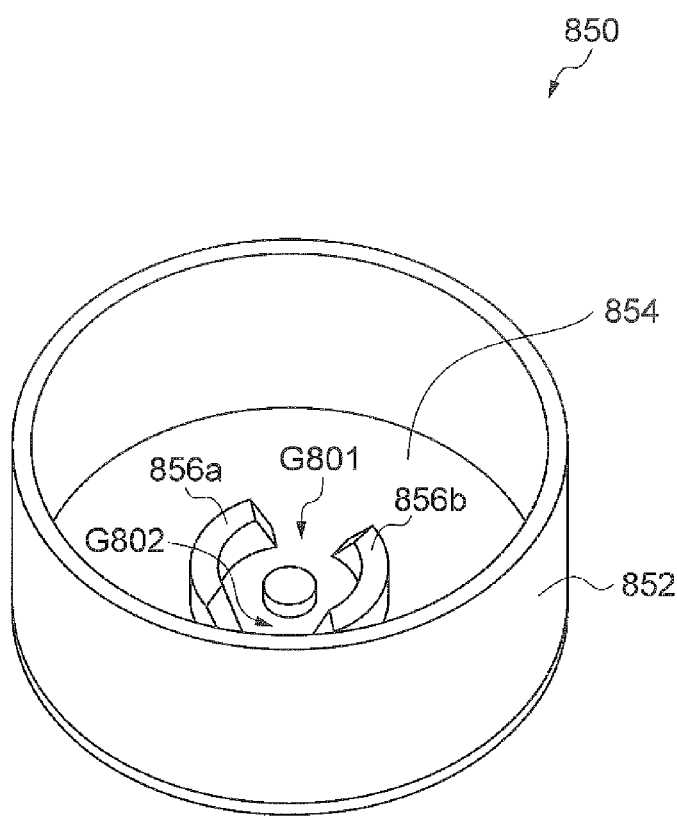
FIG. 89 is a perspective view illustrating the lower surface side of a release member.

As illustrated in FIG. 87 to FIG. 89, the release member 850 includes: a side wall part 852 having the central axis that extends along the top-bottom direction and having a cylindrical shape; and a disc-like top plate part 854 arranged in the upper end part of the side wall part 852. The inner diameter of the side wall part 852 is set to be equivalent to or slightly larger than the outer diameter of the main body part 812. A pair of elongated protrusions 856a and 856b are provided on the lower surface side (the side wall part 852 side) of the top plate part 854. The elongated protrusions 856a and 856b each have a circular arc-like shape when viewed from the central axis direction of the side wall part 852, and face each other.

The edge part in contact with the top plate part 854, of each of the elongated protrusions 856a and 856b is longer than the edge part thereof farther from the top plate part 854. Both the side edge parts of each of the elongated protrusions 856a and 856b are inclined so as to approach each other with increasing distance from the top plate part 854. Accordingly, the width of a groove G801 formed between one end of the elongated protrusion 856a and one end of the elongated protrusion 856b facing each other becomes larger with increasing distance from the top plate part 854. The width of a groove G802 formed between the other end of the elongated protrusion 856a and the other end of the elongated protrusion 856b facing each other becomes larger with increasing distance from the top plate part 854.

Figure 90:
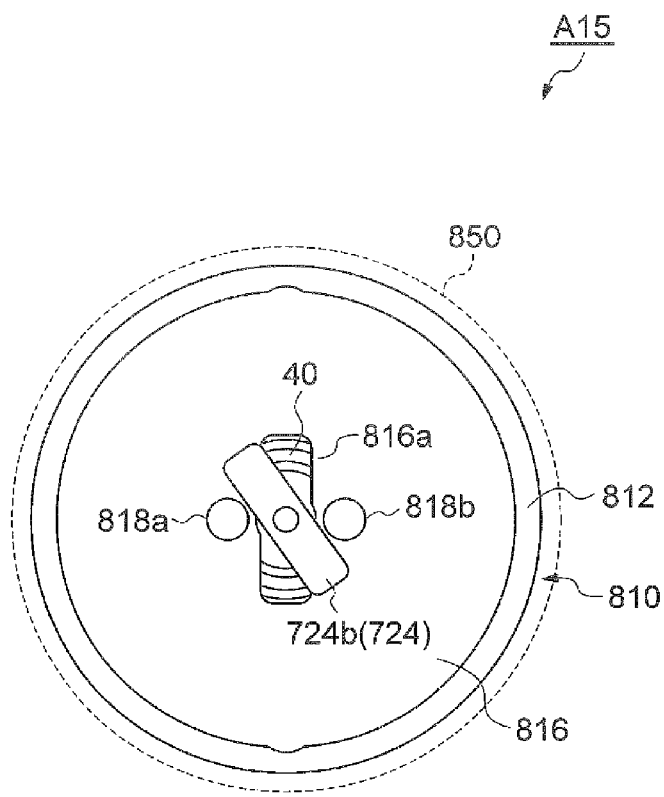
FIG. 90 is a top view illustrating a state before an operation of the applicator according to the fifteenth embodiment, from which the release member is detached.

In the locked state where the piston member 720 is locked with the casing 810 (cover part 816) and where the cover part 816 and the main body 722 compress the conical coil spring 40, as illustrated in FIG. 90, one end of the second portion 724b of the arm member 724 is close to the projection 818a, and the other end of the second portion 724b thereof is close to the projection 818b. In this state, the release member 850 is further attached to the casing 810, whereby the applicator A15 is completed. In the completed state of the applicator A15, the one end of the second portion 724b is opposed to the groove G801, and the other end of the second portion 724b is opposed to the groove G802.

Figure 91:
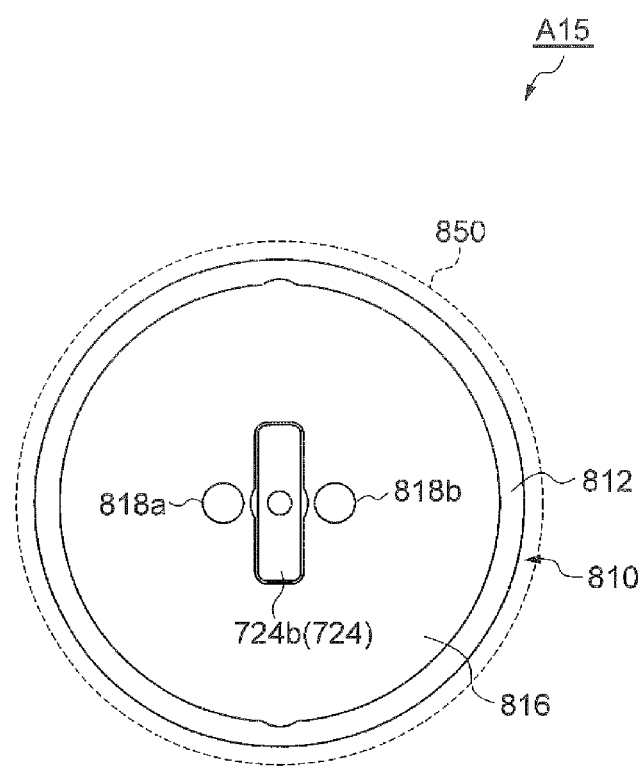
FIG. 91 is a top view illustrating a state after the operation of the applicator according to the fifteenth embodiment, from which the release member is detached.

In order to release the locking of the piston member 720, the release member 850 is pushed toward the casing 810 (main body part 812). At this time, end parts of the second portion 724b are pushed out in the circumferential direction of the main body part 812 while sliding on the side edges that form the oblique sides of the elongated protrusions 856a and 856b. If the release member 850 is further pushed, the second portion 724b of the piston member 720 turns until the second portion 724b coincides with the through-hole 816a. Consequently, a turning force is exerted on the piston member 720, with the result that the piston member 720 turns. As a result, the locking (cocking) of the piston member 720 with the casing 810 (cover part 816) is released (see FIG. 91). Then, the piston member 720 is moved, by the biasing force (elastic force) of the conical coil spring 40, outward (toward the skin) inside of the main body part 812, and the microneedle array 30 collides against the skin.

The applicator A15 according to the fifteenth embodiment as described above produces actions and effects similar to those of the applicator A14 according to the fourteenth embodiment. Further, in the applicator A15 according to the fifteenth embodiment, if the release member 850 is pushed toward the casing 810 (main body part 812), the locking (cocking) of the piston member 720 with the casing 810 (cover part 816) is released. Thus, in the state where the applicator A15 is pushed against the skin by means of the release member 850, a puncture in the skin with the microneedles 32 is made. Accordingly, when the applicator A15 is pushed against the skin, the skin is stretched by the applicator A15. As a result, at the time of the puncture, a tensile force can be applied to the surface of the skin, and hence the microneedles 32 can be more easily stuck into the skin.

[16] Other Embodiments

Figure 92:
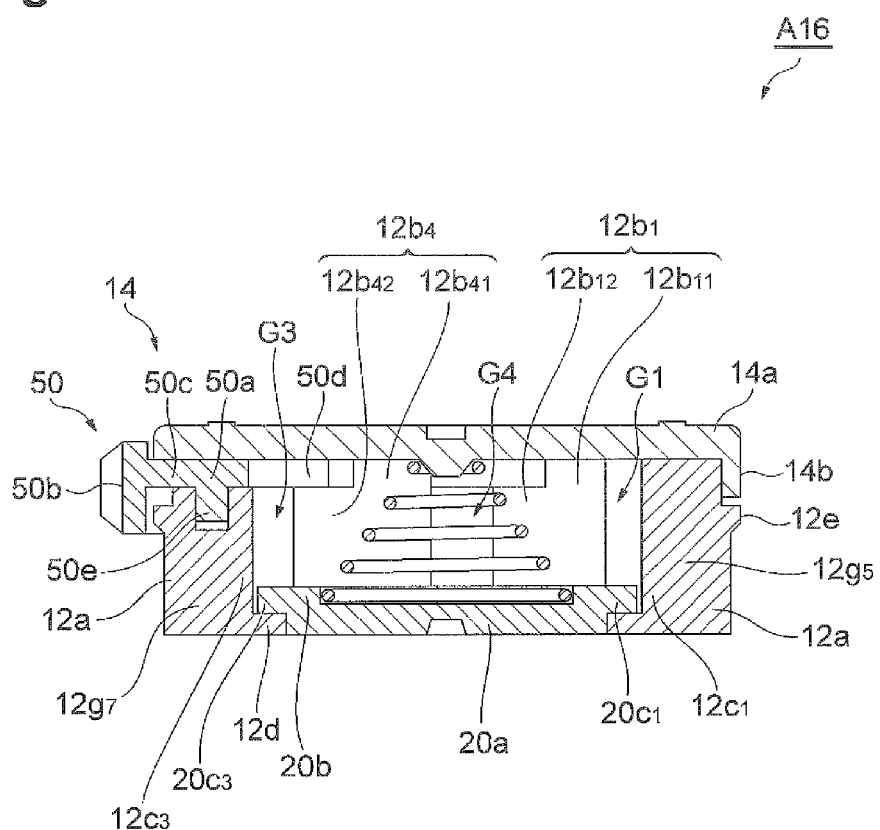
FIG. 92 is a cross sectional view illustrating a state after an operation of an applicator according to a sixteenth embodiment.

Hereinabove, embodiments of the present invention have been described in detail, but the present invention is not limited to the above-mentioned embodiments. For example, in the above-mentioned embodiments, the piston plate 20 and the microneedle array 30 are integrated with each other, but may be configured as separate members as in an applicator A16 illustrated in FIG. 92. In the case where the piston plate 20 and the microneedle array 30 are configured as separate members, after the microneedle array 30 is placed on a skin and then the applicator A16 is placed on the skin so as to be opposed to the microneedle array 30, the applicator A16 is actuated. As a result, the piston plate 20 collides against the microneedle array 30 on the skin, and a puncture into the skin is made. The applicator A16 illustrated in FIG. 92 is a modified example based on the applicator A1 according to the first embodiment, but the other applicators A2, A3, A4, A5, A6, A7, A8, A9, A10, A11, A12, A13, A14 and A15 can also be similarly modified.

Figure 93:
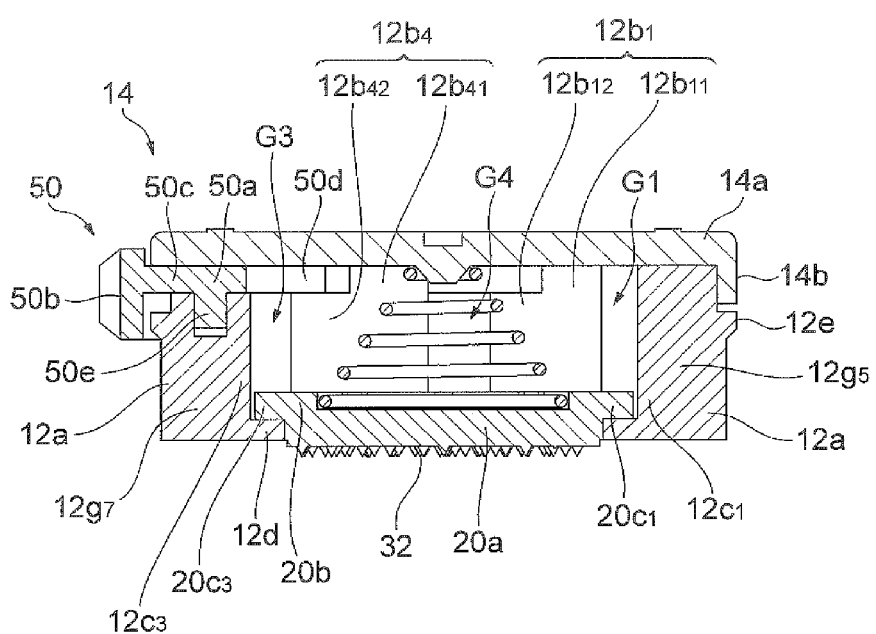
FIG. 93 is a cross sectional view illustrating a state after an operation of an applicator according to a seventeenth embodiment.

In the above-mentioned embodiments, the microneedle array 30 is integrated with the piston plate. Alternatively, as in an applicator A17 illustrated in FIG. 93, the microneedles 32 may be shaped integrally with the lower surface of the piston plate 20. The applicator A11 is different from the applicator A1 according to the first embodiment in terms of the piston plate 20. In this case, the main body 20*a* of the piston plate 20 can be regarded as being equal to the substrate of the microneedle array. That is, the microneedle array can be regarded as behaving as the piston plate 20. The applicator A17 illustrated in FIG. 93 is a modified example based on the applicator A1 according to the first embodiment, but the other applicators A2, A3, A4, A5, A6, A7, A8, A9, A10, A11, A12, A13, A14 and A15 can also be similarly modified.

In the above-mentioned embodiments, the plurality of groove parts that extend in the axial direction of the main body part of the casing are provided in the inner circumferential surface of the main body part, and the plurality of projections respectively movable inside of the groove parts are provided to the piston plate. Alternatively, as in an applicator A18 illustrated in FIG. 94, a plurality of elongated protrusions $912h_1$, $912h_2$, $912h_3$ and $912h_4$ that extend in the axial direction of a main body part 912 of a casing 910 may be provided in the inner circumferential surface of the main body part 912, and a plurality of cutout groove parts $920c_1$, $920c_2$, $920c_3$ to $920c_4$ may be provided to a piston plate 920. The applicator A18 is different from the applicator A1 according to the first embodiment in terms of the main body part 912 of the casing 910 and the piston plate 920.

Specifically, the casing 910 includes: an outer wall 912*a* having a cylindrical shape; an inner wall 912*b* having a cylindrical shape; and a bottom wall having a circular ring-like shape. The diameter of the outer wall 912*a* is larger than the diameter of the inner wall 912*b*. Thus, the outer wall 912*a* is located outside of the inner wall 912*b*. The central axis of the outer wall 912*a* is substantially coincident with the central axis of the inner wall 912*b*, but may not be coincident therewith. The outer wall 912*a* and the inner wall 912*b* are coupled to each other by coupling walls $912g_1$, $912g_2$, $912g_3$, $912g_4$, $912g_5$, $912g_6$, $912g_7$ and $912g_8$, whereby the rigidities of the two walls are enhanced.

A flange member 912*e* having a circular ring-like shape is provided at a position closer to the upper end (closer to the cover part 14) on the outer circumferential surface of the outer wall 912*a*. The flange member 912*e* protrudes outward from the outer circumferential surface of the outer wall 912*a*. A cutout part 912*f* that extends in the circumferential direction is provided between the upper end of the outer wall 912*a* and the flange member 912*e*. When the cover part 14 is attached to the main body part 912, the cutout part 912*f* forms the through-hole H together with the cutout part 14*c* of the cover part 14, and the through-hole H communicates the inside and the outside of the casing 910 with each other.

The plurality of (in FIG. 94, four) elongated protrusions $912h_1$, $912h_2$, $912h_3$ and $912h_4$ that extend in the top-bottom direction along the central axis of the main body part 912 are provided on the inner circumferential surface of the inner wall 912*b*. The elongated protrusions $912h_1$, $912h_2$, $912h_3$ and $912h_4$ are arranged in the stated order in the clockwise direction when viewed from the upper end side (the cover part 14 side) of the main body part 912, with given intervals in the circumferential direction. It is sufficient that the protruding heights of the elongated protrusions $912h_1$, $912h_2$, $912h_3$ and $912h_4$ be large enough to enable guiding the piston plate 920 to be described later in the state where the elongated protrusions $912h_1$, $912h_2$, $912h_3$ and $912h_4$ are respectively engaged with the cutout groove parts $920c_1$, $920c_2$, $920c_3$ and $920c_4$ of the piston plate 920.

The bottom wall is connected to the lower end of the outer wall 912*a* and the lower end of the inner wall 912*b*. The outer diameter of the bottom wall is equivalent to the diameter of the outer circumferential surface of the outer wall 912*a*. The inner diameter of the bottom wall is equivalent to the diameter of a circle circumscribed on the leading ends of the elongated protrusions $912h_1$, $912h_2$, $912h_3$ and $912h_4$. Thus, the bottom wall is located between adjacent ones of the elongated protrusions $912h_1$, $912h_2$, $912h_3$ and $912h_4$ when viewed from the upper end side (the cover part 14 side) of the main body part 912.

The piston plate 920 is housed in the main body part 912, and is movable in the top-bottom direction along the central axis of the main body part 912 inside of the main body part 912. The piston plate 920 includes: a disc-like main body 920*a*; and a cylindrical member 920*b* that extends upward from the periphery of the main body 920*a*. The inner diameter of the cylindrical member 920*b* is set to be larger than the maximum diameter D1 of the conical coil spring 40.

The plurality of (in FIG. 94, four) cutout groove parts $920c_1$, $920c_2$, $920c_3$ and $920c_4$ that extend in the thickness direction of the piston plate 920 are provided in the periphery of the piston plate 920. The cutout groove parts $920c_1$, $920c_2$, $920c_3$ and $920c_4$ are arranged in the stated order in the clockwise direction when viewed from above (the upper surface side of the piston plate 920 on which the conical coil spring 40 is placed), with given intervals in the circumferential direction.

The cutout groove parts $920c_1$, $920c_2$, $920c_3$ and $920c_4$ are respectively engageable with the elongated protrusions $912h_1$, $912h_2$, $912h_3$ and $912h_4$. Thus, in the state where the cutout groove parts $920c_1$, $920c_2$, $920c_3$ and $920c_4$ are respectively engaged with the elongated protrusions $912h_1$, $912h_2$, $912h_3$ and $912h_4$, the piston plate 920 can be guided in the top-bottom direction along the extending directions of the elongated protrusions $912h_1$, $912h_2$, $912h_3$ and $912h_4$ (the central axis direction of the main body part 912). Meanwhile, in the state where the piston plate 920 is located on the upper end sides of the elongated protrusions $912h_1$, $912h_2$, $912h_3$ and $912h_4$, in the case where the elongated protrusions $912h_1$, $912h_2$, $912h_3$ and $912h_4$ and the cutout groove parts $920c_1$, $920c_2$, $920c_3$ and $920c_4$ do not overlap with each other when viewed from above, the piston plate 920 can be placed on the upper ends of the elongated protrusions $912h_1$, $912h_2$, $912h_3$ and $912h_4$ and can be locked with the casing 910 (main body part 912).

A concave part 920*d* concaved inward is provided in the periphery of the piston plate 920. In the completed state of the applicator A18 (in the state where the piston plate 920 is locked with the main body part 912), the protrusion part 50*d* of the release member 50 is engaged with the concave part 920*d*. Thus, if the release member 50 is slid to the other end side of the through-hole H, the protrusion part 50*d* exerts a turning force on the piston plate 920, so that the piston plate 920 turns. If the piston plate 920 turns until the elongated protrusions 912$h_1$, 912$h_2$, 912$h_3$ and 912$h_4$ and the cutout groove parts 920$c_1$, 920$c_2$, 920$c_3$ and 920$c_4$ overlap with each other when viewed from above, the locking (cocking) of the piston plate 920 with the casing 910 (main body part 912) is released. As a result, the piston plate 920 is moved, by the biasing force (elastic force) of the conical coil spring 40, outward (toward the skin) along the elongated protrusions 920$c_1$, 920$c_2$, 920$c_3$ and 920$c_4$ (the central axis of the main body part 912) inside of the main body part 912, and the microneedle array 30 collides against the skin. At this time, the piston plate 920 abuts against the bottom wall, and hence the piston plate 920 is prevented from jumping out of the casing 910 (main body part 912).

Figure 94:
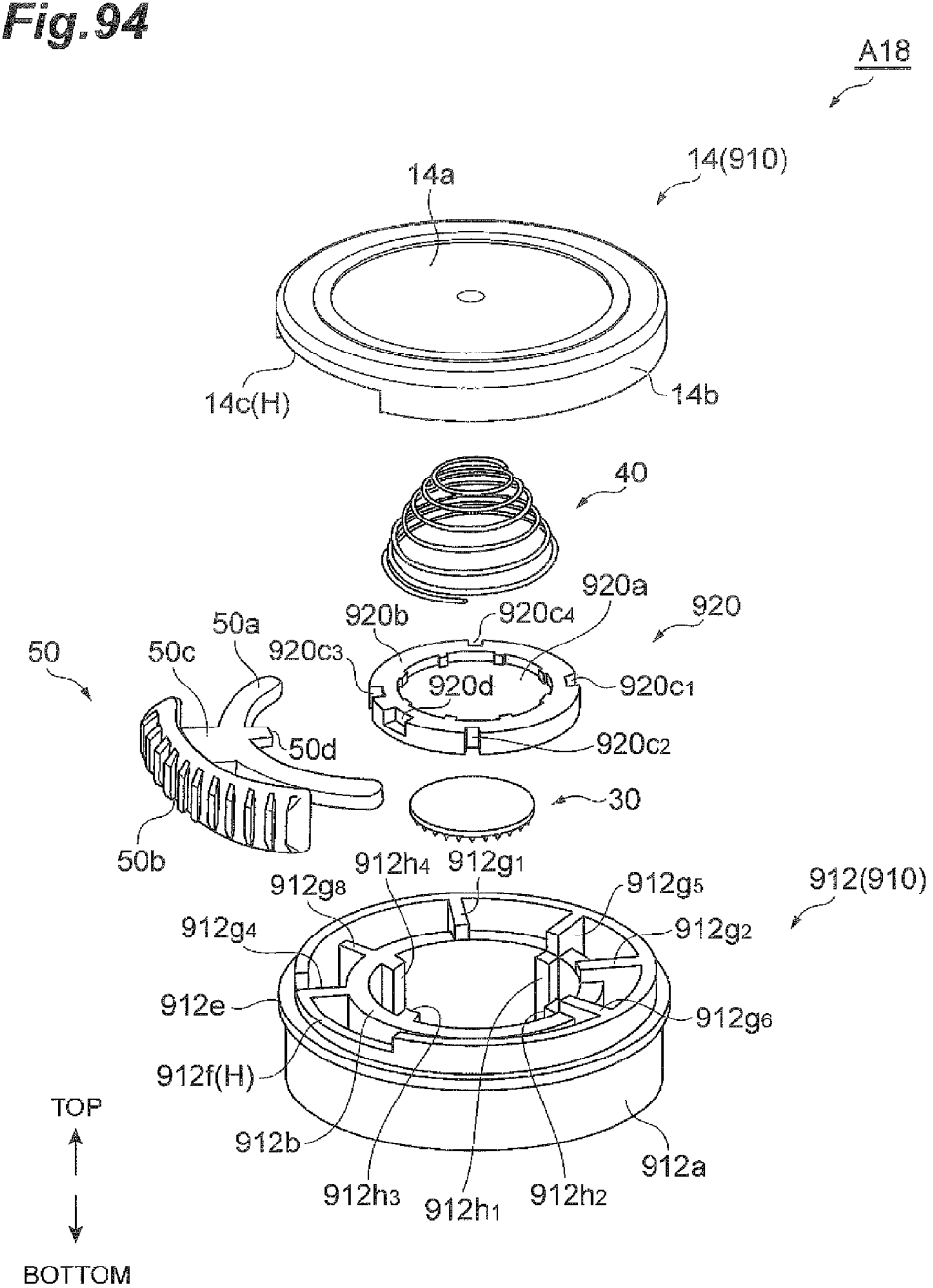
FIG. 94 is an exploded perspective view of an applicator according to an eighteenth embodiment.

The applicator A18 illustrated in FIG. 94 is a modified example based on the applicator A1 according to the first embodiment, but the other applicators A2, A3, A4, A5, A6, A7, A8, A9, A10, A12, and A13 can also be similarly modified.

In the above-mentioned embodiments, the microneedles 32 are arranged at substantially regular intervals in a zigzag (alternate) pattern on the surface of the substrate 31. Alternatively, the density of the microneedles 32 on the substrate 31 may be different. For example, the density of the microneedles 32 may be set to be higher in the vicinity of the center of the substrate 31 than in the periphery thereof, and may be set to be higher in the periphery of the substrate 31 than in the vicinity of the center thereof.

The heights of the microneedles 32 may be all the same, and may be different. In the case where the heights of the microneedles 32 are different, for example, the heights of the microneedles 32 may be set to be larger in the vicinity of the center of the substrate than in the periphery thereof, and may be set to be larger in the periphery of the substrate than in the vicinity of the center thereof.

As illustrated in (a) of FIG. 95, it is possible to use a conical coil spring 41 having both end parts that are each shaved to be flat along a virtual plane orthogonal to the central line of the conical coil spring 41, instead of the conical coil spring 40. For example, in the case where the conical coil spring 41 is adopted for the applicator A1 according to the first embodiment, the end part on the smaller diameter side of the conical coil spring 41 abuts against the cover part 14, and the end part on the larger diameter side of the conical coil spring 41 abuts against the piston plate 20. Thus, if the conical coil spring 41 is configured as described above, the contact area of the conical coil spring 41 with each of the cover part 14 and the piston plate 20 can be made larger. Thus, the conical coil spring 41 can be stably arranged inside of the casing 10.

In the above-mentioned embodiments, the conical coil spring 40 is used to exert a biasing force on the piston plate or the piston member, but non-linear coil springs having other shapes may be used. Examples of the non-linear coil springs having other shapes include: a coil spring 42 having a drum-like shape with a narrow part (see (b) of FIG. 95); and a coil spring 43 having a barrel-like shape (see (c) of FIG. 95).

In the above-mentioned embodiments, the metal wire that forms the conical coil spring 40 does not overlap when viewed from the extending direction of the central line of the conical coil spring 40. Alternatively, it is possible to use the conical coil spring 40 formed by winding a metal wire such that the metal wire overlaps when viewed from the extending direction of the central line thereof. In both of the cases, the free height h of the conical coil spring 40 can be set to be smaller than a value obtained by multiplying the wire diameter d by the total number of turns.

In the above-mentioned embodiments, the projections of the piston plate are respectively guided by the various types of groove parts, and the groove parts may pass through the main body part of the casing, and may not pass therethrough. That is, it is sufficient that the groove parts be configured as opening parts inside of which the projections of the piston plate are movable.

In the above-mentioned embodiments, the projections of the piston plate are respectively engaged with the groove parts, and the projections are respectively guided by the groove parts, whereby the piston plate is moved inside of the main body part, but means for guiding the piston plate is not limited thereto. For example, if the outer diameter of the piston plate and the inner diameter of the main body part are set to be equivalent to each other, the piston plate can also be guided inside of the main body part by sliding between the outer circumferential surface of the piston plate and the inner circumferential surface of the main body part. That is, for guiding the piston plate in the axial direction of the main body part, groove parts that extend in the axial direction thereof do not necessarily need to be formed in the main body part.

In the above-mentioned embodiments, the locking (cocking) of the piston plate with the casing (main body part) is released by exerting a turning force on the piston plate. In the above-mentioned embodiments, the locking (cocking) of the piston member with the casing (cover part) is released by exerting a turning force on the piston member. The force that is exerted on the piston plate or the piston member for releasing the locking of the piston plate or the piston member is not limited to the turning force. For example, the locking of the piston plate or the piston member may be released by moving the piston plate or the piston member in the horizontal direction with respect to the casing. Alternatively, the locking of the piston plate may be released by moving or turning a lock member in the horizontal direction without moving the piston plate that is locked with the casing (main body part) with the intermediation of the lock member. Alternatively, in the state where the piston member is locked with the casing (cover part) with the intermediation of a lock member, the locking of the piston member may be released by moving or turning the lock member in the horizontal direction without moving the piston member.

Figure 96:
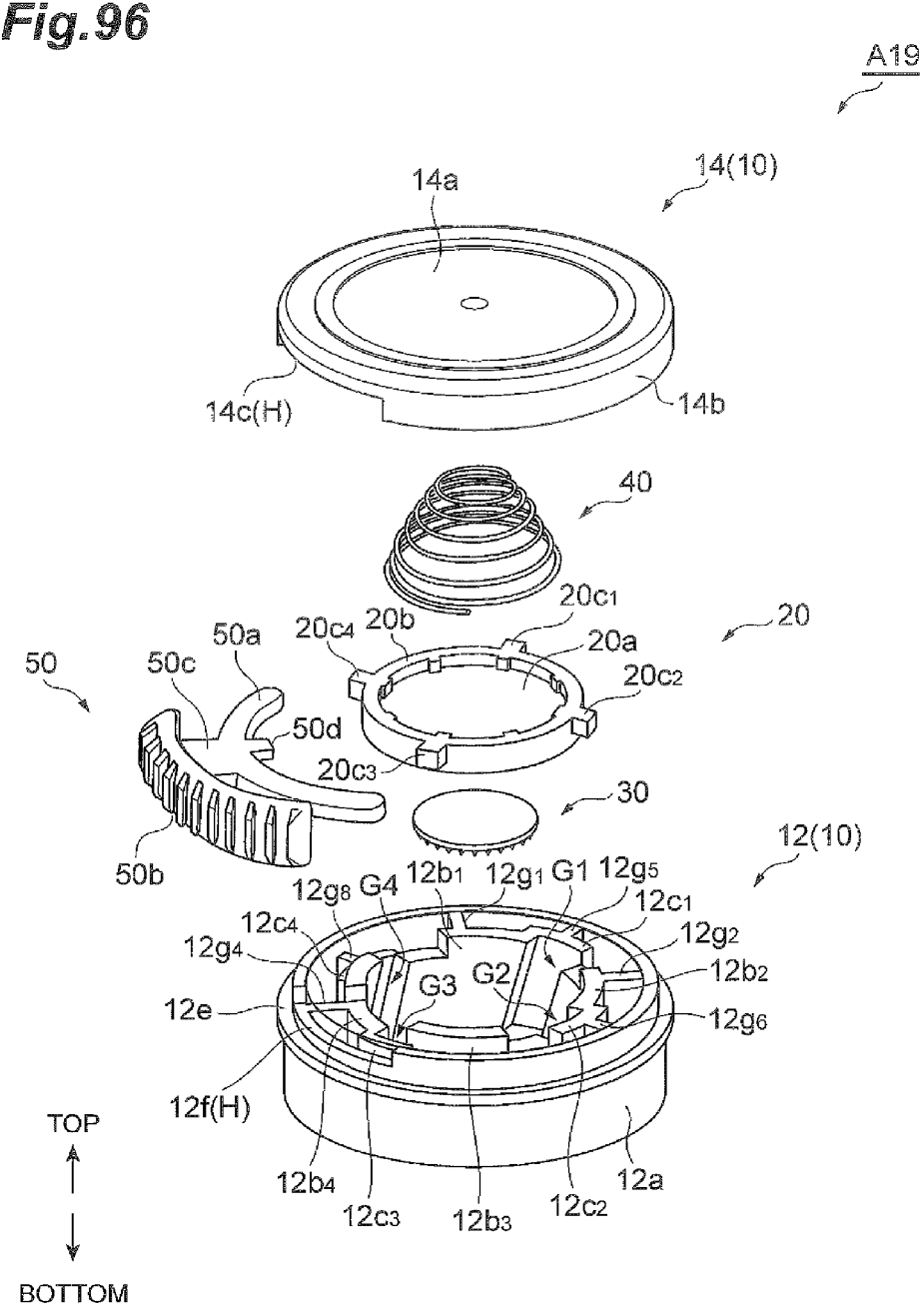
FIG. 96 is an exploded perspective view of an applicator according to a nineteenth embodiment.
Figure 97:
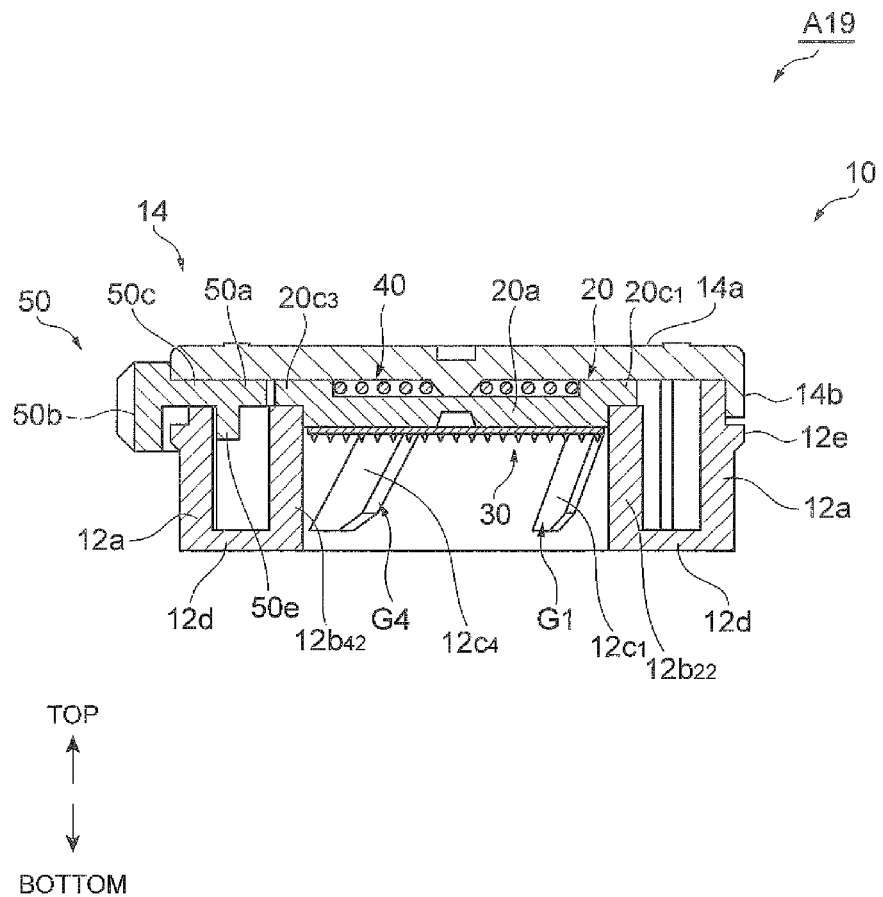
FIG. 97 is an exploded perspective view of the applicator according to the nineteenth embodiment.

As in an applicator A19 illustrated in FIG. 96 and FIG. 97, the groove parts G1, G2, G3 and G4 may extend obliquely to the central axis direction of the main body part 12 when viewed from the direction orthogonal to the central axis direction. In this case, the piston plate 20 moves while rotating inside of the main body part 12, and reaches a position for action on the skin. Thus, even in the case where an impact force is generated in the piston plate 20 when the piston plate 20 reaches the position for action on the skin and where a reaction force acts on the piston plate 20, because the groove parts G1, G2, G3 and G4 extend obliquely to the central axis direction, it is difficult for the piston plate 20 to move back along the groove parts G1, G2, G3 and G4. Accordingly, after the piston plate 20 reaches the position for action on the skin, the piston plate 20 bounces less easily toward the cover part 14. As a result, the certainty of a puncture in the skin with the microneedles 32 can be enhanced. The applicator A19 illustrated in FIG. 96 and FIG.

97 is a modified example based on the applicator A1 according to the first embodiment, but the other applicators A2, A3, A4, A5, A6, A7, A8, A9, A10, A12, and A13 can also be similarly modified.

Figure 98:
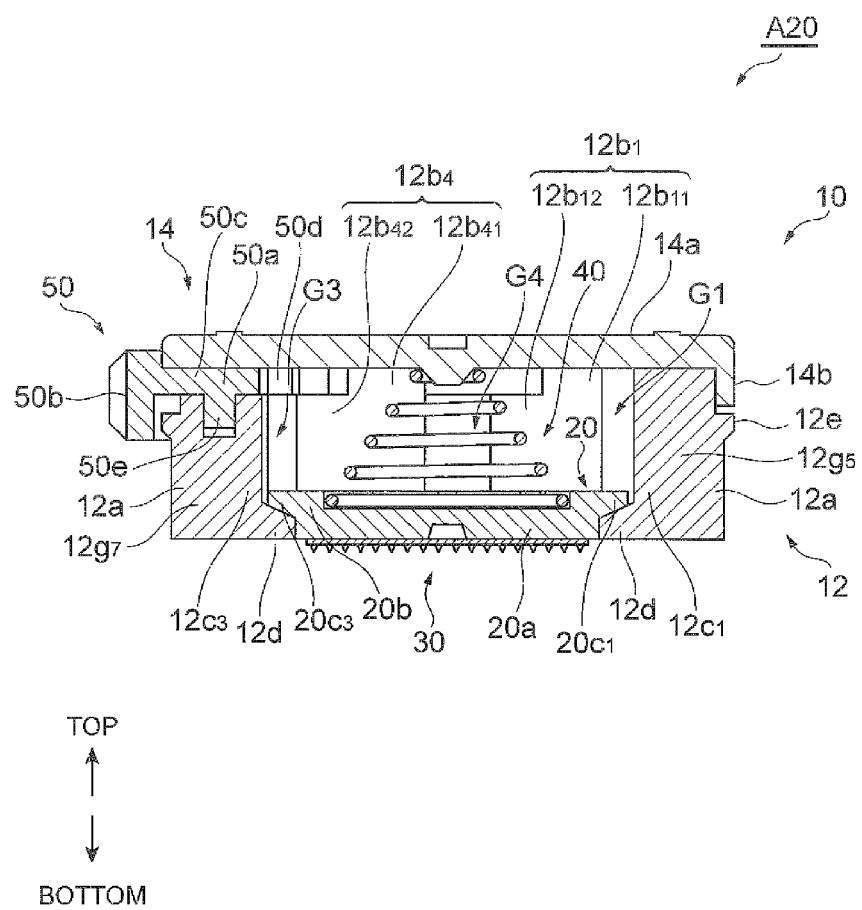
FIG. 98 is an exploded perspective view of an applicator according to a twentieth embodiment.

As in an applicator A20 illustrated in FIG. 98, surfaces facing the lower end side (the bottom wall 12$d$ side) of the main body part 12, of the projections $20c_1$, $20c_2$, $20c_3$ and $20c_4$ of the piston plate 20 may be oblique surfaces that are inclined to the central axis direction of the main body part 12 so as to approach the upper end side (the cover part 14 side) of the main body part 12 toward the outer side. Portions to be locked with the projections $20c_1$, $20c_2$, $20c_3$ and $20c_4$, of the bottom wall 12$d$ of the main body part 12 may have oblique surfaces respectively corresponding to the oblique surfaces of the projections $20c_1$, $20c_2$, $20c_3$ and $20c_4$. In this case, when the piston plate 20 reaches a position for action on the skin and the projections $20c_1$, $20c_2$, $20c_3$ and $20c_4$ of the piston plate 20 and the bottom wall 12$d$ of the main body part 12 collide against each other, the impact force generated between the projections $20c_1$, $20c_2$, $20c_3$ and $20c_4$ of the piston plate 20 and the bottom wall 12$d$ of the main body part 12 is distributed to the central axis direction of the main body part 12 and the direction orthogonal to the central axis direction thereof. Accordingly, the mechanical strength of the applicator A20 can be improved, and a collision sound generated when the projections $20c_1$, $20c_2$, $20c_3$ and $20c_4$ of the piston plate 20 and the bottom wall 12$d$ of the main body part 12 collide against each other can be reduced. Moreover, because the impact force generated when the projections $20c_1$, $20c_2$, $20c_3$ and $20c_4$ of the piston plate 20 and the bottom wall 12$d$ of the main body part 12 collide against each other is distributed, the reaction force that acts on the piston plate 20 in the central axis direction of the main body part 12 becomes smaller. Accordingly, after the collision between the projections $20c_1$, $20c_2$, $20c_3$ and $20c_4$ of the piston plate 20 and the bottom wall 12$d$ of the main body part 12, the piston plate 20 bounces less easily toward the cover part 14. As a result, the certainty of a puncture in the skin with the microneedles 32 can be enhanced. The applicator A20 illustrated in FIG. 98 is a modified example based on the applicator A1 according to the first embodiment, but the other applicators A2, A3, A4, A5, A6, A7, A8, A9, A10, A11, A12 and A13 can also be similarly modified.

In the applicator A12 according to the twelfth embodiment, the release member 550 is provided with the second protrusion parts (engagement pieces) $558a_4$ and $558b_4$ to be engaged with the piston plate 520 that has reached the position for action on the skin, but various other modes can be adopted as long as a bounce of the piston plate can be prevented by the engagement pieces. For example, engagement pieces that slightly protrude inward from the inner circumferential surface of the main body part 512 may be provided on the inner circumferential surface of the main body part 512. The heights of the engagement pieces may be set such that the piston plate 520 that is being biased by the conical coil spring 40 to move toward the position for action on the skin can climb and pass over the engagement pieces while the momentum of the piston plate 520 bounced from the skin is not enough to allow the piston plate 520 to climb over the engagement pieces. Alternatively, for example, the engagement pieces may be cantilevered, and may each have a wedge shape whose free end becomes thicker toward the leading end thereof. In this case, the piston plate 520 that is moving toward the position for action on the skin can pass over while pushing the engagement pieces aside toward the outer side of the main body part 512. After the passage of the piston plate 520, the engagement pieces return to their original positions. Thus, the leading ends of the free ends of the engagement pieces that have returned to their original positions hinder the piston plate 520 bounced from the skin from moving toward the cover part 514. The engagement pieces may be engaged with the main body 520$a$ or the cylindrical member 520$b$ of the piston plate 520, and may be engaged with the projections $520c_1$, $520c_2$, $520c_3$ and $520c_4$ of the piston plate 520.

In the applicator A13 according to the thirteenth embodiment, the first and second release members 650 and 660 are used to exert a turning force on the piston plate 620, but the applicator A13 may not include the first release member 650 located between the second release member 660 and the main body 612. In this case, a plurality of engagement projections respectively corresponding to the projections $620c_1$, $620c_2$, $620c_3$ and $620c_4$ of the piston plate 620 are provided on the inner surface of the top plate part 664 of the second release member 660. The engagement projections are located above the corresponding projections $620c_1$, $620c_2$, $620c_3$ and $620c_4$, and protrude toward the corresponding projections $620c_1$, $620c_2$, $620c_3$ and $620c_4$. The engagement projections each have an oblique side that extends obliquely to the central axis direction of the main body part 612 when viewed from the direction orthogonal to the central axis direction. The oblique sides are opposed to the corresponding projections $620c_1$, $620c_2$, $620c_3$ and $620c_4$. In this case, when a pressing force is exerted on the second release member 660 and the second release member 660 moves from the cover part 614 side of the main body part 612 to the flange part 616 side thereof, the oblique sides of the engagement projections exert a turning force on the piston plate 620 while being engaged with the corresponding projections $620c_1$, $620c_2$, $620c_3$ and $620c_4$. As a result, the locked state of the piston plate 620 is released, and the piston plate 620 reaches the position for action on the skin.

Examples

Hereinafter, the present invention is described more specifically by way of an example, but the present invention is not limited to the following example.

The puncture performance was evaluated using the applicators A1 and A9 according to the first embodiment and the ninth embodiment. For the evaluation of the puncture performance, ovalbumin (OVA) was delivered to a human skin (in vitro) using the microneedle array 30, and the transfer rate of OVA to the human skin was obtained. The puncture performance was evaluated on the basis of the transfer rate thus obtained. The transfer rate here refers to the rate of: the amount of OVA delivered to the skin; to the amount of OVA (coating C) firmly fixed to the microneedles 32.

For the applicator A1 according to the first embodiment, the total weight of the actuation part including the piston plate 20, the microneedle array 30, and the conical coil spring 40 was set to 1.24 g, whereby one type of the applicator A1 was prepared. For the applicator A9 according to the ninth embodiment, the total weight of the actuation part including the piston plate 220, the microneedle array 30, and the conical coil spring 40 was set to 1.23 g and 1.10 g, whereby two types of the applicator A9 were prepared.

The prepared microneedle array 30 was made of polylactide. The area of the substrate 31 of the microneedle array 30 was 1.13 $cm^2$. The number of the microneedles 32 of the microneedle array 30 was 640. The density of the microneedles 32 of the microneedle array 30 was 566 needles/$cm^2$. The height of each microneedle 32 of the microneedle array 30 was 500 μm. The coating range when OVA was applied to the microneedles 32 was a range of about 180 μm including the tips of the microneedles 32. The initial content of OVA coating the microneedles 32 was 51 μg.

The applicator A1, A9 was placed still on the human skin, and the microneedles 32 were stuck into the human skin by actuating the applicator A1, A9, whereby OVA was delivered into the human skin. After the delivery of OVA, the microneedle array 30 removed from the human skin was immersed in phosphate buffered saline (PBS), whereby OVA was extracted. The amount of extracted OVA was subtracted from the initial content, whereby the amount of transfer was obtained. The transfer rate was obtained from the ratio of the amount of transfer to the initial content. Further, the speed of the actuation part during the actuation of the applicator A1, A9 was measured using a laser displacement gauge (produced by Keyence Corporation; LK-H150). This speed (v [m/s]) was multiplied by the total weight (in [kg]) of the actuation part, whereby the momentum (P=m·v [Ns]) of the actuation part was obtained. In the state where the momentum thus obtained was set to the abscissa and where the transfer rate of OVA was set to the ordinate, the experimental results were plotted, so that the graph illustrated in FIG. 99 was obtained. As illustrated in FIG. 99, the transfer rate of OVA equal to or more than 50% could be obtained in the momentum range of 0.006 Ns to 0.015 Ns. Note that the momentum of the actuation part is indicative of the puncture energy when the microneedles 32 collide against the human skin.

REFERENCE SIGNS LIST 10, 110, 210, 310, 410 . . . casing
12, 212, 312, 412 . . . main body part
12f . . . cutout part
14, 116, 214, 314 . . . cover part
14c . . . cutout part
14d . . . through-hole
20, 120, 220, 320, 420 . . . piston plate
$20c_1$, $20c_2$, $20c_3$, $20c_4$, $120c_1$, $120c_2$, $120c_3$, $220c_1$, $220c_2$, $220c_3$, $220c_4$, $320c_1$, $320c_2$, $320c_3$, $420c_1$, $420c_2$, $420c_3$ . . . projection
30 . . . microneedle array
32 . . . microneedle
40 . . . conical coil spring
50, 250, 350, 450 . . . release member
50a . . . interior part
50b . . . exterior part
$50b_4$ . . . knob part
50f . . . plate-like body
112 . . . interior main body part
112b, 112c, 112d . . . guide part
114 . . . exterior main body part
$116c_1$, $116c_2$, $116c_3$ . . . projection
116e . . . mesh part
$120d_1$, $120d_2$, $120d_3$ . . . recess part
120e . . . mesh part
254c . . . protrusion part
256c . . . protrusion part
260 . . . stopper
266a, 266b . . . stopper member
414 . . . outer cover part
416 . . . inner cover part
A1, A2, A3, A4, A5, A6, A7, A8, A9, A10, A11, A12, A13 . . . applicator
G1 G2, G3, G4, G111, G112, G121, G122, G131, G132, G210, G221, G222, G230, G241, G242 . . . groove part
G310, G320, G330 . . . groove body
H . . . through-hole

The invention claimed is:

1. An applicator for transferring an active ingredient into a body through a skin by a puncture in the skin with microneedles, the applicator comprising:
  a casing including:
    a tubular main body part having a first end and a second end positioned in an axial direction; and
    a cover part arranged on the first end;
  a piston plate housed inside the casing, the piston plate including:
    a first main surface having the microneedles arranged thereon;
    a second main surface opposed to the first main surface;
    a periphery located between the first and second main surfaces; and
    a plurality of projections provided on the periphery and extending in a radial direction from the piston plate;
  a non-linear coil spring housed in the casing between the second main surface of the piston plate and the cover part of the casing, and exerting a biasing force on the piston plate;
  a plurality of groove parts formed on an inner circumferential surface of the tubular main body part, each of the plurality of groove parts including an axial part extending in the axial direction of the tubular main body part, and a circumferential part extending from a first or second end of the axial part along a circumferential direction of the tubular main body part; and
  a release member configured for turning the piston plate along the circumferential direction of the tubular main body part,
  wherein each projection of the plurality of projections of the piston plate corresponds to each groove part of the plurality of groove parts, and
  wherein the piston plate is locked within the casing with the non-linear coil spring compressed when each projection of the plurality of projections of the piston plate moves from the axial part to the circumferential part of each groove part of the plurality of groove parts, and
  wherein the release member turns the locked piston plate thereby moving the piston plate along the axial part of each of the plurality of groove parts by the biasing force to a position for transferring the active ingredient to the body through the skin.

2. The applicator according to claim 1, wherein
  a needle density of the microneedles is equal to or more than 500 needles/cm$^2$,
  a total weight of an actuation part including the piston plate, the non-linear coil spring, and the microneedles is equal to or less than 1.5 g, and
  a momentum of the actuation part actuated by the biasing force of the non-linear coil spring is 0.006 Ns to 0.015 Ns.

3. The applicator according to claim 1, wherein the circumferential part of each of the plurality of groove parts is inclined towards the cover part and towards each of the corresponding axial parts of each of the plurality of groove parts.

4. The applicator according to claim 1, wherein surfaces facing the second end of the tubular main body part of the plurality of projections are oblique surfaces inclined in the axial direction of the tubular main body part towards an outer side of the first end of the tubular main body part, and a bottom wall of the tubular main body part locking the plurality of projections has oblique surfaces respectively corresponding to the oblique surfaces of the plurality of projections.

5. The applicator according to claim 1, wherein each axial part of the plurality of groove parts is formed extending obliquely in the axial direction of the tubular main body part when viewed from a direction orthogonal to the axial direction of the tubular main body part.

6. The applicator according to claim 1, wherein a through-hole in the circumferential direction of the tubular main body part is formed in a side wall of the tubular main body part, the through-hole having two end sides,
the release member includes:
a first portion located inside of the casing and locked with the piston plate; and
a second portion connected to the first portion passing through the through-hole and located on an outer circumferential surface of the tubular main body part, and
if the second portion moves from one end side to the other end side of the through-hole, the first portion turns the piston plate, each projection of the plurality of projections respectively reaches the axial part from the circumferential part of each groove part of the plurality of groove parts, and the locked piston plate is released.

7. The applicator according to claim 1, wherein
a through-hole is formed in the cover part,
the release member includes:
a first portion located inside of the casing and locked with the piston plate; and
a second portion connected to the first portion passing through the through-hole to an outer surface of the cover part, and
if the second portion moves from one end side to another end side of the through-hole, the first portion turns the piston plate, each projection of the plurality of projections respectively reaches the axial part from the circumferential part of each groove part of the plurality of groove parts, and the locked piston plate is released.

8. The applicator according to claim 1, wherein
a through-hole is formed in the cover part,
the release member includes:
a base part arranged on an outer surface of the cover part and turnable about an axis of the tubular main body part;
a knob part attached to the base part and pivotable about a direction intersecting the axial direction of the tubular main body part; and
a transmission part extending from the base part to the inside of the casing through the through-hole and transmitting a turning force of the base part to the piston plate, and
if the transmission part moves from one end side to the other end side of the through-hole by operating the knob part, the transmission part turns the piston plate, each projection of the plurality of projections respectively reaches the axial part from the circumferential part of each groove part of the plurality of groove parts, and the locked piston plate is released.

9. The applicator according to claim 1, wherein
the release member includes an engagement part that engages the cover part with the piston plate,
the cover part and the tubular main body part are configured as separate members,
in the locked state,
when the cover part is biased by the non-linear coil spring and moves away from the piston plate and the cover part is at a separate position away from the piston plate, the engagement part of the release member does not engage the cover part with the piston plate, whereas
when a pressing force against the biasing force of the non-linear coil spring is exerted on the cover part and the cover part is at a close position adjacent to the piston plate, the engagement part of the release member engages the cover part with the piston plate, and
if the cover part is turned such that the engagement part engages the cover part with the piston plate, the engagement part turns the piston plate, each projection of the plurality of projections respectively reaches the axial part from the circumferential part of each groove part of the plurality of groove parts, and the locked piston plate is released.

10. The applicator according to claim 1, wherein
the release member faces an outer circumferential surface of the tubular main body part,
a through-hole is formed at a position on a side wall of the tubular main body part, the position being on a straight line connecting between the release member and the circumferential part of each groove part of the plurality of groove parts, and
if the release member is pushed against the plurality of projections of the locked piston plate while passing through the through-hole, turning the locked piston plate, each projection of the plurality of projections respectively reaches the axial part from the circumferential part of each groove part of the plurality of groove parts, and the locked piston plate is released.

11. The applicator according to claim 10, wherein
the release member is a plate-like body having a triangular shape,
an oblique side of the plate-like body is opposed to the through-hole, and
if the release member is pushed against the plurality of projections of the locked piston plate upon passing through the through-hole and the plurality of projections slide on the oblique side, locked piston plate, each projection of the plurality of projections respectively reaches the axial part from the circumferential part of each groove part of the plurality of groove parts, and the locked piston plate is released.

12. The applicator according to claim 10, further comprising a stopper that restricts drive of the release member thereby preventing the release member from passing through the through-hole and coming into contact with the plurality of projections of the locked piston plate.

13. The applicator according to claim 1, wherein
the release member is attached to an outside of the tubular main body part so as to be movable in the axial direction, and
when a pressing force is exerted on the release member and the release member moves from a side of the first end to a side of the second end of the tubular main body part, the release member turns the piston plate to thereby release the locked piston plate.

14. The applicator according to claim 13, wherein
the release member includes: a first release part that is attached to an outside of the tubular main body part and is movable in the axial direction; and a second release part that is arranged between the tubular main body part and the first release part and is turnable in a circumferential direction of the main body part,
the second release part is provided with: first engagement projections that protrude toward the tubular main body part and are respectively engageable with the plurality of projections of the piston plate; and second engagement projections that protrude toward the first release part, the first release part is provided with housing opening parts that respectively house the second engagement projections therein, the housing opening parts each have a side extending obliquely in the axial direction when viewed from a direction orthogonal to the axial direction, when a pressing force is exerted on the first release part and the first release part moves from the first end side to the second end side of the main body part, the second engagement projections respectively slide on the sides of the housing opening parts while abutting against the sides thereof, and the first release part turns the second release part, and along with the turn of the second release part, the first engagement projections turn the piston plate and are engaged with the plurality of projections of the piston plate, each projection of the plurality of projections respectively reaches the axial part from the circumferential part of each groove part of the plurality of groove parts, and the locked piston plate is released.

15. The applicator according to claim 13, wherein
the release member is attached to an outside of the tubular main body part and is movable in the axial direction, the release member is provided with engagement projections that are respectively located above the plurality of projections of the piston plate and respectively protrude toward the plurality of projections of the piston plate, the engagement projections each have a side extending obliquely in the axial direction when viewed from a direction orthogonal to the axial direction and opposed to each of the plurality of projections of the piston plate, and when a pressing force is exerted on the release member and the release member moves from the first end side to the second end side of the main body part, the sides of the engagement projections turn the piston plate while being respectively engaged with the plurality of projections of the piston plate, each projection of the plurality of projections respectively reaches the axial part from the circumferential part of each groove part of the plurality of groove parts, and the locked piston plate is released.

16. The applicator according to claim 1, further comprising an engagement piece engaging the piston plate.

17. The applicator according to claim 1, wherein the non-linear coil spring is a conical coil spring.

18. The applicator according to claim 17, wherein the conical coil spring is formed by a wire and the wire does not overlap when viewed from an extending direction of a central line of the conical coil spring.

19. An applicator for transferring an active ingredient into a body through a skin by a puncture in the skin with microneedles, the applicator comprising:
 a casing including:
  a tubular main body part having a first end and a second end positioned in an axial direction; and
  a cover part arranged on the first end;
 a piston plate housed in the casing, the piston plate including:
  a first main surface;
  a second main surface opposed to the first main surface;
  a periphery located between the first and second main surfaces; and
  a plurality of projections provided on the periphery and extending in a radial direction from the piston plate,
  wherein the piston plate transmits an impact force to a microneedle array provided with the microneedles when the first main surface of the piston plate collides against the microneedle array;
 a non-linear coil spring housed in the casing between the second main surface of the piston plate and the cover part of the casing, and exerting a biasing force on the piston plate;
 a plurality of groove parts formed on an inner circumferential surface of the tubular main body part, each of the plurality of groove parts including an axial part extending in the axial direction of the tubular main body part, and a circumferential part extending from a first or second end of the axial part along a circumferential direction of the tubular main body part; and
 a release member configured for turning the piston plate along the circumferential direction of the tubular main body part,
 wherein each projection of the plurality of projections of the piston plate corresponds to each groove part of the plurality of groove parts, and
 wherein the piston plate is locked within the casing with the non-linear coil spring compressed when each projection of the plurality of projections of the piston plate moves from the axial part to the circumferential part of each groove part of the plurality of groove parts, and
 wherein the release member turns the locked piston plate thereby moving the piston plate along the axial part of each of the plurality of groove parts by the biasing force to a position for transferring the active ingredient to the body through the skin.

* * * * *